US009255294B2

(12) United States Patent
Taguchi et al.

(10) Patent No.: US 9,255,294 B2
(45) Date of Patent: Feb. 9, 2016

(54) HAIR SHAPE SUSCEPTIBILITY GENE

(75) Inventors: Hiroyuki Taguchi, Haga-gun (JP); Hiroshi Yoshida, Haga-gun (JP); Chie Fuse, Haga-gun (JP); Tadao Arinami, Tsukuba (JP)

(73) Assignee: Kao Corporation, Tokyo (JP)

( * ) Notice: Subject to any disclaimer, the term of this patent is extended or adjusted under 35 U.S.C. 154(b) by 147 days.

(21) Appl. No.: 13/500,439

(22) PCT Filed: Oct. 5, 2010

(86) PCT No.: PCT/JP2010/067441
§ 371 (c)(1),
(2), (4) Date: Jun. 1, 2012

(87) PCT Pub. No.: WO2011/043330
PCT Pub. Date: Apr. 14, 2011

(65) Prior Publication Data

US 2012/0329726 A1 Dec. 27, 2012

(30) Foreign Application Priority Data

| | | |
|---|---|---|
| Oct. 5, 2009 | (JP) | 2009-231991 |
| Oct. 5, 2009 | (JP) | 2009-232001 |
| Oct. 5, 2009 | (JP) | 2009-232002 |
| Oct. 5, 2009 | (JP) | 2009-232003 |
| Oct. 5, 2009 | (JP) | 2009-232004 |
| Oct. 5, 2009 | (JP) | 2009-232035 |

(51) Int. Cl.
*C12Q 1/68* (2006.01)

(52) U.S. Cl.
CPC ........ *C12Q 1/6876* (2013.01); *C12Q 2600/148* (2013.01)

(58) Field of Classification Search
None
See application file for complete search history.

(56) References Cited

U.S. PATENT DOCUMENTS

| | | | |
|---|---|---|---|
| 6,812,339 | B1 | 11/2004 | Venter et al. |
| 2005/0208010 | A1 | 9/2005 | De Lacharriere et al. |
| 2005/0250180 | A1 | 11/2005 | Jacobs et al. |
| 2007/0065389 | A1 | 3/2007 | De Lacharriere et al. |
| 2012/0231094 | A1 | 9/2012 | Taguchi et al. |
| 2012/0276536 | A1 | 11/2012 | Taguchi et al. |

FOREIGN PATENT DOCUMENTS

| | | | |
|---|---|---|---|
| JP | 2002-238577 | | 8/2002 |
| JP | 2005-532407 | | 10/2005 |
| JP | 2006-042735 | | 2/2006 |
| JP | 2006-254735 | | 9/2006 |
| WO | WO 02/068649 | A2 | 9/2002 |
| WO | WO 2007/086526 | A1 | 8/2007 |
| WO | WO 2008/016356 | A2 | 2/2008 |
| WO | WO 2008/021290 | A2 | 2/2008 |
| WO | WO 2008/043644 | A2 | 4/2008 |

OTHER PUBLICATIONS

Honma et al., Identification of Novel Keratinocyte Differentiation Modulating Compounds by High-Throughput Screening; J Biomol Screening, vol. 11, No. 8, pp. 977-984, 2006.*

Regnier et al., Human Epidermis Reconstructed on Dermal Substrates in vitro: An Alternative to Animals in Skin Pharmacology; Skin Pharmacology, vol. 3, pp. 70-85, 1990.*

Brancaccio et al, Requirement of the forkhead gene Foxe1, a target of sonic hedgehog signaling, in hair follicle morphogenesis; Human Molecular Genetics, vol. 13, No. 21, pp. 2595-2606, 2004.*

"Notification of First Office Action," for Chinese Patent Application No. CN 201080044858.8, mailed Dec. 24, 2012, from the Patent Office of the People's Republic of China, Beijing, China.

Botchkarev, VA et al., "Edar signaling in the control of hair follicle development," J Investig Dermatol Symp Proc 10(3): 247-251, (Dec. 2005), Nature Publishing Group, New York, New York.

International Search Report (ISR) for PCT/JP2010/067443, I.A. fd: Oct. 5, 2010, mailed Dec. 7, 2010 from the Japanese Patent Office, Tokyo, Japan, (counterpart to U.S. Appl. No. 13/500,442).

International Preliminary Report on Patentability (IPRP), Chapter I of the Patent Cooperation Treaty, including the Written Opinion for PCT/JP2010/067443, I.A. fd: Oct. 5, 2010, issued May 8, 2012, from the International Bureau of WIPO, Geneva, Switzerland, (counterpart to U.S. Appl. No. 13/500,442).

International Search Report (ISR) for PCT/JP2010/067444, I.A. fd: Oct. 5, 2010, mailed Dec. 7, 2010 from the Japanese Patent Office, Tokyo, Japan, (counterpart to U.S. Appl. No. 13/500,462).

International Preliminary Report on Patentability (IPRP), Chapter I of the Patent Cooperation Treaty, including the Written Opinion for PCT/JP2010/067444, I.A. fd: Oct. 5, 2010, issued May 8, 2012, from the International Bureau of WIPO, Geneva, Switzerland, (counterpart to U.S. Appl. No. 13/500,462).

Extended European search report for EP Appl. No. 10822002.1, (counterpart to U.S. Appl. No. 13/500,442), including the supplementary European search report and the European search opinion, dated Feb. 12, 2013, European Patent Office, Munich, Germany.

(Continued)

*Primary Examiner* — Addison D Ault
(74) *Attorney, Agent, or Firm* — Sterne, Kessler, Goldstein & Fox P.L.L.C.

(57) ABSTRACT

A genetic polymorphism and a hair shape susceptibility gene that are related to hair shape, and a method for determining the genetic susceptibility to hair shape in individual test subjects are provided. Disclosed is a hair shape susceptibility gene, which overlaps with a haplotype block in 1q21.3 region (D1S2696 to D1S2346) of human chromosome 1 and comprises a portion or the entirety of the base sequence of the haplotype block, wherein the haplotype block is determined by a linkage disequilibrium analysis conducted on a single nucleotide polymorphism (SNP) marker whose allele frequency differs statistically significantly between a group having a curly hair trait and a group having a non-curly hair trait, and consists of a base sequence set forth in any one of SEQ ID NO: 1 to NO: 5.

13 Claims, 15 Drawing Sheets

(56) References Cited

OTHER PUBLICATIONS

*Homo sapiens* cysteine and glycine-rich protein 1, mRNA (cDNA clone MGC:40335 IMAGE:5244276, complete cds. Uploaded Jul. 15, 2006, NCBI Entrez Nucleotide, Accession No. BC032493 (GI:21595351) [Retrieved on Nov. 24, 2010, from the internet, www.ncbi.nlm.nih.gov/nuccore/21595351>.

*Homo sapiens* neuron navigator 1 (NAV1) mRNA, complete cds. Uploaded Jul. 1, 2002, NCBI Entrez Nucleotide, Accession No. AY043013 (GI:21654876) [Retrieved on Nov. 24, 2010, from the internet, www.ncbi.nlm.nih.gov/nuccore/21654876>.

*Homo sapiens* importin 9 (IPO9), mRNA, Uploaded Feb. 11, 2008, NCBI Entrez Nucleotide, Accession No. NM_018085 (GI:112734865) [Retrieved on Nov. 24, 2010, from the internet, www.ncbi.nlm.nih.gov/nuccore/112734865?sat=NCBI &satkey=20569420>.

*Homo sapiens* shisa homolog 4 (Xenopus laevis) (SHISA4), mRNA, Uploaded Sep. 3, 2009, NCBI Entrez Nucleotide, Accession No. NM_198149 (GI:39930574) [Retrieved on Nov. 24, 2010, from the internet, www.ncbi.nlm.nih.gov/nuccore/39930574?sat=NCBI &satkey=32433675>.

*Homo sapiens* nuclear casein kinase and cyclin-dependent kinase substrate 1 (NUCKS1), mRNA, Uploaded Feb. 1, 2009, NCBI Entrez Nucleotide, Accession No. NM_022731 (GI:181336713) [Retrieved on Nov. 24, 2010, from the internet, www.ncbi.nlm.nih.gov/nuccore/181336713?sat=NCBI&satkey=27783208>.

*Homo sapiens* organic anion transporter 3 (OAT3), mRNA, complete cds. Uploaded Mar. 9, 1999, NCBI Entrez Nucleotide, Accession No. AF097491 (GI:4378058), [Retrieved on Nov. 29, 2010, from the internet, www.ncbi.nlm.nih.gov/nuccore/4378058>.

*Homo sapiens* phosphofurin acidic cluster sorting protein 1 (PACS1), mRNA, complete cds. Uploaded Sep. 20, 2009, NCBI Entrez Nucleotide, Accession No. NM_018026 (GI:30089915), [Retrieved on Nov. 29, 2010, from the internet, www.ncbi.nlm.nih.gov/nuccore/30089915?sat=NCBI&satkey=32698503>.

*Homo sapiens* kinesin light chain 2 (KLC2), transcript variant 2, mRNA, Uploaded Sep. 3, 2009, NCBI Entrez Nucleotide, Accession No. NM_001134774 (GI:198041727), [Retrieved on Nov. 29, 2010, from the internet, www.ncbi.nlm.nih.gov/nuccore/198041727?sat=NCBI&satkey=32519240>.

*Homo sapiens* RAB1B, member RS oncogene family (RAB1B), mRNA, Uploaded Feb. 1, 2009, NCBI Entrez Nucleotide, Accession No. NM_030981 (GI:116014337), retrieved on Nov. 29, 2010, from the internet, www.ncbi.nlm.nih.gov/nuccore/116014337?sat=NCBI &satkey=27780408>.

*Homo sapiens* cornichon homolog 2 (*Drosophila*) (CNIH2), mRNA, Uploaded Aug. 6, 2009, NCBI Entrez Nucleotide, Accession No. NM_182553 (GI:32698937), retrieved on Nov. 29, 2010, from the internet, www.ncbi.nlm.nih.gov/nuccore/32698937?sat=NCBI &satkey=31931907>.

*Homo sapiens* Yip1 interacting factor homolog A (S. cerevisiae) (YIF1A), mRNA, Uploaded Aug. 2, 2009, NCBI Entrez Nucleotide, Accession No. NM_020470 (GI:170932463), retrieved on Nov. 29, 2010, from the internet, www.ncbi.nlm.nih.gov/nuccore/170932463?sat=NCBI&satkey=31767219>.

*Homo sapiens* transmembrance protein 151A (TMEM151A), mRNA, Uploaded Aug. 6, 2009, NCBI Entrez Nucleotide, Accession No. NM_153266 (GI:221136815), retrieved on Nov. 29, 2010, from the internet, www.ncbi.nlm.nih.gov/nuccore/NM_153266.3.

*Homo sapiens* CD248 molecule, endosialin (CD248), mRNA, Uploaded Feb. 1, 2009, NCBI Entrez Nucleotide, Accession No. NM_020404 (GI:45387956), retrieved on Nov. 29, 2010, from the internet, www.ncbi.nlm.nih.gov/nuccore/45387956?sat=NCBI &satkey=27783461>.

*Homo sapiens* oral cancer overexpressed 1 (ORAOV1), mRNA, Uploaded Aug. 6, 2009, NCBI Entrez Nucleotide, Accession No. NM_153451 GI:56676315), retrieved on Nov. 29, 2010, from the internet, www.ncbi.nlm.nih.gov/nuccore/56676315?sat=NCBI &satkey=31931818>.

*Homo sapiens* keratin associated protein 5-8 (KRTAP5-8), mRNA, Uploaded May 1, 2008, NCBI Entrez Nucleotide, Accession No. NM_021046 (GI:123173776), retrieved on Nov. 29, 2010, from the internet, www.ncbi.nlm.nih.gov/nuccore/123173776?sat=NCBI &satkey=22245774>.

*Homo sapiens* keratin associated protein 5-9 (KRTAP5-9), mRNA, Uploaded Feb. 26, 2008, NCBI Entrez Nucleotide, Accession No. NM_005553 (GI:123702037), retrieved on Nov. 29, 2010, from the internet, www.ncbi.nlm.nih.gov/nuccore/123702037?sat=NCBI &satkey=20831141>.

*Homo sapiens* keratin associated protein 5-10 (KRTAP5-10), mRNA, Uploaded May 1, 2008, NCBI Entrez Nucleotide, Accession No. NM_001012710 (GI:60593039), retrieved on Nov. 29, 2010, from the internet, www.ncbi.nlm.nih.gov/nuccore/60593039?sat=NCBI&satkey=22247595>.

Kimura, K. et al., "Diversification of transcriptional modulation: Large-scale identification and characterization of putative alternative promoters of human gene," Genome Research 16: 55-65, Jan. 2006, Cold Spring Harbor Laboratory Press, Woodbury, NY.

Klacansky, I. et al., "Cell-type-specific patterns of gene expression, GenBank: locus FW48121.1" Feb. 21, 2008, XP055052019, Retrieved from the internet: www.ncbi.nlm.nih.gov/nuccore/fw548121, retrieved Feb. 1, 2013.

Mou, C, et al., "Enhanced ectodysplasin-A receptor (EDAR) signaling alters multiple fiber characteristics to produce the East Asian hair form," Hum Mutat, 29(12): 1405-1411 (Dec. 2008), Wiley-Liss, New York, NY.

Notification of First Office Action, for Chinese Patent Application No. CN 201080044857.3, mailed Dec. 24, 2012, from the Patent Office of the People's Republic of China, Beijing, China (counterpart to U.S. Appl. No. 13/500,462).

Notification of First Office Action, for Chinese Patent Application No. CN 201080044856.9, mailed Dec. 25, 2012, from the Patent Office of the People's Republic of China, Beijing, China (counterpart to U.S. Appl. No. 13/500,442).

Tand, D. et al., "Advances in Method for SNP Detection," J. Shanghai Jiaotong University (Agricultural Science) 25(2):405-418 (Apr. 2007), China Academic Journal Electronic Publishing House, Beijing, China.

Wang, Q-s. et al., "Review of Association Analyses of Haplotype with Traits," J. Shanghai Jiaotong University (Agricultural Science) 26(3):255-257 (Jun. 2008),China Academic Journal Electronic Publishing House, Beijing, China.

International Search Report (ISR) for PCT/JP2010/067441, I.A. fd: Oct. 5, 2010, mailed Nov. 30, 2010 from the Japanese Patent Office, Tokyo, Japan.

International Preliminary Report on Patentability (IPRP), Chapter I of the Patent Cooperation Treaty, including the Written Opinion for PCT/JP2010/067441, I.A. fd: Oct. 5, 2010, issued May 8, 2012, from the International Bureau of WIPO, Geneva, Switzerland.

*Homo sapiens* annexin A9 (ANXA9), mRNA, Uploaded May 1, 2008, NCBI Entrez Nucleotide, Accession No. NM_003568 (GI:145864464), retrieved on Nov. 15, 2010, from the internet, www.ncbi.nlm.nih.gov/nuccore/145864464?sat=NCBI &satkey=22246716>.

*Homo sapiens* family with sequence similarity 63, member A (FAM63A), transcript variant 2, mRNA, Uploaded Aug. 5, 2009, NCBI Entrez Nucleotide, Accession No. NM_001040217 (GI:253795485), retrieved on Nov. 15, 2010, from the internet, www.ncbi.nlm.nih.gov/nuccore/NM_001040217.2>.

*Homo sapiens* late cornified envelope 5A (LCE5A), mRNA, Uploaded Sep. 20, 2009, NCBI Entrez Nucleotide, Accession No. NM_178438 (GI:110578661), retrieved on Nov. 15, 2010, from the internet, www.ncbi.nlm.nih.gov/nuccore/110578661?sat=NCBI &satkey=32699481>.

*Homo sapiens* cysteine-rich C-terminal 1 (CRCT1), mRNA, Uploaded Oct. 9, 2008, NCBI Entrez Nucleotide, Accession No. NM_019060 (GI:209180483), retrieved on Nov. 15, 2010, from the internet, www.ncbi.nlm.nih.gov/nuccore/209180483?sat=NCBI &satkey=25519550>.

*Homo sapiens* late cornified envelope 2B (LCE2B), mRNA, Uploaded Feb. 22, 2009, NCBI Entrez Nucleotide, Accession No. NM_014357 (GI:223633914), retrieved on Nov. 15, 2010, from the internet, www.ncbi.nlm.nih.gov/nuccore/223633914?sat=NCBI &satkey=28460288>.

(56) References Cited

OTHER PUBLICATIONS

*Homo sapiens* late cornified envelope 2A (LCE2A), mRNA, Uploaded Feb. 13, 2009, NCBI Entrez Nucleotide, Accession No. NM_178428 (GI:57242769), retrieved on Nov. 15, 2010, from the internet, www.ncbi.nlm.nih.gov/nuccore/57242769?sat=NCBI &satkey=283933204>.
*Homo sapiens* sperm mitochondria-associated cysteine-rich protein (SMCP), nuclear gene encoding mitochondrial protein, mRNA, Uploaded Feb. 11, 2008, NCBI Entrez Nucleotide, Accession No. NM_030663 (GI:25121988), retrieved on Nov. 15, 2010, from the internet, www.ncbi.nlm.nih.gov/nuccore/25121988?sat=NCBI &satkey=20570171>.
*Homo sapiens* involucrin (IVL), mRNA, Uploaded Sep. 20, 2009, NCBI Entrez Nucleotide, Accession No. NM_005547 (GI:44890058), retrieved on Nov. 15, 2010, from the internet, www.ncbi.nlm.nih.gov/nuccore/44890058?sat=NCBI &satkey=32698100>.
Altshuler, D et al., "The common PPARγPro12Ala polymorphism is associated with decreased risk of type 2 diabetes," Nat Genet 26(1): 76-80 (Sep. 2000), Nature Pub. Co, New York, NY.
Cullen SI et al, "Acquired Progressive Kinking of the Hair," Arch Dermatol 125: 252-255 (Feb. 1989), American Medical Assn, Chicago, IL.
Du, X et al., "Velvet, a Dominant *Egfr* Mutation That Causes Wavy Hair and Defective Eyelid Development in Mice," Genetics 166: 331-340 (Jan. 2004), Genetics Society of America, Bethesda, MD.
Fujimoto, A, et al., "A scan for genetic determinants of human hair morphology: *EDAR* is associated with Asian hair thickness," Hum Mol Genet 17: 835-843 (Mar. 2008), IRL Press at Oxford University Press, Oxford, England.
Hanis, CL et al., "A genome-wide search for human non-insulin-dependent (type 2) diabetes genes reveal a major susceptibility locus on chromosome 2," Nat Genet 13(2): 161-166 (Jun. 1996), Nature Pub. Co, New York, NY.
Kjaer, KW et al.. "Novel Connexin 43 (GJA1) mutation causes oculo-dento-digital dysplasia with curly hair," Am J Med Genet A, 127A(2): 152-157 (Jun. 2004), Wiley-Blackwell, Hoboken, N.J.
Mann, GB et al., "Mice with a null mutation of the TGFα gene have abnormal skin architecture, wavy hair, and curly whiskers and often develop corneal inflammation," Cell 73(2): 249-261 (Apr. 1993), MIT Press, Cambridge, MA.
Medland, SE et al., "Common variants in the trichohyalin gene are associated with straight hair in Europeans," Am J Hum Genet 85(5): 750-755 (Nov. 2009), American Society of Human Genetics, Baltimore, MD.
Møller, LB et al., "Identification and analysis of 21 novel disease-causing amino acid substitutions in the conserved part of ATP7A," Hum Mutat 26(2): 84-93 (Aug. 2005), Wiley-Liss, New York, NY.
Norgett, EE et al,, "Recessive mutation in desmoplakin disrupts desmoplakin-intermediate filament interactions and causes dilated cardiomyopathy, woolly hair and keratoderma," Hum Mol Genet 9: 2761-2766 (Nov. 2000), IRL Press at Oxford University Press, Oxford, England.
Rostand, J et al., "An Atlas of Human Genetics," Hutchinson Scientific & Technical, London, England, pp. 26-29, 1964.
Sabeti, PC et al., "Genome-wide detection and characterization of positive selection in human populations," Nature 449(7164): 913-918 (Oct. 2007), plus supplementary online material, Nature Publishing Group, Basingstoke, England.
Sulem, P. et al., "Genetic determinants of hair, eye and skin pigmentation in Europeans," Nat Genet 39(12): 1443-1452 (Dec. 2007), Nature Pub. Co., New York, NY.
Thibaut, S, et al., "Human hair shape is programmed from the bulb," Br J Dermatol 152(4): 632-638 (Apr. 2005), Blackwell Scientific Publications, Oxford, England.
Extended European search report including the supplementary European search report and the European search opinion, mailed May 17, 2013, for EP Application No. 10822000.5, the European Patent Office, Rijswijk, Netherlands.
Yusuke: "Submitted SNP (ss) Details: ss4940242," NCBI-DbSNP database, NCBI Bethesda, MD, submitted Aug. 1, 2002, retrieved from the internet: www.ncbi.nlm.nih.gov/SNP/snp_ss.cgi?subsnp_id=4940242 retrieved on Apr. 16, 2013.
Extended European search report including the supplementary European search report and the European search opinion, mailed Jun. 7, 2013, for EP Application No. 10822003.9, the European Patent Office, Munich, Germany.
Stoll, M et al., "Genetic variation in *DLG5* is associated with inflammatory bowel disease," Nat Genet, May 2004; 36(5): 476-480, Nature Pub. Co, New York, NY.
Shimomura, Y et al., "Disruption of P2RY5, an orphan G protein-coupled receptor, underlies autosomal recessive woolly hair," Nat Genet, Mar. 2008; 40(3): 335-339, Nature Pub. Co, New York, NY.
Schlake, T, "Segmental *Igfbp5* expression is specifically associated with the bent structure of zigzag hairs," Mech Dev, Sep. 2005; 122(9): 988-997, Elsevier, Limerick, Ireland.
Excerpted file history of U.S. Appl. No. 13/500,442: Final Office action mailed Sep. 10, 2014, Reply to first Office action filed Aug. 21, 2014; first Office action mailed Apr. 21, 2014; reply to Restriction/election of species requirements filed Jan. 23, 2014; and Restriction/election of species requirement mailed Nov. 27, 2013.
Excerpted file history of U.S. Appl. No, 13/500,462: final Office action mailed Sep. 10, 2014, Reply to first Office action filed Aug. 21, 2014; first Office action mailed Apr. 21, 2014; reply to restriction/election of species requirements filed Jan. 23, 2014; and restriction/election of species requirement mailed Nov. 27, 2013.
Hindorff, LA et al., "Genetic architecture of cancer and other complex diseases: lessons learned and future directions," Carcinogenesis, Jul. 2011; 32: 945-954, IRL Press, Oxford, England.
Liu, X et al., "Genetic variants at 5p12 and risk of breast cancer in Han Chinese," J Hum Genet, Oct. 2012; 57(10): 638-641, Nature Pub. Group, London, England.
*Homo sapiens* cysteine and glycine-rich protein 1 (CSRP1), transcript variant 1, mRNA, NCBI Accession NM_004078, version NM_004078.2 (GI:221316625), Jun. 24, 2009, last modification Feb. 26, 2014, printed from www.ncbi.nlm.nih.gov/nuccore/NM_004078.
Xie, Ji-sheng et al., "Difference in the polymorphism of exon 5 +3953C/T of interleukin-1 beta gene between Guangxi Zhuang population and Han population," Chinese J Clin. Rehabilitation 10:154-156 (Oct. 2006), Shenyang Shi, China.
Excerpted file history of U.S. Appl. No. 13/500,442: Applicants' Amendment and Reply filed Mar. 9, 2015, filed with the USPTO, Alexandria, VA.
Excerpted file history of U.S. Appl. No. 13/500,462: Applicants' Amendment and Reply filed Mar. 9, 2015, filed with the USPTO, Alexandria, VA.

* cited by examiner

HAIR SHAPE SUSCEPTIBILITY GENE

REFERENCE TO SEQUENCE LISTING SUBMITTED ELECTRONICALLY

The content of the electronically submitted substitute sequence listing, file name 2537_0670006SequenceListing_ascii.txt; size 219,923 bytes; and date of creation Apr. 4, 2012, filed herewith, is incorporated herein by reference in its entirety.

FIELD OF THE INVENTION

The present invention relates to a gene related to hair shape, determination of genetic susceptibility to hair shape, detection and/or determination of the type of hair shape, a marker for screening an ingredient effective for the regulation of hair shape, and a use of the marker.

BACKGROUND OF THE INVENTION

The natural shape of human hair is generally classified into straight hair, wavy hair (wave hair), curled hair, and kinky hair (or coiled hair), depending on the degree of curl of the hair. Since the shape of hair and hairstyle constitutes one of the traits that can be easily recognized as physical features of human being, and also serve as an important factor that determines the first impression of a person, the shape of hair and hairstyle is a matter of great interest from a cosmetic viewpoint, irrespective of gender and age. In the case of kinky hair or curled hair with a high degree of curl, the person has trouble that the degree of freedom in hairstyle is limited so that desired styling cannot be achieved. On the other hand, even in the case of straight hair, the person also has trouble that the hair cannot be volumized, and bare skin is easily shown through.

As methods for changing the shape of hair and hairstyle, hairdressing using various hairstyling agents or hair dryers/hair irons, wave/straight permanent treatments, and the like are being extensively carried out. However, although these operations can effectively modify the shape of hair, the operations have no effect on the causative factor that determines the hair shape. These operations, which are the solutions to the above described troubles, are not fundamental solutions but are merely temporary, and in order to maintain the shape of hair and hairstyle, these operations must be repeated frequently. However, on the contrary, these operations cause increased damage to hair, and consequently impair the cosmetic value. For this reason, there is a demand for the development of a method for the intrinsic regulation of hair shape, by which the hair shape can be changed from the beginning of hair growth.

Searching for a causative factor that determines the hair shape and identifying a causative gene thereof are expected to provide useful information in the development of a method for the intrinsic regulation of hair shape. In regard to the factors or genes related to hair shape, there have been reports on the genetic diseases that bring changes to the shape of hair (Non-Patent Documents 1 to 3), acquired kinky hair caused by drugs (Non-Patent Document 4), curly hair model animals (Non-Patent Documents 5 and 6), an the like. However, the factors or genes disclosed in these documents are merely a special example which affect the hair shape, and are not adequate to be considered as causative factors that determine the natural shape of human hair.

Meanwhile, along with the rapid progress in the genome analysis technology in recent years, the correlation between diseases and genes is being gradually clarified. Particularly, not only for so-called genetic diseases that are defined by variation or abnormality of a single gene, but also for polygenic diseases characterized by low penetrance (the ratio of onset of a certain disease in an individual having a variation in a certain gene), such as highly frequent common diseases including lifestyle diseases such as diabetes and hypertension, search for causative genes using non-parametric linkage analysis techniques such as affected sib-pair linkage analysis is frequently carried out (see, for example, Non-Patent Document 7). Further, based on the hypothesis that the variation of a disease-associated gene for a common disease is a highly frequent genetic polymorphism (common variant), and that although the variation is present in healthy persons as well, the prevalence is significantly high in patients (Common Disease-Common Variant), search for causative genes by means of linkage disequilibrium analysis using a genetic polymorphism (for example, SNP (Single Nucleotide Polymorphism)) is also actively carried out throughout the world (see, for example, Non-Patent Document 8).

More recently, with the progress in the international HapMap Project, a database of general polymorphisms (SNP) of high frequencies such as one million loci or more in four human populations has been established, and research is being conducted on common diseases as well as on general traits in which the phenotype varies with the human race or population, for example, skin color, hair color, and eye color (see, for example, Non-Patent Documents 9 and 10).

Similarly, also in regard to the natural shape of human hair, it can be contemplated that the natural hair shape is a general trait in which the phenotype varies with the human race or population. In general, many Asian people have straight hair, while African people predominantly have kinky hair (or curled hair). Indo-European people have a high ratio of having a trait of wavy hair (wave hair), which is intermediate of the two. The mode of inheritance was first observed by Rostand, J., et al., and they reported that curly hair is an autosomal (semi) dominant trait over straight hair (Non-Patent Document 11). Furthermore, descriptions on the curly hair trait may also be found in the human Mendelian inheritance database of the NCBI (OMIM, http://www.ncbi.nlm.nih.gov/omim/). However, in regard to causative genes that determine the natural shape of human hair, systematic research on genome analysis has not been completed, and no such genes have been found yet.

PRIOR ART DOCUMENTS

Non-Patent Documents

Non-Patent Document 1: Norgett E E et al., Hum. Mol. Genet. 9(18), p. 2761-2766, 2000

Non-Patent Document 2: Moller L B et al., Hum. Mutat. 26 (2), p. 84-93, 2005

Non-Patent Document 3: Kjaer K W et al., Am. J. Med. Genet. A. 127A(2), p. 152-157, 2004

Non-Patent Document 4: Cullen S I et al., Arch. Dermatol. 125(2), p. 252-255, 1989

Non-Patent Document 5: Du X et al. Genetics. 166(1), p. 331-340, 2004

Non-Patent Document 6: Mann G B et al., Cell. 73 (2), p. 249-61, 1993

Non-Patent Document 7: Hanis C L et al., Nat. Genet. 13 (2), p 161-166, 1996

Non-Patent Document 8: Altshuler D et al., Nat. Genet. 26(1), p. 76-80, 2000

Non-Patent Document 9: Sulem P et al., Nat. Genet. 39(12), p. 1443-1452, 2007

Non-Patent Document 10: Sabeti P C et al., Nature. 449 (7164), p. 913-918, 2007

Non-Patent Document 11: Rostand J et al., "An Atlas of Human Genetics", Hutchinson Scientific & Technical, London, pp. 26-29, 1964

SUMMARY OF THE INVENTION

The present invention provides a hair shape susceptibility gene, which overlaps with a haplotype block in 1q21.3 region (D1S2696 to D1S2346) of human chromosome 1 and includes a portion or the entirety of the base sequence of the haplotype block, wherein the haplotype block is determined by a linkage disequilibrium analysis conducted on a single nucleotide polymorphism (SNP) marker whose allele frequency differs statistically significantly between a group having a curly hair trait and a group having a non-curly hair trait, and consists of a base sequence set forth in any one of SEQ ID NO: 1 to NO: 5.

The present invention also provides a hair shape determining marker, which is an oligo- or polynucleotide containing a partial base sequence of the base sequence of the haplotype block described above, or a complementary strand thereof, wherein the partial base sequence consists of a contiguous base sequence containing one or more single nucleotide polymorphisms (SNPs), wherein the SNPs include an SNP whose allele frequency differs statistically significantly between a group having a curly hair trait and a group having a non-curly hair trait and an SNP linked to the SNP.

Furthermore, the present invention provides a method for determining the genetic susceptibility of a test subject to hair shape, the method including the following steps (a) to (c):

(a) preparing a genomic DNA derived from a test subject;

(b) detecting, from the genomic DNA, in the haplotype block, a single nucleotide polymorphism (SNP) which exists in the haplotype block described above and whose allele frequency differs statistically significantly between a group having a curly hair trait and a group having a non-curly hair trait, and a single nucleotide polymorphism (SNP) that is linked to the SNP; and (c) determining, if the allele frequency of the detected relevant SNP is statistically significantly higher in the group of curly hair people than in the group of non-curly hair people, that the test subject has a genetic predisposition to curly hair, and if the allele frequency of the detected SNP is statistically significantly higher in an arbitrary group of non-curly hair people than in the group of curly hair people, that the test subject does not have a genetic predisposition to curly hair.

The present invention also provides a method for determining the genetic susceptibility of a test subject to hair shape, the method including:

identifying, for any one or more nucleotides of the nucleotide numbers as indicated in the following table that are present in the base sequences set forth in SEQ ID NO:1 to NO:5 in the genomic DNA derived from a test subject, whether the nucleotide is nucleotide (i) or nucleotide (ii); and determining, when the nucleotide is nucleotide (i), that the test subject has a predisposition to curly hair, and when the nucleotide is nucleotide (ii), that the test subject does not have a predisposition to curly hair.

TABLE 1

| SEQ ID NO. | Nucleotide Number | Nucleotide (i) (having predisposition) | Nucleotide (ii) (no predisposition) |
|---|---|---|---|
| 1 | 1 | G | A |
| | 2405 | G | T |
| | 5874 | A | G |
| | 7121 | T | C |
| | 8494 | A | C |
| | 18980 | A | T |
| | 23252 | C | T |
| 2 | 2355 | G | A |
| | 2569 | A | G |
| | 3897 | G | A |
| | 8196 | T | C |
| | 9510 | C | T |
| | 13643 | G | C |
| | 15387 | G | G |
| | 15708 | C | A |
| | 16017 | T | G |
| | 17106 | C | T |
| | 17453 | C | T |
| | 17579 | T | C |
| | 17634 | T | A |
| | 26924 | G | A |
| | 28383 | C | T |
| | 31275 | G | C |
| | 31301 | G | T |
| | 31653 | G | A |
| | 31903 | C | T |
| | 32209 | G | A |
| | 33199 | C | T |
| | 33822 | G | A |
| | 34100 | C | T |
| | 35791 | G | A |
| | 36884 | A | G |
| | 37072 | A | G |
| | 37365 | T | A |
| | 37613 | C | G |
| | 38062 | A | G |
| | 39063 | C | T |
| | 46580 | C | A |
| | 49618 | G | C |
| | 50164 | T | A |
| | 50278 | A | G |
| | 50662 | T | G |
| | 50822 | C | T |
| | 50981 | G | A |
| | 51133 | C | A |
| | 51263 | T | G |
| | 51397 | C | T |
| 3 | 2509 | A | G |
| | 5167 | C | T |
| | 8449 | G | T |
| | 17598 | A | G |
| | 18481 | C | T |
| | 20891 | G | C |
| | 21734 | T | C |
| | 23382 | T | A |
| 4 | 1 | C | T |
| | 3308 | T | C |
| | 4715 | A | G |
| | 4985 | T | C |
| | 6354 | A | C |
| | 8553 | T | C |
| | 8818 | G | C |
| 5 | 1 | T | C |
| | 540 | A | C |
| | 759 | T | C |
| | 1007 | G | A |
| | 1018 | A | G |
| | 1075 | C | G |
| | 1939 | A | G |
| | 3440 | G | A |

Furthermore, the present invention provides a reagent for the determination of the genetic susceptibility of a test subject to hair shape, the reagent including a probe and/or a primer, which hybridizes with the hair shape determining marker of the present invention under stringent conditions.

The present invention also provides a kit for the determination of the genetic susceptibility of a test subject to hair shape, the kit including the reagent described above.

Furthermore, the present invention provides a method for screening a hair shape regulating agent, the method including the following steps (a) and (b):

(a) administering a test substance to a cell containing the hair shape susceptibility gene of the present invention; and (b) selecting, among the administered test substances, a substance which converts the type of the polymorphism of the nucleotide in a marker with a single nucleotide polymorphism (SNP) that is present on the hair shape susceptibility gene or in the vicinity thereof, and the allele frequency of which differs statistically significantly between a group having a curly hair trait and a group having a non-curly hair trait, or a single nucleotide polymorphism (SNP) that is linked to the SNP, to another type of polymorphisms, as a hair shape regulating agent.

Furthermore, the present invention provides a marker for the type of hair shape, consisting of a polynucleotide consisting of a base sequence set forth in SEQ ID NO:44, SEQ ID NO:46, SEQ ID NO:48, SEQ ID NO:50 or SEQ ID NO:52, or a base sequence complementary thereto, or a partial polynucleotide of the polynucleotide, or consisting of a polypeptide consisting of an amino acid sequence set forth in SEQ ID NO:45, SEQ ID NO: 47, SEQ ID NO:49, SEQ ID NO: 51 or SEQ ID NO: 53, or a partial polypeptide thereof.

The present invention also provides a primer for amplifying the marker for the type of hair shape of the present invention, the primer including a partial polynucleotide of a polynucleotide consisting of a base sequence set forth in SEQ ID NO:44, SEQ ID NO:46, SEQ ID NO:48, SEQ ID NO:50 or SEQ ID NO:52, or a base sequence complementary thereto.

The present invention also provides a probe for detecting the marker for the type of hair shape of the present invention, the probe including a polynucleotide consisting of a base sequence set forth in SEQ ID NO:44, SEQ ID NO:46, SEQ ID NO:48, SEQ ID NO:50 or SEQ ID NO:52, or a base sequence complementary thereto, or a partial polynucleotide of the polynucleotide.

The present invention also provides an antibody for detecting the marker for the type of hair shape of the present invention, the antibody being capable of specifically recognizing a polypeptide consisting of an amino acid sequence set forth in SEQ ID NO:45, SEQ ID NO:47, SEQ ID NO:49, SEQ ID NO:51 or SEQ ID NO:53, or a partial polypeptide of the polypeptide.

Furthermore, the present invention provides a method for detecting and/or determining the type of hair shape, the method including the following steps (a) to (c):

(a) measuring the amount of expression of the marker for the type of hair shape of the present invention in a sample derived from a test subject;

(b) comparing the results in the measurement obtained from step (a) with the results of non-curly hair people; and (c) determining the type of hair shape based on the results obtained from (b).

The present invention also provides a method for evaluating or selecting a hair shape regulating agent, the method including the following steps (a) to (d):

(a) contacting a test substance with a tissue or cell capable of expressing the hair shape susceptibility gene of the present invention or a protein encoded by the gene;

(b) measuring the amount of expression of the gene or the protein in the cell contacted with a test substance;

(c) comparing the amount of expression measured in step (b) with the amount of expression of the gene or the protein in a control tissue or cell that has not been contacted with the test substance; and (d) selecting, based on the results obtained in step (c), a test substance which increases or decreases the amount of expression of the gene or the protein, as a hair shape regulating agent.

The present invention also provides a method for evaluating or selecting a hair shape regulating agent, the method including the following steps (a) to (c):

(a) introducing, to a cell capable of expressing the hair shape susceptibility gene for the type of hair shape of the present invention, a fusion gene of the regulatory region of the hair shape susceptibility gene and a reporter gene, and culturing the cell in the presence and in the absence of a test substance;

(b) measuring the amount of expression of an expression product of the reporter gene in the cell culture cultured in the presence of the test substance, and comparing the amount with the amount of expression of an expression product of the reporter gene in the cell culture cultured in the absence of the test substance; and (c) selecting, based on the comparison results obtained from step (b), a test substance which increases or decreases the amount of the expression product of the reporter gene, as a hair shape regulating agent.

The present invention also provides a method for evaluating or selecting a hair shape regulating agent, the method including the following steps (a) to (c):

(a) contacting a test substance with an aqueous solution, a cell or a cell fraction prepared from the cell containing a protein encoded by the hair shape susceptibility gene of the present invention;

(b) measuring the function or activity of the protein in the aqueous solution, cell or cell fraction that has been contacted with the test substance, and comparing the function or activity with that in a control aqueous solution, a control cell or a control cell fraction which has not been contacted with the test substance; and (c) selecting, based on the comparison results obtained from step (b), a test substance which increases or decreases the function or activity of the protein, as a hair shape regulating agent.

The present invention also provides a method for regulating the type of hair shape, the method including controlling the expression of the hair shape susceptibility gene of the present invention in the human hair root area.

According to an embodiment, the hair shape susceptibility gene of the present invention is selected from ANXA9, FAM63A, LCE5A, CRCT1, LCE2B, LCE2A, SMCP and IVL.

According to an embodiment of the hair shape determining marker of the present invention, the SNPs include an SNP in a nucleotide selected from the group consisting of the following nucleotides:

(1) in the base sequence set forth in SEQ ID NO:1, nucleotides represented by Nucleotide Numbers 1 (dbSNP Database ID: rs3754211, A or G), 2405 (rs3754210, T or G), 5874 (rs16832604, G or A), 7121 (rs2305814, C or T), 8494 (rs7532008, C or A), 18980 (rs1673160, T or A), and 23252 (rs771205, T or C);

(2) in the base sequence set forth in SEQ ID NO:2, nucleotides represented by Nucleotide Numbers 2355 (rs11581947, A or G), 2569 (rs6658925, G or A), 3897 (rs2105117, A or G), 8196 (rs1053590, C or T), 9510 (rs548252, T or C), 13643 (rs493133, C or G) 15387

(rs1970283, C or G), 15708 (rs1001834, A or C), 16017 (rs11205018, G or T), 17106 (rs545418, T or C), 17453 (rs12116609, T or C), 17579 (rs526099, C or T), 17634 (rs525960, A or T), 26924 (rs4845443, A or G), 28383 (rs569032, T or C), 31275 (rs528427, C or G), 31301 (rs478926, T or G), 31653 (rs1337338, A or G), 31903 (rs6587681, T or C), 32209 (rs1856120, A or G), 33199 (rs474086, T or C), 33822 (rs578382, A or G), 34100 (rs549044, T or C), 35791 (rs1123567, A or G), 36884 (rs1538083, G or A), 37072 (rs1538082, G or A), 37365 (rs7532535, A or T), 37613 (rs7518654, G or C), 38062 (rs533917, G or A), 39063 (rs564107, T or C), 46580 (rs7530609, A or C), 49618 (rs4240885, C or G), 50164 (rs4240886, A or T), 50278 (rs4240887, G or A), 50662 (rs6687126, G or T), 50822 (rs6674451, T or C), 50981 (rs7550769, A or G), 51133 (rs7529157, A or C), 51263 (rs1988805, G or T), and 51397 (rs7529441, T or C);

(3) in the base sequence set forth in SEQ ID NO:3, nucleotides represented by Nucleotide Numbers 2509 (rs11205072, G or A), 5167 (rs3753453, T or C), 8449 (rs3737859, T or G), 17598 (rs3904414, G or A), 18481 (rs12074783, T or C), 20891 (rs3908717, C or G), 21734 (rs3904415, C or T), and 23382 (rs11205079, A or T);

(4) in the base sequence set forth in SEQ ID NO:4, nucleotides represented by Nucleotide Numbers 1 (rs16834715, T or C), 3308 (rs12022319, C or T), 4715 (rs4845490, G or A), 4985 (rs4845491, C or T), 6354 (rs3737861, C or A), 8553 (rs16834728, C or T), and 8818 (rs4845492, C or G); and (5) in the base sequence set forth in SEQ ID NO:5, nucleotides represented by Nucleotide Numbers 1 (rs1854779, C or T), 540 (rs1683.4751, C or A), 759 (rs4523473, C or T), 1007 (rs11205131, A or G), 1018 (rs7528862, G or A), 1075 (rs7517189, G or C), 1939 (rs2229496, G or A), and 3440 (rs913996, A or G).

According to another embodiment, the hair shape determining marker consists of a contiguous base sequence having a length of 10 to 601 nucleotides.

According to an embodiment of the reagent for the determination of the genetic susceptibility of a test subject to hair shape of the present invention, the probe and/or the primer hybridized with a region containing the SNP listed in the items (1) to (5) described above.

According to an embodiment of the marker for the type of hair shape of the present invention, the partial polynucleotide is a polynucleotide of 15 bases or more.

According to an embodiment of the method of the present invention for detecting and/or determining the type of hair shape, the sample derived from a test subject is an RNA prepared from a biological sample collected from the test subject, or a complementary polynucleotide transcribed from the RNA.

According to another embodiment of the method of the present invention for detecting and/or determining the type of hair shape, the step (a) is a step for contacting a biological sample collected from a test subject with an antibody for detecting the marker for the type of hair shape of the present invention, and measuring the amount of the marker for the type of hair shape of the present invention in the biological sample that has been bound with the antibody.

According to another embodiment of the method of the present invention for detecting and/or determining the type of hair shape, the biological sample collected from the test subject is derived from an epithelial tissue or epithelial cell.

BRIEF DESCRIPTION OF THE DRAWINGS

FIG. 10-1 is a graph showing the amounts of expression of the hair shape susceptibility gene in the scalp hair roots of a curly hair group and a straight hair group, A: ANXA9 gene, B: CRCT1 gene;

FIG. 10-2 is a graph showing the amounts of expression of the hair shape susceptibility gene in the scalp hair roots of a curly hair group and a straight hair group, C: LCE2B gene, D: LCE2A gene;

FIG. 10-3 is a graph showing the amounts of expression of the hair shape susceptibility gene in the scalp hair roots of a curly hair group and a straight hair group, E: IVL gene;

DETAILED DESCRIPTION OF THE INVENTION

Figure 1:
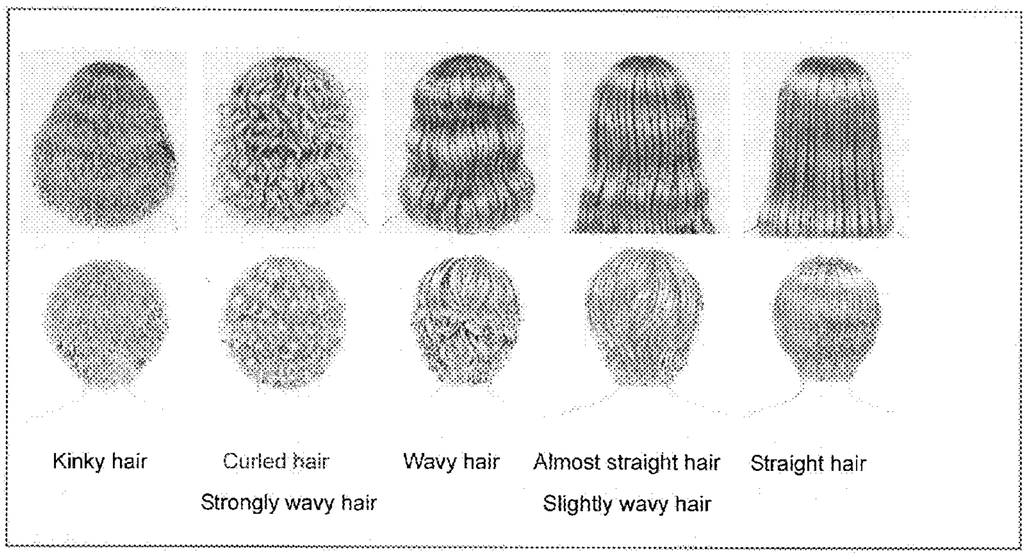
FIG. 1 is a set of images of the phenotypes of hair shape.

The present invention relates to the provision of a genetic polymorphism and a hair shape susceptibility gene that are related to the natural shape of human hair such as curly hair or straight hair, and the provision of a method for determining the genetic susceptibility of individual test subjects to hair shape based on this information. Furthermore, the present invention relates to the provision of a reagent and a reagent kit, which are useful for conveniently carrying out the method. In addition, the present invention relates to the provision of a marker (polynucleotide or polypeptide) for detecting and determining the natural shape of human hair such as curly hair or straight hair, and to the use of the marker, such as the detection and/or determination of the type of hair shape or the evaluation and selection of an ingredient effective for the regulation of hair shape using the marker.

The inventors of the present invention set a goal of finding a causative gene that determines the natural shape of human hair, and conducted a genome analysis directed to a Japanese family lines having curly hair, a group of Japanese curly hair people and a group of Japanese non-curly hair people. As a result, the inventors identified genetic polymorphisms related to hair shape, that is, hair shape susceptibility SNP markers, and also identified hair shape susceptibility genes in the 1q21.3 region of chromosome 1. The inventors of the present invention also investigated the relations between hair shape and the gene expression of various genes in the hair root area, and found that the amount of expression of the hair shape susceptibility genes in the hair root area differs significantly between non-curly hair people and curly hair people. These genes are hair shape susceptibility genes, and can serve as markers for detecting and/or determining the type of hair shape. Based on these findings, the inventors of the present invention finally completed the present invention.

According to the present invention, a hair shape susceptibility gene related to the natural shape of human hair such as curly hair or straight hair, a hair shape susceptibility SNP marker, and a hair shape determining marker utilizing these are provided. When the hair shape susceptibility gene, the SNP marker, and the hair shape determining marker of the present invention are analyzed in detail, research on the mechanism of the hair formation related to the hair shape, and application research such as the development of an adequate method for promoting the regulation of hair shape are made available.

According to the method for determining the genetic susceptibility to hair shape of a test subject of the present invention, search for a gene that serves as a main factor that determines the hair shape of individual test subjects, and determination of the susceptibility of individual test subjects to the acquired changes of hair shape, that is, the degree of risk of the future change in the hair shape, can be more conveniently and rapidly carried out. Furthermore, based on the results, an adequate method for regulating the hair shape for individual persons can be provided. Further, the determination method can be carried out more conveniently and rapidly, by the reagent for the determination of genetic susceptibility of a test subject to hair shape of the present invention and the kit including the reagent.

According to the present invention, the shape or nature of hair such as curly hair or kinky hair can be detected and determined without damaging the hair. Furthermore, a substance selected according to the method of the present invention for screening an ingredient effective for the regulation of hair shape can be used as a hair shape regulating agent that is effective for the regulation of hair shape, and can also be used for the preparation of a pharmaceutical product, a quasi-drugs, cosmetic materials, health foods and the like, which all contain the agent. Further, according to the present invention, a method for regulating the hair shape using the hair shape susceptibility SNP marker obtained by the present invention can be provided.

1. DEFINITIONS OF TERMS USED IN PRESENT INVENTION

The indication of base sequences (nucleotide sequences), nucleic acids and the like by means of abbreviations in the present specification is as recommended by the specifications of IUPAC-IUB (IUPAC-IUB Communication on Biological Nomenclature (Eur. J. Biochem. 138, 9, 1984), "Guidelines for the preparation of specifications containing base sequences or amino acid sequences" (edited by the Japanese Patent Office), and the symbols conventionally used in the art.

The term "DNA" as used in the present specification encompasses not only a double-strand DNA, but also single-strand DNAs such as a sense strand and an anti-sense strand constituting the double-strand DNA. Unless particularly stated otherwise, the term "gene" as used herein encompasses all of a double-stranded DNA including human genome DNA, a single-stranded DNA (sense strand) and a single-stranded DNA having a sequence complementary to the sense strand (anti-sense strand), and fragments thereof. Unless particularly stated otherwise, the term "gene" as used herein is, intended to indicate any of a regulatory region, a coding region, an exon and an intron without discrimination. Further, the "gene" or "DNA" encompasses a "gene" or "DNA" represented by a specific base sequence, as well as a "gene" or "DNA" which encodes a homologue, a derivative or a variant of a protein encoded by the "gene" or "DNA" represented by a specific base sequence, provided that they have a biological function equivalent to that of the protein.

Furthermore, according to the present invention, the terms "nucleotide", "oligonucleotide" and "polynucleotide" have the same meanings as nucleic acid, and they are intended to encompass both DNA and RNA. The DNA encompasses all of cDNA, genomic DNA and synthetic DNA. The RNA encompasses all of total RNA, mRNA, rRNA and synthetic RNA. Further, the "nucleotide", "oligonucleotide" and "polynucleotide" may be double-stranded or single-stranded, and in the case of a "nucleotide" (or an "oligonucleotide" or "polynucleotide") having a certain sequence, unless particularly stated otherwise, the "nucleotide" is intended to collectively mean "nucleotide" (or an "oligonucleotide" or "polynucleotide") having a sequence complementary to the sequence. Furthermore, when the "nucleotide" (or "oligonucleotide" or "polynucleotide") is RNA, the nucleotide symbol "T" indicated in the base sequence may be replaced with "U".

The term "polynucleotide having a complementary base sequence" means a polynucleotide that is in a complementary relation in terms of nucleotide (i.e., complementary strand or anti-sense strand), to a polynucleotide having an arbitrary base sequence (sense strand). A complementary base sequence encompasses a sequence that is completely complementary to the subject base sequence, as well as a base sequence that can be hybridized with the subject base sequence under stringent conditions. Here, the stringent conditions may conventionally refer to washing conditions of approximately "1×SSC, 0.1% SDS, 37° C.", and more stringent hybridization conditions may be approximately "0.5×SSC, 0.1% SDS, 42° C.", and even more stringent hybridization conditions may be approximately "0.1×SSC, 0.1% SDS, 65° C.". Furthermore, a person having ordinary skill in the art can determine stringent hybridization conditions according to general textbooks (for example, Sambrook, J. & Russell, D., 2001, Molecular Cloning: a Laboratory Manual, 3$^{rd}$ edition, Cold Spring Harbor, N.Y.: cold Spring Harbor Laboratory). An example of a base sequence that can be hybridized with a subject base sequence under stringent conditions may be a base sequence having a homology of 90% or higher, and preferably 95% or higher, with the subject base sequence.

The term "protein" or "polypeptide" encompasses a "protein" or "polypeptide" represented by a specific base sequence or amino acid sequence, as well as a fragment, a homologue, a derivative and a variant thereof, provided that they all have a biological function equivalent to that of the "protein" or "polypeptide". Meanwhile, the variant encompasses a naturally occurring allele variant, a variant that does not occur naturally, and a variant having an amino acid sequence modified by artificial deletion, substitution, addition and insertion. In addition, examples of the variant include those having a homology in the amino acid sequence of 80% or higher, preferably 90% or higher, more preferably 95% or higher, and even more preferably 98% or higher, with a protein or polypeptide having no variation.

According to the present specification, the homology of amino acid sequences and base sequences is calculated by the Lipman-Pearson method (Science, 227, 1435, 1985). Specifically, the homology is calculated by performing an analysis using a homology analysis (Search homology) program in the genetic information processing software Genetyx-Win (Software Development Co., Ltd.), and by setting the parameter, Unit size to compare (ktup), at 2.

The term "antibody" encompasses a polyclonal antibody, a monoclonal antibody, a chimeric antibody, a single-chain antibody, and portions of the antibodies described above which have antigen-binding properties, such as Fab fragments, and fragments produced by a Fab expression library.

In regard to the term "genetic polymorphism" as used herein, when there are two or more genetically determined alleles, the term refers to such an allele gene. Specifically, in a human population, when variation(s) such as substitution, deletion, insertion, dislocation and inversion of one or plural nucleotides exist at a specific region in the genome of one or plural individuals with respect to the genomic sequence of one certain individual, the variation is called "genetic polymorphism" if it is statistically ensured that the variation is not a mutation occurring in the one or plural individuals, or if it can be genetically demonstrated that the variation is not a specific variation in the individuals but occurs in the population at a frequency of 1% or greater. Examples of the "genetic polymorphism" as used herein include substitution of one nucleotide with another nucleotide, that is, a single nucleotide polymorphism (SNP); deletion or insertion of one to several tens of nucleotides (DIP); a region includes repetition of units of sequence consisting of 2 to several tens of nucleotides as one unit, where the number of the repetition is different (when the unit repeated in the region consists of 2 to 4 nucleotides, it is referred to as a microsatellite polymorphism, and when the unit repeated in the region consists of several to several tens of nucleotides, it is referred to as a VNTR (Variable Number of Tandem Repeat); and the like.

The term "hair shape" as used herein refers to the tendency of the overall shape of hair in the head area, which attributes to the shape of individual hairs, such as straight hair, wavy hair or wave hair, curled hair, or kinky hair or coiled hair.

The term "curly hair" as used herein is, unless particularly stated otherwise, a term which collectively refers to the shape other than straight hair in the case of contrasting with straight hair. Therefore, according to the present specification, in the case of contrasting with the "curly hair", unless particularly stated otherwise, the "straight hair" and the "non-curly hair" are considered to have the same meaning. The "curly hair", "non-curly hair" and "straight hair" are of relative nature, and can be defined by various methods that will be described below. The "curly hair trait", "non-curly hair trait", and "straight hair trait" refer to the phenotypes representing the "curly hair", "non-curly hair" and "straight hair", respectively.

The term "hair shape susceptibility gene" as used herein refers to a causative gene that determines the hair shape which is a polygenic trait, and the term "hair shape susceptibility SNP marker" refers to the nucleotide at a site which represents an SNP associated with the trait of hair shape of the individual.

According to the present specification, the terms "genetic susceptibility to hair shape", "hair shape determining marker" and "marker for the type of hair shape" respectively refer to the genetic predisposition related to the specific hair shape possessed by an individual, and a marker for determining the predisposition.

The term "Affected Sib-Pair Linkage Analysis" as used herein refers to one technique for estimating the location of a target gene (e.g., disease susceptibility gene or the like) using linkage, and is a representative analysis technique for non-parametric linkage analysis which does not assume any mode of inheritance (e.g., autosomal dominant inheritance, recessive heredity, sex-linked gene, or the like) or the penetrance. In the affected sib-pair linkage analysis, family lines including sibs (e.g., brothers and sisters) that are affected (or have a particular trait) are collected, calculation of the likelihood is carried out on the basis of the data obtained by observation of these family lines, and the genetic locus regions of the marker linked to the disease (or the particular trait) are narrowed down. In the case of a group of general (i.e., not affected, or not having a particular trait) sibs, in one genetic locus, a child receives one of the two alleles of one parent (even if the one parent is a homozygote, the alleles are considered to be different from each other). Therefore, in this case, there exist a case in which the sibs receive the same allele, and a case in which the sibs receive different alleles. Since each of the two alleles of a child originates one allele from each of the parents, when the question of how many identical alleles sibs will receive from their parents is considered, there are three cases such as 0, 1 and 2. These three cases are said to have an IBD (Identity By Descent) of 0, 1 and 2, respectively. When a number of sib-pairs are considered, the numbers of the pairs having an IBD=0, the pairs having an IBD=1, and the pairs having an IBD=2 should be counted, and the proportion of the numbers constitutes a certain proportion (1:2:1) according to the probability laws. On the contrary, when sibs that are affected (or have a particular trait) are collected, and the same investigation is carried out with this group, if an observed marker gene is linked to the disease (or the particular trait), this ratio (1:2:1) is deviated (i.e., the number of the pairs having an IBD=2 increases, and the number of the pairs having an IBD=0 decreases). In addition, for a marker gene which is not linked to a gene that is related to the disease (or the particular trait), it can be considered that the ratio has the same distribution (1:2:1) as any arbitrary sibs. In the affected sib-pair linkage analysis, the likelihood of observation data is calculated by utilizing this hypothesis, by taking the difference of the ratio of shared alleles in affected sib-pairs as an index. The likelihood is represented by the following formula:

$$L(Z) = \prod_{j=1}^{N} \sum_{i=0}^{2} ZiWij$$

wherein Wij represents the probability that the affected sib-pair of the $i^{th}$ family line has an IBD=i. The variable is Z=(Z0, Z1, Z2), and the degree of freedom is 2 (Z2=1−Z1−Z0, there are only two independent variables of Z0 and Z1). The ratio with the likelihood in the case where a marker gene and a gene associated with a disease (or a particular trait) are not linked (that is, Z0=0.25, Z1=0.5, Z2=0.25) is taken, and the value of Z which gives the maximum likelihood is determined by the likelihood maximization method (maximum likelihood estimation).

The term "gene frequency" as used herein refers to the proportion occupied by the allele at a genetic locus among the total number of genes present in a group.

The term "haplotype" as used herein means a combination of genetic variations existing in one allele (haploid).

The term "linkage disequilibrium analysis" or "haplotype analysis" as used herein means an analysis of the degree of the intensity of linkage disequilibrium in a genomic region.

The term "linkage disequilibrium" as used herein refers to a phenomenon in the population genetics, in which a non-random correlation is observed in a group between alleles or genetic markers (polymorphisms) at plural genetic loci, that is, the frequency of such a particular combination (haplotype) is significantly increased. They are generally on the same chromosome and constitute genetic linkage, but there are occasions in which even if the alleles are linked, linkage disequilibrium is not observed. Further, in some exceptional cases, linkage disequilibrium may be seen over different chromosomes. For example, when a genetic locus X has alleles a and b (these exist at the same frequency), and a neighboring genetic locus Y has alleles c and d (these exist at the same frequency), the haplotype ac, which is a combination of the respective genetic polymorphisms, is expected to exist at a frequency of 0.25 in the group. When the frequency of the haplotype ac is higher than such an expected value, that is, when a specific genotype denoted as ac appears frequently, it is said that the allele ac is in linkage disequilibrium. Linkage disequilibrium is occurred as a result that the time of natural selection or introduction into a group of a particular combination of alleles is evolutionarily recent, and may be occurred as a result that linked alleles have not reached equilibrium. Therefore, the mode of linkage disequilibrium varies with different groups, such as nations or races, and even in the case where the allele ac in a certain group is in linkage disequilibrium, there are occasions in which the allele ad is in a relation of linkage disequilibrium in other groups. The detection of genetic polymorphism in the linkage disequilibrium is effective in detecting the susceptibility to a disease, regardless of whether the polymorphism itself directly causes the disease. For example, in regard to an allele a of a certain genetic locus X, although the allele is not a causative genetic factor of a disease, the allele may exhibit susceptibility to a disease through the linkage disequilibrium with an allele c of a genetic locus Y.

The "haplotype block" as used herein is defined as a region that is categorized as a genome region for which most of the historical recombination has not been acknowledged, and includes strong linkage disequilibrium. Identification of a haplotype block can be appropriately achieved by those having ordinary skill in the art based on the strength of the linkage disequilibrium, but for example, the identification can be carried out according to the report of Gabriel, et al. (Gabriel, S. B., et al., Science, 296 (5576), p. 2225-2229, 2002). The term "strong linkage disequilibrium" as used herein means the state in which the upper limit of the 95% confidence interval of the linkage disequilibrium coefficient D', which is calculated in a linkage disequilibrium analysis, exceeds 0.98, and the lower limit is higher than 0.7. The phrase "there is an evidence of strong historical recombination" means a state in which the upper limit of the 95% confidence interval of the linkage disequilibrium coefficient D' is lower than 0.9.

The term "minor allele" as used herein means an allele having a low gene frequency when two alleles exist in one genetic locus.

According to the present specification, the terms "gene frequency" and "allele frequency" are used for the same meaning, and are terms meaning the proportion occupied by a particular allele in an arbitrary group of genes.

The phrase "statistically significantly different" as used herein means a state in which when a test is carried out according to any statistical technique, the risk (p value) is less than 0.1%, preferably less than 0.07%, even more preferably less than 0.05%, and still more preferably less than 0.01%.

2. IDENTIFICATION OF HAIR SHAPE SUSCEPTIBILITY GENE AND HAIR SHAPE SUSCEPTIBILITY SNP MARKER

Search and identification of a causative gene that determines the natural shape of human hair which is a multifactorial general trait (hair shape susceptibility gene), can be carried out by a genetic statistical analysis using a technique for trait mapping. That is, SNP(s) that are in the linkage disequilibrium state with the hair shape susceptibility gene can be effectively selected through the identification of curly hair trait loci by an affected sib-pair linkage analysis and a case-control association analysis on the curly hair trait loci, and a gene present in a haplotype block containing the SNP(s) can be identified as a hair shape susceptibility gene.

The identification of the hair shape susceptibility gene and the hair shape susceptibility SNP marker of the present invention can be carried out, as will be described specifically in Examples below, by performing an identification method having the following steps:

(i) a step of defining hair shapes, and collecting curly hair family lines, people having a curly hair trait (case), and people having a straight hair trait (control);

(ii) a step of performing an affected sib-pair linkage analysis directed to the entire genome using samples derived from the curly hair family lines, and identifying a curly hair trait locus;

(iii) a step of selecting plural SNP markers which are not unevenly distributed over the entire region in the curly hair trait locus identified in step (ii);

(iv) a step of performing typing of the SNP markers selected in step (iii) using case-derived and control-derived samples, comparing the results of the typing through a statistical processing, and identifying a SNP marker that is recognized to have a significant difference, as a hair shape susceptibility SNP marker;

(v) a step of determining, with regard to the hair shape susceptibility SNP marker, a region where linkage disequilibrium is recognized within an object candidate region and a hair shape susceptibility SNP marker is contained (haplotype block), using the HapMap PHASE data of the International HapMap Project Database, and thereby identifying the hair shape susceptibility gene; and (vi) a step of determining, for the haplotype extracted from the haplotype block specified in step (v), a SNP locus that is linked with the hair shape susceptibility SNP marker locus determined in step (iv) using the HapMap PHASE data of the International HapMap Project Database, and additionally identifying the SNP thus-determined as an additional hair shape susceptibility SNP marker.

The step (i) is a step of defining hair shapes (curly hair or straight hair) and collecting analysis objects for trait mapping. In regard to the trait mapping, it is necessary to handle the subject trait quantitatively to a certain extent, and thus, the operation of defining hair shape, by which the objects are defined to have a curly hair trait or a straight hair trait, constitutes an important step when the trait mapping is carried out. There are a variety of human hair shapes, and the method for measurement thereof and the method for classification or defining are also various. For instance, examples of the method of defining hair shapes include a method of binarizing the hair shape, in such a manner that curly hair=1 and straight hair=0; a method of measuring the degree of curly hair by any method and quantifying the degree; and a method that is well known to those having ordinary skill in the art (for example, see, Japanese Patent Application Laid-Open (JP-A) No. 2005-350801, JP-A No. 2008-268229, Japanese Patent No. 4159515, and the like), but the method is not limited to these. As a more specific example of the method of defining hair shapes, there may be mentioned a method of classifying hair shapes into several grades (for example, 2 to 10 grades, preferably 3 to 8 grades, and more preferably 5 to 7 grades) based on the features such as the overall shape, the degree of curl of the hair (radius of curl), the frequency of the appearance of curl, and/or the synchrony of curl with the groups of hair in the surroundings; and defining, in regard to such classifications, a hair shape having a tendency of a small radius of curl, such as kinky hair and curled hair or strongly wavy hair, as a curly hair trait, and defining a hair shape having a tendency of a large radius of curl, such as wavy hair, almost straight hair or slightly wavy hair, or straight hair, as a straight hair trait.

The step (ii) is a step of carrying out an affected sib-pair linkage analysis on the entire genome using samples derived from a curly hair family line. The constituent members of the curly hair family line for carrying out the affected sib-pair linkage analysis are sibs (a pair among brothers and sisters, two people) determined to have the curly hair trait by the step (i). More preferably, the constituent members consist of a family of 4 people (or 3 people) including the parents of the sibs, and other brothers and sisters (irrespective of the hair shape) or grandparents may also be further added. Furthermore, the number of the curly hair family lines needed to carry out the affected sib-pair linkage analysis can be determined by estimating and/or observing the frequency in the population of the curly hair trait, the frequency of the causative gene (allele frequency), the sib relative risk, or the like, and calculating the number by through simulation. However, the number of the curly hair family line needed is generally 50 family lines to several hundred family lines.

The genetic marker used in the affected sib-pair linkage analysis is not particularly limited as long as it is a genetic polymorphism, but a microsatellite that exists uniformly in the genome and has a large number of alleles is used with preference. A kit for amplifying and detecting a microsatellite (linkage mapping set) is commercially available from Applied Biosystems Corp. (ABI). Meanwhile, in the present invention, ABI PRISM Linkage Mapping Set-MD 10 v2.5 (manufactured by ABI) which covers human chromosome at an average interval of 9.2 cM, and ABI PRISM Linkage Mapping Set-HD 5 v2.5 (manufactured by ABI) which covers human chromosome at an average interval of 5 cM were used.

Furthermore, the microsatellite that serves as a genetic marker can be arbitrarily selected, and can be retrieved from the Comprehensive Human Genetic Maps of the Mammalian Genotyping Service (http://research.marshfieldclinic.org/genetics/GeneticResearch/compMaps.asp), NCBI (http://www.ncbi.nlm.nih.gov/) and the like. In this case, it is preferable to select a microsatellite which exists in the genome at an interval of 0.1 to several cM, and has many alleles and high heterozygosity. Furthermore, microsatellite markers can be added to a chromosome in which linkage has been recognized, and the linkage region can be narrowed (detailed mapping). Meanwhile, for the PCR primer for amplifying and detecting the microsatellites that have been arbitrarily selected and added, the base sequence can be retrieved from the NCBI (http://www.ncbi.nlm.nih/gov/), and the primer can be produced based on the retrieved sequence according to an ordinary method using, for example, a commercially available nucleotide synthesizer. At this time, it is preferable to label the probe with a radioactive substance, a fluorescent substance, a chemiluminescent substance, an enzyme or the like so that the detection of the amplification product can be achieved rapidly and easily.

In the affected sib-pair linkage analysis, PCR is carried out using a genomic DNA derived from a curly hair family line as a template, and using a linkage mapping set (ABI) or an amplification primer of a microsatellite marker arbitrarily selected, and thus an amplification product (fragment) is detected. The operations of PCR and the detection of the amplification product can be carried out according to ordinary methods. At this time, when various amplification primers are labeled with different fluorescent dyes (for example, any dyes emitting different fluorescent light, such as 6-FAM (blue), VIC (green), or NED (yellow)), even if amplification products having an identical size are obtained, plural amplification primers can be rapidly detected by separately discriminating the various fluorescent colors.

A statistical test of the linkage can be carried out using commercially available or publicly disclosed genetic statistic software programs which are capable of non-parametric analysis (for example, Genehunter, Linkage Package, Mapmaker/sibs, and the like).

The determination of the region where linkage is recognized was based on the criteria for obtaining a false positive linkage, according to the guidelines provided by Lander and Kruglyak (Nat. Genet., 11 (3), 241-247, 1995) shown below. The guidelines by Lander and Kruglyak (linkage analysis over the entire genome with a multifactorial disease) has come to be actively carried out, but in the linkage analysis of individual genes, the determination of whether the gene function can be causative is also added. However, since the gene function is not taken into consideration in that stage in the analysis of the entire genome, determination criteria (threshold) of significance purely in terms of mathematical genetics are required. Thus, they provided criteria for significance of linkage as shown in the following Table 2 according to simulations.

TABLE 2

| | |
|---|---|
| Suggestive Linkage | $P < 7.4 \times 10^{-4}$ |
| (Criteria for obtaining a result of one false positive linkage from the entire genome) | LOD > 2.2 |
| Significant Linkage | $P < 2.2 \times 10^{-5}$ |
| (Criteria for obtaining a result of 0.05 false positive linkages from the entire genome) | LOD > 3.6 |
| High Significant Linkage | $P < 3.0 \times 10^{-7}$ |
| (Criteria for obtaining a result of 0.01 false positive linkages from the entire genome) | LOD > 5.4 |

Through this process, the whole chromosome can be screened, and a region on the chromosome where linkage with the curly hair trait is recognized can be detected. Through further detailed mapping, a specific region on the chromosome can be identified as a curly hair trait locus. The region identified as such is a region where the presence of a hair shape susceptibility gene is strongly suggested.

The step (iii) is a step of selecting, in the curly hair trait locus region identified in the step (ii), plural SNP markers which are not unevenly distributed over the entire region. The SNP markers can be selected by using various databases related to SNP, such as the dbSNP database (http://www.ncbi.nim.nih.gov/SNP/) and the JSNP database (http://snp.ims.u-tokyo.ac.jp/index_ja.html).

Upon the selection of the SNP marker, a SNP which is useful for the identification of a hair shape susceptibility gene is selected. Specifically, in a Japanese group, a SNP having a gene frequency of minor allele of 10% or greater, and more preferably 15% or greater, is selected. When a SNP having such a gene frequency is used, a SNP marker having high reliability can be selected.

In addition, when a SNP marker is selected by using the gene frequency as an index, there are occasions in which the SNP marker is unevenly distributed in a specific narrow region. In this case, if all of the selected SNP markers are used in the identification of a hair shape susceptibility gene, the experiment becomes complicated, and it is also not very effective that SNPs which are neighboring with each other are in the state of linkage disequilibrium. Therefore, it is preferable to select and use SNP markers which are present at a certain interval from one another. As such, when uneven distribution of markers is eliminated by providing a certain interval between them, a comprehensive association analysis can be carried out over the entire object candidate region, and the identification of the hair shape susceptibility gene can be easily carried out. The distance between adjacent SNP markers that are selected as such is preferably 5 kb or greater, and more preferably 5 kb to 10 kb. If this distance is too long, there is a possibility that a region may occur where the extent of the strength of mutual linkage disequilibrium between SNP markers cannot be checked. Furthermore, if this distance is too short, there are so many SNPs for which strong mutual linkage disequilibrium is recognized, and therefore, it is not efficient.

In the comprehensive selection of SNP markers over the entire object candidate region, apart from this distance between SNP markers, the state of scattering of markers in the object candidate region, that is, the number of markers per unit distance of genome, can be expressed as "marker density." The marker density is 0.5 SNPs or more, preferably 1 SNP or more, and more preferably 1 SNP to 2 SNPs, per 10 kb of genome. If the marker density is too low, the distance between markers is too long, and there is a possibility that a region may occur where the degree of the strength of linkage disequilibrium between SNP markers cannot be checked, as described above. On the other hand, if the marker density is too high, the distance between markers is too short, and as described above, markers are selected overcrowdedly, so that in the case of identifying a hair shape susceptibility gene, a large amount of experiment is needed, which is not so efficient.

The step (iv) is a step of carrying out a case-control association analysis for the SNP markers selected in step (iii). The case-control association analysis is a method of comparing the allele frequencies for a certain hereditary marker between a case (affected people: people having the curly hair trait) group and a control (control people: people having the straight hair trait), and detecting a marker which can exhibit a significant difference in the allele frequency between the two groups. For example, samples derived from people having the curly hair trait (case) and people having the straight hair trait (control) are used, and typing is carried out. The results are compared by statistical processing, and a SNP marker with which a significant difference is recognized is identified as a hair shape susceptibility SNP marker. The sample required for trait mapping is not particularly limited as long as the sample contains genomic DNA, but examples include blood such as peripheral blood, body fluids such as saliva and sweat, somatic cells, and tissues or organs including somatic cells. The number of case and control required to perform a case-control association analysis can be estimated based on the frequency in a population having the curly hair trait, the gene frequency (allele frequency) causative of the trait, the genotype relative risk, and the like, but the number is generally 50 to several thousand people. Furthermore, it is possible to obtain a relatively high power of test by a stepwise refinement method under the conditions of limited sample size, limited number of typing operations or the like. Furthermore, the case and the control are preferably constituted of the same human race as the race for which the hair shape susceptibility gene is specified, and for example, in order to identify a hair shape susceptibility gene of Japanese people, it is preferable that the object of analysis be constituted of Japanese people.

As the method for SNP typing, methods that are well known to those having ordinary skill in the art, such as PCR-SSCP, PCR-RLFP, PCR-SSO, PCR-ASP, a direct sequencing method, SNaPshot, dHPLC, a Sniper method, and a MALDI-TOF/MS method, can be used (see, for example, Nojima, Hiroshi, Ed., "Forefront of Genomic Drug Discovery", p. 44-p. 54, Yodosha Co., Ltd., 2001). For example, it is effective to utilize TaqMan SNP Genotyping Assays (registered trademark) (manufactured by ABI), and to employ a SNP typing method which utilizes a TaqMan system.

The association analysis is typically achieved by comparing the gene frequency of each of the SNP markers between the case group and the control group, and carrying out a $\chi^2$ test on whether the difference in the frequency is statistically meaningful or not (see, University of Tokyo, College of Arts and Sciences, Department of Social Sciences, Statistics Section, Edited, "Tokeigaku Nyumon—Kisotokeigaku I (Introduction to Statistics—Fundamental Statistics I)", University of Tokyo Press, 1991). However, the association analysis may also be carried out based on the genotype frequency for each SNP marker, the genotype frequency in the case of employing a dominant (or recessive) model, the frequency of allele in terms of positive ratio, and the like. Furthermore, in addition to the $\chi^2$ test, the association analysis can be carried out by any other well-known statistical processing, as long as, it is possible to compare the case group and the control group, that is, to test the relations between a phenotype that can be divided into plural groups such as a trait and a disease, and a genetic polymorphism.

Meanwhile, in order to evaluate the typing error of a genotype, and the validity of sampling, a Hardy-Weinberg equilibrium test is carried out. Hardy-Weinberg equilibrium is well known in the field of genome statistics, and in which when two alleles (for example, C and T) exists as in an SNP or the like, and the respective frequencies in a group are represented by p and q ($p+q=1$), the genotype frequencies of C/C homo, C/T hetero and T/T homo may be represented by $p^2$, $2pq$ and $q^2$, respectively ($p^2+2pq+q^2=1$). When an association analysis is carried out, it is desirable that the Hardy-Weinberg equilibrium is established for the control group. However, the selected SNP marker can be evaluated as valid as long as the number of alleles, whose genotype frequency is statistically significantly different from Hardy-Weinberg equilibrium, is in a predictable range of the significance level (typically, $p=0.01$ to $0.05$).

According to an embodiment, typing is carried out for the respective samples obtained from a case group and a control group, and a significant difference test is carried out by a $\chi^2$ test by four methods involving the genotype, allele type, dominance model and recessive model. That is, if a certain genetic variation is causative of hair shape change, the difference in the allele frequency or the like between the case and the control can be predicted. In regard to the test, when the association analysis is carried out on a relatively small number of objects, or when the power of test of the significant difference between the objects is increased, the level of significance is set loose. When the number of objects is relatively large, or when the significant difference is strictly determined, the level of significance can be set strict. A SNP which exhibits a significant difference in the gene frequency by a test is identified as a hair shape susceptibility SNP marker.

The step (v) that is subsequently carried out is a step of identifying a hair shape susceptibility gene by determining, in connection with the hair shape susceptibility SNP marker determined as described above, a region where linkage disequilibrium is recognized in an object candidate region and the hair shape susceptibility SNP marker is included (haplotype block), using the HapMap PHASE data of the International HapMap Project Database.

The analysis of haplotype (linkage disequilibrium analysis) is a method well known to those having ordinary skill in the art, and can be carried out by various linkage disequilibrium analyses that are conventionally carried out (for example, Kamatani, Naoyuki, Edited., "Post-Genome Jidai no Iden Tokeigaku (Genetic Statistics in Post-Genomic Era)", p. 183-201, Yodosha Co., Ltd., 2002). The haplotype analysis can be carried out using various genetic statistics software programs that are commercially available or made public (for example, Haploview, Arlequin, SNP disease-associated analysis software, SNPalyze (registered trademark) (manufactured by Dynacom Co., Ltd.), and the like). More specifically, the linkage disequilibrium coefficient D' (pair-wise LD coefficient) is calculated and an analysis is carried out, through a linkage disequilibrium analysis based on the EM algorithm (Laird, N.: "The EM Algorithm", Chap. 14, pp. 509-520, Handbook of Statistics, Vol. 9, Computational Statistics, C. R. Rao (ed.), Elsevier Science Publishers B.V., 1993). More specifically, in the haplotype analysis, it is analyzed whether linkage disequilibrium exists between the hair shape susceptibility SNP marker specified above and another SNP marker, and the region where linkage disequilibrium exists is identified as the haplotype block. The other SNP marker used in the linkage disequilibrium analysis can be freely selected among the SNPs existing in the upstream and the downstream of the genome sequence with respect to the hair shape susceptibility SNP marker. For example, the linkage disequilibrium analysis may be sequentially carried out for the SNPs present from proximal positions to distal positions of the hair shape susceptibility SNP marker, or the linkage disequilibrium analysis may be carried out for arbitrarily selected SNPs at distal positions to determine an approximate haplotype block region, and then be carried out for SNPs at more proximal positions to determine a more specific haplotype block region. The number of the other SNP markers used in the linkage disequilibrium analysis is 4 SNPs or more including the hair shape susceptibility SNP marker, preferably 20 SNPs or more, and even more preferably 32 SNPs or more, and the analysis is carried out for a series of SNP marker groups including these plural SNP markers. Here, the linkage disequilibrium coefficient D' is obtained from the following equation when, in two SNPs, the respective alleles of a first SNP are designated as (A, a), the respective alleles of a second SNP are designated as (B, b), and the respective frequencies of four haplotypes (AB, Ab, aB, ab) are designated as $P_{AB}$, $P_{Ab}$, $P_{aB}$, and $P_{ab}$. Furthermore, Min $[(P_{AB}+P_{aB})\ (P_{aB}+P_{ab})\ (P_{AB}+P_{Ab})\ (P_{Ab}+P_{ab})]$ in the equation means that the smaller value between the values of $(P_{AB}+P_{aB})\ (P_{aB}+P_{ab})$ and $(P_{AB}+P_{Ab})\ (P_{Ab}+P_{ab})$ is taken.

$$D'=(P_{AB}P_{ab}-P_{Ab}P_{aB})/\mathrm{Min}[(P_{AB}+P_{aB})(P_{aB}+P_{ab}),\ (P_{AB}+P_{Ab})(P_{Ab}+P_{ab})]$$

The number of markers in the SNP marker group may appropriately vary with the size of the region forming the haplotype block related to the hair shape susceptibility gene to be identified (linkage disequilibrium block). Furthermore, when a discontinuity of blocks can be predicted in advance, it is also possible to carry out the analysis on about 6 SNPs located over the blocks. Furthermore, it is also acceptable to carry out a linkage disequilibrium analysis for a hair shape susceptibility SNP marker and 5 SNPs each existing on both sides of the SNP marker, 11 SNPs in total. If necessary, the number of markers to be analyzed may be increased.

As the linkage disequilibrium analysis is carried out, a region where SNPs are linked within an object candidate region (a haplotype block including the group of SNP markers among which strong linkage disequilibrium is recognized) is determined. For example, the linkage disequilibrium coefficient D' is calculated for all combinations between 2 SNPs for the selected SNP markers, combinations showing the relation: D'>0.9 are selected, and a series of regions including a region sandwiched between the remotest SNPs among them are detected. Subsequently, D' is calculated between three consecutive SNPs that are adjacent to the region in the outside of the detected region and the SNPs in the region. Even among any combinations thus calculated, when it is verified that D' is 0.9 or less, the region is specified as a "haplotype block."

When a haplotype block is determined in this manner, for example, in connection with that region, genes present in the haplotype block under attention can be determined using a database associated with the genome, or the like. Furthermore, even in the case of not using a database, the base sequence in the vicinity of SNP markers present in the haplotype block region are determined by ordinary methods, and genes can also be determined from the base sequence.

The step (vi) is a step of determining, for the haplotype extracted from the haplotype block specified in step (v), a SNP locus that is linked to the locus of the hair shape susceptibility SNP marker identified in the step (iv) using the HapMap PHASE data of the International HapMap Project Database, and additionally identifying the SNP thus-determined as an additional hair shape susceptibility SNP marker.

In the step (v), it is possible to extract all haplotypes consisting of the respective nucleotides of the SNP marker group used in the haplotype analysis, while simultaneously determining the haplotype block, and to thereby determine the frequency of the haplotype or the like.

When the combinations of the respective nucleotides of the extracted haplotype, that is, the SNP marker group, are compared, a SNP locus that is linked to the locus of the hair shape susceptibility SNP marker identified in the step (iv) can be identified, and the SNP locus thus identified can be designated as an additional hair shape susceptibility SNP marker.

Through the steps (i) to (vi), a chromosome region where linkage with curly hair is recognized is determined, and then a hair shape susceptibility SNP marker is selected from the chromosome region. Furthermore, through a haplotype analysis of the selected SNP marker, a haplotype block and gene in the chromosome region that are related to hair shape are identified. Thereafter, a SNP locus that is linked to the locus of the hair shape susceptibility SNP marker is further determined, and thereby, a hair shape susceptibility SNP marker that is present in the haplotype block or gene can be identified.

Examples of the chromosome region where linkage to curly hair is recognized, which is determined in the steps described above, include chromosome 1 and chromosome 11, more specifically the 1q21.3 region of chromosome 1 (a region between microsatellites D1S2696 and D1S2346) (maximum LOD score=3.60). These regions are determined as curly hair trait loci, and it is strongly suggested that hair shape susceptibility genes exist in these regions.

Examples of the haplotype block specified by the steps described above include, among the genomic regions of human chromosome 1, a 23,252-bp region represented by the base sequence set forth in SEQ ID NO:1, a 56,552-bp region represented by the base sequence set forth in SEQ ID NO:2, a 23,382-bp region represented by the base sequence set forth in SEQ ID NO:3, a 8,818-bp region represented by the base sequence set forth in SEQ ID NO:4, and a 3,440-bp region represented by the base sequence set forth in SEQ ID NO:5.

A gene which overlaps with such a haplotype block, and contains a portion or the entirety of the base sequence of the haplotype block, is identified as a hair shape susceptibility gene. Here, the "gene which overlaps with the haplotype block" means both a gene which has the same base sequence as that of a partial region of the haplotype block, and a gene which has the same base sequence as the base sequence of the entire region of the haplotype block. Further, a single nucleotide polymorphism (SNP) which exists in such a haplotype block, and whose allele frequency is statistically significantly different between a group having a curly hair trait and a group having a non-curly hair trait, and an SNP that is linked to the SNP, are identified as hair shape susceptibility SNP markers.

Examples of the gene which overlaps with the 23,252-bp haplotype block represented by the base sequence set forth in SEQ ID NO:1 include ANXA9 gene and FAM63A gene on human chromosome 1. ANXA9 gene is a gene represented by GeneID: 8416 in the Entrez Gene Database (http://www.ncbi.nlm.nih.gov/gene), and as shown in Example 5 and FIG. 5, the entire length of the base sequence overlaps with the haplotype block described above. Furthermore, FAM63A gene is a gene represented by GeneID: 55793 in the Entrez Gene Database, and as shown in Example 5 and FIG. 5, a portion of the base sequence overlaps with the haplotype block described above.

Examples of the hair shape susceptibility SNP marker present in the base sequence set forth in SEQ ID NO:1 include nucleotides represented by Nucleotide Numbers 1 (dbSNP Database ID: rs3754211, A or G), 2405 (rs3754210, T or G), 5874 (rs16832604, G or A), 7121 (rs2305814, C or T), 8494 (rs7532008, C or A), 18980 (rs1673160, T or A), and 23252 (rs771205, T or C). A preferred example may be a nucleotide represented by Nucleotide Number 7121 (rs2305814, C or T).

Examples of the gene which overlaps with the 56,552-bp haplotype block represented by the base sequence set forth in SEQ ID NO: 2 include LCE5A gene and CRCT1 gene on human chromosome 1. LCE5A gene is a gene represented by GeneID: 254910 in the Entrez Gene Database, and as shown in Example 5 and FIG. 6, the entire length of the base sequence overlaps with the haplotype block described above. Further, CRCT1 gene is a gene represented by GeneID: 54544 in the Entrez Gene Database, and as shown in Example 5 and FIG. 6, the entire length of the base sequence overlaps with the haplotype block described above.

Examples of the hair shape susceptibility SNP markers present in the base sequence set forth in SEQ ID NO:2 include nucleotides represented by Nucleotide Numbers 2355 (rs11581947, A or G), 2569 (rs6658925, G or A), 3897 (rs2105117, A or G), 8196 (rs1053590, C or T), 9510 (rs548252, T or C), 13643 (rs493133, C or G), 15387 (rs1970283, C or G), 15708 (rs1001834, A or C), 16017 (rs11205018, G or T), 17106 (rs545418, T or C), 17453 (rs12116609, T or C), 17579 (rs526099, C or T), 17634 (rs525960, A or T), 26924 (rs4845443, A or G), 28383 (rs569032, T or C), 31275 (rs528427, C or G), 31301 (rs478926, T or G), 31653 (rs1337338, A or G), 31903 (rs6587681, T or C), 32209 (rs1856120, A or G), 33199 (rs474086, T or C), 33822 (rs578382, A or G), 34100 (rs549044, T or C), 35791 (rs1123567, A or G), 36884 (rs1538083, G or A), 37072 (rs1538082, G or A), 37365 (rs7532535, A or T), 37613 (rs7518654, G or C), 38062 (rs533917, G or A), 39063 (rs564107, T or C), 46580 (rs7530609, A or C), 49618 (rs4240885, C or G), 50164 (rs4240886, A or T), 50278 (rs4240887, G or A), 50662 (rs6687126, G or T), 50822 (rs6674451, T or C), 50981 (rs7550769, A or G), 51133 (rs7529157, A or C), 51263 (rs1988805, G or T), and 51397 (rs7529441, T or C). A preferred example may be a nucleotide represented by Nucleotide Number 8196 (rs1053590, C or T).

Examples of the gene which overlaps with the 23,382-bp haplotype block represented by the base sequence set forth in SEQ ID NO: 3 include LCE2B gene and LCE2A gene on human chromosome 1. LCE2B gene is a gene represented by GeneID: 26239 in the Entrez Gene Database, and as shown in Example 5 and FIG. 7, the entire length of the base sequence overlaps with the haplotype block described above. Further, LCE2A gene is a gene represented by GeneID: 353139 in the Entrez Gene Database, and as shown in Example 5 and FIG. 7, the entire length of the base sequence overlaps with the haplotype block described above.

Examples of the hair shape susceptibility SNP marker present in the base sequence set forth in SEQ ID NO:3 include nucleotides represented by Nucleotide Numbers 2509 (rs11205072, G or A), 5167 (rs3753453, T or C), 8449 (rs3737859, T or G), 17598 (rs3904414, G or A), 18481 (rs12074783, T or C), 20891 (rs3908717, C or G), 21734 (rs3904415, C or T), and 23382 (rs11205079, A or T). Preferred examples include nucleotides represented by Nucleotide Numbers 5167 (rs3753453, T or C), 8449 (rs3737859, T or G), 17598 (rs3904414, G or A), and 20891 (rs3908717, C or G).

Examples of the gene which overlaps with the 8,818-bp haplotype block represented by the base sequence set forth in SEQ ID NO:4 include SMCP gene on human chromosome 1. SMCP gene is a gene represented by GeneID: 4184 in the Entrez Gene Database, and as shown in Example 5 and FIG. 8, a portion of the nucleotide overlaps with the haplotype block described above.

Examples of the hair shape susceptibility SNP marker present in the base sequence set forth in SEQ ID NO:4 include nucleotides represented by Nucleotide Numbers 1 (rs16834715, T or C), 3308 (rs12022319, C or T), 4715 (rs4845490, G or A), 4985 (rs4845491, C or T), 6354 (rs3737861, C or A), 8553 (rs16834728, C or T), and 8818 (rs4845492, C or G). A preferred example may be a nucleotide represented by Nucleotide Number 6354 (rs3737861, C or A).

Examples of the gene which overlaps with the 3,440-bp haplotype block represented by the base sequence set forth in SEQ ID NO:5 include IVL gene on human chromosome 1. IVL gene is a gene represented by GeneID: 3713 in the Entrez Gene Database, and as shown in Example 5 and FIG. 9, a portion of the base sequence overlaps with the haplotype block described above.

Examples of the hair shape susceptibility SNP markers present in the base sequence set forth in SEQ ID NO:5 include nucleotides represented by Nucleotide Numbers 1 (rs1854779, C or T), 540 (rs16834751, C or A), 759 (rs4523473, C or T), 1007 (rs11205131, A or G), 1018 (rs7528862, G or A), 1075 (rs7517189, G or C), 1939 (rs2229496, G or A), and 3440 (rs913996, A or G). Preferred examples include nucleotides represented by Nucleotide Numbers 759 (rs4523473, C or T), 1939 (rs2229496, G or A), and 3440 (rs913996, A or G).

3. HAIR SHAPE DETERMINING MARKER

The present invention also provides a hair shape determining marker in the 1q21.3 region (D1S2696 to D1S2346) of human chromosome 1, which is an oligo- or polynucleotide, or a complementary strand thereof, wherein the oligo- or polynucleotide contains a partial base sequence of the base sequence of a haplotype block that is determined by a linkage disequilibrium analysis for a SNP marker whose allele frequency is statistically significantly different between a group having a curly hair trait and a group having a non-curly hair trait and consists of a base sequence set forth in any one of SEQ ID NO:1 to NO:5, and wherein the partial base sequence consists of a contiguous base sequence containing one or more single nucleotide polymorphisms (SNPs) wherein the SNPs include an SNP whose allele frequency is statistically significantly different between a group having a curly hair trait and a group having a non-curly hair trait, and an SNP linked to the SNP.

The oligo- or polynucleotides, or complementary strands thereof, defined by these base sequences contain one or more a hair shape susceptibility SNP marker that is a single nucleotide polymorphism (SNP) which is present in a haplotype block represented by a base sequence set forth in any one of SEQ ID NO:1 to NO:5 and whose allele frequency is statistically significantly different between a group having a curly hair trait and a group having a non-curly hair trait, or an SNP linked to the SNP. When these oligo- or polynucleotides, or complementary strands thereof, are detected, the genetic predisposition of hair shape in a test subject can be examined and/or determined. Therefore, these oligo- or polynucleotides, or complementary strand thereof can be defined and used as markers for determining the genetic predisposition of hair shape possessed by an individual.

The length (nucleotide length) of these oligo- or polynucleotides, or complementary strands, is desirably a length which is specifically recognized in human genome, and there are no particular limitations on the limit. The length is usually equal to or more than 10-mers and equal to or fewer than 1000-mers, preferably equal to or more than 20-mers and equal to or fewer than 500-mers, and more preferably equal to or more than 20-mers and equal to or fewer than 100-mers. Therefore, if necessary, the length can be set to, for example, 11 nucleotides containing a hair shape susceptibility SNP marker present in a haplotype block represented by a base sequence set forth in SEQ ID NO:1 to NO:5 (preferably including 5 nucleotides each on the 5' side and the 3' side of the hair shape susceptibility SNP marker), 21 nucleotides (preferably including 10 nucleotides each on the 5' side and the 3' side of the hair shape susceptibility SNP marker), 101 nucleotides (preferably including 50 nucleotides each on the 5' side and the 3' side of the hair shape susceptibility SNP marker), 601 nucleotides (preferably including 300 nucleotides each on the 5' side and the 3' side of the hair shape susceptibility SNP marker), or the like.

Examples of the hair shape susceptibility SNP marker used in the present invention, which should be included in the hair shape determining marker of the present invention, include the following:

(1) nucleotides represented by Nucleotide Numbers 1 (dbSNP Database ID: rs3754211, A or G), 2405 (rs3754210, T or G), 5874 (rs16832604, G or A), 7121 (rs2305814, C or T), 8494 (rs7532008, C or A), 18980 (rs1673160, T or A) and 23252 (rs771205, T or C) in the base sequence set forth in SEQ ID NO:1;

(2) nucleotides represented by Nucleotide Numbers 2355 (rs11581947, A or G), 2569 (rs6658925, G or A), 3897 (rs2105117, A or G), 8196 (rs1053590, C or T), 9510 (rs548252, T or C), 13643 (rs493133, C or G), 15387 (rs1970283, C or G), 15708 (rs1001834, A or C), 16017 (rs11205018, G or T), 17106 (rs545418, T or C), 17453 (rs12116609, T or C), 17579 (rs526099, C or T), 17634 (rs525960, A or T), 26924 (rs4845443, A or G), 28383 (rs569032, T or C), 31275 (rs528427, C or G), 31301 (rs478926, T or G), 31653 (rs1337338, A or G), 31903 (rs6587681, T or C), 32209 (rs1856120, A or G), 33199 (rs474086, T or C), 33822 (rs578382, A or G), 34100 (rs549044, T or C), 35791 (rs1123567, A or G), 36884 (rs1538083, G or A), 37072 (rs1538082, G or A), 37365 (rs7532535, A or T), 37613 (rs7518654, G or C), 38062 (rs533917, G or A), 39063 (rs564107, T or C), 46580 (rs7530609, A or C), 49618 (rs4240885, C or G), 50164 (rs4240886, A or T), 50278 (rs4240887, G or A), 50662 (rs6687126, G or T), 50822 (rs6674451, T or C), 50981 (rs7550769, A or G), 51133 (rs7529157, A or C), 51263 (rs1988805, G or T) and 51397(rs7529441, T or C) in the base sequence set forth in SEQ ID NO:2;

(3) nucleotides represented by Nucleotide Numbers 2509 (rs11205072, G or A), 5167 (rs3753453, T or C), 8449 (rs3737859, T or G), 17598 (rs3904414, G or A), 18481 (rs12074783, T or C), 20891 (rs3908717, C or G), 21734 (rs3904415, C or T) and 23382 (rs11205079, A or T) in the base sequence set forth in SEQ ID NO:3;

(4) nucleotides represented by Nucleotide Numbers 1 (rs16834715, T or C), 3308 (rs12022319, C or T), 4715 (rs4845490, G or A), 4985 (rs4845491, C or T), 6354 (rs3737861, C or A), 8553 (rs16834728, C or T) and 8818 (rs4845492, C or G) in the base sequence set forth in SEQ ID NO:4; and (5) nucleotides represented by Nucleotide Numbers 1 (rs1854779, C or T), 540 (rs16834751, C or A), 759 (rs4523473, C or T), 1007 (rs11205131, A or G), 1018 (rs7528862, G or A), 1075 (rs7517189, G or C), 1939 (rs2229496, G or A) and 3440 (rs913996, A or G) in the base sequence set forth in SEQ ID NO: 5.

Among the nucleotides described above, the nucleotide represented by Nucleotide Number 7121 (rs2305814, C or T) in the base sequence set forth in SEQ ID NO:1, the nucleotide represented by Nucleotide Number 8196 (rs1053590, C or T) in the base sequence set forth in SEQ ID NO:2, the nucleotide represented by Nucleotide Numbers 5167 (rs3753453, T or C), 8449 (rs3737859, T or G), 17598 (rs3904414, G or A) and 20891 (rs3908717, C or G) in the base sequence set forth in SEQ ID NO:3, the nucleotide represented by Nucleotide Number 6354 (rs3737861, C or A) in the base sequence set forth in SEQ ID NO:4, and the nucleotide represented by Nucleotide Numbers 759 (rs4523473, C or T), 1939 (rs2229496, G or A), and 3440 (rs913996, A or G) in the base sequence set forth in SEQ ID NO:5 are preferred.

It is desirable that the hair shape susceptibility SNP marker be located at the center or near the center of the hair shape determining marker of the present invention (for example, within 100 nucleotides, preferably 50 nucleotides, more preferably 30 nucleotides, even more preferably 10 nucleotides, and still more preferably 5 nucleotides, from the center), but it is not necessarily required. Furthermore, when two or more hair shape susceptibility SNP markers are included in the hair shape determining marker of the present invention, all of the hair shape susceptibility SNP markers may be located at the center or near the center of the hair shape determining marker of the present invention; one of the hair shape susceptibility SNP markers is located at the center or near the center, while the others may be located at any positions; or all of the hair shape susceptibility SNP markers may not be located at the center or near the center.

Specific examples of the hair shape determining marker of the present invention in which the hair shape susceptibility SNP marker is located at the center include, for example, in the case where a SNP is contained in the nucleotide represented by Nucleotide Number 7121 (dbSNP Database ID: rs2305814, C or T) in the base sequence set forth in SEQ ID NO:1, a 11-mer polynucleotide consisting of nucleotides from Nucleotide Number 7116 to Nucleotide Number 7126 of SEQ ID NO:1, a 21-mer polynucleotide consisting of nucleotides from Nucleotide Number 7111 to Nucleotide Number 7131 of SEQ ID NO:1, a 101-mer polynucleotide consisting of nucleotides from Nucleotide Number 7021 to Nucleotide Number 7221 of SEQ ID NO:1, and a 601-mer polynucleotide consisting of nucleotides from Nucleotide Number 6821 to Nucleotide Number 7421 of SEQ ID NO: 1. Furthermore, complementary strands of these can also be used. In the same manner, the base sequences of markers containing other SNPs are also determined.

4. METHOD FOR DETERMINING GENETIC SUSCEPTIBILITY TO HAIR SHAPE

The present invention also provides a method for determining the genetic susceptibility (genetic predisposition) of a test subject to hair shape. The method for determining the genetic susceptibility to hair shape of the present invention includes the following steps (a) and (b), and there are no particular limitations on the limit:

(a) a step of preparing a genomic DNA derived from a test subject; and (b) a step of detecting, from the genomic DNA, a single nucleotide polymorphism (SNP) whose allele frequency is statistically significantly different between a group having a curly hair trait and a group having a non-curly hair trait, and being present in a haplotype block in the 1q21.3 region (D1S2696 to D1S2346) of human chromosome 1 that is determined by a linkage disequilibrium analysis on a single nucleotide polymorphism (SNP) marker whose allele frequency is statistically significantly different between a group having a curly hair trait and a group having a non-curly hair trait, and that consists of a base sequence set forth in any one of SEQ ID NO: 1 to NO: 5, and a single nucleotide polymorphism (SNP) linked to the SNP.

The step (a) (extraction of a genomic DNA) and the step (b) (detection of SNPs) can be carried out using a known method (for example, Birren Bruce et al., Genome Analysis, Vol. 4/A Laboratory Manual Mapping Genomes, Cold Spring Harbor Laboratory, NY, 1999).

In the step (a), the genomic DNA derived from a test subject can be obtained from a material such as all cells (including cultured cells; however, reproductive cells are excluded), tissues (including cultured tissues), organs, or body fluids (for example, blood, saliva, lymph fluid, respiratory tract mucosa, semen, sweat, urine, and the like), which have been isolated from the test subject, clinical specimens therefrom, and the like. The material is preferably leukocytes or monocytes separated from peripheral blood, and is more suitably leukocytes. These materials can be isolated according to those methods usually used in clinical tests.

For example, in the case of using leukocytes as the material, first, leukocytes are separated from the peripheral blood isolated from a test subject, according to an ordinary method. Subsequently, Proteinase K and sodium dodecyl sulfate (SDS) are added to the leukocytes thus obtained to degrade and denature proteins, and then phenol/chloroform extraction is carried out to thereby obtain genomic DNA (including RNA). The RNA can be eliminated with an RNase as necessary. Meanwhile, the extraction of genomic DNA is not limited to the method described above, and can be carried out using a method well-known in the art (for example, Joseph Sambrook et al., Molecular Cloning: A Laboratory Manual (3 Vol. set), Cold Spring Harbor Laboratory, NY, 2001) or using a commercially available DNA extraction kit or the like. Furthermore, if necessary, the DNA containing the 1q21.3 region of human chromosome 1, or a DNA containing a haplotype block represented by a base sequence set forth in any one of SEQ ID NO: 1 to NO:5 in the genomic region of human chromosome 1, may be isolated. The isolation of the DNA can be carried out by PCR using a primer which hybridizes with the 1q21.3 region or with the corresponding haplotype block and using the genomic DNA as a template, or the like.

In the step (b), detected from the genomic DNA obtained in the step (a) is an SNP which is a polymorphism present in a haplotype block in the 1q21.3 region (D1S2696 to D1S2346) of human chromosome 1 that has a base sequence set forth in any one of SEQ ID NO:1 to NO:5 and that is determined by a linkage disequilibrium analysis on a single nucleotide polymorphism (SNP) marker whose allele frequency is statistically different between a group having a curly hair trait and a group having a non-curly hair trait, and the allele frequency of which is higher in any curly hair people group than in any non-curly hair people group, or a SNP that is linked to the SNP. The base sequences set forth in SEQ ID NO:1 to NO:5 include the 23,252-bp base sequence set forth in SEQ ID NO:1, the 56,552-bp base sequence set forth in SEQ ID NO:2, the 23,382-bp base sequence set forth in SEQ ID NO:3, the 8,818-bp base sequence set forth in SEQ ID NO:4, and the 3,440-bp base sequence set forth in SEQ ID NO:5, in the genomic region of human chromosome 1.

The method for determination of the present invention preferably further includes the following step (c):

(c) a step of determining, if the allele frequency of the detected SNP is statistically significantly higher in the curly hair people group than in the non-curly hair people group, that the test subject has a genetic predisposition to curly hair, and if the allele frequency of the detected SNP is statistically significantly higher in any non-curly hair people group than in the curly hair people group, that the test subject does not have a genetic predisposition to curly hair.

An example of the step (c) may be a step of identifying, for any one or more nucleotides of the nucleotide numbers as indicated in the following table that are present in the base sequences set forth in SEQ ID NO:1 to NO:5 in the genomic DNA derived from a test subject, whether the nucleotide is nucleotide (i) or nucleotide (ii); and determining, when the nucleotide is nucleotide (i), that the test subject has a predisposition to curly hair, and when the nucleotide is nucleotide (ii), that the test subject does not have a predisposition to curly hair.

TABLE 3

| SEQ ID NO. | Nucleotide Number | Nucleotide (i) (having predisposition) | Nucleotide (ii) (No predisposition) |
|---|---|---|---|
| 1 | 1 | G | A |
| | 2405 | G | T |
| | 5874 | A | G |
| | 7121 | T | C |
| | 8494 | A | C |
| | 18980 | A | T |
| | 23252 | C | T |
| 2 | 2355 | G | A |
| | 2569 | A | G |
| | 3897 | G | A |
| | 8196 | T | C |
| | 9510 | C | T |
| | 13643 | G | C |
| | 15387 | G | G |
| | 15708 | C | A |
| | 16017 | T | G |
| | 17106 | C | T |
| | 17453 | C | T |
| | 17579 | T | C |
| | 17634 | T | A |
| | 26924 | G | A |
| | 28383 | C | T |
| | 31275 | G | C |
| | 31301 | G | T |
| | 31653 | G | A |
| | 31903 | C | T |
| | 32209 | G | A |
| | 33199 | C | T |
| | 33822 | G | A |
| | 34100 | C | T |
| | 35791 | G | A |
| | 36884 | A | G |
| | 37072 | A | G |
| | 37365 | T | A |
| | 37613 | C | G |
| | 38062 | A | G |
| | 39063 | C | T |
| | 46580 | C | A |
| | 49618 | G | C |
| | 50164 | T | A |
| | 50278 | A | G |
| | 50662 | T | G |
| | 50822 | C | T |
| | 50981 | G | A |
| | 51133 | C | A |
| | 51263 | T | G |
| | 51397 | C | T |
| 3 | 2509 | A | G |
| | 5167 | C | T |
| | 8449 | G | T |
| | 17598 | A | G |
| | 18481 | C | T |
| | 20891 | G | C |
| | 21734 | T | C |
| | 23382 | T | A |
| 4 | 1 | C | T |
| | 3308 | T | C |
| | 4715 | A | G |
| | 4985 | T | C |
| | 6354 | A | C |
| | 8553 | T | C |
| | 8818 | G | C |
| 5 | 1 | T | C |
| | 540 | A | C |
| | 759 | T | C |
| | 1007 | G | A |
| | 1018 | A | G |
| | 1075 | C | G |
| | 1939 | A | G |
| | 3440 | G | A |

More specifically, the method of the present invention for determining genetic susceptibility of a test subject to hair shape includes any one step of the following (1) to (70).

(1) In the base sequence set forth in SEQ ID NO:1, it is identified whether the nucleotide represented by Nucleotide Number 1 is A or G, and it is determined, when the nucleotide is G, that the test subject has a predisposition to curly hair, or when the nucleotide is A, the test subject does not have a predisposition to curly hair;

(2) in the base sequence set forth in SEQ ID NO:1, it is identified whether the nucleotide represented by Nucleotide Number 2405 is T or G, and it is determined, when the nucleotide is G, that the test subject has a predisposition to curly hair, or when the nucleotide is T, the test subject does not have a predisposition to curly hair;

(3) in the base sequence set forth in SEQ ID NO:1, it is identified whether the nucleotide represented by Nucleotide Number 5874 is G or A, and it is determined, when the nucleotide is A, that the test subject has a predisposition to curly hair, or when the nucleotide is G, the test subject does not have a predisposition to curly hair;

(4) in the base sequence set forth in SEQ ID NO:1, it is identified whether the nucleotide represented by Nucleotide Number 7121 is C or T, and it is determined, when the nucleotide is T, that the test subject has a predisposition to curly hair, or when the nucleotide is C, the test subject does not have a predisposition to curly hair;

(5) in the base sequence set forth in SEQ ID NO:1, it is identified whether the nucleotide represented by Nucleotide Number 8494 is C or A, and it is determined, when the nucleotide is A, that the test subject has a predisposition to curly hair, or when the nucleotide is C, the test subject does not have a predisposition to curly hair;

(6) in the base sequence set forth in SEQ ID NO:1, it is identified whether the nucleotide represented by Nucleotide Number 18980 is T or A, and it is determined, when the nucleotide is A, that the test subject has a predisposition to curly hair, or when the nucleotide is T, the test subject does not have a predisposition to curly hair;

(7) in the base sequence set forth in SEQ ID NO:1, it is identified whether the nucleotide represented by Nucleotide Number 23252 is T or C, and it is determined, when the nucleotide is C, that the test subject has a predisposition to curly hair, or when the nucleotide is T, the test subject does not have a predisposition to curly hair;

(8) in the base sequence set forth in SEQ ID NO:2, it is identified whether the nucleotide represented by Nucleotide Number 2355 is A or G, and it is determined, when the nucleotide is G, that the test subject has a predisposition to curly hair, or when the nucleotide is A, the test subject does not have a predisposition to curly hair;

(9) in the base sequence set forth in SEQ ID NO:2, it is identified whether the nucleotide represented by Nucleotide Number 2569 is G or A, and it is determined, when the nucleotide is A, that the test subject has a predisposition to curly hair, or when the nucleotide is G, the test subject does not have a predisposition to curly hair;

(10) in the base sequence set forth in SEQ ID NO:2, it is identified whether the nucleotide represented by Nucleotide Number 3897 is A or G, and it is determined, when the nucleotide is G, that the test subject has a predisposition to curly hair, or when the nucleotide is A, the test subject does not have a predisposition to curly hair;

(11) in the base sequence set forth in SEQ ID NO:2, it is identified whether the nucleotide represented by Nucleotide Number 8196 is C or T, and it is determined, when the nucleotide is T, that the test subject has a predisposition to curly hair, or when the nucleotide is C, the test subject does not have a predisposition to curly hair;

(12) in the base sequence set forth in SEQ ID NO:2, it is identified whether the nucleotide represented by Nucleotide Number 9510 is T or C, and it is determined, when the nucleotide is C, that the test subject has a predisposition to curly hair, or when the nucleotide is T, the test subject does not have a predisposition to curly hair;

(13) in the base sequence set forth in SEQ ID NO:2, it is identified whether the nucleotide represented by Nucleotide Number 13643 is C or G, and it is determined, when the nucleotide is G, that the test subject has a predisposition to curly hair, or when the nucleotide is C, the test subject does not have a predisposition to curly hair;

(14) in the base sequence set forth in SEQ ID NO:2, it is identified whether the nucleotide represented by Nucleotide Number 15387 is C or G, and it is determined, when the nucleotide is G, that the test subject has a predisposition to curly hair, or when the nucleotide is C, the test subject does not have a predisposition to curly hair;

(15) in the base sequence set forth in SEQ ID NO:2, it is identified whether the nucleotide represented by Nucleotide Number 15708 is A or C, and it is determined, when the nucleotide is C, that the test subject has a predisposition to curly hair, or when the nucleotide is A, the test subject does not have a predisposition to curly hair;

(16) in the base sequence set forth in SEQ ID NO:2, it is identified whether the nucleotide represented by Nucleotide Number 16017 is G or T, and it is determined, when the nucleotide is T, that the test subject has a predisposition to curly hair, or when the nucleotide is G, the test subject does not have a predisposition to curly hair;

(17) in the base sequence set forth in SEQ ID NO:2, it is identified whether the nucleotide represented by Nucleotide Number 17106 is T or C, and it is determined, when the nucleotide is C, that the test subject has a predisposition to curly hair, or when the nucleotide is T, the test subject does not have a predisposition to curly hair;

(18) in the base sequence set forth in SEQ ID NO:2, it is identified whether the nucleotide represented by Nucleotide Number 17453 is T or C, and it is determined, when the nucleotide is C, that the test subject has a predisposition to curly hair, or when the nucleotide is T, the test subject does not have a predisposition to curly hair;

(19) in the base sequence set forth in SEQ ID NO:2, it is identified whether the nucleotide represented by Nucleotide Number 17579 is C or T, and it is determined, when the nucleotide is T, that the test subject has a predisposition to curly hair, or when the nucleotide is C, the test subject does not have a predisposition to curly hair;

(20) in the base sequence set forth in SEQ ID NO:2, it is identified whether the nucleotide represented by Nucleotide Number 17634 is A or T, and it is determined, when the nucleotide is T, that the test subject has a predisposition to curly hair, or when the nucleotide is A, the test subject does not have a predisposition to curly hair;

(21) in the base sequence set forth in SEQ ID NO:2, it is identified whether the nucleotide represented by Nucleotide Number 26924 is A or G, and it is determined, when the nucleotide is G, that the test subject has a predisposition to curly hair, or when the nucleotide is A, the test subject does not have a predisposition to curly hair;

(22) in the base sequence set forth in SEQ ID NO:2, it is identified whether the nucleotide represented by Nucleotide Number 28383 is T or C, and it is determined, when the nucleotide is C, that the test subject has a predisposition to curly hair, or when the nucleotide is T, the test subject does not have a predisposition to curly hair;

(23) in the base sequence set forth in SEQ ID NO:2, it is identified whether the nucleotide represented by Nucleotide Number 31275 is C or G, and it is determined, when the nucleotide is G, that the test subject has a predisposition to curly hair, or when the nucleotide is C, the test subject does not have a predisposition to curly hair;

(24) in the base sequence set forth in SEQ ID NO:2, it is identified whether the nucleotide represented by Nucleotide Number 31301 is T or G, and it is determined, when the nucleotide is G, that the test subject has a predisposition to curly hair, or when the nucleotide is T, the test subject does not have a predisposition to curly hair;

(25) in the base sequence set forth in SEQ ID NO:2, it is identified whether the nucleotide represented by Nucleotide Number 31653 is A or G, and it is determined, when the nucleotide is G, that the test subject has a predisposition to curly hair, or when the nucleotide is A, the test subject does not have a predisposition to curly hair;

(26) in the base sequence set forth in SEQ ID NO:2, it is identified whether the nucleotide represented by Nucleotide Number 31903 is T or C, and it is determined, when the nucleotide is C, that the test subject has a predisposition to curly hair, or when the nucleotide is T, the test subject does not have a predisposition to curly hair;

(27) in the base sequence set forth in SEQ ID NO:2, it is identified whether the nucleotide represented by Nucleotide Number 32209 is A or G, and it is determined, when the nucleotide is G, that the test subject has a predisposition to curly hair, or when the nucleotide is A, the test subject does not have a predisposition to curly hair;

(28) in the base sequence set forth in SEQ ID NO:2, it is identified whether the nucleotide represented by Nucleotide Number 33199 is T or C, and it is determined, when the nucleotide is C, that the test subject has a predisposition to curly hair, or when the nucleotide is T, the test subject does not have a predisposition to curly hair;

(29) in the base sequence set forth in SEQ ID NO:2, it is identified whether the nucleotide represented by Nucleotide Number 33822 is A or G, and it is determined, when the nucleotide is G, that the test subject has a predisposition to curly hair, or when the nucleotide is A, the test subject does not have a predisposition to curly hair;

(30) in the base sequence set forth in SEQ ID NO:2, it is identified whether the nucleotide represented by Nucleotide Number 34100 is T or C, and it is determined, when the nucleotide is C, that the test subject has a predisposition to curly hair, or when the nucleotide is T, the test subject does not have a predisposition to curly hair;

(31) in the base sequence set forth in SEQ ID NO:2, it is identified whether the nucleotide represented by Nucleotide Number 35791 is A or G, and it is determined, when the nucleotide is G, that the test subject has a predisposition to curly hair, or when the nucleotide is A, the test subject does not have a predisposition to curly hair;

(32) in the base sequence set forth in SEQ ID NO:2, it is identified whether the nucleotide represented by Nucleotide Number 36884 is G or A, and it is determined, when the nucleotide is A, that the test subject has a predisposition to curly hair, or when the nucleotide is G, the test subject does not have a predisposition to curly hair;

(33) in the base sequence set forth in SEQ ID NO:2, it is identified whether the nucleotide represented by Nucleotide Number 37072 is G or A, and it is determined, when the nucleotide is A, that the test subject has a predisposition to curly hair, or when the nucleotide is G, the test subject does not have a predisposition to curly hair;

(34) in the base sequence set forth in SEQ ID NO: 2, it is identified whether the nucleotide represented by Nucleotide Number 37365 is A or T, and it is determined, when the nucleotide is T, that the test subject has a predisposition to curly hair, or when the nucleotide is A, the test subject does not have a predisposition to curly hair;

(35) in the base sequence set forth in SEQ ID NO:2, it is identified whether the nucleotide represented by Nucleotide Number 37613 is G or C, and it is determined, when the nucleotide is C, that the test subject has a predisposition to curly hair, or when the nucleotide is G, the test subject does not have a predisposition to curly hair;

(36) in the base sequence set forth in SEQ ID NO:2, it is identified whether the nucleotide represented by Nucleotide Number 38062 is G or A, and it is determined, when the nucleotide is A, that the test subject has a predisposition to curly hair, or when the nucleotide is G, the test subject does not have a predisposition to curly hair;

(37) in the base sequence set forth in SEQ ID NO:2, it is identified whether the nucleotide represented by Nucleotide Number 39063 is T or C, and it is determined, when the nucleotide is C, that the test subject has a predisposition to curly hair, or when the nucleotide is T, the test subject does not have a predisposition to curly hair;

(38) in the base sequence set forth in SEQ ID NO:2, it is identified whether the nucleotide represented by Nucleotide Number 46580 is A or C, and it is determined, when the nucleotide is C, that the test subject has a predisposition to curly hair, or when the nucleotide is A, the test subject does not have a predisposition to curly hair;

(39) in the base sequence set forth in SEQ ID NO:2, it is identified whether the nucleotide represented by Nucleotide Number 49618 is C or G, and it is determined, when the nucleotide is G, that the test subject has a predisposition to curly hair, or when the nucleotide is C, the test subject does not have a predisposition to curly hair;

(40) in the base sequence set forth in SEQ ID NO:2, it is identified whether the nucleotide represented by Nucleotide Number 50164 is A or T, and it is determined, when the nucleotide is T, that the test subject has a predisposition to curly hair, or when the nucleotide is A, the test subject does not have a predisposition to curly hair;

(41) in the base sequence set forth in SEQ ID NO:2, it is identified whether the nucleotide represented by Nucleotide Number 50278 is G or A, and it is determined, when the nucleotide is A, that the test subject has a predisposition to curly hair, or when the nucleotide is G, the test subject does not have a predisposition to curly hair;

(42) in the base sequence set forth in SEQ ID NO:2, it is identified whether the nucleotide represented by Nucleotide Number 50662 is G or T, and it is determined, when the nucleotide is T, that the test subject has a predisposition to curly hair, or when the nucleotide is G, the test subject does not have a predisposition to curly hair;

(43) in the base sequence set forth in SEQ ID NO:2, it is identified whether the nucleotide represented by Nucleotide Number 50822 is T or C, and it is determined, when the nucleotide is C, that the test subject has a predisposition to curly hair, or when the nucleotide is T, the test subject does not have a predisposition to curly hair;

(44) in the base sequence set forth in SEQ ID NO:2, it is identified whether the nucleotide represented by Nucleotide Number 50981 is A or G, and it is determined, when the nucleotide is G, that the test subject has a predisposition to curly hair, or when the nucleotide is A, the test subject does not have a predisposition to curly hair;

(45) in the base sequence set forth in SEQ ID NO:2, it is identified whether the nucleotide represented by Nucleotide Number 51133 is A or C, and it is determined, when the nucleotide is C, that the test subject has a predisposition to curly hair, or when the nucleotide is A, the test subject does not have a predisposition to curly hair;

(46) in the base sequence set forth in SEQ ID NO:2, it is identified whether the nucleotide represented by Nucleotide Number 51263 is G or T, and it is determined, when the nucleotide is T, that the test subject has a predisposition to curly hair, or when the nucleotide is G, the test subject does not have a predisposition to curly hair;

(47) in the base sequence set forth in SEQ ID NO:2, it is identified whether the nucleotide represented by Nucleotide Number 51397 is T or C, and it is determined, when the nucleotide is C, that the test subject has a predisposition to curly hair, or when the nucleotide is T, the test subject does not have a predisposition to curly hair;

(48) in the base sequence set forth in SEQ ID NO:3, it is identified whether the nucleotide represented by Nucleotide Number 2509 is G or A, and it is determined; when the nucleotide is A, that the test subject has a predisposition to curly hair, or when the nucleotide is G, the test subject does not have a predisposition to curly hair;

(49) in the base sequence set forth in SEQ ID NO:3, it is identified whether the nucleotide represented by Nucleotide Number 5167 is T or C, and it is determined, when the nucleotide is C, that the test subject has a predisposition to curly hair, or when the nucleotide is T, the test subject does not have a predisposition to curly hair;

(50) in the base sequence set forth in SEQ ID NO:3, it is identified whether the nucleotide represented by Nucleotide Number 8449 is T or G, and it is determined, when the nucleotide is G, that the test subject has a predisposition to curly hair, or when the nucleotide is T, the test subject does not have a predisposition to curly hair;

(51) in the base sequence set forth in SEQ ID NO:3, it is identified whether the nucleotide represented by Nucleotide Number 17598 is G or A, and it is determined, when the nucleotide is A, that the test subject has a predisposition to curly hair, or when the nucleotide is G, the test subject does not have a predisposition to curly hair;

(52) in the base sequence set forth in SEQ ID NO:3, it is identified whether the nucleotide represented by Nucleotide Number 18481 is T or C, and it is determined, when the nucleotide is C, that the test subject has a predisposition to curly hair, or when the nucleotide is T, the test subject does not have a predisposition to curly hair;

(53) in the base sequence set forth in SEQ ID NO:3, it is identified whether the nucleotide represented by Nucleotide Number 20891 is C or G, and it is determined, when the nucleotide is G, that the test subject has a predisposition to curly hair, or when the nucleotide is C, the test subject does not have a predisposition to curly hair;

(54) in the base sequence set forth in SEQ ID NO:3, it is identified whether the nucleotide represented by Nucleotide Number 21734 is C or T, and it is determined, when the nucleotide is T, that the test subject has a predisposition to curly hair, or when the nucleotide is C, the test subject does not have a predisposition to curly hair;

(55) in the base sequence set forth in SEQ ID NO:3, it is identified whether the nucleotide represented by Nucleotide Number 23382 is A or T, and it is determined, when the nucleotide is T, that the test subject has a predisposition to curly hair, or when the nucleotide is A, the test subject does not have a predisposition to curly hair;

(56) in the base sequence set forth in SEQ ID NO:4, it is identified whether the nucleotide represented by Nucleotide Number 1 is T or C, and it is determined, when the nucleotide is C, that the test subject has a predisposition to curly hair, or when the nucleotide is T, the test subject does not have a predisposition to curly hair;

(57) in the base sequence set forth in SEQ ID NO:4, it is identified whether the nucleotide represented by Nucleotide Number 3308 is C or T, and it is determined, when the nucleotide is T, that the test subject has a predisposition to curly hair, or when the nucleotide is C, the test subject does not have a predisposition to curly hair;

(58) in the base sequence set forth in SEQ ID NO:4, it is identified whether the nucleotide represented by Nucleotide Number 4715 is G or A, and it is determined, when the nucleotide is A, that the test subject has a predisposition to curly hair, or when the nucleotide is G, the test subject does not have a predisposition to curly hair;

(59) in the base sequence set forth in SEQ ID NO:4, it is identified whether the nucleotide represented by Nucleotide Number 4985 is C or T., and it is determined, when the nucleotide is T, that the test subject has a predisposition to curly hair, or when the nucleotide is C, the test subject does not have a predisposition to curly hair;

(60) in the base sequence set forth in SEQ ID NO:4, it is identified whether the nucleotide represented by Nucleotide Number 6354 is C or A, and it is determined, when the nucleotide is A, that the test subject has a predisposition to curly hair, or when the nucleotide is C, the test subject does not have a predisposition to curly hair;

(61) in the base sequence set forth in SEQ ID NO:4, it is identified whether the nucleotide represented by Nucleotide Number 8553 is C or T, and it is determined, when the nucleotide is T, that the test subject has a predisposition to curly hair, or when the nucleotide is C, the test subject does not have a predisposition to curly hair;

(62) in the base sequence set forth in SEQ ID NO:4, it is identified whether the nucleotide represented by Nucleotide Number 8818 is C or G, and it is determined, when the nucleotide is G, that the test subject has a predisposition to curly hair, or when the nucleotide is C, the test subject does not have a predisposition to curly hair;

(63) in the base sequence set forth in SEQ ID NO:5, it is identified whether the nucleotide represented by Nucleotide Number 1 is C or T, and it is determined, when the nucleotide is T, that the test subject has a predisposition to curly hair, or when the nucleotide is C, the test subject does not have a predisposition to curly hair;

(64) in the base sequence set forth in SEQ ID NO:5, it is identified whether the nucleotide represented by Nucleotide Number 540 is C or A, and it is determined, when the nucleotide is A, that the test subject has a predisposition to curly hair, or when the nucleotide is C, the test subject does not have a predisposition to curly hair;

(65) in the base sequence set forth in SEQ ID NO:5, it is identified whether the nucleotide represented by Nucleotide Number 759 is C or T, and it is determined, when the nucleotide is T, that the test subject has a predisposition to curly hair, or when the nucleotide is C, the test subject does not have a predisposition to curly hair;

(66) in the base sequence set forth in SEQ ID NO:5, it is identified whether the nucleotide represented by Nucleotide Number 1007 is A or G, and it is determined, when the nucleotide is G, that the test subject has a predisposition to curly hair, or when the nucleotide is A, the test subject does not have a predisposition to curly hair;

(67) in the base sequence set forth in SEQ ID NO:5, it is identified whether the nucleotide represented by Nucleotide Number 1018 is G or A, and it is determined, when the nucleotide is A, that the test subject has a predisposition to curly hair, or when the nucleotide is G, the test subject does not have a predisposition to curly hair;

(68) in the base sequence set forth in SEQ ID NO:5, it is identified whether the nucleotide represented by Nucleotide Number 1075 is G or C, and it is determined, when the nucleotide is C, that the test subject has a predisposition to curly hair, or when the nucleotide is G, the test subject does not have a predisposition to curly hair;

(69) in the base sequence set forth in SEQ ID NO:5, it is identified whether the nucleotide represented by Nucleotide Number 1939 is G or A, and it is determined, when the nucleotide is A, that the test subject has a predisposition to curly hair, or when the nucleotide is G, the test subject does not have a predisposition to curly hair; or

(70) in the base sequence set forth in SEQ ID NO:5, it is identified whether the nucleotide represented by Nucleotide Number 3440 is A or G, and it is determined, when the nucleotide is G, that the test subject has a predisposition to curly hair, or when the nucleotide is A, the test subject does not have a predisposition to curly hair.

In addition, the SNP detected in the method of the present invention for determining the genetic susceptibility (genetic predisposition) to hair shape may be any one of the SNPs described above, or may be two or more thereof. Preferably, two or more SNPs are detected, and thereby, the type or the presence or absence of the genetic predisposition of the test subject to the hair shape, which is a general polygenic trait, can be made clear, while a gene which serves as a main factor determining the hair shape of the test subject can be retrieved with higher accuracy.

The detection of the SNPs can be carried out by directly determining the base sequence of the 1q21.3 region of human chromosome 1 further isolated from a sample containing the genomic DNA, or the base sequence of the haplotype block represented by the base sequences set forth in SEQ ID NO:1 to NO:5 in the genomic regions of human chromosome 1. Alternatively, as a method for detecting a polymorphism, in addition to the method of directly determining the gene sequence of the region as described above, there are available a method of determining, when the polymorphism sequence is a restriction enzyme recognition site, the genotype by using the difference in the restriction enzyme cleavage pattern (hereinafter, called RFLP); and methods based on hybridization using a polymorphism-specific probe (for example, a method of determining the type of polymorphism by attaching particular probes on a chip, a glass slide or a nylon film and detecting the difference in the intensity of hybridization with respect to those probes, or a method of determining the genotype by detecting the efficiency of hybridization of a specific probe as the amount of the probe decomposed by a polymerase during amplification of the two strands of a template; a method of detecting the temperature difference in the fusion of two strands by tracing the temperature change of fluorescence emitted by a certain type of two-stranded specific fluorescent dye, and thereby determining the polymorphism; a method of attaching complementary sequences to the two ends of a polymorphic site-specific oligo-probe, and determining the genotype by utilizing the difference between the case where the probe makes a secondary structure within the molecules of the probe itself due to temperature, and the case where the probe hybridizes with the target region; and the like). Further examples include methods of carrying out a nucleotide extension reaction by a polymerase from a template-specific primer, and determining a nucleotide that is accepted to the polymorphic site at that time (a method of using dideoxynucleotides, including fluorescently labeling each of them and detecting the fluorescence of each, and a method of detecting the accepted dideoxynucleotides by mass spectrometry); a method of recognizing the presence or absence of a complementary base pair or a non-complementary base pair at a mutation site by means of an enzyme, subsequent to a template-specific primer; and the like.

Now, conventionally well-known, representative methods for detecting genetic polymorphisms will be listed below, but the present invention is not at all intended to be limited to these: (a) a RFLP (restriction enzyme-cleaved fragment length polymorphism) method; (b) a PCR-SSCP method (analysis of single-stranded DNA higher structure polymorphism, Biotechniques, 16, p. 296-297, 1994, and Biotechniques, 21, p. 510 to 514, 1996); (c) an ASO hybridization method (Clin. Chim. Acta., 189, p. 153-157, 1990); (d) a direct sequencing method (Biotechniques, 11, p. 246-249, 1991); (e) an ARMS method (Nuc. Acids Res., 19, p. 3561-3567, 1991, and Nuc. Acids Res., 20, p. 4831-4837, 1992); (f) a denaturant concentration gradient gel electrophoresis (DGGE) method (Biotechniques, 27, p. 1016-1018, 1999); (g) an RNaseA cleavage method (DNA Cell Biol 14, p. 87-94, 1995); (h) a chemical cleavage method (Biotechniques, 21, p. 216-218, 1996); (i) a DOL method (Genome Res., 8, p. 549-556, 1998); (j) a TaqMan-PCR method (Genet. Anal., 14, p. 143-149, 1999, and J. Clin. Microbiol., 34, p. 2933-2936, 1996); (k) an invader method (Science, 5109, p. 778-783, 1993, J. Bio. Chem., 30, p. 21387-21394, 1999, and Nat. Biotechnol., 17, p. 292-296, 1999); (1) a MALDI-TOF/MS method (Genome Res., 7, p. 378-388, 1997, and Eur. J. Clin. Chem. Clin. Biochem., 35, p. 545-548, 1997); (m) a TDI method (Proc. Natl. Acad. Sci. USA, 94, p. 10756-10761, 1997); (n) a molecular beacon method (Nat. Biotechnol., 16, p. 49-53, 1998); (O) a dynamic allele specific hybridization (DASH) method (Nat. Biotechnol., 17, p. 87-88, 1999); (p) a padlock probe method (Nat. Genet., 3, p. 225-232, 1998); (q) a DNA chip or DNA microarray (Nakamura, Yusuke, et al., "SNP Idenshi Takei no Senryaku (Strategy for SNP Gene Polymorphism)", Nakayama Shoten Co., Ltd., p. 128-135, 2000); and (R) an ECA method (Anal. Chem., 72, p. 1334-1341, 2000).

Those described above are representative methods for gene polymorphism detection; however, the method of the present invention for determining the genetic susceptibility (genetic predisposition) to hair shape is not limited to these, and any other gene polymorphism detection methods that are already known or will be developed in the future can be broadly used. Furthermore, in regard to the gene polymorphism detection of the present invention, these methods for gene polymorphism detection may be used singly, or two or more methods can also be used in combination. Hereinafter, as representative methods, the TaqMan-PCR method and the invader method that are used in the Examples described below will be explained in more detail.

(1) TaqMan-PCR Method

The TaqMan-PCR method is a method of using a fluorescent-labeled, allele-specific oligonucleotide (TaqMan probe), and PCR by a Taq DNA polymerase. As the TaqMan probe, an oligonucleotide containing a contiguous base sequence of about 15 to about 30 nucleotides, which is a partial base sequence of a haplotype block represented by any one of SEQ ID NO:1 to NO:5 in the genomic region of human chromosome 1, and contains one or more of polymorphic sites described above (for example, a nucleic acid probe contained in the reagent for hair shape determination of the present invention that will be described below), is used. The probe is labeled with a fluorescent dye such as FAM or VIC at the 5'-terminal, and with a quencher (quenching substance) such as TAMRA at the 3'-terminal, respectively, and in the state as received, since the quencher absorbs the fluorescent energy, fluorescence is not detected. It is preferable to produce probes for both alleles, and to label the probes with fluorescent dyes having different fluorescence wavelengths for batch detection (for example, FAM for one allele and VIC for the other). Furthermore, the 3'-terminal is phosphorylated so that a PCR extension reaction from the TaqMan probe does not occur. When a PCR is carried out using a primer which is designed to amplify a partial sequence of the genomic DNA containing a region that hybridizes with the TaqMan probe, as well as a TaqDNA polymerase, the TaqMan probe hybridizes with the template DNA, and at the same time, an extension reaction from the PCR primer occurs. However, when the extension reaction proceeds, the hybridized TaqMan probe is cleaved due to the 5' nuclease activation of the Taq DNA polymerase, and the fluorescent dye is released and is no longer affected by the quencher, so that fluorescence is detected. With the amplification of the template, the fluorescence intensity increases exponentially. For example, in the detection of a polymorphism in the nucleotide represented by Nucleotide Number 7121 (rs2305814, C or T) in the base sequence set forth in SEQ ID NO:1, when an allele-specific oligonucleotide containing the nucleotide (having a length of about 15 to about 30-mers; the C allele is labeled with FAM, and the T allele is labeled with VIC, respectively, at the 5'-terminals, and the 3'-terminals are both labeled with TAMRA) is used as the TaqMan probe, if the genotype of the test subject is CC or TT, high fluorescence intensity of FAM or VIC is recognized in the respective cases, while the other fluorescence is almost unrecognizable. On the other hand, if the genotype of the test subject is CT, fluorescence of both FAM and VIC is detected.

(2) Invader Method

In the invader method, unlike the TaqMan-PCR method, the allele-specific oligonucleotide (allele probe) itself is not labeled, and the oligonucleotide has a sequence having no complementarity to the template DNA on the 5' side of the nucleotides at the polymorphic site (flap) and has a complementary sequence specific to the template on the 3' side. In the invader method, use is made of an oligonucleotide having a complementary sequence specific to the 3' side of the polymorphic site of the template (invader probe; the nucleotides corresponding to the polymorphic site, which is the 5'-terminal of the probe, are arbitrary), and a FRET (Fluorescence Resonance Energy Transfer) probe characterized in that the 5' side has a sequence capable of adopting a hairpin structure, and the sequence contiguous from the nucleotides forming pairs with the nucleotides of the 5'-terminal to the 3' side when a hairpin structure is formed, is a sequence complementary to the flap of the allele probe. The 5'-terminal of the FRET probe is fluorescent labeled (for example, FAM, VIC, or the like), and a quencher (for example, TAMRA, or the like) is bonded in the vicinity thereof, so that in the state as received (hairpin structure), fluorescence is not detected. When the template genomic DNA is allowed to react with the allele probe and the invader probe, upon the complementary binding of the three entities, the 3'-terminal of the invader probe penetrates into the polymorphic site. When the single-stranded portion of the allele probe (that is, the flap portion on the 5' side from the nucleotides of the polymorphic site) is cut using an enzyme which recognizes the structure of this polymorphic site (Cleavase), the flap complementarily binds with the FRET probe, and the polymorphic site of the flap penetrates into the hairpin structure of the FRET probe. When Cleavase recognizes and cleaves this structure, the fluorescent dye used to label the terminal of the FRET probe is released and is no longer affected by the quencher, and thus fluorescence is detected. An allele probe whose nucleotides of the polymorphic site do not match with the template is not cleaved by Cleavase, since an allele probe which is not cleaved can also hybridize with the FRET probe, fluorescence is similarly detected. However, because the reaction efficiency is different, in the allele probe whose nucleotides of the polymorphic site match the template, the fluorescence intensity is markedly stronger than that of the allele probe which does not match. Usually, it is preferable to have the template DNA amplified by PCR using a primer capable of amplifying the region containing the portions where the allele probe and the invader probe hybridize, before the template DNA is allowed to react with the three kinds of probes and Cleavase.

The hair shape of a person can be freely changed by a permanent treatment, a styling agent treatment, brushing or the like, and also can change in an acquired manner, through changes in aging, metabolism, and the like. For this reason, it is difficult to correctly determine or classify the intrinsic natural hair shape of a person based only on the phenotype. Furthermore, since the hair shape can be considered as a general trait of complicated polygenicity, it can be speculated that for individual persons, the gene which serves as a main causative factor for determining the hair shape among the hair shape susceptibility genes of the present invention described above, may vary in different individuals. Therefore, when the genetic predisposition to hair shape is examined and/or determined, a method for regulating the hair shape appropriate for the individuals can be provided.

Furthermore, according to the method, the susceptibility to an acquired change in the hair shape of a test subject, that is, the risk of hair shape change, can be determined. The risk of hair shape change can be mechanically determined using the polymorphisms described above as the reference (index), without requiring the judgment of a person having expertise such as a doctor. Accordingly, the method of the present invention can also be used as a method for detecting the risk of hair shape change.

Through the method of the present invention for determining the genetic susceptibility (genetic predisposition) of a test subject to hair shape, the type or the presence or absence of the genetic predisposition of the test subject to hair shape, which is a general polygenic trait, can be made clear, and a gene which serves as the main causative factor that determines the hair shape of the test subject can be searched among the hair shape susceptibility genes of the present invention. Furthermore, appropriate measures for promoting the regulation of hair shape in the test subject can be devised based on the results of the search. Therefore, the present invention is extremely useful as a method for the examination and/or determination for the fundamental regulation of hair shape.

5. REAGENT FOR DETERMINATION OF GENETIC SUSCEPTIBILITY (GENETIC PREDISPOSITION) TO HAIR SHAPE AND KIT INCLUDING THE REAGENT

The present invention also provides a reagent to be used in the determination method of the present invention, and a kit including the reagent. That is, the reagent for determination of the present invention and the kit including the reagent include a nucleic acid probe and/or a primer capable of detecting one or more SNPs selected from the group consisting of an SNP in the 1q21.3 region (D1S2696 to D1S2346) of human chromosome 1, which is determined by a linkage disequilibrium analysis on a single polynucleotide polymorphism (SNP) marker whose allele frequency is statistically significantly different between a group having a curly hair trait and a group having a non-curly hair trait, and is present in a haplotype block having a 23,252-bp base sequence set forth in SEQ ID NO: 1, a 56,552-bp base sequence set forth in SEQ ID NO:2, a 23,382-bp base sequence set forth in SEQ ID NO:3, a 8,818-bp base sequence set forth in SEQ ID NO:4, or a 3,440-bp base sequence set forth in SEQ ID NO:5, and which has a higher allele frequency in an arbitrary curly hair people group than in an arbitrary non-curly hair people group, and an SNP linked to the SNP.

According to an embodiment, the nucleic acid probe used in the reagent for determination of the present invention and the kit including the reagent, is a nucleic acid which specifically hybridizes with the region of a genomic DNA containing the nucleotides of the SNP site to be detected in the method for examination and/or determination of the present invention, and is, for example, a probe which specifically hybridizes with the hair shape determining marker sequence of the present invention. The nucleic acid probe is not particularly limited in the length (length of nucleotides in the portion that hybridizes with the genomic DNA), as long as the nucleic acid probe is specific to a target site to be hybridized and can easily detect polymorphisms. For example, the length is about 10 nucleotides or more, preferably about 15 nucleotides or more, more preferably about 15 to about 600 nucleotides, even more preferably about 15 to about 200 nucleotides, and still more preferably about 15 to about 50 nucleotides. Meanwhile, the phrase "specifically hybridizes with a target site (sequence)" means that cross-hybridization with another DNA does not occur significantly under standard hybridization conditions, preferably under stringent hybridization conditions (for example, conditions described in Joseph Sambrook et al., Molecular Cloning: A Laboratory Manual (3 Vol. set), Cold Spring Harbor Laboratory, NY, 2001). Suitably, the nucleic acid probe preferably has a base sequence complementary to the base sequence of a region containing nucleotides of the polymorphic site to be detected; however, if such specific hybridization is possible, the nucleic acid probe does not need to be completely complementary.

The nucleic acid probe may contain an additional sequence appropriate for the detection of polymorphism (a sequence which is not complementary to the genomic DNA). For example, the allele probe used in the invader method has an additional sequence called flap, at the 5'-terminal of the nucleotides of the polymorphic site. Furthermore, the probe may also be labeled with an appropriate labeling agent, for example, a radioisotope (for example, $^{125}I$, $^{131}I$, $^{3}H$, and $^{14}C$), an enzyme (for example, β-galactosidase, β-glucosidase, alkali phosphatase, peroxidase, malate dehydrogenase, or the like), a fluorescent substance (for example, fluorescamine, fluorescein isothiocyanate, or the like), or a luminescent substance (for example, luminol, a luminol derivative, luciferin, lucigenin, or the like). Alternatively, the probe may also be further bonded, in the vicinity of a fluorescent substance (for example, FAM, VIC, or the like), with a quencher (quenching substance) which absorbs the fluorescent energy emitted by the fluorescent substance. In such an embodiment, the fluorescent substance and the quencher are separated at the time of the detection reaction, and fluorescence is detected.

The nucleic acid probe can also be used after being immobilized on an arbitrary solid phase. For this reason, the reagent of the present invention and the kit including the reagent can be provided as an immobilized probe in which the probe is immobilized on an arbitrary solid support (for example, a gene chip, a cDNA microarray, an oligo-DNA array, a membrane filter, or the like, on which a probe is immobilized). Suitably, the immobilized probe is provided as a DNA chip for hair shape susceptibility gene detection.

The solid support used in immobilization is not particularly limited as long as nucleic acid can be immobilized thereon, and examples include a glass plate, a nylon membrane, microbeads, a silicon chip, a capillary, other supports, or the like. The immobilization of a nucleic acid on a solid support may be carried out by a method of mounting a previously synthesized nucleic acid on a solid phase, or by a method of synthesizing a target nucleic acid on a solid phase. The immobilization method is, for example, in the case of a DNA microarray, well known in the art according to the type of the immobilization probe, e.g., a commercially available spotter (manufactured by Amersham Biosciences Corp.), or the like (for example, in situ synthesis of oligonucleotides by photolithographic technology (Affymetrix, Inc.) or inkjet technology (Rosetta Inpharmatics, Inc.), and the like).

The nucleic acid primer used in the reagent for determination of the present invention and the kit including the reagent, may be any nucleic acid primer as long as it is designed to be capable of specifically hybridizing with the region of a genomic DNA containing the nucleotides of the SNP site to be detected in the method for examination and/or determination of the present invention, and specifically amplifying the nucleic acid sequence. For example, the primer is a primer which specifically hybridizes with the nucleic acid sequence of the hair shape determining marker of the present invention and amplifies the hair shape determining marker. Here, the phrase "specifically hybridizes with a target site (sequence)" means that cross-hybridization with another DNA does not occur significantly under the standard hybridization conditions, preferably under stringent hybridization conditions (for example, the conditions described in Joseph Sambrook et al., Molecular Cloning: A Laboratory Manual (3 Vol. set), Cold Spring Harbor Laboratory, NY, 2001).

The method for amplifying the nucleic acid sequence using a primer is not particularly limited as long as it is a method ordinarily used in the art. For example, generally, a PCR method is broadly used, but examples include RCA (Rolling Circle Amplification; Proc. Natl. Acad. Sci., Vol. 92, 4641-4645 (1995)), ICAN (Isothermal and Chimeric primer-initiated Amplification of Nucleic acids), LAMP (Loop-Mediated Isothermal Amplification of DNA; Bio Industry, vol. 18, No. 2 (2001)), NASBA (Nucleic acid Sequence-based Amplification method; Nature, 350, 91-(1991)), TMA (Transcription Mediated Amplification method; J. Clin. Microbiol. Vol. 31, 3270-(1993), and the like). The number and type of the nucleic acid primer required for amplification can vary depending on the amplification method. For example, in the case of using a PCR method, the required primer may be a pair of nucleic acid primers, which is a combination of a nucleic acid containing a base sequence having about 10 to about 50 nucleotides, preferably about 15 to about 50 nucleotides, and more preferably about 15 to about 30 nucleotides, that is a partial base sequence of a haplotype block represented by a base sequence set forth in any one of SEQ ID NO:1 to NO:5 in the genomic region of human chromosome 1, and specifically hybridizes with a portion of the complementary strand sequence on the 5' side relative to the nucleotides of the polymorphic site to be detected, and a nucleic acid containing a base sequence having about 10 to about 50 nucleotides, preferably about 15 to about 50 nucleotides, and more preferably about 15 to about 30 nucleotides, that is the partial base sequence and specifically hybridizes with a portion of the complementary strand sequence on the 3' side relative to the nucleotides of the polymorphic site, the fragment of the nucleic acid to be amplified by the combination of nucleic acids having a length of about 50 to about 1000 nucleotides, preferably about 50 to about 500 nucleotides, and more preferably about 50 to about 200 nucleotides.

The primer may also contain an additional sequence appropriate for the detection of polymorphism (a sequence that is not complementary to the genomic DNA), for example, a linker sequence. Further, the primer may also be labeled with an appropriate labeling agent, for example, a radioisotope (for example, $^{125}I$, $^{131}I$, $^{3}H$, or $^{14}C$), an enzyme (for example, β-galactosidase, β-glucosidase, alkali phosphatase, peroxidase, or malate dehydrogenase), a fluorescent substance (for example, fluorescamine, or fluorescein isothiocyanate), a luminescent substance (for example, luminol, a luminol derivative, luciferin, lucigenin, or the like), or the like.

Preferably, the nucleic acid probe and/or primer used in the reagent for determination of the present invention and the kit including the reagent include the hair shape susceptibility SNP marker of the present invention, that is, the nucleotides shown below:

(1) nucleotides represented by Nucleotide Numbers 1 (db-SNP Database ID: rs3754211, A or G), 2405 (rs3754210, T or G), 5874 (rs16832604, G or A), 7121 (rs2305814, C or T), 8494 (rs7532008, C or A), 18980 (rs1673160, T or A) and 23252 (rs771205, T or C) in the base sequence set forth in SEQ ID NO: 1;

(2) nucleotides represented by Nucleotide Numbers 2355 (rs11581947, A or G), 2569 (rs6658925, G or A), 3897 (rs2105117, A or G), 8196 (rs1053590, C or T), 9510 (rs548252, T or C), 13643 (rs493133, C or G), 15387 (rs1970283, C or G), 15708 (rs1001834, A or C), 16017 (rs11205018, G or T), 17106 (rs545418, T or C), 17453 (rs12116609, T or C), 17579 (rs526099, C or T), 17634 (rs525960, A or T), 26924 (rs4845443, A or G), 28383 (rs569032, T or C), 31275 (rs528427, C or G), 31301 (rs478926, T or G), 31653 (rs1337338, A or G), 31903 (rs6587681, T or C), 32209 (rs1856120, A or G), 33199 (rs474086, T or C), 33822 (rs578382, A or G), 34100 (rs549044, T or C), 35791 (rs1123567, A or G), 36884 (rs1538083, G or A), 37072 (rs1538082, G or A), 37365 (rs7532535, A or T), 37613 (rs7518654, G or C), 38062 (rs533917, G or A), 39063 (rs564107, T or C), 46580 (rs7530609, A or C), 49618 (rs4240885, C or G), 50164 (rs4240886, A or T), 50278 (rs4240887, G or A), 50662 (rs6687126, G or T), 50822 (rs6674451, T or C), 50981 (rs7550769, A or G), 51133 (rs7529157, A or C), 51263 (rs1988805, G or T) and 51397 (rs7529441, T or C) in the base sequence set forth in SEQ ID NO:2;

(3) nucleotides represented by Nucleotide Numbers 2509 (rs11205072, G or A), 5167 (rs3753453, T or C), 8449 (rs3737859, T or G), 17598 (rs3904414, G or A), 18481 (rs12074783, T or C), 20891 (rs3908717, C or G), 21734 (rs3904415, C or T) and 23382 (rs11205079, A or T) in the base sequence set forth in SEQ ID NO:3;

(4) nucleotides represented by Nucleotide Numbers 1 (rs16834715, T or C), 3308 (rs12022319, C or T), 4715 (rs4845490, G or A), 4985 (rs4845491, C or T), 6354 (rs3737861, C or A), 8553 (rs16834728, C or T) and 8818 (rs4845492, C or G) in the base sequence set forth in SEQ ID NO:4; and (5) nucleotides represented by Nucleotide Numbers 1 (rs1854779, C or T), 540 (rs16834751, C or A), 759 (rs4523473, C or T), 1007 (rs11205131, A or G), 1018 (rs7528862, G or A), 1075 (rs7517189, G or C), 1939 (rs2229496, G or A) and 3440 (rs913996, A or G) in the base sequence set forth in SEQ ID NO:5.

More preferably, the nucleic acid probe and/or primer used in the reagent for determination of the present invention and the kit including the reagent, contains a nucleotide represented by Nucleotide Number 7121 (rs2305814, C or T) in the base sequence set forth in SEQ ID NO:1; a nucleotide represented by Nucleotide Number 8196 (rs1053590, C or T) in the base sequence set forth in SEQ ID NO:2; nucleotides represented by Nucleotide Numbers 5167 (rs3753453, T or C), 8449 (rs3737859, T or G), 17598 (rs3904414, G or A), and 20891 (rs3908717, C or G) in the base sequence set forth in SEQ ID NO:3; a nucleotide represented by Nucleotide Number 6354 (rs3737861, C or A) in the base sequence set forth in SEQ ID NO:4; and nucleotides represented by Nucleotide Numbers 759 (rs4523473, C or T), 1939 (rs2229496, G or A), and 3440 (rs913996, A or G) in the base sequence set forth in SEQ ID NO:5.

As the nucleic acid probe having the nucleotides of the polymorphic sites described above, a nucleic acid having the nucleotides of any one of the alleles for various polymorphic sites can be used, or two nucleic acids having the nucleotides each respectively corresponding to each of the alleles can also be used, depending on the method for detecting polymorphism used. Meanwhile, in regard to the invader probe used in the invader method, the nucleotides of the polymorphic site (that is, the nucleotides at the 3'-terminal) may be any arbitrary nucleotides.

The nucleic acid probe and/or primer used in the reagent for determination of the present invention and the kit including the reagent may be a DNA or an RNA, and may be single-stranded or double-stranded. In the case of being double-stranded, the nucleic acid probe and/or primer may be any one of a double-stranded DNA, a double-stranded RNA, and a DNA/RNA hybrid. The nucleic acid probe and/or primer can be produced, based on the information of the base sequence, according to an ordinary method using, for example, a commercially available nucleotide synthesizer.

The nucleic acid probe and/or primer described above can be respectively separately (or if possible, in a mixed state) dissolved in water or an appropriate buffer solution (for example, TE buffer, or the like) to an appropriate concentration (for example, 1 to 50 μM, or the like at ×2 to 20 concentration), and can be stored at about −20° C. The reagent for determination of the present invention and the kit including the reagent may further include, as constituents, other components necessary for carrying out the method, for example, a buffer for hybridization reaction, an enzyme for nucleic acid amplification reaction, a buffer and other necessary reagents, a reagent for labeling, a reagent for label detection, and apparatuses needed for those reactions or procedure, depending on the method for detecting polymorphism used. For example, when the reagent and the kit including the reagent are for polymorphism detection according to a TaqMan-PCR method, the reagent and the kit including the reagent can further include a 10×PCR reaction buffer solution, a 10× aqueous solution of $MgCl_2$, a 10× aqueous solution of dNTPs, a Taq DNA polymerase (5 U/μL) and the like.

The reagent for determination of the present invention and the kit including the reagent can be used for the examination and/or determination of the genetic susceptibility (genetic predisposition) to hair shape.

6. USE OF HAIR SHAPE SUSCEPTIBILITY GENE OR PROTEIN ENCODING THE GENE

In regard to the hair shape susceptibility gene identified by the procedure described above or an expression product thereof, the expression or activity changes in association with the hair shape. Therefore, the hair shape susceptibility gene and an expression product thereof can be used as a marker for the type of hair shape for detecting and/or determining the type of hair shape of a test subject. Alternatively, when the amount of expression of the hair shape susceptibility gene or an expression product thereof is measured and evaluated, the evaluation or selection of a regulating agent for the hair shape of a person can be carried out. Furthermore, alternatively, when the amount of expression of the hair shape susceptibility gene or an expression product thereof is controlled, the hair shape of a person can be regulated.

According to the present invention, the person who can serve as an object in need of the detection and/or determination of the type of hair shape or the regulation of hair shape, is not particularly limited to a specific human race or group, but Asian race is preferred, while Japanese people are more preferred.

The hair shape susceptibility gene and an expression product thereof that are used as the hair shape determining marker may be a gene which overlaps with the haplotype block having the base sequence set forth in any one of SEQ ID NO:1 to NO:5 or an expression product thereof. However, preferred examples include ANXA9 gene, FAM63A gene, LCE5A gene, CRCT1 gene, LCE2B gene, LCE2A gene, SMCP gene and IVL gene, and expression products thereof, and among these ANXA9 gene, LCE2B gene, LCE2A gene, IVL gene and CRCT1 gene, and expression products thereof are more preferred.

ANXA9 gene is a gene containing a polynucleotide set forth in SEQ ID NO:44, and AXNA9 protein encoded by the gene has an amino acid sequence set forth in SEQ ID NO:45. ANXA9 gene is reported as a member of calcium-dependent phospholipid-binding proteins (Nguyen V T et al., J. Biol. Chem., 275(38), p. 29466-76, 2000). The gene can be accessed at the NCBI gene database under GeneID: 8416. The gene can be acquired by a known technique for gene manipulation. ANXA9 protein can be obtained by expressing a gene containing a polynucleotide set forth in SEQ ID NO:44, or can also be produced by a general chemical synthesis method, according to the amino acid sequence information set forth in SEQ ID NO:45.

As shown in the Examples that will be described below, gene expression in the hair root area of curly hair people and non-curly hair people among Japanese people was analyzed, and it was found that as compared with the non-curly hair group, the amount of expression of ANXA9 gene significantly decreases in the curly hair group. Further, when a substance having a hair straightening action, such as common morning glory, is administered, curly hair is alleviated, and the amount of expression of ANXA9 gene is increased.

LCE2B gene is a gene containing a polynucleotide set forth in SEQ ID NO:46, and LCE2B protein encoded by the gene has an amino acid sequence set forth in SEQ ID NO:47. LCE2B gene is reported as a gene that is expressed in the course of terminal differentiation of epidermal cells (Jackson B et al., J. Invest. Dermatol., 124 (5), p. 1062-70, 2005). The gene can be accessed at the NCBI gene database under GeneID: 26239. The gene can be acquired by a known technique for gene manipulation. LCE2B protein can be obtained by expressing a gene containing a polynucleotide set forth in SEQ ID NO:46, or can also be produced by a general chemical synthesis method according to the amino acid sequence information set forth in SEQ ID NO:47.

As shown in the Examples that will be described below, gene expression in the hair root area of curly hair people and non-curly hair people among Japanese people was analyzed, and it was found that as compared with the non-curly hair group, the amount of expression of LCE2B gene significantly decreases in the curly hair group.

LCE2A gene is a gene containing a polynucleotide set forth in SEQ ID NO:48, and LCE2A protein encoded by the gene has an amino acid sequence set forth in SEQ ID NO:49. LCE2A gene is reported as a gene that is expressed in the course of terminal differentiation of epidermal cells (Jackson B et al., J. Invest. Dermatol., 124 (5), p. 1062-70, 2005). The gene can be accessed at the NCBI gene database under GeneID: 353139. The gene can be acquired by a known technique for gene manipulation. LCE2A protein can be obtained by expressing a gene containing a polynucleotide set forth in SEQ ID NO:48, or can also be produced by a general chemical synthesis method according to the amino acid sequence information set forth in SEQ ID NO:49.

As shown in the Examples that will be described below, gene expression in the hair root area of curly hair people and non-curly hair people among Japanese people was analyzed, and it was found that as compared with the non-curly hair group, the amount of expression of LCE2A gene significantly decreases in the curly hair group.

IVL gene is a gene containing a polynucleotide set forth in SEQ ID NO: 50, and IVL protein encoded by the gene has an amino acid sequence set forth in SEQ ID NO:51. IVL gene is reported as a gene that is expressed in the course of terminal differentiation of epidermal cells (Eckert R L et al., J. Invest. Dermatol., 100(5), p. 613-7, 1993). The gene can be accessed at the NCBI gene database under GeneID: 3713. The gene can be acquired by a known technique for gene manipulation. IVL protein can be obtained by expressing a gene containing a polynucleotide set forth in SEQ ID NO: 50, or can also be produced by a general chemical synthesis method according to the amino acid sequence information set forth in SEQ ID NO:51.

As shown in the Examples that will be described below, gene expression in the hair root area of curly hair people and non-curly hair people among Japanese people was analyzed, and it was found that as compared with the non-curly hair group, the amount of expression of IVL gene significantly increases in the curly hair group. Further, when a substance having a hair curling action, such as passion flower, is administered, hair curling is promoted, and the amount of expression of IVL gene is increased.

CRCT1 gene is a gene containing a polynucleotide set forth in SEQ ID NO:52, and CRCT1 protein encoded by the gene has an amino acid sequence set forth in SEQ ID NO:53. CRCT1 gene is reported as a gene encoding a protein which participates in the terminal differentiation of epithelial cells (Marenholz I et al., Genome Res., 11 (3), p. 341-55, 2001). The gene can be accessed at the NCBI gene database under GeneID: 54544. The gene can be acquired by a known technique for gene manipulation. CRCT1 protein can be obtained by expressing a gene containing a polynucleotide set forth in SEQ ID NO:52, or can also be produced by a general chemical synthesis method, according to the amino acid sequence information set forth in SEQ ID NO:53.

As shown in the Examples that will be described below, gene expression in the hair root area of curly hair people and non-curly hair people among Japanese people was analyzed, and it was found that as compared with the non-curly hair group, the amount of expression of CRCT1 gene significantly decreases in the curly hair group. Further, when a substance having a hair straightening action, such as common morning glory, is administered, curly hair is alleviated, and the amount of expression of CRCT1 gene is increased.

(1) Polynucleotide Marker for Detecting and/or Determining Type of Hair Shape

According to the present invention, the marker for detecting and/or determining the type of hair shape (marker for the type of hair shape) may be a polynucleotide having the base sequence of the hair shape susceptibility gene of the present invention, or a partial polynucleotide thereof. Examples of the marker for the type of hair shape of the present invention include a polynucleotide consisting of the base sequence of ANXA9 gene, FAM63A gene, LCE5A gene, CRCT1 gene, LCE2B gene, LCE2A gene, SMCP gene or IVL gene; preferably a polynucleotide consisting of the base sequence of ANXA9 gene, LCE2B gene, LCE2A gene, IVL gene or CRCT1 gene; more preferably a polynucleotide consisting of the base sequence set forth in SEQ ID NO:44, SEQ ID NO:46, SEQ ID NO:48, SEQ ID NO:50 or SEQ ID NO:52, polynucleotides consisting of base sequences complementary to these, and partial polynucleotides thereof.

Furthermore, the marker for the type of hair shape of the present invention can contain a strain consisting of a base sequence which is in a further complementary relation with respect to the base sequence of the polynucleotide consisting of complementary base sequence or a partial polynucleotide thereof described above.

The polynucleotides described above and complementary strands thereof may be respectively used as the marker of the present invention in a single-stranded form, or may also be used as the marker of the present invention in a double-stranded form.

Examples of the partial polynucleotide include a partial polynucleotide of the polynucleotide consisting of the base sequence of the hair shape susceptibility gene of the present invention or a base sequence complementary to this, in which the partial polynucleotide has, for example, a length of contiguous 15 nucleotides or more. The length of the partial polynucleotide can be appropriately set in accordance with the use.

(2) Primer for Amplifying Marker for Type of Hair Shape, and Probe for Detecting the Marker A partial polynucleotide of the polynucleotide consisting of the base sequence of the hair shape susceptibility gene of the present invention or a base sequence complementary to this, can serve as a primer for amplifying the marker for the type of hair shape. Preferably, the primer amplifies a polynucleotide consisting of the base sequence set forth in SEQ ID NO:44, SEQ ID NO:46, SEQ ID NO:48, SEQ ID NO:50 or SEQ ID NO:52, or a base sequence complementary to this, or a partial polynucleotide of such a polynucleotide.

Furthermore, a polynucleotide consisting of the base sequence of the hair shape susceptibility gene of the present invention or abase sequence complementary to this, or a partial polynucleotide thereof, can serve as a probe for detecting the marker for the type of hair shape. Preferably, the probe detects a polynucleotide consisting of the base sequence set forth in SEQ ID NO:44, SEQ ID NO:46, SEQ ID NO:48, SEQ ID NO:50 or SEQ ID NO:52, or a base sequence complementary to this, or a partial polynucleotide of such a polynucleotide.

That is, a primer for specifically recognizing and amplifying an RNA produced as a result of the expression of ANXA9 gene, LCE2B gene, LCE2A gene, IVL gene or CRCT1 gene, or a polynucleotide derived therefrom, or a probe for specifically detecting the RNA or the polynucleotide derived therefrom, is included the primer or probe described above.

Specifically, the polynucleotide or partial polynucleotide can be used as a primer or a probe according to an ordinary method, in the methods known to specifically detect a particular gene, such as a Northern Blotting method, an RT-PCR method, and an in situ hybridization method.

In the case of using the polynucleotide or partial polynucleotide as a primer, the nucleotide length thereof is usually 15 to 100 nucleotides, preferably 15 to 50 nucleotides, and more preferably 15 to 35 nucleotides.

Furthermore, in the case of using the polynucleotide or partial polynucleotide as a detection probe, one having a nucleotide length of usually 15 nucleotides or more, preferably 15 to 1000 nucleotides, and more preferably 100 to 1000 nucleotides, may be used.

Here, the term "specifically recognizes" means that, as in the case where, for example, in a Northern Blotting method, a polynucleotide consisting of a base sequence set forth in SEQ ID NO:44, SEQ ID NO:46, SEQ ID NO:48, SEQ ID NO:50 or SEQ ID NO:52, or a base sequence complementary to this, or a partial polynucleotide thereof can be specifically detected, and as in the case where, for example, in an RT-PCR method, the polynucleotide is specifically produced, the detected substance or the product can be considered as a polynucleotide consisting of a base sequence set forth in SEQ ID NO: 44, SEQ ID NO:46, SEQ ID NO: 48, SEQ ID NO: 50 or SEQ ID NO: 52, or a base sequence complementary to this, or a partial polynucleotide thereof.

The partial polynucleotide of a polynucleotide consisting of a base sequence set forth in SEQ ID NO:44, SEQ ID NO:46, SEQ ID NO:48, SEQ ID NO or SEQ ID NO:52, or a base sequence complementary to this, can be designed based on the base sequence of ANXA9 gene, LCE2B gene, LCE2A gene, IVL gene or CRCT1 gene as set forth in the sequence numbers described above, for example, through the software programs of Primer 3 or Vector NTI. The candidate sequence of the primer or probe thus obtainable, or a sequence containing the sequence in a portion, can be designed as a primer or a probe.

(3) Polypeptide Marker for Detecting and/or Determining Type of Hair Shape

Like the hair shape susceptibility genes listed above, expression products of these genes (proteins encoded by the hair shape susceptibility genes, or polypeptides derived therefrom, or partial polypeptides thereof) can also serve as the marker (polypeptide) for the type of hair shape.

Examples of the expression products include ANXA9 protein, FAM63A protein, LCE5A protein, CRCT1 protein, LCE2B protein, LCE2A protein, SMCP protein, and IVL protein (or also referred to as ANXA9, FAM63A, LCE5A, CRCT1, LCE2B, LCE2A, SCMP and IVL), which are proteins encoded by ANXA9 gene, FAM63A gene, LCE5A gene, CRCT1 gene, LCE2B gene, LCE2A gene, SMCP gene and IVL gene, respectively; polypeptides derived from these proteins; and partial polypeptides thereof. Preferred examples include ANXA9, LCE2B, LCE2A, IVL and CRCT1, polypeptides derived from these, and partial polypeptides thereof.

More preferably, the expression products are proteins encoded by polynucleotides consisting of base sequences set forth in SEQ ID NO:44, SEQ ID NO:46, SEQ ID NO:48, SEQ ID NO:50 and SEQ ID NO:52, and even more preferably, proteins having amino acid sequences set forth in SEQ ID NO:45, SEQ ID NO:47, SEQ ID NO:49, SEQ ID NO:51 and SEQ ID NO:53.

Furthermore, the expression products also include proteins which have amino acid sequences resulting from deletions, substitutions or additions of one or several amino acids in the amino acid sequences set forth in SEQ ID NO:45, SEQ ID NO:47, SEQ ID NO:49, SEQ ID NO:51 and SEQ ID NO:53, and having biological functions equivalent to and/or having equivalent immunological activity to those of proteins consisting of the amino acid sequences set forth in SEQ ID NO:45, SEQ ID NO:47, SEQ ID NO:49, SEQ ID NO:51 and SEQ ID NO:53 (so-called homologues of ANXA9, LCE2B, LCE2A, IVL or CRCT1).

Here, examples of proteins which have equivalent biological functions include proteins that are equivalent to ANXA9, LCE2B, LCE2A, IVL or CRCT1 in terms of the biochemical or pharmacological functions. Further, examples of proteins having equivalent immunological activity include proteins that have an ability to induce a specific immune reaction in an appropriate animal or cells thereof, and to bind specifically to the antibodies to ANXA9, LCE2B, LCE2A, IVL or CRCT1.

Meanwhile, an indicator that determines the substitution, insertion or deletion of amino acid residues can be found by using a computer program well known to those having ordinary skill in the art, for example, DNA Star software program. For example, the number of variations is typically 10% or less of the total number of amino acids, preferably 5% or less of the total number of amino acids, and more preferably 1% or less of the total number of amino acids. Furthermore, from the viewpoint of maintaining the structure of protein, the amino acid to be substituted is preferably an amino acid having properties that are similar to those of amino acids before substitution in terms of the polarity, charge, solubility, hydrophobicity, hydrophilicity, amphiphilicity and the like of the amino acid.

The partial polypeptide may be a polypeptide consisting of at least 5 contiguous amino acids, and preferably 10 to 100 amino acids, in an amino acid sequence encoded by the hair shape susceptibility gene of the present invention (for example, an amino acid sequence set forth in SEQ ID NO:45, SEQ ID NO:47, SEQ ID NO: 49, SEQ ID NO: 51 or SEQ ID NO:53), and having a biological function and/or immunological activity equivalent to those of an expression product of the hair shape susceptibility gene of the present invention (for example, ANXA9, LCE2B, LCE2A, IVL or CRCT1).

The polypeptide encoded by the hair shape susceptibility gene of the present invention can be obtained by operations of DNA cloning, establishment of various plasmids, transfection of the plasmids to a host, culture of the transformant, and collection of protein from the culture, based on the base sequence information of the hair shape susceptibility gene. These operations can be carried out according to known methods, for example, the methods described in Molecular Cloning, T. Maniatis et al., CSH Laboratory (1983); DNA Cloning, D M. Glover, IRL PRESS (1985); and the like.

Specifically, the polypeptide can be obtained by producing a recombinant DNA (e.g., expression vector) that can be expressed by a gene encoding ANXA9, LCE2B, LCE2A, IVL or CRCT1 in a desired host cell, introducing this into a host cell to thereby transform the recombinant DNA, culturing the transformant, and collecting the target protein from the culture thus obtainable.

Furthermore, the polypeptide encoded by the hair shape susceptibility gene of the present invention can also be produced by a general chemical synthesis method in accordance with an amino acid sequence encoded by the hair shape susceptibility gene.

(4) Antibody Specifically Recognizing Marker (Polypeptide) for Type of Hair Shape An antibody which specifically recognizes a polypeptide consisting of an amino acid sequence encoded by the hair shape susceptibility gene of the present invention or a partial polypeptide thereof, may be an antibody for detecting the marker (polypeptide) for the type of hair shape described above.

As will be described below, when such an antibody is used, the presence or absence of the expression of the marker (polypeptide) for the type of hair shape (for example, ANXA9, LCE2B, LCE2A, IVL, CRCT1, or a polypeptide derived therefrom, or a partial polypeptide thereof) in a tissue of a test subject, and the level of the expression of the marker can be detected. Specifically, when a portion of the hair root area of a test subject or the like is collected by a biopsy method or the like, a protein is produced therefrom according to an ordinary method, and the antibody of the present invention is used according to an ordinary method in, for example, a known detection method such as a Western Blotting method or an ELISA method, the marker (polypeptide) for the type of hair shape present in the tissue can be detected.

The antibody for the detection of the type of hair shape may be a polyclonal antibody or a monoclonal antibody, which are both directed to the marker (polypeptide) for the type of hair shape as an immunizing antigen.

These antibodies can be produced according to known methods (Current protocols in Molecular Biology, edited by Ausubel et al., (1987) published by John Wiley and Sons, Section 11.12-11.13). Specifically, a polyclonal antibody can be obtained by immunizing a non-human animal such as a rabbit with a polypeptide consisting of an amino acid sequence encoded by the hair shape susceptibility gene of the present invention (for example, ANXA9, LCE2B, LCE2A, IVL or CRCT1), which has been expressed in *Escherichia coli* or the like and purified by ordinary methods, or with a partial polypeptide of the polypeptide above synthesized according to an ordinary method, collecting the polyclonal antibody from the blood serum of the immunized animal according to an ordinary method.

On the other hand, a monoclonal antibody can be obtained from a hybridoma cell prepared by immunizing a non-human animal such as a mouse with the polypeptide expressed in *Escherichia coli* or the like and purified according to ordinary methods as described above, or a partial polypeptide thereof, and subjecting spleen cells obtained from the animal and myeloma cells to cell fusion (Current protocols in Molecular Biology, edited by Ausubel et al., (1987), published by John Wiley and Sons, Section 11.4-11.11).

The partial polypeptide used herein is an oligopeptide having a partial amino acid sequence of a polypeptide consisting of an amino acid sequence encoded by the hair shape susceptibility gene of the present invention (for example, ANXA9, LCE2B, LCE2A, IVL or CRCT1). It is not necessary for the partial polypeptide to have a functional biological activity, but it is preferable that the partial polypeptide has the same immunogenic characteristics as those of proteins consisting of the amino acid sequences described above. For example, there may be mentioned an oligopeptide consisting of at least 8 contiguous amino acids, preferably 15 amino acids, and more preferably 20 amino acids, in the amino acid sequences described above, which oligopeptide has immunogenic characteristics equivalent to those of proteins consisting of the amino acid sequences described above, preferably ANXA9, LCE2B, LCE2A, IVL and CRCT1.

The production of an antibody to such a partial polypeptide can be carried out by increasing the immunological response using various adjuvants depending on the host. Although there are no limitations, examples of such adjuvants include Freund's adjuvant; mineral gels such as aluminum hydroxide; surface-active substances such as lysolecithin, pluronic polyol, polyanions, peptides, oil emulsifying agents, keyhole limpet hemocyanin, and dinitrophenol; and human adjuvants such as *bacillus* Calmette-Guerin (BCG) and *corynebacterium parvum.*

(5) Detection and/or Determination of Type of Hair Shape

Detection/determination of the type of hair shape involves collecting a portion of hair root tissue or the like of a test subject by a biopsy method or the like, and detecting and/or determining the type of hair shape by using the marker for the type of hair shape of the present invention contained in the tissue as an indicator. For example, in the method described above, the type of hair shape is detected and/or determined by measuring the expression level (amount of expression) of the hair shape susceptibility gene of the present invention (for example, ANXA9 gene, LCE2B gene, LCE2A gene, IVL gene, or CRCT1 gene), a complementary strand thereof, or a partial polynucleotide thereof, or the amount of expression of a protein derived from the gene (for example, ANXA9, LCE2B, LCE2A, IVL, or CRCT1), a homologue thereof, or a partial polypeptide thereof.

Furthermore, the method for detection/determination of the present invention is also used, for example, in the case where a pharmaceutical product, a cosmetic product or the like for alleviating curly hair is administered to a curly hair person, so as to determine the presence or absence or the degree of an alleviation of the curly hair.

1) Biological Sample

Examples of the biological sample used herein include epithelial tissue or epithelial cells of a test subject, for example, a tissue containing cells that are capable of expressing the hair shape susceptibility gene of the present invention (for example ANXA9 gene, LCE2B gene, LCE2A gene, IVL gene, or CRCT1 gene), such as hair root area or skin; an RNA prepared from this tissue; a polynucleotide further prepared from the RNA; and a protein prepared from the tissue described above. These RNA, polynucleotide and protein can be prepared, for example, by collecting a portion of the hair root area of a test subject by a biopsy method or the like, and then according to ordinary methods.

2) Detection and/or Measurement of Marker

The detection and measurement of a marker may vary depending on the type of the biological sample used as the object of measurement, and specifically, the detection and measurement are carried out as follows.

(i) Case of Using RNA as Biological Sample of Measurement

In the case of using an RNA as a biological sample, the detection and measurement is carried out by detecting and measuring the expression level of a marker (polynucleotide) for the type of hair shape of the present invention in the RNA, for example, ANXA9 gene, LCE2B gene, LCE2A gene, IVL gene, CRCT1 gene, a partial polynucleotide thereof, or the like.

Here, specifically, the measurement of the amount of expression of the marker can be carried out by carrying out a known method such as a Northern Blotting method, an RT-PCR method, a DNA chip analysis method, or an in situ hybridization analysis method, using a primer for amplifying a polynucleotide that can serve as the marker of the present invention described above, or a probe for detecting the polynucleotide.

In the case of using a Northern Blotting method, when the probe of the present invention is used, the presence or absence of the expression of the marker (for example, ANXA9 gene, LCE2B gene, LCE2A gene, IVL gene, CRCT1 gene, or a partial polynucleotide thereof) in the RNA, and the level of the expression can be detected and measured.

Specifically, there may be mentioned a method in which, first, the probe DNA is labeled with a radioisotope ($^{32}P$, $^{33}P$, or the like; RI), a fluorescent substance or the like; subsequently, the labeled disease marker thus obtainable is hybridized with an RNA derived from a biological tissue of a test subject that has been transferred onto a nylon membrane or the like according to an ordinary method; and then the double strand of the labeled disease marker (DNA) and the RNA thus formed is detected and measured by measuring the signal originating from the labeled material (RI, a fluorescent substance or the like) of the labeled disease marker with a radiation detector (BAS-1800 II, manufactured by Fujifilm Holdings Corp.), a fluorescence detector or the like.

Furthermore, a method using an AlkPhos Direct™ Labelling and Detection System (manufactured by Amersham Pharamcia Biotech, Inc.) can also be available, in which the method includes labeling a probe DNA according to the protocol of AlkPhos Direct™, hybridizing the probe DNA with an RNA derived from a biological tissue of a test subject, and then detecting and measuring the signal originating from the labeled material of the probe DNA with a multibioimager STORM860 (manufactured by Amersham Pharmacia Biotech, Inc.).

In the case of using an RT-PCR method, the presence or absence of the expression of the marker in the RNA, and the level of the expression can be detected and measured using the primer of the present invention. Specifically, first, a cDNA is prepared from an RNA derived from a biological tissue of a test subject according to an ordinary method, and by using this cDNA as a template, a pair of primers (a forward strand which binds to the cDNA (minus strand) and a reverse strand which binds to the plus strand) prepared from the marker polynucleotide of the present invention is hybridized with the cDNA, so that the region of the target marker can be amplified. Thereafter, a PCR method is carried out according to an ordinary method, and thus the amplified double-stranded DNA thus obtained is detected.

For the detection of the amplified double-stranded DNA, a method of detecting a labeled double-stranded DNA produced by carrying out the PCR using primers which have been labeled in advance with R1, a fluorescent substance or the like; a method of transferring the produced double-stranded DNA onto a nylon membrane or the like according to an ordinary method, hybridizing this double-stranded DNA by using a labeled disease marker as a probe, and detecting the hybridization product; and the like can be used. The labeled double-stranded DNA product thus produced can be measured with an Agilent 2100 Bioanalyzer (manufactured by Yokogawa Analytical Systems, Inc.) or the like. Furthermore, an RT-PCR reaction solution is prepared using SYBR (registered trademark) Green RT-PCR Reagents (manufactured by Applied Biosystems, Inc.) according to the protocol, the reaction solution is allowed to react with ABI PRIME (registered trademark) 7700 Sequence Detection System (manufactured by Applied Biosystems), and the reaction product may be detected. The detection and measurement of the level of expression of the marker (polynucleotide) for the type of hair shape of the present invention in the RNA of a test subject using such an RT-PCR method, will be described in Examples.

In the case of using a DNA chip analysis, a DNA chip bonded with the DNA probe (single-stranded or double-stranded) of the present invention is provided, and this is hybridized with a cRNA prepared from an RNA derived from a biological tissue of a test subject according to a conventional method, the two strands of the DNA and cRNA thus formed are bound with a labeled probe prepared from the marker polynucleotide of the present invention, and thereby, the presence or absence of the expression of the marker of the present invention and the level of the expression can be detected and measured.

Furthermore, DNA chip capable of detecting and measuring the level of expression of the marker of the present invention can also be used as the DNA chip. As the DNA chip, for example, GeneChip (registered trademark) Human Genome U133 plus 2 manufactured by Affymetrix, Inc. may be used.

(ii) Case of Using Protein as Biological Sample of Object of Measurement

When a protein is used as an object of measurement, the measurement is carried out by contacting the antibody of the present invention with a biological sample, detecting the marker (polypeptide) for the type of hair shape of the present invention in the biological sample, which has been bound to the antibody, for example, ANXA9, LCE2B, LCE2A, IVL, CRCT1 or a partial polypeptide thereof, and measuring the amount (level) of the marker.

Here, the measurement of the amount of protein binding can be carried out by using a known method such as a Western Blotting method.

The Western Blotting method can be carried out by using the antibody of the present invention as a primary antibody, subsequently; labeling the primary antibody using, as a secondary antibody, an antibody which binds to the primary antibody labeled with a radioisotope such as $^{125}I$, a fluorescent substance, an enzyme such as horse radish peroxidase (HRP), or the like; and determining the signals originating from these labeled substances with a radiation meter, a fluorescence detector or the like. Furthermore, after using the antibody of the present invention as the primary antibody, the primary antibody is detected using an ECL Plus Western Blotting Detection System (manufactured by Amersham Pharmacia Biotech, Inc.) according to the protocol, and measurement can be made using a multibioimager STORM 860 (manufactured by Amersham Pharmacia Biotech, Inc.).

3) Determination of Type of Hair Shape

The determination of the type of hair shape can be carried out by comparing the level of the marker of the present invention (for example, the level of gene expression of ANXA9 gene, LCE2B gene, LCE2A gene, IVL gene or CRCT1 gene, the amount of ANXA9, LCE2B, LCE2A, IVL or CRCT1, or the like) in a biological sample of a test subject, which has been measured as described above, with the corresponding level of a non-curly hair person, and determining the difference between the two levels.

The comparison of the level of expression of the marker polynucleotide or polypeptide between the biological sample of a test subject and the biological sample of a non-curly hair person can be carried out by carrying out the measurements directed to the biological sample of a test subject and the biological sample of a non-curly hair person in parallel. Furthermore, even if the measurements are not carried out in parallel, the average level or a statistical median value of the level of gene expression of the marker polynucleotide (ANXA9 gene, LCE2B gene, LCE2A gene, IVL gene, CRCT1 gene, a partial polynucleotide thereof, or the like) or the level of expression of the marker polypeptide (ANXA9, LCE2B, LCE2A, IVL, CRCT1, a partial polypeptide thereof, or the like), which has been determined in advance in the tissues of plural (at least 2, preferably 3 or more, and more preferably 5 or more) non-curly hair persons under the same measurement conditions, can be used for the comparison with the test subjects, as the measured value for the test subject with the level of expression of the marker polynucleotide or polypeptide of a non-curly hair.

The determination of the type of hair shape of a test subject can be carried out by using, as an index, the extent of increase or decrease (for example, higher or lower by two times or more, and preferably three times or more) in the case of comparing the gene expression level of the marker polynucleotide (ANXA9 gene, LCE2B gene, LCE2A gene, IVL gene, CRCT1 gene, a partial polynucleotide thereof, or the like) or the expression level of the marker polypeptide (ANXA9, LCE2B, LCE2A, IVL, CRCT1, a partial polypeptide thereof, or the like) in the tissue of the test subject, with the level of a non-curly hair person.

For example, if the expression level of ANXA9 gene or ANXA9 protein of the test subject is lower than such a level of a non-curly hair person, the test subject can be determined as a curly hair person, or is suspected to have the onset of curly hair in the future.

Furthermore, for example, if the expression level of LCE2B gene or LCE2B protein of the test subject is lower than such a level of a non-curly hair person, the test subject can be determined as a curly hair person, or is suspected to have the onset of curly hair in the future.

Further, for example, if the expression level of LCE2A gene or LCE2A protein of the test subject is lower than such a level of a non-curly hair person, the test subject can be determined as a curly hair person, or is suspected to have the onset of curly hair in the future.

For example, if the expression level of IVL gene or IVL protein of the test subject is higher than such a level of a non-curly hair person, the test subject can be determined as a curly hair person, or is suspected to have the onset of curly hair in the future.

For example, if the expression level of CRCT1 gene or CRCT1 protein of the test subject is lower than such a level of a non-curly hair person, the test subject can be determined as a curly hair person, or is suspected to have the onset of curly hair in the future.

7. METHOD FOR REGULATING HAIR SHAPE

When the nucleotides located at the hair shape susceptibility SNP marker of the present invention are modified, the hair shape of individuals can be regulated.

That is, the present invention also provides a method for regulating the hair shape of an individual. According to an embodiment, the method may be a non-therapeutic method for regulating hair shape for cosmetic purposes, and can be carried out by a beautician or a barber. Meanwhile, according to the present specification, the term “non-therapeutic” is a concept which does not encompass medical acts, that is, acts of remedy to human body through treatment.

The method can be achieved by modifying the nucleotides located at the hair shape susceptibility SNP markers of the present invention listed above. The specific technique is not particularly limited as long as it is a method capable of achieving the purpose described above, and conventionally known methods and techniques that will be developed in the future can all be used; however, for example, a method of utilizing genetic recombination may be used.

Alternatively, the method for regulating hair shape of the present invention is carried out by controlling the expression of the hair shape susceptibility gene of the present invention in the hair root area of a person in need of regulation of hair shape (for example, suppression of curly hair or kinky hair, or waving of scalp hair).

For example, in a person who is worried about curly hair or kinky hair, curly hair or kinky hair can be suppressed by inducing or promoting the expression of a hair shape susceptibility gene whose expression contributes to the phenotype of straight hair, for example, ANXA9 gene, LCE2B gene, LCE2A gene or CRCT1 gene. Alternatively, curly hair or kinky hair can be suppressed by inhibiting the expression of a hair shape susceptibility gene whose expression contributes to the phenotype of curly hair or kinky hair, for example, IVL gene. On the other hand, in a person who wishes for waving of the scalp hair, waving can be expressed or promoted by inducing or promoting the expression of a hair shape susceptibility gene whose expression contributes to the phenotype of curly hair or kinky hair, for example, IVL gene. Alternatively, waving can be expressed or promoted by inhibiting the expression of a hair shape susceptibility gene whose expression contributes the phenotype of straight hair, for example, ANXA9 gene, LCE2B gene, LCE2A gene, or CRCT1 gene.

For example, in the case of suppressing curly hair or kinky hair, the expression level of ANXA9 gene, LCE2B gene, LCE2A gene or CRCT1 gene in the human hair root area may be brought to a value equal to or higher than the mRNA expression level of the gene in a non-curly hair person, and for example, it is desirable to increase the expression level to a value of about 3 to 10 times higher or more. On the other hand, in the case of intending to promote waving, the expression level of ANXA9 gene, LCE2B gene, LCE2A gene, or CRCT1 gene may be brought to a value lower than the mRNA expression level of the gene in a non-curly hair person, and for example, it is desirable to decrease the expression level to a value of about 3 to 10 times lower or less.

Furthermore, for example, in the case of suppressing curly hair or kinky hair, the expression level of IVL gene in the human hair root area may be brought to a value equal to or lower than the mRNA expression level of the gene in a non-curly hair person, and for example, it is desirable to decrease the expression level to a value of about 3 to 10 times lower or less. On the other hand, in the case of intending to promote waving, the expression level of IVL gene may be brought to a value higher than the mRNA expression level of the gene in a non-curly hair person, and for example, it is desirable to increase the expression level to a value of about 3 to 10 times higher or more.

The suppression, induction or promotion of the expression of a hair shape susceptibility gene in the human hair root area can be carried out according to an ordinary method. For example, in the suppression of gene, a method based on an antisense nucleotide, for example, a technique based on a method of inhibiting the translation from mRNA, or the like, may be used, and in the induction or promotion, a technique of expressing a hair shape susceptibility gene through gene transduction by means of a viral vector or the like may be used, or the like. Furthermore, in the suppression of the expression of a protein encoded by a hair shape susceptibility gene can be basically realized by a technique of suppressing the expression of the gene, and in the induction or promotion of the expression of the protein, a technique of expressing the gene at a high level, as well as a technique of direct intracutaneous injection of a human recombinant protein of the protein, or the like may be used.

The gene transduction utilizing an antisense nucleotide can be carried out in the same manner as in the methods n ordinarily used in gene therapy. For example, gene transduction can be carried out by a method of directly administering an antisense oligonucleotide or a chemical modification product thereof into the body of a test subject and thereby suppressing the expression of the hair shape susceptibility gene of the present invention, or a method of introducing an antisense RNA to a target cell of a patient and thereby suppressing the expression of the hair shape susceptibility gene of the present invention in the cell.

Here, the term “antisense nucleotide” encompasses an antisense oligonucleotide, an antisense RNA, an antisense DNA and the like, which all correspond to a portion of at least 8 nucleotides or more in a hair shape susceptibility gene of the present invention. Examples of the chemical modification products thereof include derivatives which are capable of increasing the transferability into cells or stability in the cells, such as phosphorothioates, phosphorodithioates, alkyl phosphotriesters, alkylphosphonates, and alkyl phosphoamidates ("Antisense RNA and DNA", published by WILEY-LISS, 1992, pp. 1-50; J. Med. Chem. 36, 1923-1937 (1993)).

The antisense nucleotide or a chemical modification product thereof can suppress the expression of a hair shape susceptibility gene, that is, the expression of a protein encoded by a hair shape susceptibility gene, by binding to a sense strand mRNA in a cell, and can thereby control the function (activity) of the protein.

In the method of directly administering an antisense oligonucleotide or a chemical modification product thereof into a living body, an antisense oligonucleotide or a chemical modification product thereof used therein may have a length of preferably 5 to 200 nucleotides, more preferably 8 to 25 nucleotides, and most preferably 12 to 25 nucleotides. Upon the administration, the antisense oligonucleotide or a chemical modification product thereof can be formulated into a preparation using a stabilizer, a buffer solution, a solvent and the like that are ordinarily used.

In the method of introducing an antisense RNA into a target cell of a test subject, the antisense RNA used therein may have a length of preferably 100 nucleotides or more, more preferably 300 nucleotides or more, and even more preferably 500 nucleotides or more. Furthermore, this method encompasses an in vivo method of introducing an antisense gene into the cells of a living body, and an ex vivo method of first introducing an antisense gene into the cells that have been extracted out of body, and returning the cells into the body (see Nikkei Science, April 1994, pp. 20-45; Gekkan Yakuji (Pharmaceuticals Monthly) 36 (1), 23-48 (1994); Jikken Igaku (Experimental Medicine) Special Issue, 12 (15), whole page; and the like). Among these, an in vivo method is preferred, and examples thereof include a viral transduction method (a method of using a recombinant virus) and a non-viral transduction method (see the various documents described above).

As the method of using a recombinant virus, for example, methods of inserting an antisense nucleotide of MLTK gene into the genome of a virus such as retrovirus, adenovirus, adeno-associated virus, herpes virus, vaccinia virus, polio virus, or Sindbis virus, and introducing the product into the living body, may be used. Among these methods, methods of using retrovirus, adenovirus, adeno-associated virus and the like are particularly preferred. As the non-viral transduction method, a liposome method, a lipofectin method and the like may be used, and particularly, a liposome method is preferred. As other non-viral transduction methods, for example, a microinjection method, a calcium phosphate method, an electroporation method and the like may also be used.

A preparation composition for gene transduction contains, as active ingredients, the antisense nucleotide described above or a chemical modification product thereof, recombinant viruses containing these, infected cells to which these viruses have been introduced, and the like.

The administration of the composition to a test subject can be carried by, for example, intravenous, intraarterial, subcutaneous, or intramuscular administration in an appropriate dosage form such as an injection, and can be introduced by directly administering the composition through the skin of a patient. In the case of employing an in vivo method, the composition for gene transduction can be formulated into a dosage form such as an injection containing an antisense nucleotide of a hair shape susceptibility gene, as well as a form in which, for example, a viral vector containing an antisense nucleotide of a hair shape susceptibility gene that is embedded in a liposome or a membrane-fused liposome (Sendai virus (HVJ)-liposome, or the like). These liposome dosage forms include a suspending agent, a freezing agent, a centrifuge concentration freezing agent, and the like. Furthermore, the composition for gene transduction can also be formulated into a form of a culture fluid of cells infected with a virus to which a vector containing the antisense nucleotide of a hair shape susceptibility gene has been introduced. The amount of administration of the active ingredient in these various preparation forms can be appropriately adjusted on the basis of the severity of the disease intended to treat, the age and body weight of the patient, and the like. Usually, in the case of an antisense nucleotide for a hair shape susceptibility gene, the amount of administration may be an amount by which about 0.0001 to 100 mg, and preferably about 0.001 to 10 mg, is administered once in several days to several months to an adult as a test subject.

In the case of a retrovirus vector containing an antisense nucleotide, the amount can be selected in the range of an amount which gives a retrovirus titer of about $1\times10^3$ pfu to $1\times10^{15}$ pfu per day per kg of the patient's body weight. In the case of a cell having an antisense nucleotide introduced therein, an amount of about $1\times10^4$ cells/body to $1\times10^{15}$ cells/body may be administered.

8. METHOD FOR EVALUATION OR SELECTION OF HAIR SHAPE REGULATING AGENT

The present invention also provides a method for evaluating or selecting a hair shape regulating agent (screening method).

The screening method may be carried out by, for example, steps such as described below:

(a) a step of administering a test substance into a cell containing the hair shape susceptibility gene of the present invention; and (b) a step of selecting, among the administered test substances, a substance which converts a nucleotide polymorphism of the hair shape susceptibility SNP marker of the present invention present on the hair shape susceptibility gene or the vicinity thereof, for example, on the haplotype block containing the gene, to another polymorphism, as a hair shape regulating agent.

The cell used in the step (a) (step of administering a test substance) may be any cell which can be introduced a haplotype block in the genomic region of human chromosome 1 represented by a base sequence set forth in any one of SEQ ID NO: 1 to NO: 5, or a gene which at least overlaps with the haplotype block, that is, the hair shape susceptibility gene of the present invention, and can retain the gene stably, and there are no particular limitations on the origin of the cell (for example, the cell is not limited to a prokaryotic cell or a eukaryotic cell, or to an insect cell or an animal cell, or the like). Meanwhile, gene transduction, cell culture and the like can be carried out by arbitrarily using any methods conventionally known in the art (for example, Joseph Sambrook et al., Molecular Cloning: A Laboratory Manual (3 Vol. Set), Cold Spring Harbor Laboratory, NY, 2001; The Japanese Tissue Culture Association, Ed., "Technology of Tissue Culture, 3rd Edition, Fundamentals and Applications", Asakura Shoten, 1996; and the like). The cell can be effectively utilized as a screening tool in the method for evaluating or selecting a substance effective for regulating the hair shape (screening method).

There are no particular limitations on the test substance that is administered. Examples include single compounds such as a natural compound, an organic compound, an inorganic compound, a protein and a peptide; and arbitrary compounds or compositions such as a compound library, expression products of a gene library, a cell extract, a cell culture supernatant, products of a fermentation microorganism, a marine extract, and a vegetable extract.

In regard to the step (b) (step of selecting a hair shape regulating agent), the presence or absence of the conversion of a nucleotide polymorphism and the type of the nucleotide after conversion are detected. The method for detecting the presence or absence of the conversion of a nucleotide polymorphism and the type of the converted nucleotide may be a method of directly measuring the type of nucleotides, or a method capable of indirectly evaluating the change of nucleotides. Examples of the method of directly measuring nucleotides include methods that are well known to those having ordinary skill in the art, such as PCR-SSCP, PCR-RLFP, PCR-SSO, PCR-ASP, a direct sequencing method, SNaPshot, dHPLC, a Sniper method, and a MALDI-TOF/MS method. Examples of the method of indirectly evaluating nucleotides include methods of measuring a function, activity, the amount of a specific mRNA, or the amount of a protein, which may be produced/increased, or lost/decreased as a result of the conversion of the target nucleotides.

The substance selected by the method can be used as a hair shape regulating agent effective for the regulation of hair shape, and can also be used for the preparation of a pharmaceutical product, a quasi-drug, a cosmetic material, a health food, or the like, which all contain the agent. When the selected substance is further subjected to other pharmacological tests, clinical tests and toxicology tests as necessary, a hair shape regulating agent that is more effective and safe to human beings can be obtained.

Alternatively, the screening method described above can be carried out by using, for example, the expression of a hair shape susceptibility gene of the present invention or a protein encoded by the gene in a tissue or cell capable of expressing the gene or protein, as an indicator.

Specifically, the screening method can be carried out by the following steps (a) to (d):

(a) a step for contacting a test substance with a tissue or cell capable of expressing the hair shape susceptibility gene of the present invention or a protein encoded by the gene;

(b) a step of measuring the amount of expression of the gene or the protein in the tissue or cell;

(c) a step of comparing the amount of expression measured in step (b) with the amount of expression of the gene or the protein in a control tissue or cell which has not been contacted with the test substance; and (d) a step of selecting, based on the results of step (c), a test substance which decreases or increases the amount of expression of the gene or the protein, as a hair shape regulating agent.

Here, as the tissue or cell capable of expressing the hair shape susceptibility gene of the present or a protein encoded by the gene, the type of the tissue or cell does not matter as long as the tissue or cell which expresses the gene or the protein. However, examples include a tissue or a cell of a mammal, for example, the skin tissue, hair root area tissue (hair follicle tissue), epidermal keratinocytes, hair root area-derived cells, an established epithelial cell line, and the like, all collected from a human being. The cell also includes a transformant which has been transformed with the hair shape susceptibility gene of the present invention (an expression vector having the gene).

The contact between the tissue or cell and a test substance can be carried out by, for example, adding the test substance in advance to a culture fluid to a predetermined concentration, and then placing the tissue or cell in the culture fluid, or by adding the test substance to a culture fluid in which the tissue or cell is placed, to a predetermined concentration.

Examples of the culture fluid include DMEM medium, MCDB medium, Willams'E medium, RPMI1640 medium, DMEM/HamF12 (1:1) medium, various commercially available media for epithelial cells, and the like, and appropriately agar or gelatin may also be added. Furthermore, if necessary, an antibiotic substance, an amino acid, blood serum, a growth factor, a biological extract, and the like may also be added.

Tissue culture can be carried out by, for example, inserting a collected hair root area tissue (hair follicle tissue) into a 24-well plate to which a culture fluid has been added, and culturing the tissue usually for 10 to 30 days, and preferably 1 to 21 days, in a gas phase of air containing $CO_2$ at a temperature of 37° C.

Furthermore, cell culture can be carried out by, for example, inserting cells into a 24-well plate to which a culture fluid has been added, and culturing the cells usually for 1 to 7 days, and preferably 1 to 3 days, in a gas phase of air containing $CO_2$ at a temperature of 37° C.

The measurement (quantification) of the expression of the gene can be carried out according to the method described in connection with the detection/measurement of a marker for the type of hair shape described above ((5)-2)-(i)). That is, the measurement can be carried out by performing a known method such as a Northern Blotting method, an RT-PCR method, a DNA chip analysis method, or an in situ hybridization analysis method, using a primer for amplifying a polynucleotide that can serve as the marker of the present invention, or a probe for detecting the polynucleotide.

Furthermore, the measurement (quantification) of the expression of the protein can be carried out according to the method described in connection with the detection/measurement of a marker for the type of hair shape described above ((5)-2)-(ii)). That is, the measurement can be achieved according to a known method such as a Western Blotting method, using an antibody which recognizes the marker (polypeptide) for the type of hair shape of the present invention.

2) The measurement of the expression level of the hair shape susceptibility gene of the present invention can also be carried out by introducing into a cell line a fusion gene in which a reporter gene such as, for example, luciferase gene, is linked to a gene region controlling the expression of the gene (regulatory region), and measuring the amount or activity of a protein derived from the reporter gene.

That is, the method for evaluating or selecting a hair shape regulating agent according to the present invention can be carried out by the following steps of (a) to (c):

(a) a step of introducing a fusion gene of the regulatory region of a hair shape susceptibility gene of the present invention and a reporter gene, into a cell capable of expressing the hair shape susceptibility gene of the present invention, and culturing the cell in the presence and in the absence of a test substance;

(b) a step of measuring the amount of expression of an expression product of the reporter gene in the cell culture cultured in the presence of the test substance, and comparing the amount with the amount of expression of an expression product of the reporter gene in the cell culture cultured in the absence of the test substance; and (c) a step of selecting, based on the comparison results obtained in step (b), a test substance which increases or decreases the amount of expression of the reporter gene expression product, as a hair shape regulating agent.

As the reporter gene, a structural gene of an enzyme which catalyzes a light emission reaction or a color reaction is preferred. Specifically, examples include the luciferase gene described above, secreted alkali phosphatase gene, chloramphenichol acetyltransferase gene, β-glucuronidase gene, β-galactosidase gene, aequorin gene, and the like.

Furthermore, as the regulatory region of the hair shape susceptibility gene, for example, about 1 kb to about 10 kb, and preferably about 2 kb, in the upstream of the transcription initiation site of the gene can be used, and for example, the regions having base sequences set forth in SEQ ID NO: 54 to NO: 58 in ANXA9 gene, LCE2B gene, LCE2A gene, IVL gene or CRCT1 gene, respectively, may be used. The preparation of a fusion gene and the measurement of the activity originating from a reporter gene can be carried out by known methods.

A substance which decreases the amount of expression of the hair shape susceptibility gene may be a substance which suppresses the expression of or promotes the degradation of a mRNA complementary to the polynucleotide constituting the gene, and a substance which decreases the amount of expression of a protein encoded by the hair shape susceptibility gene may be a substance which suppresses the expression of the hair shape susceptibility gene or a protein thereof, or promotes the degradation of the gene or a protein thereof, and consequently decreases the amount of expression of the protein.

A substance which increases the amount of expression of the hair shape susceptibility gene of the present invention may be a substance which promotes the expression of or suppresses the degradation of a mRNA complementary to the polynucleotide constituting the gene, and a substance which increases the amount of expression of a protein encoded by the hair shape susceptibility gene may be a substance which promotes the expression of the hair shape susceptibility gene or a protein thereof, or suppresses the degradation of the gene or a protein thereof, and consequently increases the amount of expression of the protein.

A substance which increases the amount of expression of the hair shape susceptibility gene or a protein encoded by the gene serves as a reducing or promoting agent for curly hair or kinky hair. For example, a substance which increases the amount of expression of ANXA9 gene, LCE2B gene, LCE2A gene or CRCT1 gene or a protein encoded thereby can serve as a reducing or improving agent for curly hair or kinky hair, while a substance which decreases the expression of such a gene or protein can serve as a promoting agent for curly hair or kinky hair, or a waving promoting agent. Furthermore, for example, a substance which increases the amount of expression of IVL gene or a protein encoded thereby can serve as a promoting agent for curly hair or kinky hair, or a waving promoting agent, while a substance which decreases the expression of the gene or protein can serve as a reducing or improving agent for curly hair or kinky hair. Such a hair shape regulating agent can function as a pharmaceutical product, a cosmetic product or the like for an amelioration of curly hair or kinky hair, or for the promotion of waving of scalp hair, when administered to a human being.

3) Furthermore, the method for evaluating or selecting the hair shape regulating agent of the present invention can be carried out by using the function (activity) of a protein encoded by the hair shape susceptibility gene of the present invention as an indicator.

Examples of the function or activity of the protein include the acetylcholine receptor activity (Nguyen V T et al., J. Biol. Chem., 275(38), p. 29466-76, 2000), and phosphatidylserine binding ability (Goebeler V et al., FEES Lett. 546(2-3), p. 359-64, 2003). The amount of the protein and the function or activity thereof have a certain correlation. Therefore, when the measurement of the function or activity of the protein described above is measured instead of the measurement of the amount of the protein, an evaluation or selection of a hair shape regulating agent can be carried out.

Specifically, the evaluation or selection is carried out by the following steps (a), (b) and (c):

(a) a step for contacting a test substance with an aqueous solution, tissue cells, or a cell fraction prepared from the tissue cells containing a protein encoded by the hair shape susceptibility gene of the present invention;

(b) a step of measuring the function or activity of the protein in the aqueous solution, tissue cells or cell fraction that has been contacted with the test substance, and comparing the function or activity with the function or activity of the protein in a control aqueous solution, control cells or control cell fraction which has not been contacted with the test substance; and (c) a step of selecting, based on the comparison results of the step (b), a test substance which increases or decreases the function or activity of the protein.

As the aqueous solution containing a protein encoded by the hair shape susceptibility gene, examples include aqueous solutions of ANXA9, LCE2B, LCE2A, IVL or CRCT1, as well as a tissue cell lysate, a nucleus extract, and cell culture supernatant which contain such a protein, and the like. The cell used herein may be a cell which expresses the hair shape susceptibility gene of the present invention (for example, ANXA9 gene, LCE2B gene, LCE2A gene, IVL gene, or CRCT1 gene), and has a protein encoded by such a gene as an expression product. Specifically, a tissue or cell of a mammal, for example, the skin tissue, hair root area tissue (hair follicle tissue), epidermal keratinocytes, hair root area-derived cells, an established epithelial cell line, and the like, all collected from a human being, can be used. The cell also includes a transformant which has been transformed with the hair shape susceptibility gene of the present invention (or an expression vector having the gene). Examples of host cells used in the transformation include well known cells such as Hela cell, COS cell, HEK293 cell, MDCK cell, CHO cell, and HL60 cell. Furthermore, a cell fraction means one of various fractions derived from the cells described above, and includes, for example, a cell membrane fraction, a cell cytoplasm fraction, a cell nucleus fraction, and the like.

The activity of a protein encoded by the hair susceptibility gene of the present invention can be measured, for example, in the case of measuring the acetylcholine receptor activity or the phosphatidylserine binding ability, by known methods such as a binding assay, a co-immunoprecipitation method, a pulldown assay, a two-hybrid method (Y2H), a fluorescence polarization method, and a time-resolved fluorescence resonance energy transfer (TR-FRET) method (for example, Hiromitsu Nakauchi, Ed., "Immunological Protocol", Yodosha Co., Ltd., 2004; Tadaomi Takenawa, Ed., "Optimal Methods Clarifying Protein Interaction", Biotechnology Journal, Vol. 5, No. 6, Yodosha Co., Ltd., 2005). That is, the activity can be measured by immobilizing a protein encoded by a hair shape susceptibility gene on a membrane or a plate using an aqueous solution containing the protein, and detecting the amount of radioisotope-labeled acetylcholine or phosphatidylserine binding to the protein. A substance which suppresses (decreases) the function (activity) of the protein may be a substance which decreases the acetylcholine receptor activity or the phosphatidylserine binding ability, while a substance which enhances (increases) the function (activity) of the protein may be a substance which increases the acetylcholine receptor activity or the phosphatidylserine binding ability. For example, a substance which enhances the function (activity) of ANXA9, LCE2B, LCE2A or CRCT1 can serve as an ameliorating agent for curly hair or kinky hair, and a substance which suppresses the function (activity) of such a protein can serve as a waving promoting agent. Furthermore, for example, a substance which enhances the function (activity) of IVL can serve as a waving promoting agent, while a substance which suppresses the function (activity) of such a protein can serve as an ameliorating agent for curly hair or kinky hair.

EXAMPLES

Hereinafter, the present invention will be described by way of Examples.

Example 1

Definition of Hair Shape and Collection of Curly Hair Family Lines

In the present Example, an affected sib-pair linkage analysis and a case-control association analysis were carried out on a Japanese group, in order to identify the hair shape susceptibility gene.

In general, hair shape varies with the human race, and the people of the Asian race relatively more frequently have straight hair, while the people of the African race mainly have kinky hair (or curled hair). A large proportion of the people of the Indo-European race have a trait of wavy hair (wave hair) which is intermediate of the two. Since a Japanese group is a straight hair-dominant group, people having a curly hair trait as the hair shape were defined as the affected (case), while the straight hair trait was defined as the control (control). In a genetic analysis such as a linkage analysis, it is necessary to handle the object traits quantitatively to a certain extent, and thus, for example, a method of binarizing the traits in such a manner that curly hair=1 and straight hair=0, or a method of measuring the degree of curly hair by a certain method, and quantifying the degree were considered. However, in the current situation, due to a wide variety of hair shapes of human being, the method for measurement or classification has not been sufficiently established. Thus, first, an accurate classification of the phenotypes of hair shape was carried out. The hair shape is defined by the overall feature of the hair and the degree of curl (curl radius). Furthermore, factors defining the hair shape include not only the curl characteristics of a single hair, but also the synchrony of curl with the groups of hair in the surroundings. Thus, the phenotypes of hair shape were classified as indicated in Table 4, based on the actual states of hair shape in various human races. This classification is applicable to various racial groups, including Japanese groups. Furthermore, FIG. 1 presents images of the phenotypes of hair shape.

TABLE 4

Classification of phenotypes of hair shape

| | Feature | Curl radius | Type of hair shape |
|---|---|---|---|
| Type 1 | Hair which exhibits one curl in overall even if the length of the hair changes, or has one curl only at the hair tips | 9.5 cm or larger over the entire hair, or 3 cm or larger only at the hair tip | Straight hair |
| | | Smaller than 9.5 cm over the entire hair, or smaller than 3 cm only at the hair tip | Almost straight hair, or slightly wavy hair |
| Type 2 | Hair which has several repeated curls along the length of the hair with an inherent curl radius, and has a curl period synchronizing with the hair in the surroundings | 9.5 cm or larger over the entire hair | Almost straight hair, or slightly wavy hair |
| | | Equal to or larger of 3 cm and smaller than 9.5 cm over the entire hair | Wavy hair |
| | | Smaller than 3 cm over the entire hair | Curly hair, or strongly wavy hair |
| Type 3 | Hair in which individual hairs have finely repeated curls, and the curl period does not synchronize with the hair in the surroundings | | Kinky hair |

On the other hand, the phenotype is the hair shape is a quantitative trait which can be continuously changed in a group, and it has been not established to which extent should be determined as the curly hair trait or as the straight hair trait. In the present invention, among the classifications based on the actual states of hair shape, kinky hair, and curly hair or strongly wavy hair are defined as the curly hair traits, and wavy hair, almost straight hair or slightly wavy hair, and straight hair are defined as the straight hair (non-curly hair) traits.

As such, the phenotypes of hair shape could be accurately classified, but in regard to the collection of the objects of genetic analysis, the following problem to be solved emerged. That is, problems arise when the hair at the time point of collection is markedly short and it is impossible to evaluate the shape, and when the original hair shape has changed by permanent treatment, hair dyeing, and chemical treatments by various styling agents. For this reason, all candidates who could become the objects of a genetic analysis were each requested to submit a photograph of the candidate himself/herself that was taken at a time when the phenotype of the hair shape could be discriminated (for example, childhood). That is, it is a photograph of a hair state which is not a markedly short hair and has not been subjected to a chemical treatment of hair. At the same time, all of the candidates were requested to submit several hair strands. The submitted hair strands were subjected to a detailed shape evaluation of torsion or kink of the hair, crimp, curl characteristics, and the like under water immersion conditions by which the effect of chemical treatment is lost. The objects of a genetic analysis were determined based on the evaluation of hair shape from the submitted photographs of the candidates themselves, and the evaluation of the shape of the submitted hair, and finally based on an investigation of hair shape through interviews.

As such, it took about two years to collect curly hair family lines of 68 families with 283 members among 3000 or more candidates applied from all over Japan. The specific details include 41 groups of two siblings, 22 groups of three siblings, 4 groups of four siblings, and one group of five siblings, and 100 pairs were defined as the final affected sib-pairs (brothers or sisters having the curly hair trait). Since it was predicted that this number of sib-pairs was sufficient to characterize the genetic locus in consideration of the strength of the genetic factor and the risk in the siblings, it was decided to carry out an affected sib-pair linkage analysis.

In regard to the collection of specimens from the objects of the genetic analysis, specimens were collected only when an approval was granted in advance by the ethics committee, subsequently the person in charge of the implementation of informed consent explained the contents of the study to the objects using a written explanation, and written consent was obtained.

A doctor or a nurse collected about 20 mL of blood from each of the objects of the genetic analysis. The genomic DNA was extracted from the blood specimen using PUREGENE Genomic DNA Purification Kit (manufactured by Gentra Systems, Inc.) according to the manual. The genomic DNA was dissolved in 2 mL of a DNA Hydration Solution, the concentration was measured, and the solution was stored at 4° C. The average yield of the genomic DNA was 576.2 g/20 ml of blood.

Example 2

Affected Sib-Pair Linkage Analysis on Entire Genome

In the present Example, an affected sib-pair linkage analysis covering the entire genome was carried out for the first time on the Japanese curly hair family lines. To briefly describe the principle of this method, since siblings that are affected have inherited from their parents an allele causative of a disease, the siblings necessarily share the allele. On the other hand, the number of alleles shared by brothers is 1 (a value based on the null hypothesis). When many cases of allele sharing could be observed from the number of alleles based on the null hypothesis by examining the number of alleles shared by many affected sib-pairs, it was determined that linkage was recognized.

The affected sib-pair linkage analysis was carried out using a linkage mapping set (ABI PRISM Linkage Mapping Set-MD 10 v2.5) manufactured by Applied Biosystems, Inc. (ABI). This is a set of 400 fluorescent primers for typing in total, intended to amplify microsatellites, which are short repeating sequences rich in polymorphisms that are evenly scattered in the genome, and the kit covers human chromosome at an average interval of 9.2 cm.

The genomic DNA prepared in Example 1 was used as a template, and PCR (GeneAmp PCR System 9700G, manufactured by ABI) was carried out using a linkage mapping set. Detection of the amplification product (fragment) was carried out using an ABI PRISM 3100 Genetic Analyzer (manufactured by ABI). The fluorescent primer set for typing includes primers labeled with three types of fluorescent dyes such as 6-FAM (blue), VIC (green) and NED (yellow), and therefore, even with fragments of the same size, three types of colors can be separately discriminated. Accordingly, large amounts of samples could be rapidly processed.

The typing of the fragments was carried out by means of Genotyper Software v3.7 (manufactured by ABI) and GeneScan Software (manufactured by ABI).

A statistical test of the linkage was carried out using Genehunter v2.1_r5 Software (Kruglyak, L. et al., Am. J. Hum. Genet., 58(6), 1347-1363, 1996), which is a non-parametric analysis. Determination of the region where linkage is recognized was carried out according to the guidelines of Lander and Kruglyak (Nat. Genet., 11 (3), 241-247, 1995) as described below, based on the criteria for obtaining false positive linkage.

A linkage analysis came to be actively carried out over the entire genome through the guidelines of Lander and Kruglyak (polygenic diseases), but in a linkage analysis of individual genes, the determination of whether the gene function can be a cause of a disease, is also needed. However, in an analysis over the entire genome, since the gene function is not taken into consideration at that stage, determination criteria (threshold values) that are purely meaningful in terms of mathematical genetics are required. Thus, they have provided significant linkage criteria as shown in the following Table 5, according to simulation results.

TABLE 5

| | |
|---|---|
| Suggestive Linkage<br>(Criteria for obtaining one false positive linkage result over the entire genome) | $P < 7.4 \times 10^{-4}$<br>LOD > 2.2 |
| Significant Linkage<br>(Criteria for obtaining 0.05 false positive linkage results over the entire genome) | $P < 2.2 \times 10^{-5}$<br>LOD > 3.6 |
| High Significant Linkage<br>(Criteria for obtaining 0.01 false positive linkage results over the entire genome) | $P < 3.0 \times 10^{-7}$<br>LOD > 5.4 |

Figure 2:
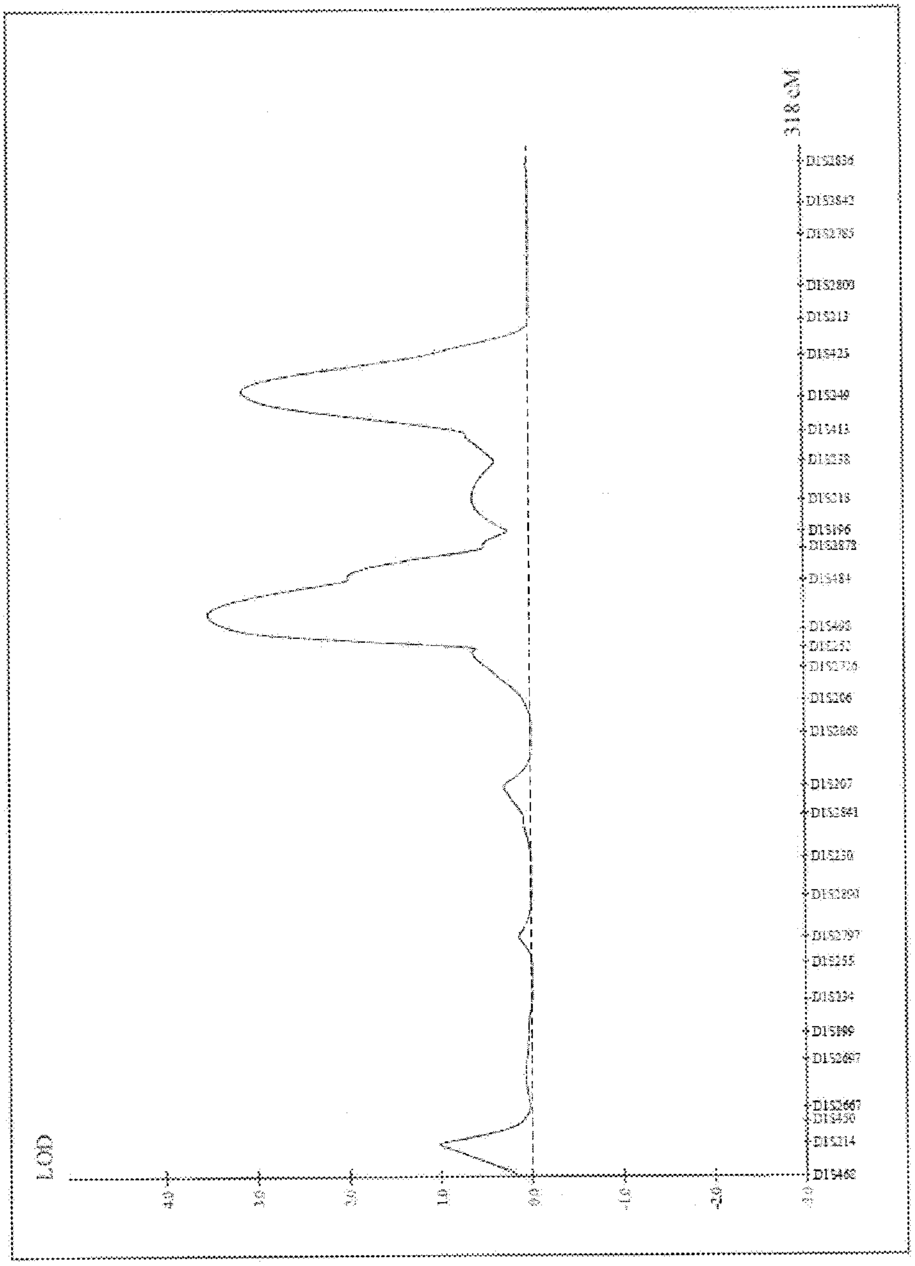
FIG. 2 is a diagram showing microsatellite markers and the maximum LODs obtained by an affected sib-pair linkage analysis on chromosome 1.
Figure 3:
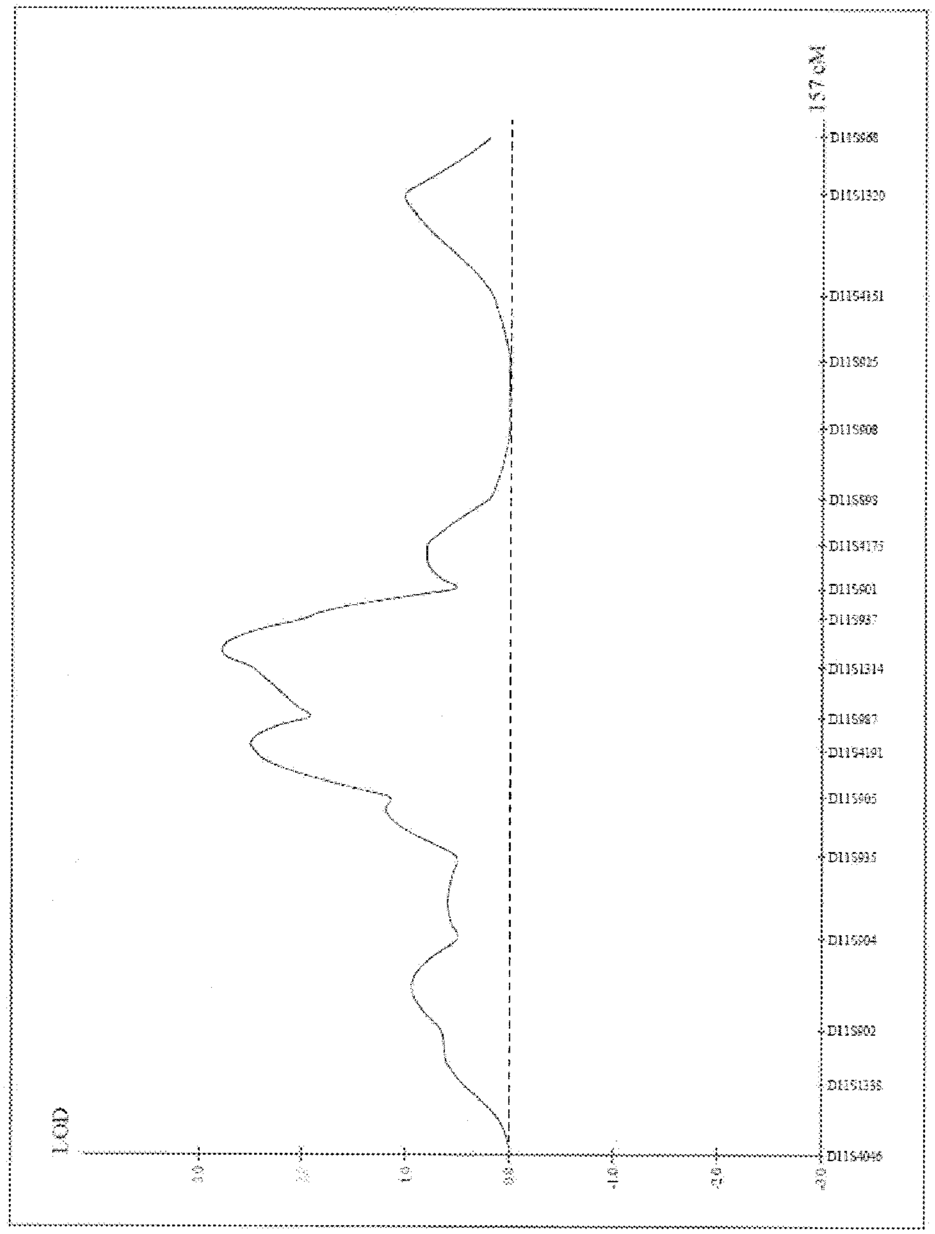
FIG. 3 is a diagram showing microsatellite markers and the maximum LODs obtained by an affected sib-pair linkage analysis on chromosome 11.

As a result of the screening of whole chromosome, linkages were recognized on chromosome 1 and chromosome 11. The results are respectively presented in FIG. 2 and FIG. 3. As shown in FIG. 2, in chromosome 1, a maximum LOD score of 3.49 was obtained in the 1q21 to 1823.1 region (near D1S498), and a maximum LOD score of 3.13 was obtained in the 1q32 to 1q41 region (D1S249-D1S213). As shown in FIG. 3, in chromosome 11, a maximum LOD score of 2.78 was obtained in the 11q12 to 11813.5 region (D11S905 to D11S937). The values thus obtained satisfied the criteria of Suggestive Linkage defined by Lander and Kruglyak. Therefore, the curly hair trait locus could be specified on chromosome 1 and chromosome 11, and it was strongly suggested that hair shape susceptibility genes exist in these regions.

Example 3

Detailed Mapping in Candidate Regions

Subsequently, chromosome 1 where linkages was recognized in Example 2 was subjected to an affected sib-pair linkage analysis (detailed mapping) by further using microsatellite markers, for the purpose of narrowing the linkage regions.

The microsatellites used as a marker for the detailed mapping were searched using Comprehensive human genetic maps of the Mammalian Genotyping Service (http://research-.marshfieldclinic.org/genetics/GeneticResearch/compMaps.asp). Microsatellites which were present in the genome at an interval of 1 to 2 cM and had high heterozygosity were selected. Furthermore, the fluorescent primers for typing, which were intended to amplify the microsatellites, were designed based on the Genome Database Project (GDB) (http://www.gdb.org/). Here, although the GDB has terminated the operation, currently retrieval and design can be carried out through the NCBI (http://www.ncbi.nlm.nih.gov/). Fluorescent primers for typing manufactured by ABI were used, and for some of the fluorescent primers for typing, those included in a linkage mapping set (ABI PRISM Linkage Mapping Set-HD 5 v2.5, manufactured by ABI) were used. The microsatellites used as the markers for detailed mapping, and the fluorescent primers for typing are presented in Table 6-1 and Table 6-2 (see SEQ ID NO:6 to NO:43).

TABLE 6-1

Microsatellites used as markers for detailed mapping, and fluorescent primers for typing

| ABI | Microsatellite | | Location (cM) | GenBank Accession | Heterozygosity | Amplification product (fragment) size | Label | Forward primer | Reverse primer |
|---|---|---|---|---|---|---|---|---|---|
| MD10 | AFM249zg9 | D1S252 | 150.27 | Z17138 | 0.82 | 99-119 | | | |
| | GATA12A07 | D1S534 | 151.88 | G07791 | 0.83 | 196-212 | VIC | AGCACATAGCAGGCACTAGC (SEQ ID NO: 6) | CGATTGTGCCACTACACAGT (SEQ ID NO: 7) |
| | AFMa297xg9 | D1S2696 | 153.59 | Z52819 | 0.88 | 159-185 | 6-FAM | AAAAATGAGTCCAGTAGAAGCCT (SEQ ID NO: 8) | AGCCAGATTTACATCCCAG (SEQ ID NO: 9) |
| MD10 | AFM336xb1 | D1S498 | 155.89 | Z24441 | 0.82 | 183-205 | | | |
| | AFM207yh6 | D1S2346 | 158.75 | Z51162 | 0.83 | 89-115 | VIC | TATCTTGCCCTGCACC (SEQ ID NO: 10) | AAGTGGGTCTCCCCAG (SEQ ID NO: 11) |
| | AFMb009zb9 | D1S2721 | 161.05 | Z53073 | 0.74 | 233-247 | VIC | TTGCTCGGCCAGAGTCT (SEQ ID NO: 12) | ACGCATCACACCTGGCTAGT (SEQ ID NO: 13) |
| | AFMa127wh9 | D1S506 | 163.34 | Z24627 | 0.58 | 123-141 | VIC | GGGCCTATGGCTGGAA (SEQ ID NO: 14) | GGCTATGCTGGGGCAA (SEQ ID NO: 15) |
| HD5 | AFMa133ye5 | D1S2635 | 165.62 | Z52215 | 0.86 | 142-159 | | | |
| | AFMb334xb1 | D1S2771 | 168.52 | Z53685 | 0.72 | 243-259 | 6-FAM | TCAGTTCCATAGGCTGACG (SEQ ID NO: 16) | CATTGCTGATGCTGGAGG (SEQ ID NO: 17) |
| MD10 | AFM297wb9 | D1S484 | 169.68 | Z24182 | 0.64 | 136-142 | | | |
| MD10 | AFMa057ze5 | D1S2878 | 177.86 | Z51743 | 0.84 | 169-195 | | | |
| | AFMb316zb9 | D1S2762 | 179.10 | Z53529 | 0.81 | 232-250 | NED | CCTTAATTGTGGTGTTGGT (SEQ ID NO: 18) | AAAAATCTGGAAGGCATAAA (SEQ ID NO: 19) |
| MD10 | AFM063xg9 | D1S196 | 181.49 | Z16503 | 0.73 | 267-279 | | | |
| | AFMb359xf5 | D1S2799 | 183.19 | Z53881 | 0.87 | 191-209 | 6-FAM | AGCAAGACCCTGTCTCAAAA (SEQ ID NO: 20) | TGGATAGCTTTCCACCACT (SEQ ID NO: 21) |
| HD5 | AFM248wg5 | D1S452 | 188.85 | Z23809 | 0.76 | 119-131 | | | |
| MD10 | AFM157xe7 | D1S218 | 191.52 | Z16701 | 0.83 | 266-286 | | | |
| | AFM123yc5 | D1S460 | 194.32 | Z23379 | 0.84 | 145-159 | 6-FAM | ACAAGGTGACCGGAAAGACC (SEQ ID NO: 22) | AGCTCTGGCAAGTTGAAGGA (SEQ ID NO: 23) |
| HD5 | AFMc025xh9 | D1S2818 | 198.30 | Z54047 | 0.70 | 258-268 | | | |
| | AFM348tg1 | D1S2848 | 200.96 | Z51502 | 0.82 | 105-123 | VIC | ATCTGGGTTCACTATTAAACAGAGT (SEQ ID NO: 24) | TGGGCAAGGTAGAATATGTG (SEQ ID NO: 25) |
| MD10 | AFM205xg1 | D1S238 | 202.73 | Z16920 | 0.86 | 272-302 | | | |
| HD5 | AFMa057vb5 | D1S2877 | 205.40 | Z51735 | 0.72 | 143-157 | | | |
| HD5 | AFM031xd12 | D1S412 | 209.15 | Z23298 | 0.71 | 129-147 | | | |

TABLE 6-1-continued

Microsatellites used as markers for detailed mapping, and fluorescent primers for typing

| ABI | Microsatellite | | Location (cM) | GenBank Accession | Heterozygosity | Amplification product (fragment) size | Label | Forward primer | Reverse primer |
|---|---|---|---|---|---|---|---|---|---|
| MD10 | AFM165xc9 | D1S413 | 212.44 | Z23420 | 0.77 | 246-262 | | | |
| | UT492 | D1S373 | 214.08 | L16266 | 0.90 | 283-330 | VIC | GGGTGACAGAGCAAGACTC (SEQ ID NO: 26) | CCCTGACCTCCCTTACAGA (SEQ ID NO: 27) |
| | AFM136xa7 | D1S1723 | 215.17 | Z51003 | 0.83 | 167-181 | NED | AACTGTGTCCAGCAGCAACT (SEQ ID NO: 28) | TATGTGCCTGTTGTGTGCAT (SEQ ID NO: 29) |
| | AFMa190xd5 | D1S2655 | 216.82 | Z52412 | 0.90 | 224-260 | VIC | AGGGTCCCCAAAGAGCCTTC (SEQ ID NO: 30) | ATGGCAGCACATCCTGCTTC (SEQ ID NO: 31) |
| | AFMa224xc1 | D1S2668 | 218.46 | Z52594 | 0.77 | 233-247 | VIC | AATCACTTGAACCTGGGAG (SEQ ID NO:32) | ACTGACTGGCTGTTTCTGAG (SEQ ID NO:33) |

TABLE 6-2

| ABI | Microsatellite | | Location (cM) | GenBank Accession | Heterozygosity | Amplification product (fragment) size | Label | Forward primer | Reverse primer |
|---|---|---|---|---|---|---|---|---|---|
| MD10 | AFM234wf6 | D1S249 | 220.65 | Z17051 | 0.87 | 155-185 | | | |
| HD5 | AFMa290xd1 | D1S2692 | 222.84 | Z52805 | 0.87 | 276-316 | | | |
| | AFMa082wf9 | D1S2891 | 224.50 | Z51920 | 0.75 | 211-273 | 6-FAM | ACTGCTTATTCGGAGTTGGA (SEQ ID NO: 34) | CCAAGAGTTTTCTTAGCA AATCAC (SEQ ID NO: 35) |
| HD5 | AFM224xc1 | D1S245 | 227.81 | Z17011 | 0.83 | 239-257 | | | |
| | AFM108ya3 | D1S205 | 229.13 | Z16585 | 0.80 | 94-112 | 6-FAM | CTGAGCACAGCAGTGGTCTC (SEQ ID NO: 36) | AAGGCTTATCAAGAGCGA GG (SEQ ID NO: 37) |
| MD10 | AFM203zb6 | D1S425 | 231.11 | Z23538 | 0.81 | 92-108 | | | |
| | GATA87F04 | D1S2141 | 233.38 | G07856 | 0.82 | 236-263 | 6-FAM | AGACTTACAGCACTGGCTGC (SEQ ID NO: 38) | TGCTCCTAGGAAAGGAAA CA (SEQ ID NO: 39) |
| | AFM297xc1 | D1S2827 | 234.52 | Z51306 | 0.78 | 142-152 | 6-FAM | GCTTCTGGCCTCTGTCA (SEQ ID NO: 40) | AATTTTGCGTGTGTGTGC (SEQ ID NO: 41) |
| HD5 | AFM184yf6 | D1S227 | 238.52 | Z16806 | 0.71 | 61-75 | | | |
| | AFMa052zd1 | D1S2871 | 241.26 | Z51685 | 0.84 | 215-241 | NED | TGAAGTGTGCATTCTNTACA TCA (SEQ ID NO: 42) | CGAGACATTTGCATCATC A (SEQ ID NO: 43) |
| MD10 | AFM147xf8 | D1S213 | 242.34 | Z16668 | 0.86 | 104-124 | | | |

Figure 4:
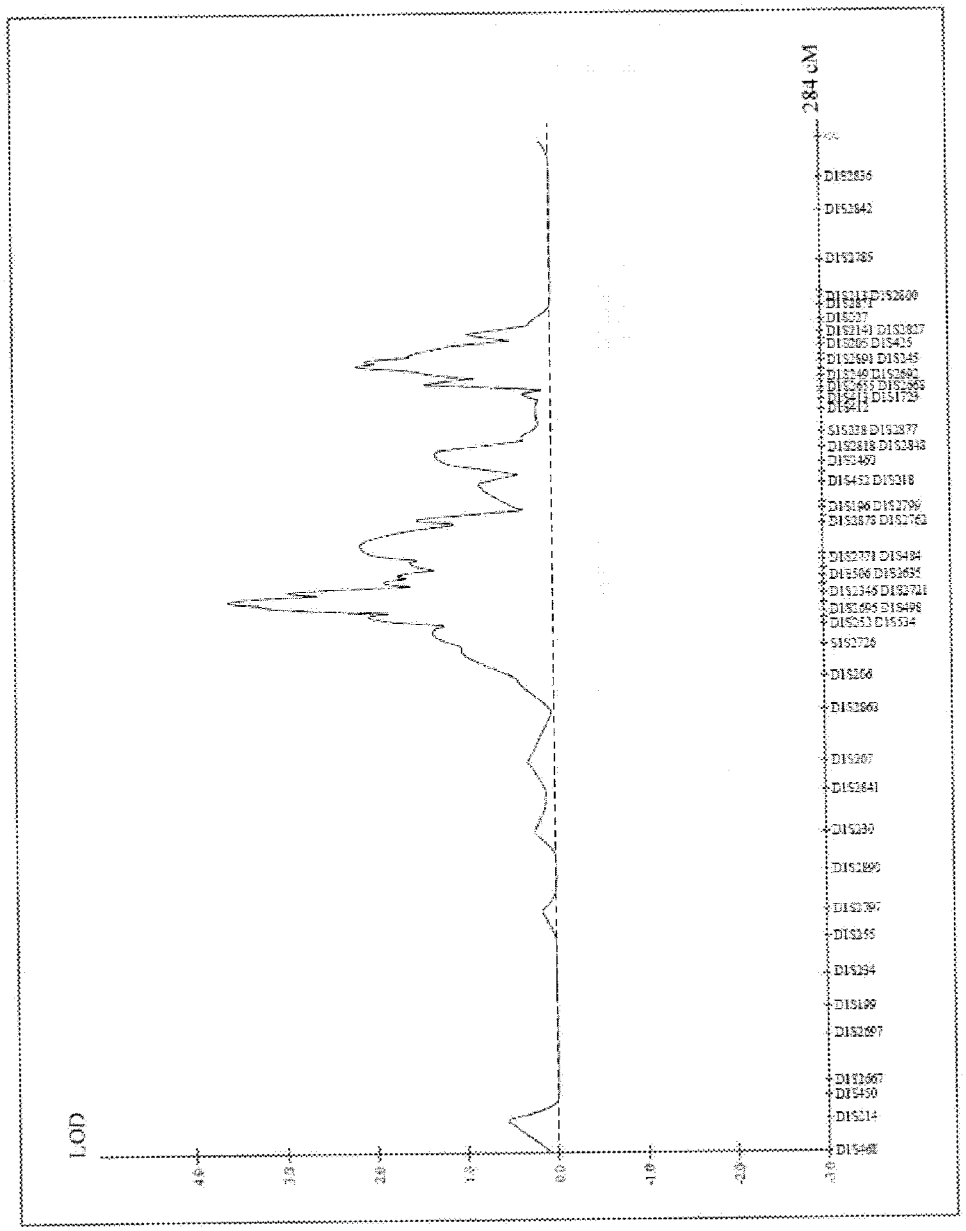
FIG. 4 is a diagram showing microsatellite markers and the maximum LODs obtained by an affected sib-pair linkage analysis on chromosome 1.

The results obtained by carrying out an affected sib-pair linkage analysis (detailed mapping) on chromosome 1 in the same manner as in Example 2, are presented in FIG. 4. As shown in FIG. 4, a maximum LOD score of 3.60 was obtained in the 1q21.3 region (D1S2696-D1S2346), and a maximum LOD score of 2.14 was obtained in the 1832.1 to 1q32.2 region (D1S249 to D1S2891). The values thus obtained were considered to satisfy the criteria of Significant Linkage and Suggestive Linkage, respectively, defined by Lander and Kruglyak as described in Example 2. Therefore, the curly hair trait loci on chromosome 1 could be narrowed, and it was strongly suggested that hair shape susceptibility genes exist in these regions.

Example 4

Case-Control Association Analysis

In order to identify a hair shape susceptibility gene from the 1q21.3 region (D1S2696 to D1S2346). on chromosome 1, where strong linkage was recognized in Example 3 above, a comparison of the allele frequency for the single nucleotide polymorphism (SNP) markers present in the region was made by a case-control association analysis.

Since it is necessary that the cases (affected: those having the curly hair trait) and the controls (control: those having the straight hair trait) consist of people of the same race as the race for whom the hair shape susceptibility gene is identified, in the present invention, non-family related Japanese people having the curly hair trait and non-family related Japanese people having the straight hair trait were employed as objects. Objects were collected in the same manner according to the criteria described in Example 1, and genomic DNA was obtained from each of 43 non-family related Japanese people having the curly hair trait and 51 non-family related Japanese people having the straight hair trait.

With reference to the dbSNP database (http://www.ncbi.nlm.nih.gov/SNP/) and the JSNP database (http://snp.ims.u-tokyo.ac.jp/index_ja.html), SNPs which represented certain regions in the region to be analyzed, and had a gene frequency of the minor allele of 10% or higher in a panel of Japanese people, were selected as SNPs to be typed. Thus, 32 SNPs were selected from the region to be analyzed.

The typing of SNPs was carried out according to a TaqMan PCR method, using TaqMan SNP Genotyping Assays (manufactured by ABI, formerly known as Assays-on-Demand or Assays-by-Design). Furthermore, the apparatuses of Applied Biosystems 7900HT Fast Real-time PCR System (manufactured by ABI) and Applied Biosystems 7500 Real-time PCR System (manufactured by ABI) were used. The method was carried out according to the respective manuals attached to the apparatuses.

The typing data thus obtained were totalized for each of the cases and the controls, and a significant difference test was carried out through a $\chi^2$ test by four methods involving the genotype, allele type, dominant model and recessive model. That is, if any genetic variation is causative of changes in the hair shape, differences in the allele frequency and the like are expected between the cases and the controls. Furthermore, in the present Example, since the association analysis was carried out on a relatively small number of objects, the significance level was set at $p<0.05$. Further, in some part, the significance level was set to be loose ($p<0.07$) in order to increase the power of the test.

As a result, it was found that nine SNPs shown in the following items (a) to (i) exhibit statistically significant ($p<0.05$) differences between the cases and the controls.

(a) In SNP:rs1053590 (single nucleotide polymorphism represented by Nucleotide Number 8196 in the base sequence set forth in SEQ ID NO:2), the proportion of homozygous C-allele carriers was significantly higher in the people having the straight hair trait as compared with the people having the curly hair strait (Table 7-1).

(b) In SNP:rs3753453 (single nucleotide polymorphism represented by Nucleotide Number 5167 in the base sequence set forth in SEQ ID NO:3), the proportion of homozygous C-allele carriers was significantly higher in the people having the curly hair trait as compared with the people having the straight hair trait, and even by the genotype, a significant difference was observed between the people having the straight hair trait and the people having the curly hair trait (Table 7-2).

(c) In SNP:rs3737859 (single nucleotide polymorphism represented by Nucleotide Number 8449 in the base sequence set forth in SEQ ID NO:3), the proportion of homozygous G-allele carriers was significantly higher in the people having the curly hair trait as compared with the people having the straight hair trait, and even by the genotype, a significant difference was observed between the people having the straight hair trait and the people having the curly hair trait (Table 7-3).

(d) In SNP:rs3904414 (single nucleotide polymorphism represented by Nucleotide Number 17598 in the base sequence set forth in SEQ ID NO:3), the proportion of homozygous A-allele carriers was significantly higher in the people having the curly hair trait as compared with the people having the straight hair trait, and even by the genotype, a significant difference was observed between the people having the straight hair trait and the people having the curly hair trait (Table 7-4).

(e) In SNP:rs3908717 (single nucleotide polymorphism represented by Nucleotide Number 20891 in the base sequence set forth in SEQ ID NO:3), the proportion of homozygous G-allele carriers was significantly higher in the people having the curly hair trait as compared with the people having the straight hair trait, and even by the genotype, a significant difference was observed between the people having the straight hair trait and the people having the curly hair trait (Table 7-5).

(f) In SNP:rs3737861 (single nucleotide polymorphism represented by Nucleotide Number 6354 in the base sequence set forth in SEQ ID NO:4), the proportion of homozygous A-allele carriers was significantly higher in the people having the curly hair trait as compared with the people having the straight hair trait, and even by the allele type, a significant difference was observed between the people having the straight hair trait and the people having the curly hair trait (Table 7-6).

(g) In SNP:rs4523473 (single nucleotide polymorphism represented by Nucleotide Number 759 in the base sequence set forth in SEQ ID NO:5), the proportion of homozygous T-allele carriers was significantly higher in the people having the curly hair trait as compared with the people having the straight hair trait, and even by the allele type, a significant difference was observed between the people having the straight hair trait and the people having the curly hair trait (Table 7-7).

(h) In SNP:rs2229496 (single nucleotide polymorphism represented by Nucleotide Number 1939 in the base sequence set forth in SEQ ID NO:5), the proportion of homozygous A-allele carriers was significantly higher in the people having the curly hair trait as compared with the people having the straight hair trait, and even by the allele type, a significant difference was observed between the people having the straight hair trait and the people having the curly hair trait (Table 7-8).

(i) In SNP:rs913996 (single nucleotide polymorphism represented by Nucleotide Number 3440 in the base sequence set forth in SEQ ID NO:5), the proportion of homozygous G-allele carriers was significantly higher in the people having the curly hair trait as compared with the people having the straight hair trait, and even by the allele type, a significant difference was observed between the people having the straight hair trait and the people having the curly hair trait (Table 7-9).

Furthermore, it was found that even one SNP shown in the following item (j) exhibit a difference between the cases and the controls.

(j) In SNP:rs2305814 (single nucleotide polymorphism represented by Nucleotide Number 7121 in the base sequence set forth in SEQ ID NO:1), the proportion of homozygous T-allele carriers was higher ($p=0.066$) in the people having the curly hair trait as compared with the people having the straight hair trait (Table 7-10). These ten SNPs all satisfied the Hardy-Weinberg equilibrium. Therefore, these ten SNPs were determined to be hair shape susceptibility SNPs, and their relations with hair shape were confirmed.

TABLE 7-1

| Association analysis on SNP: rs1053590 | | | | | |
|---|---|---|---|---|---|
| | SNP: rs1053590 | | | | |
| | Allele type | | Genotype | | |
| | C | T | CC | CT | TT |
| Curly hair trait | 70.3% | 29.7% | 43.2% | 54.1% | 2.7% |
| Straight hair trait (control) | 80.4% | 19.6% | 64.7% | 31.4% | 3.9% |
| p value ($\chi^2$ test) | Allele type | | 0.120 | | |
| | Genotype | | 0.102 | | |
| | CC vs CT, TT | | 0.045 | | |

TABLE 7-2

| Association analysis on SNP: rs3753453 | | | | | |
|---|---|---|---|---|---|
| | SNP: rs3753453 | | | | |
| | Allele type | | Genotype | | |
| | T | C | TT | TC | CC |
| Curly hair trait | 66.3% | 33.7% | 46.5% | 39.5% | 14.0% |
| Straight hair trait (control) | 76.5% | 23.5% | 52.9% | 47.1% | 0.0% |
| p value ($\chi^2$ test) | Allele type | | 0.122 | | |
| | Genotype | | 0.022 | | |
| | TT, TC vs CC | | 0.006 | | |

TABLE 7-3

| Association analysis on SNP: rs3737859 | | | | | |
|---|---|---|---|---|---|
| | SNP: rs3737859 | | | | |
| | Allele type | | Genotype | | |
| | G | T | GG | GT | TT |
| Curly hair trait | 33.7 | 66.3 | 14.0 | 39.5 | 46.5 |
| Straight hair trait (control) | 23.5 | 76.5 | 0.0 | 47.1 | 52.9 |
| p value ($\chi^2$ test) | Allele type | | 0.122 | | |
| | Genotype | | 0.022 | | |
| | GG vs GT, TT | | 0.006 | | |

TABLE 7-4

| Association analysis on SNP: rs3904414 | | | | | |
|---|---|---|---|---|---|
| | SNP: rs3904414 | | | | |
| | Allele type | | Genotype | | |
| | G | A | GG | GA | AA |
| Curly hair trait | 67.1% | 32.9% | 46.3% | 41.5% | 12.2% |
| Straight hair trait (control) | 77.0% | 23.0% | 54.0% | 46.0% | 0.0% |
| p value ($\chi^2$ test) | Allele type | | 0.136 | | |
| | Genotype | | 0.039 | | |
| | GG, GA vs AA | | 0.011 | | |

TABLE 7-5

| Association analysis on SNP: rs3908717 | | | | | |
|---|---|---|---|---|---|
| | SNP: rs3908717 | | | | |
| | Allele type | | Genotype | | |
| | C | G | CC | CG | GG |
| Curly hair trait | 67.9% | 32.1% | 47.6% | 40.5% | 11.9% |
| Straight hair trait (control) | 76.5% | 23.5% | 52.9% | 47.1% | 0.0% |
| p value ($\chi^2$ test) | Allele type | | 0.190 | | |
| | Genotype | | 0.040 | | |
| | CC, CG vs GG | | 0.011 | | |

TABLE 7-6

| Association analysis on SNP: rs3737861 | | | | | |
|---|---|---|---|---|---|
| | SNP: rs3737861 | | | | |
| | Allele type | | Genotype | | |
| | A | C | AA | AC | CC |
| Curly hair trait | 48.8% | 51.2% | 31.0% | 35.7% | 33.3% |
| Straight hair trait (control) | 33.3% | 66.7% | 13.7% | 39.2% | 47.1% |
| p value ($\chi^2$ test) | Allele type | | 0.032 | | |
| | Genotype | | 0.116 | | |
| | AA vs AC, CG | | 0.044 | | |

TABLE 7-7

| Association analysis on SNP: rs4523473 | | | | | |
|---|---|---|---|---|---|
| | SNP: rs4523473 | | | | |
| | Allele type | | Genotype | | |
| | T | C | TT | TC | CC |
| Curly hair trait | 47.7% | 52.3% | 30.2% | 34.9% | 34.9% |
| Straight hair trait (control) | 32.4% | 67.6% | 11.8% | 41.2% | 47.1% |
| p value ($\chi^2$ test) | Allele type | | 0.032 | | |
| | Genotype | | 0.082 | | |
| | TT vs TC, CC | | 0.026 | | |

TABLE 7-8

| Association analysis on SNP: rs2229496 | | | | | |
|---|---|---|---|---|---|
| | SNP: rs2229496 | | | | |
| | Allele type | | Genotype | | |
| | G | A | GG | GA | AA |
| Curly hair trait | 53.6% | 46.4% | 35.7% | 35.7% | 26.8% |
| Straight hair trait (control) | 67.6% | 32.4% | 47.1% | 41.2% | 11.8% |
| p value ($\chi^2$ test) | Allele type | | 0.050 | | |
| | Genotype | | 0.120 | | |
| | GG, GA vs AA | | 0.041 | | |

TABLE 7-9

Association analysis on SNP: rs913996

| | SNP: rs913996 | | | | |
|---|---|---|---|---|---|
| | Allele type | | Genotype | | |
| | G | A | GG | GA | AA |
| Curly hair trait | 47.7% | 52.3% | 30.2% | 34.9% | 34.9% |
| Straight hair trait (control) | 32.4% | 67.6% | 11.8% | 41.2% | 47.1% |

| | | |
|---|---|---|
| p value ($\chi^2$ test) | Allele type | 0.032 |
| | Genotype | 0.082 |
| | GG vs GA, AA | 0.026 |

TABLE 7-10

Association analysis on SNP: rs2305814

| | SNP: rs2305814 | | | | |
|---|---|---|---|---|---|
| | Allele type | | Genotype | | |
| | C | T | CC | CT | TT |
| Curly hair trait | 55.4% | 44.6% | 35.1% | 40.5% | 24.3% |
| Straight hair trait (control) | 65.7% | 34.3% | 41.2% | 49.0% | 9.8% |

| | | |
|---|---|---|
| p value ($\chi^2$ test) | Allele type | 0.167 |
| | Genotype | 0.184 |
| | CC, CT vs TT | 0.066 |

Example 5

Haplotype Analysis

As a result of the analyses in Example 4, ten hair shape susceptibility SNPs were found. Further, a haplotype analysis was carried out in order to found a correlation between hair shape and polymorphisms that are present in the surrounding regions of the SNPs, particularly those that have not been typed, and to identify hair shape susceptibility genes.

In the analysis, the linkage disequilibrium coefficient D' (pair-wise LD coefficient) based on the EM algorithm was calculated using Haploview 4.1 Software (Barrett, J C, et al., Bioinformatics, 21 (2), 263-265, 2005), and the analysis was carried out. A linkage disequilibrium analysis was carried out on the SNPs found above and the SNPs present in the surrounding regions, using the HapMap PHASE data of the International HapMap Project Database (HapMap Data ReI 21/PhaseII July 06, on NCBI Build 35 assembly, dbSNP b125). Meanwhile, the analysis panel consisted of JPT+CHB (Japanese people in Tokyo, Japan, and Chinese people of Han race in Beijing, China).

The method for inferring the haplotype block used the confidence interval (Gabriel, S B, et al., Science, 296 (5576), p. 2225-2229, 2002). That is, it can be considered that the haplotype blocks to be determined are mostly in the genome range where historical recombination has not been recognized, and strong linkage disequilibrium exists within the regions. Usually, when the upper limit of the 95% confidence interval of the linkage disequilibrium coefficient D' is lower than 0.9, the region is considered as a region having an evidence of historical recombination. On the other hand, when the upper limit of the 95% confidence interval of D' is higher than 0.98 and the lower limit is higher than 0.7, the region can be considered as a region where strong linkage disequilibrium exists.

As a result, haplotype blocks of the following items (1) to (5) containing the ten hair shape susceptibility SNPs shown below were found.

Figure 5:
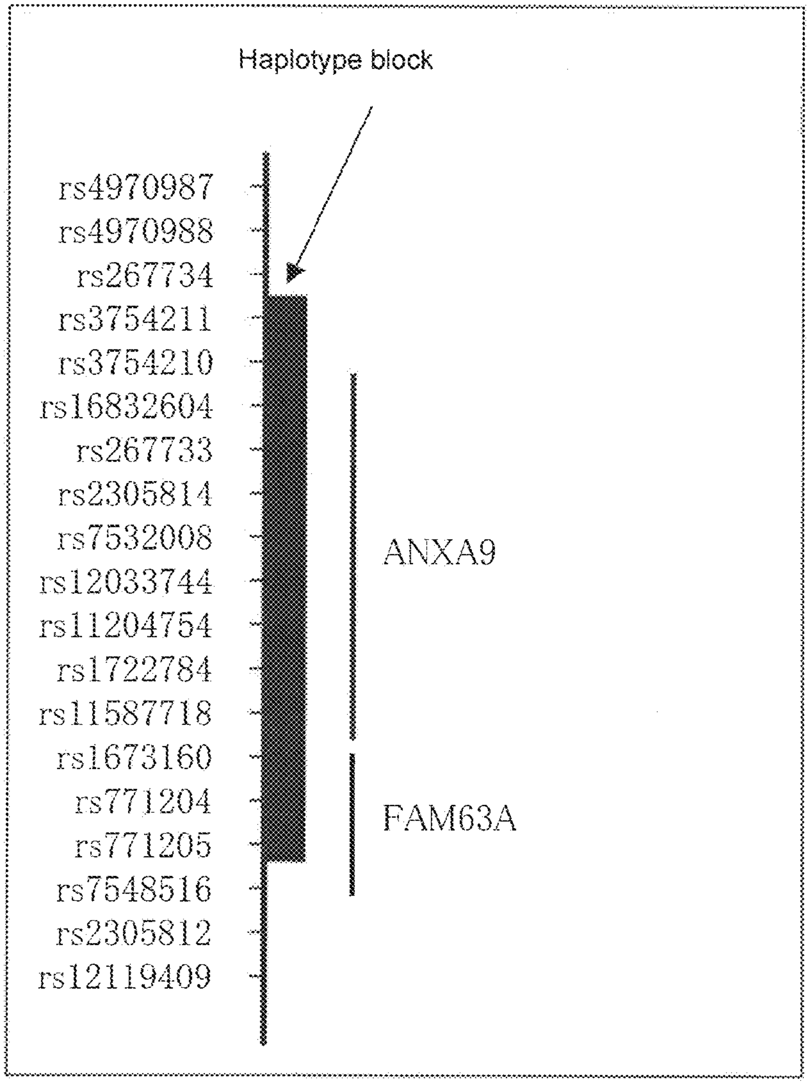
FIG. 5 is a conceptual diagram of a 23,252-bp haplotype block represented by a base sequence set forth in SEQ ID NO:1, which contains SNP: rs2305814 and extends from SNP: rs3754211 to SNP: rs771205.

(1) A 23,252-bp haplotype block ranging from SNP: rs3754211 to SNP:rs771205 and containing SNP:rs2305814, and represented by the base sequence set forth in SEQ ID NO:1 (FIG. 5). This haplotype block was a region containing ANXA9 gene and FAM63A gene. From this result, ANXA9 gene and FAM63A gene were identified as hair shape susceptibility genes.

Figure 6:
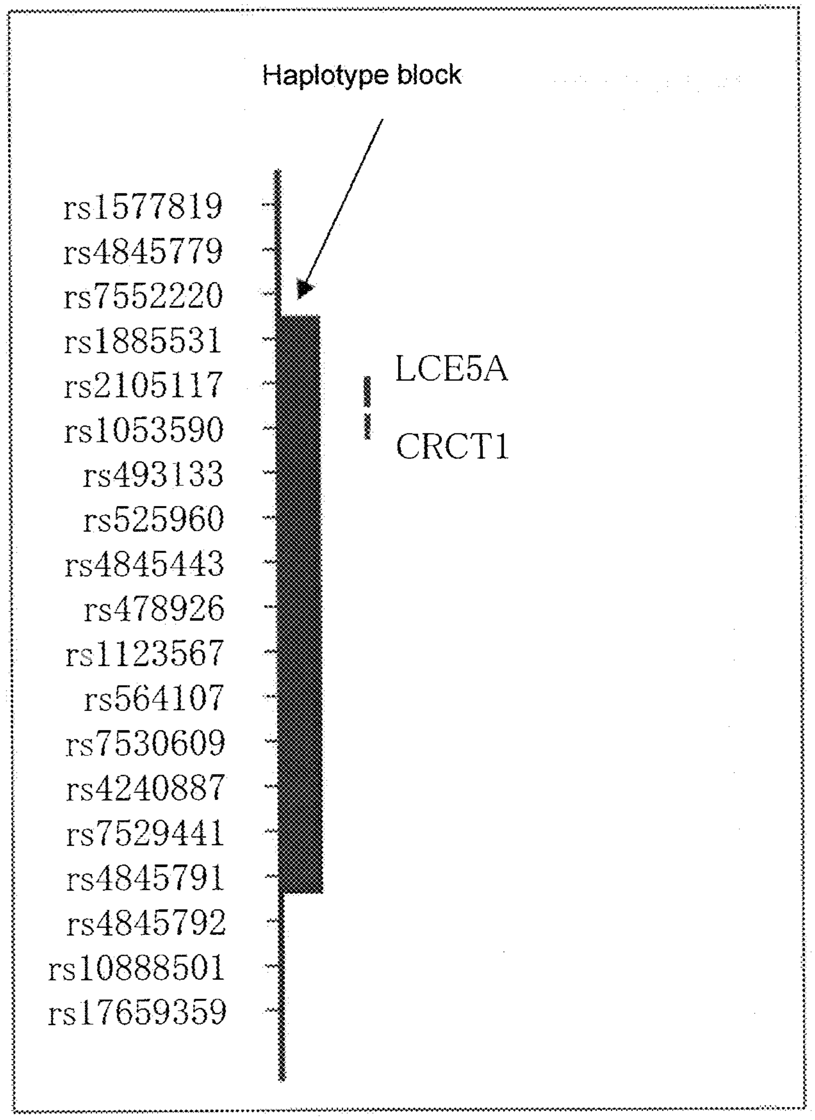
FIG. 6 is a conceptual diagram of a 56,552-bp haplotype block represented by a base sequence set forth in SEQ ID NO:2, which contains SNP: rs1053590 and extends from SNP: rs1885531 to SNP: rs4845791.

(2) A 56,552-bp haplotype block ranging from SNP: rs1885531 to SNP:rs484791 and containing SNP:rs1053590, and represented by the base sequence set forth in SEQ ID NO:2 (FIG. 6). This haplotype block was a region containing LCE5A gene and CRCT1 gene. From this result, LCE5A gene and CRCT1 gene were identified as hair shape susceptibility gene.

Figure 7:
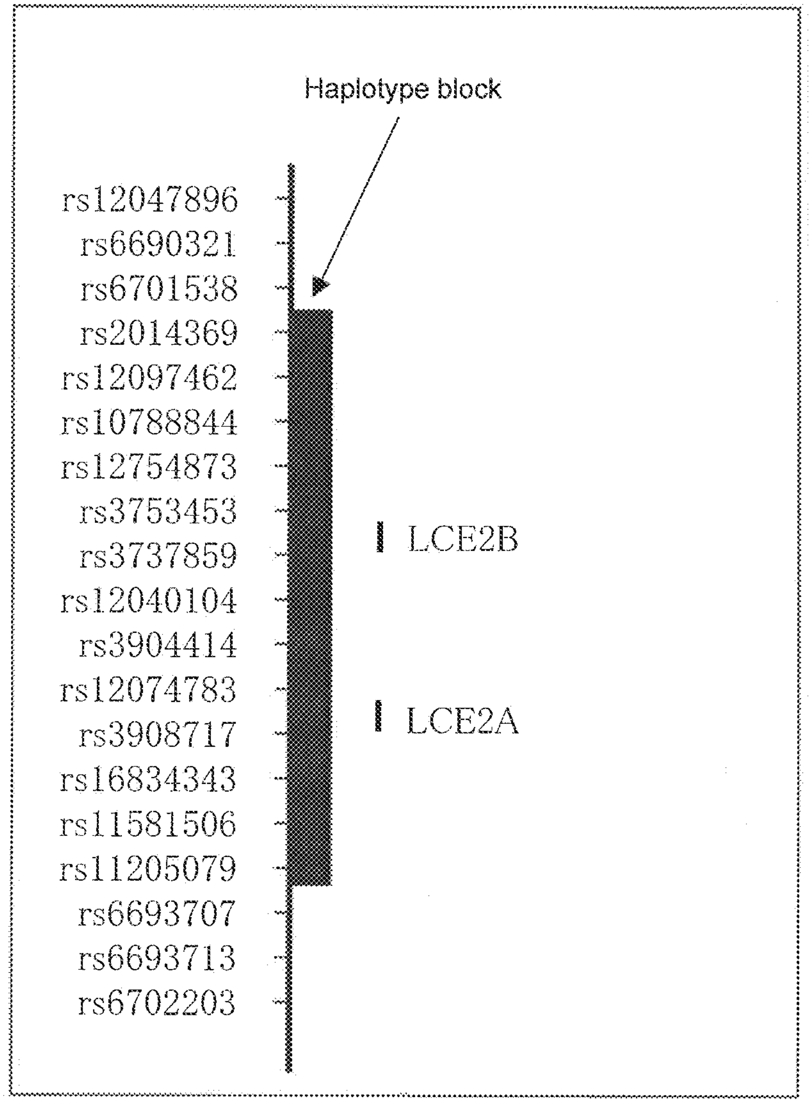
FIG. 7 is a conceptual diagram of a 23,382-bp haplotype block represented by a base sequence set forth in SEQ ID NO:3, which contains SNP: rs3753453, SNP: rs3737859, SNP: rs3904414 and SNP: rs3908717, and extends from SNP: rs2014369 to SNP: rs11205079.

(3) A 23,382-bp haplotype block ranging from SNP: rs2014369 to SNP: rs11205079 and containing SNP: rs3753453, SNP:rs3737859, SNP:rs3904414 and SNP: rs3908717, and represented by the base sequence set forth in SEQ ID NO:3 (FIG. 7). This haplotype block was a region containing LCE2B gene and LCE2A gene. From this result, LCE2B gene and LCE2A gene were identified as hair shape susceptibility genes.

Figure 8:
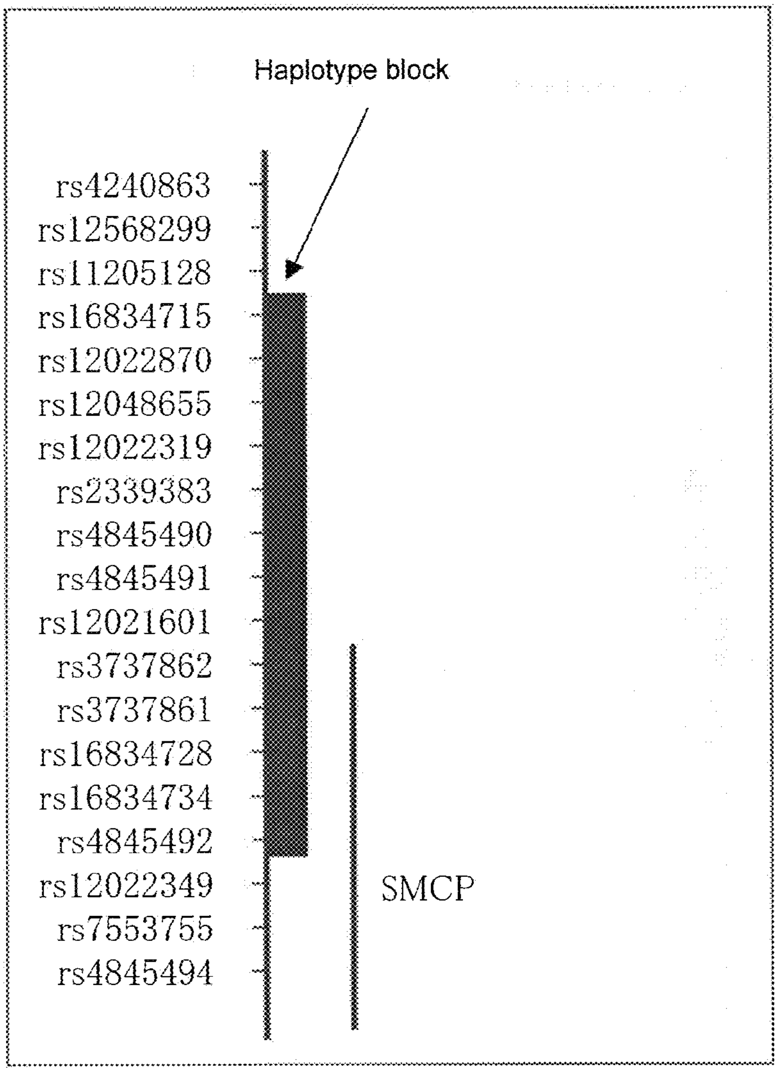
FIG. 8 is a conceptual diagram of a 8,818-bp haplotype block represented by a base sequence set forth in SEQ ID NO:4, which contains SNP: rs3737861 and extends from SNP: rs16834715 to SNP: rs4845492.

(4) A 8,818-bp haplotype block ranging from SNP: rs16834715 to SNP:rs4845492 and containing SNP: rs3737861, and represented by the base sequence set forth in SEQ ID NO:4 (FIG. 8). This haplotype block was a region containing SMCP gene. From this result, SMCP gene was identified as a hair shape susceptibility gene.

Figure 9:
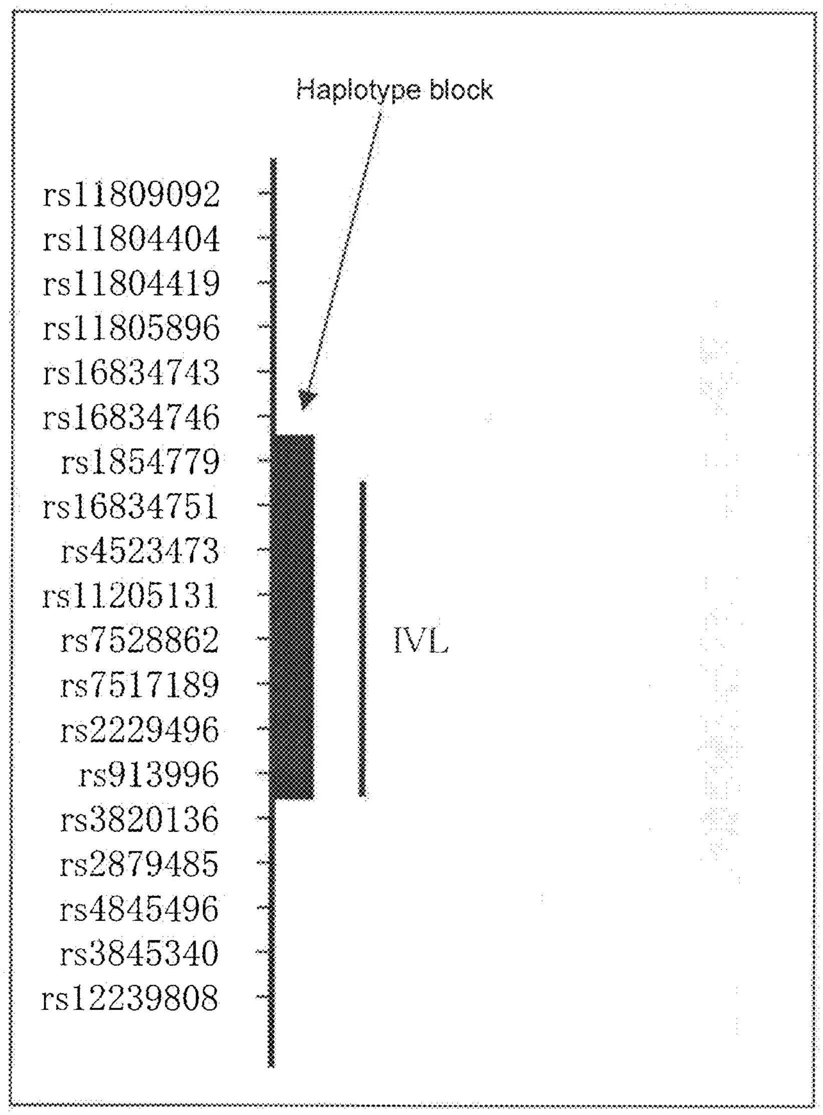
FIG. 9 is a conceptual diagram of a 3,440-bp haplotype block represented by a base sequence set forth in SEQ ID NO:5, which contains SNP: rs4523473, SNP: rs2229496 and SNP: rs913996, and extends from SNP: rs1854779 to SNP: rs913996.
Figures 1, 10:
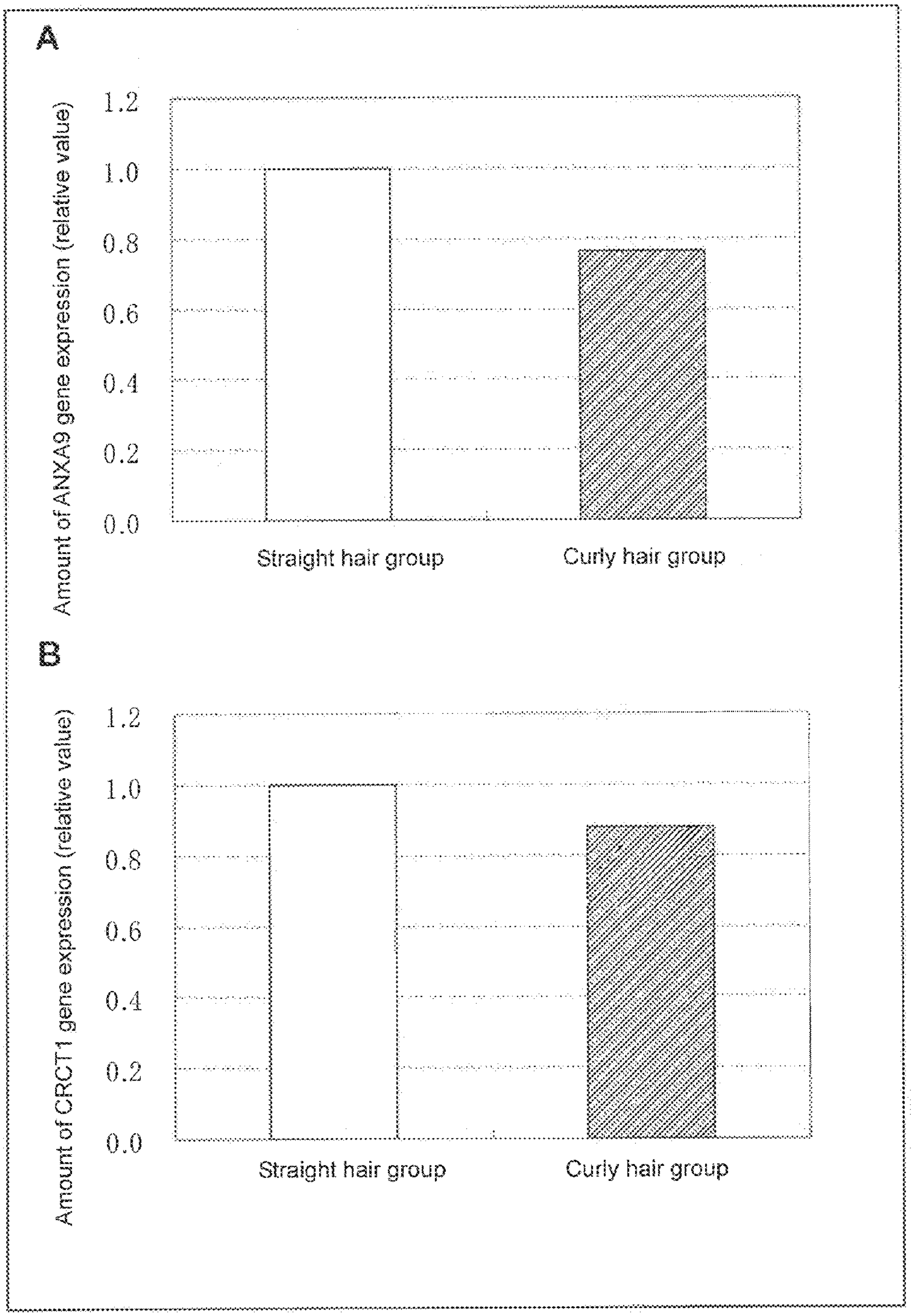
Figures 2, 10:
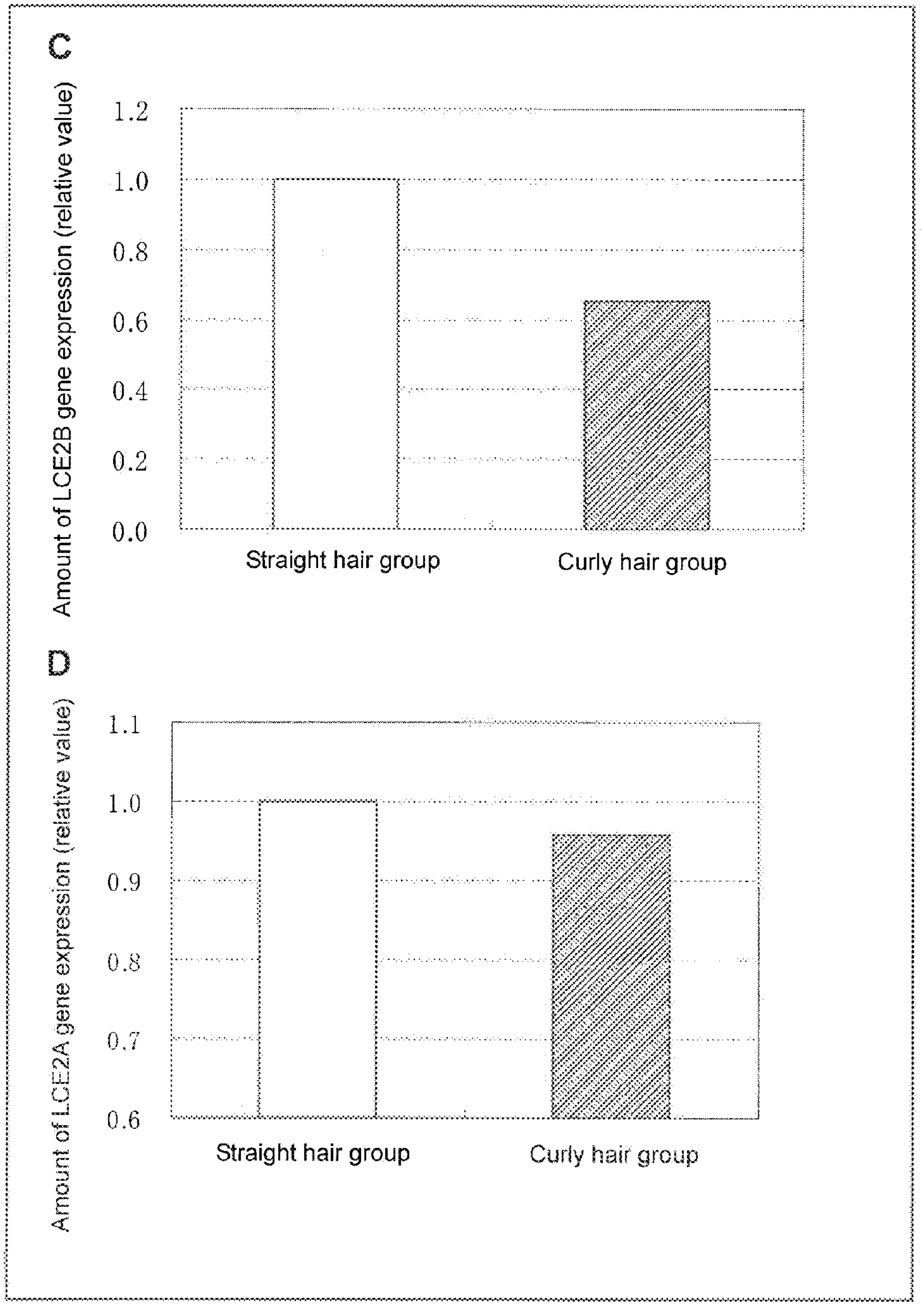
Figures 3, 10:
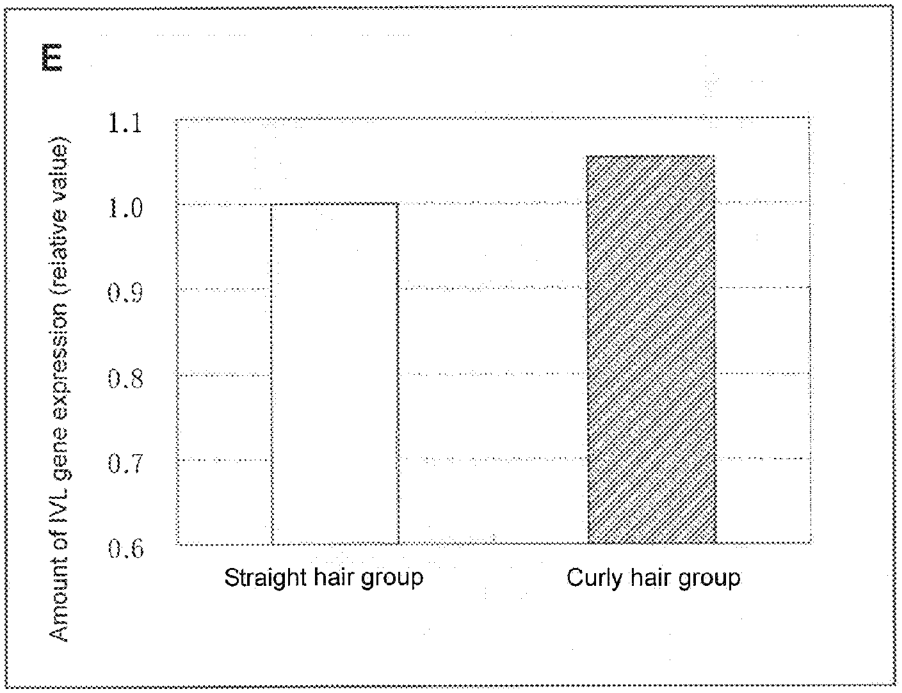

(5) A 3,440-bp haplotype block ranging from SNP: rs1854779 to SNP:rs913996 and containing SNP:rs4523473, SNP:rs2229496 and SNP:rs913996, and represented by the base sequence set forth in SEQ ID NO:5 (FIG. 9). This haplotype block was a region containing IVL gene. From this result, IVL gene was identified as a hair shape susceptibility gene.

Example 6

Identification of Hair Shape Susceptibility SNP Marker

While haplotype blocks were found in the haplotype analysis in Example 5, a haplotype was extracted from each of the haplotype blocks using the same Haploview 4.1 Software (Barrett, J C et al., Bioinformatics, 21(2), 263-265, 2005). By comparing the respective nucleotide combinations of the extracted haplotypes, that is, the SNP marker groups, SNP loci that were linked to the hair shape susceptibility SNP marker loci were identified. The SNP loci thus identified can be identified as additional hair shape susceptibility SNP markers.

As a result, additional hair shape susceptibility SNP markers shown below were respectively found in the haplotype blocks of (1) to (5) shown in Example 4.

(1) 23,252-bp haplotype block represented by the base sequence set forth in SEQ ID NO:1: There were nine principal haplotypes in this haplotype block (Table 8). As the SNP loci that are linked to a hair shape susceptibility SNP marker, SNP:rs2305814, additional six hair shape susceptibility SNP markers shown below were identified.

SNP:rs3754211 (single nucleotide polymorphism represented by Nucleotide Number 1 in the base sequence set forth in SEQ ID NO:1), SNP:rs3754210 (single nucleotide polymorphism represented by Nucleotide Number 2405), SNP: rs16832604 (single nucleotide polymorphism represented by Nucleotide Number 5874), SNP:rs7532008 (single nucleotide polymorphism represented by Nucleotide Number 8494), SNP:rs1673160 (single nucleotide polymorphism represented by Nucleotide Number 18980), and SNP:rs771205 (single nucleotide polymorphism represented by Nucleotide Number 23252).

TABLE 8

| SNP Marker | Nucleotide number in base sequence set forth in SEQ ID NO: 1 | Haplotype 1 | 2 | 3 | 4 | 5 | 6 | 7 | 8 | 9 | Hair shape susceptibility SNP |
|---|---|---|---|---|---|---|---|---|---|---|---|
| rs3754211 | 1 | A | G | G | A | G | A | A | A | A | O |
| rs3754210 | 2405 | G | G | G | T | G | G | G | G | T | O |
| rs16832604 | 5874 | A | A | A | G | A | A | A | A | G | O |
| rs2305814 | 7121 | C | T | T | C | C | C | C | T | C | O (Example 4) |
| rs7532008 | 8494 | C | A | A | C | C | A | C | A | C | O |
| rs12033744 | 9072 | G | A | G | G | G | G | G | G | G | |
| rs11204754 | 9398 | C | C | T | C | C | T | C | T | C | |
| rs1722784 | 10013 | A | A | G | A | A | G | A | G | A | |
| rs11587718 | 11422 | C | T | T | C | C | T | C | T | C | |
| rs1673160 | 18980 | T | A | A | T | T | A | A | A | T | O |
| rs771204 | 22306 | A | A | A | G | A | A | A | A | G | |
| rs771205 | 23252 | C | C | C | T | C | C | C | C | C | O |

(2) 56,552-bp haplotype block represented by the base sequence set forth in SEQ ID NO:2: There were ten principal haplotypes in this haplotype block (Table 9-1 to Table 9-3). As SNP loci that are linked to a hair shape susceptibility SNP marker, SNP: rs1053590, additional 39 hair shape susceptibility SNP markers shown below were identified.

SNP:rs11581947 (single nucleotide polymorphism represented by Nucleotide Number 2355 in the base sequence set forth in SEQ ID NO:2), SNP:rs6658925 (single nucleotide polymorphism represented by Nucleotide Number 2569), SNP:rs2105117 (single nucleotide polymorphism represented by Nucleotide Number 3897), SNP:rs548252 (single nucleotide polymorphism represented by Nucleotide Number 9510), SNP:rs493133 (single nucleotide polymorphism represented by Nucleotide Number 13643), SNP:rs1970283 (single nucleotide polymorphism represented by Nucleotide Number 15387), SNP:rs1001834 (single nucleotide polymorphism represented by Nucleotide Number 15708), SNP: rs11205018 (single nucleotide polymorphism represented by Nucleotide Number 16017), SNP:rs545418 (single nucleotide polymorphism represented by Nucleotide Number 17106), SNP:rs12116609 (single nucleotide polymorphism represented by Nucleotide Number 17453), SNP:rs526099 (single nucleotide polymorphism represented by Nucleotide Number 17579), SNP:rs525960 (single nucleotide polymorphism represented by Nucleotide Number 17634), SNP: rs4845443 (single nucleotide polymorphism represented by Nucleotide Number 26924), SNP:rs569032 (single nucleotide polymorphism represented by Nucleotide Number 28383), SNP:rs528427 (single nucleotide polymorphism represented by Nucleotide Number 31275), SNP:rs478926 (single nucleotide polymorphism represented by Nucleotide Number 31301), SNP:rs1337338 (single nucleotide polymorphism represented by Nucleotide Number 31653), SNP: rs6587681 (single nucleotide polymorphism represented by Nucleotide Number 31903), SNP:rs1856120 (single nucleotide polymorphism represented by Nucleotide Number 32209), SNP:rs474086 (single nucleotide polymorphism represented by Nucleotide Number 33199), SNP:rs578382 (single nucleotide polymorphism represented by Nucleotide Number 33822), SNP:rs549044 (single nucleotide polymorphism represented by Nucleotide Number 34100), SNP: rs1123567 (single nucleotide polymorphism represented by Nucleotide Number 35791), SNP:rs1538083 (single nucleotide polymorphism represented by Nucleotide Number 36884), SNP:rs1538082 (single nucleotide polymorphism represented by Nucleotide Number 37072), SNP:rs7532535 (single nucleotide polymorphism represented by Nucleotide Number 37365), SNP:rs7518654 (single nucleotide polymorphism represented by Nucleotide Number 37613), SNP: rs533917 (single nucleotide polymorphism represented by Nucleotide Number 38062), SNP:rs564107 (single nucleotide polymorphism represented by Nucleotide Number 39063), SNP:rs7530609 (single nucleotide polymorphism represented by Nucleotide Number 46580), SNP:rs4240885 (single nucleotide polymorphism represented by Nucleotide Number 49618), SNP:rs4240886 (single nucleotide polymorphism represented by Nucleotide Number 50164), SNP: rs4240887 (single nucleotide polymorphism represented by Nucleotide Number 50278), SNP:rs6687126 (single nucleotide polymorphism represented by Nucleotide Number 50662), SNP:rs6674451 (single nucleotide polymorphism represented by Nucleotide Number 50822), SNP:rs7550769 (single nucleotide polymorphism represented by Nucleotide Number 50981), SNP:rs7529157 (single nucleotide polymorphism represented by Nucleotide Number 51133), SNP: rs1988805 (single nucleotide polymorphism represented by Nucleotide Number 51263), and SNP:rs7529441 (single nucleotide polymorphism represented by Nucleotide Number 51397).

TABLE 9-1

| SNP marker | Nucleotide number in base sequnce set forth in SEQ ID NO: 2 | Haplotype 1 | 2 | 3 | 4 | 5 | 6 | 7 | 8 | 9 | 10 | Hair shape susceptibility SNP |
|---|---|---|---|---|---|---|---|---|---|---|---|---|
| rs1885531 | 1 | G | T | G | G | T | G | G | T | G | T | |
| rs1415432 | 422 | A | G | A | A | G | A | A | G | A | G | |
| rs7521430 | 1464 | G | G | G | T | G | G | T | G | G | G | |
| rs11581947 | 2355 | A | G | A | G | G | A | G | G | A | G | O |
| rs6658925 | 2569 | G | A | G | A | A | G | A | A | G | A | O |
| rs2105117 | 3897 | A | G | A | G | G | A | G | G | A | G | O |
| rs2282298 | 4013 | | | | | | | | | | | |
| rs4845441 | 5189 | T | C | T | C | C | T | C | C | T | T | |
| rs3753450 | 5787 | T | T | G | T | T | T | T | T | T | T | |
| rs2297760 | 6802 | T | T | T | C | T | T | C | T | T | T | |
| rs16834168 | 7914 | G | G | G | A | G | G | G | G | G | G | |
| rs1053590 | 8196 | C | T | C | T | T | C | T | T | C | T | O (Example 4) |
| rs488393 | 9316 | A | G | A | G | G | A | G | G | A | A | |
| rs548252 | 9510 | T | C | T | C | C | T | C | C | T | C | O |
| rs4845783 | 12327 | A | G | A | A | G | A | A | G | A | A | |
| rs10888491 | 12390 | G | A | G | A | A | G | A | A | A | G | |
| rs499697 | 12922 | A | G | A | A | G | A | A | G | A | G | |
| rs493133 | 13643 | C | G | C | G | G | C | G | G | C | G | O |
| rs1970283 | 15387 | C | G | C | G | G | C | G | G | C | G | O |
| rs1001834 | 15708 | A | C | A | C | C | A | C | C | A | C | O |
| rs1538084 | 15780 | C | A | C | C | A | C | C | C | C | A | |
| rs11205018 | 16017 | G | T | G | T | T | G | T | T | G | T | O |
| rs545418 | 17106 | T | C | T | C | C | T | C | C | T | C | O |
| rs12116609 | 17453 | T | C | T | C | C | T | C | C | T | C | O |
| rs526099 | 17579 | C | T | C | T | T | C | T | T | C | T | O |
| rs525960 | 17634 | A | T | A | T | T | A | T | T | A | T | O |
| rs4845443 | 26924 | A | G | A | G | G | A | G | G | A | G | O |
| rs569032 | 28383 | T | C | T | C | C | T | C | C | T | C | O |
| rs16834184 | 29986 | G | G | G | G | G | C | G | G | G | G | |
| rs6662637 | 30116 | G | G | A | G | G | G | G | G | G | G | |
| rs528427 | 31275 | C | G | C | G | G | C | G | G | C | G | O |
| rs478926 | 31301 | T | G | T | G | G | T | G | G | T | G | O |
| rs1337338 | 31653 | A | G | A | G | G | A | G | G | A | G | O |
| rs6587681 | 31903 | T | C | T | C | C | T | C | C | T | C | O |
| rs1856120 | 32209 | A | G | A | G | G | A | G | G | A | G | O |
| rs474086 | 33199 | T | C | T | C | C | T | C | C | T | C | O |
| rs578382 | 33822 | A | G | A | G | G | A | G | G | A | G | O |
| rs549044 | 34100 | T | C | T | C | C | T | C | C | T | C | O |
| rs1123567 | 35791 | A | G | A | G | G | A | G | G | A | G | O |
| rs1538083 | 36884 | G | A | G | A | A | G | A | A | G | A | O |
| rs1538082 | 37072 | G | A | G | A | A | G | A | A | G | A | O |
| rs7532535 | 37365 | A | T | A | T | T | A | T | T | A | T | O |
| rs7518654 | 37613 | G | C | G | C | C | G | C | C | G | C | O |
| rs533917 | 38062 | G | A | G | A | A | G | A | A | G | A | O |
| rs564107 | 39063 | T | C | T | C | C | T | C | C | T | C | O |
| rs7530609 | 49580 | A | C | A | C | C | A | C | C | A | C | O |
| rs6587688 | 49390 | C | T | C | C | T | C | C | T | C | T | |

TABLE 9-2

| SNP marker | Nucleotide number in base sequence set forth in SEQ ID NO: 2 | Haplotype 1 | 2 | 3 | 4 | 5 | 6 | 7 | 8 | 9 | 10 | Hair shape susceptibility SNP |
|---|---|---|---|---|---|---|---|---|---|---|---|---|
| rs4240885 | 49618 | C | G | C | G | G | C | G | G | C | G | O |
| rs4240886 | 50164 | A | T | A | T | T | A | T | T | A | T | O |
| rs4240887 | 50278 | G | A | G | A | A | G | A | A | G | A | O |
| rs6687126 | 50662 | G | T | G | T | T | G | T | T | G | T | O |
| rs6674451 | 50822 | T | C | T | C | C | T | C | C | T | C | O |
| rs7550769 | 50981 | A | G | A | G | G | A | G | G | A | G | O |
| rs7529157 | 51133 | A | C | A | C | C | A | C | C | A | C | O |
| rs1988805 | 51263 | G | T | G | T | T | G | T | T | G | T | O |
| rs7529441 | 51397 | T | C | T | C | C | T | C | C | T | C | O |

TABLE 9-2-continued

| SNP marker | Nucleotide number in base sequence set forth in SEQ ID NO: 2 | Haplotype 1 | 2 | 3 | 4 | 5 | 6 | 7 | 8 | 9 | 10 | Hair shape susceptibility SNP |
|---|---|---|---|---|---|---|---|---|---|---|---|---|
| rs4845790 | 56528 | T | T | T | T | C | T | T | T | T | T | |
| rs4845791 | 56552 | A | A | A | A | G | A | A | A | A | A | |
| rs1885531 | 1 | G | T | G | G | T | G | G | T | G | T | |
| rs1415432 | 422 | A | G | A | A | G | A | A | G | A | G | |
| rs7521430 | 1464 | G | G | G | T | G | G | T | G | G | G | |
| rs11581947 | 2355 | A | G | A | G | G | A | G | G | A | G | O |
| rs6658925 | 2569 | G | A | G | A | A | G | A | A | G | A | O |
| rs2105117 | 3897 | A | G | A | G | G | A | G | G | A | G | O |
| rs2282298 | 4013 | C | G | C | G | G | C | G | G | C | G | |
| rs4845441 | 5189 | T | C | T | C | C | T | C | C | T | T | |
| rs3753450 | 5787 | T | T | G | T | T | T | T | T | T | T | |
| rs2297760 | 6802 | T | T | T | C | T | T | C | T | T | T | |
| rs16834168 | 7914 | G | G | G | A | G | G | G | G | G | G | |
| rs1053590 | 8196 | C | T | C | T | T | C | T | T | C | T | O (Example 4) |
| rs488393 | 9316 | A | G | A | G | G | A | G | G | A | A | |
| rs548252 | 8510 | T | C | T | C | C | T | C | C | T | C | O |
| rs4845783 | 12327 | A | G | A | A | G | A | A | G | A | A | |
| rs10888491 | 12390 | G | A | G | A | A | G | A | A | A | G | |
| rs499697 | 12922 | A | G | A | A | G | A | A | G | A | G | |
| rs493133 | 13643 | C | G | C | G | G | C | G | G | C | G | O |
| rs1970283 | 15387 | C | G | C | G | G | C | G | G | C | G | O |
| rs1001834 | 15708 | A | C | A | C | C | A | C | C | A | C | O |
| rs1538084 | 15780 | C | A | C | C | A | C | C | C | C | A | |
| rs11205018 | 16017 | G | T | G | T | T | G | T | T | G | T | O |
| rs545418 | 17106 | T | C | T | C | C | T | C | C | T | C | O |
| rs12116609 | 17453 | T | C | T | C | C | T | C | C | T | C | O |
| rs526099 | 17579 | C | T | C | T | T | C | T | T | C | T | O |
| rs525960 | 17634 | A | T | A | T | T | A | T | T | A | T | O |
| rs4845443 | 26924 | A | G | A | G | G | A | G | G | A | G | O |
| rs569032 | 28383 | T | C | T | C | C | T | C | C | T | C | O |
| rs16834184 | 29986 | G | G | G | G | G | C | G | G | G | G | |
| rs6662637 | 30116 | G | G | A | G | G | G | G | G | G | G | |
| rs528427 | 31275 | C | G | C | G | G | C | G | G | C | G | O |
| rs478926 | 31301 | T | G | T | G | G | T | G | G | T | G | O |
| rs1337338 | 31653 | A | G | A | G | G | A | G | G | A | G | O |
| rs6587681 | 31903 | T | C | T | C | C | T | C | C | T | C | O |
| rs1856120 | 32209 | A | G | A | G | G | A | G | G | A | G | O |
| rs474086 | 33199 | T | C | T | C | C | T | C | C | T | C | O |
| rs578382 | 33822 | A | G | A | G | G | A | G | G | A | G | O |

TABLE 9-3

| SNP marker | Nucleotide number in base sequence set forth in SEQ ID NO: 2 | Haplotype 1 | 2 | 3 | 4 | 5 | 6 | 7 | 8 | 9 | 10 | Hair shape susceptibility SNP |
|---|---|---|---|---|---|---|---|---|---|---|---|---|
| rs549044 | 34100 | T | C | T | C | C | T | C | C | T | C | O |
| rs1123567 | 35791 | A | G | A | G | G | A | G | G | A | G | O |
| rs1538083 | 36884 | G | A | G | A | A | G | A | A | G | A | O |
| rs1538082 | 37072 | G | A | G | A | A | G | A | A | G | A | O |
| rs7532535 | 37365 | A | T | A | T | T | A | T | T | A | T | O |
| rs7518654 | 37613 | G | C | G | C | C | G | C | C | G | C | O |
| rs533917 | 38062 | G | A | G | A | A | G | A | A | G | A | O |
| rs564107 | 39063 | T | C | T | C | C | T | C | C | T | C | O |
| rs7530609 | 46580 | A | C | A | C | C | A | C | C | A | C | O |
| rs6587688 | 49390 | C | T | C | C | T | C | C | T | C | T | |
| rs4240885 | 49618 | C | G | C | G | G | C | G | G | C | G | O |
| rs4240886 | 50164 | A | T | A | T | T | A | T | T | A | T | O |
| rs4240887 | 50278 | G | A | G | A | A | G | A | A | G | A | O |
| rs6687126 | 50662 | G | T | G | T | T | G | T | T | G | T | O |

TABLE 9-3-continued

| SNP marker | Nucleotide number in base sequence set forth in SEQ ID NO: 2 | Haplotype 1 | 2 | 3 | 4 | 5 | 6 | 7 | 8 | 9 | 10 | Hair shape susceptibility SNP |
|---|---|---|---|---|---|---|---|---|---|---|---|---|
| rs6674451 | 50822 | T | C | T | C | C | T | C | C | T | C | O |
| rs7550769 | 50981 | A | G | A | G | G | A | G | G | A | G | O |
| rs7529157 | 51133 | A | C | A | C | C | A | C | C | A | C | O |
| rs1988805 | 51263 | G | T | G | T | T | G | T | T | G | T | O |
| rs7529441 | 51397 | T | C | T | C | C | T | C | C | T | C | O |
| rs4845790 | 56528 | T | T | T | T | C | T | T | T | T | T | |
| rs4845791 | 56552 | A | A | A | A | G | A | A | A | A | A | |

(3) 23,382-bp haplotype block represented by the base sequence set forth in SEQ ID NO:3: There were nine principal haplotypes in this haplotype block (Table 10). As SNP loci that are linked to a hair shape susceptibility SNP marker, SNP: rs3753453, SNP:rs3737859, SNP:rs3904414 or SNP: rs3908717, additional four hair shape susceptibility SNP markers shown below were identified.

SNP:rs11205072 (single nucleotide polymorphism represented by Nucleotide Number 2509 in the base sequence set forth in SEQ ID NO:3), SNP:rs12074783 (single nucleotide polymorphism represented by Nucleotide Number 18481), SNP:rs3904415 (single nucleotide polymorphism represented by Nucleotide Number 21734), and SNP:rs11205079 (single nucleotide polymorphism represented by Nucleotide Number 23382).

TABLE 10

| SNP marker | Nucleotide number in base sequence set forth in SEQ ID NO: 3 | Haplotype 1 | 2 | 3 | 4 | 5 | 6 | 7 | 8 | 9 | Hair shape susceptibility SNP |
|---|---|---|---|---|---|---|---|---|---|---|---|
| rs2014369 | 1 | T | T | C | C | C | C | C | C | C | |
| rs2014368 | 7 | T | T | C | C | C | C | C | C | C | |
| rs12097462 | 1115 | A | A | C | C | C | C | C | C | C | |
| rs11576287 | 1991 | A | A | A | A | T | A | A | A | T | |
| rs10788844 | 2303 | A | A | C | C | C | C | C | C | C | |
| rs1925663 | 2484 | A | A | T | T | T | T | T | T | T | |
| rs11205072 | 2509 | G | G | A | A | G | A | G | A | A | O |
| rs11205073 | 3363 | A | A | C | C | C | C | C | C | C | |
| rs12754873 | 4275 | C | C | C | C | T | C | T | C | C | |
| rs3753453 | 5167 | T | T | C | C | T | C | T | C | C | O (Example 4) |
| rs3753452 | 5560 | C | T | C | C | C | C | C | C | C | |
| rs3737859 | 8449 | T | T | G | G | T | G | T | G | G | O (Example 4) |
| rs10888508 | 9159 | C | C | A | A | C | C | C | C | A | |
| rs1332509 | 9724 | A | A | T | T | T | T | T | T | T | |
| rs12040104 | 15127 | C | C | C | A | C | C | C | A | C | |
| rs3904413 | 17476 | T | T | C | C | C | C | C | C | C | |
| rs3904414 | 17598 | G | G | A | A | G | A | G | A | A | O (Example 4) |
| rs11205078 | 18437 | G | G | A | A | A | A | A | A | A | |
| rs12074783 | 18481 | T | T | C | C | T | C | T | C | C | O |
| rs4845317 | 19319 | A | A | G | G | G | G | G | G | G | |
| rs3908717 | 20891 | C | C | G | G | C | G | C | G | G | O (Example 4) |
| rs17661905 | 20983 | T | T | T | T | C | T | C | T | T | |
| rs16834343 | 21327 | A | A | G | A | A | G | A | A | G | |
| rs3904415 | 21734 | C | C | T | T | C | T | C | T | T | O |
| rs11581506 | 22237 | A | A | G | G | G | G | G | G | G | |
| rs11587581 | 23044 | C | C | T | T | T | T | T | T | T | |
| rs7543194 | 23198 | T | T | C | C | C | C | C | C | C | |
| rs11205079 | 23382 | A | A | T | T | A | T | A | T | T | O |

(4) 8,818-bp haplotype block represented by the base sequence set forth in SEQ ID NO:4: There were three principal haplotypes in this haplotype block (Table 11). As an SNP locus that is linked to a hair shape susceptibility SNP marker, SNP:rs3737861, additional six hair shape susceptibility SNP markers shown below were identified.

SNP:rs16834715 (single nucleotide polymorphism represented by Nucleotide Number 1 in the base sequence set forth in SEQ ID NO:4), SNP:rs12022319 (single nucleotide polymorphism represented by Nucleotide Number 3308), SNP: rs4845490 (single nucleotide polymorphism represented by Nucleotide Number 4715), SNP:rs4845491 (single nucleotide polymorphism represented by Nucleotide Number 4985), SNP:rs16834728 (single nucleotide polymorphism represented by Nucleotide Number 8553), and SNP: rs4845492 (single nucleotide polymorphism represented by Nucleotide Number 8818).

TABLE 11

| SNP marker | Nucleotide number in base sequence set forth in SEQ ID NO: 4 | Haplotype 1 | Haplotype 2 | Haplotype 3 | Hair shape susceptibility SNP |
|---|---|---|---|---|---|
| rs16834715 | 1 | T | C | C | ○ |
| rs12022870 | 1816 | A | G | G | |
| rs12048655 | 1967 | G | T | T | |
| rs12022319 | 3308 | C | T | C | ○ |
| rs2339383 | 4039 | A | C | C | |
| rs4845490 | 4715 | G | A | G | ○ |
| rs4845491 | 4985 | C | T | C | ○ |
| rs12021601 | 5738 | T | G | G | |
| rs3737862 | 6322 | A | G | G | |
| rs3737861 | 6354 | C | A | C | ○ (Example 4) |
| rs16834728 | 8553 | C | T | C | ○ |
| rs16834734 | 8694 | C | T | T | |
| rs4845492 | 8818 | C | G | C | ○ |

(5) 3,440-bp haplotype block represented by base sequence set forth in SEQ ID NO: 5: There were three principal haplotypes in this haplotype block (Table 12). As SNP loci that are linked to a hair shape susceptibility SNP marker, SNP: rs4523473, SNP:rs2229496 or SNP: rs913996, additional five hair shape susceptibility SNP markers shown below were identified.

SNP:rs1854779 (single nucleotide polymorphism represented by Nucleotide Number 1 in the base sequence set forth in SEQ ID NO:5), SNP:rs16834751 (single nucleotide polymorphism represented by Nucleotide Number 540), SNP: rs11205131 (single nucleotide polymorphism represented by Nucleotide Number 1007), SNP:rs7528862 (single nucleotide polymorphism represented by Nucleotide Number 1018), and SNP: rs7517189 (single nucleotide polymorphism represented by Nucleotide Number 1075).

TABLE 12

| SNP marker | Nucleotide number in base sequence set forth in SEQ ID NO: 5 | Haplotype 1 | Haplotype 2 | Haplotype 3 | Hair shape susceptibility SNP |
|---|---|---|---|---|---|
| rs1854779 | 1 | C | T | C | ○ |
| rs16834751 | 540 | C | A | C | ○ |
| rs4523473 | 759 | C | T | C | ○ (Example 4) |
| rs11205131 | 1007 | A | G | G | ○ |
| rs7528862 | 1018 | G | A | G | ○ |
| rs7517189 | 1075 | G | C | G | ○ |
| rs2229496 | 1939 | G | A | G | ○ (Example 4) |
| rs913996 | 3440 | A | G | A | ○ (Example 4) |

Example 7

Analysis of Gene Expression in Scalp Hair Roots in Curly Hair People and Straight Hair People Ten curly hair people and ten straight hair people were collected according to the classifications of Example 1, and an analysis was carried out on the expression of the hair shape susceptibility gene in the scalp hair roots of each test subject. In regard to the collection of specimens from the test subjects, an approval was granted in advance by the ethics committee, subsequently the person in charge of the implementation of informed consent explained the contents of the study to the objects using a written explanation, and written consent was obtained.

About 60 scalp hair strands per person were pulled out from all over the whole head of each test subject, and only those scalp hair root parts that were determined to be in the growth period from the shape of the hair root part, were collected in a petri dish filled with ice-cooled PBS (manufactured by Invitrogen, Inc.). Under a stereoscopic microscope and using forceps and a needle teeth, the outer hair root sheath and the inner hair root sheath were removed from the hair root part as much as possible, and the hair root of the hair shaft only (hair shaft keratinized region) was separated and prepared. The hair shaft keratinized region was introduced in a 1.5-mL tube containing 0.5 mL of an RNA extraction solution, ISOGEN (manufactured by Nippon Gene Co., Ltd.), and the tissue was sufficiently crushed with a mini codeless grinder and a homogenization pestle. 0.5 mL of ISOGEN and 200 μL of chloroform were added thereto, and the mixture was sufficiently stirred in a vortex mixer and then was centrifuged (15000 rpm, for 15 minutes) using a small-sized microcentrifuge. Thus, about 500 μL of an aqueous phase containing RNA was collected. 50 μL of 3 M sodium acetate and 1 μL of Ethachinmate (manufactured by Nippon Gene Co., Ltd.) were added to the collected solution, and the mixture was sufficiently stirred. Furthermore, 1 mL of isopropanol was added and stirred, and the mixture was centrifuged (15000 rpm, for 20 minutes) with a small-sized microcentrifuge to precipitate total RNA. The supernatant was discarded, and then 75% ethanol was added to the precipitate. The mixture was centrifuged again (15000 rpm, for 10 minutes) with a small-sized microcentrifuge. The supernatant was discarded, and the precipitate was dried in air and was dissolved in 20 μL of Nuclease-free Water (manufactured by Invitrogen, Inc.). A portion of this was used to measure the RNA concentration using an absorption spectrometer (GeneQuant: manufactured by Pharmacia AB, or NonoDrop: manufactured by Nanodrop Technologies, Inc.), or RiboGreen RNA Reagent and Kit (manufactured by Invitrogen, Inc.). cDNA was synthesized from 1 fig of the total RNA thus obtained using QuantiTect Reverse Transcription Kit (manufactured by Qiagen N.V.) according to the attached protocol, and the cDNA was used in the quantification of the amount of gene expression by PCR.

The quantification of the amount of gene expression was carried out using TaqMan (registered trademark) Gene Expression Assays manufactured by Applied Biosystems, Inc. (ABI). According to the attached protocol, the synthesized cDNA, a primer & probe set specific to the gene to be detected and quantified, a real-time PCR reagent and the like (manufactured by ABI) were mixed, and fragments of the gene to be detected and quantified were amplified with Applied Biosystems 7500 Real-Time PCR System (manufactured by ABI). At this time, real-time PCR was carried out in the same manner using a known cDNA derived from an standard hair shaft keratinized region sample, and a calibration curve was produced. Thus, standardization of the amount of gene expression was carried out. Furthermore, standardization of the amount of expression of the gene to be detected and quantified was carried out using GAPDH gene as an internal standard, and also employing KRT31 gene and KRT85 gene, which is recognized to be uniformly expressed in the sample hair shaft keratinized region, as internal standards.

As a specific primer & probe set for the detection and quantification of the amount of expression of ANXA9 gene, Assay Number Hs00185977_m1 of TaqMan (registered trademark) Gene Expression Assays (manufactured by ABI) was used.

In order to detect and quantify the amount of expression of LCE2B gene, Assay Number Hs00863535_g1 of TaqMan (registered trademark) Gene Expression Assays (manufactured by ABI) was used as a specific primer & probe set.

In order to detect and quantify the amount of expression of LCE2A gene, Assay Number Hs00820278_sH of TaqMan (registered trademark) Gene Expression Assays (manufactured by ABI) was used as a specific primer & probe set.

In order to detect and quantify the amount of expression of IVL gene, Assay Number Hs00846307_s1 of TaqMan (registered trademark) Gene Expression Assays (manufactured by ABI) was used as a specific primer & probe set.

As a specific primer & probe set for detecting and quantifying the amount of expression of CRCT1 gene, Assay Number Hs00219416_m1 of TaqMan (registered trademark) Gene Expression Assays (manufactured by ABI) was used.

The amounts of expression of the hair shape susceptibility genes in the scalp hair roots of the curly hair group and the straight hair group are presented in FIG. 10A to FIG. 10E. From the results shown in FIG. 10, decreases in the amount of expression of ANXA9 gene, LCE2B gene, LCE2A gene and CRCT1 gene were observed and an increase in the amount of expression of IVL gene was observed in the curly hair group, as compared with the straight hair group. Therefore, it was made clear that ANXA9 gene, LCE2B gene, LCE2A gene, IVL gene, and CRCT1 gene are hair shape susceptibility genes serving as indicators for the evaluation of hair shape, and the measurement of the amounts of expression of these genes in the hair root area is valuable.

Example 8

Screening of Substance Regulating Amount of Expression of Hair Shape Susceptibility Gene Normal human neonatal foreskin epidermal keratinocytes (KK-4009, manufactured by Kurabo Industries, Ltd.) were used in the screening. Normal human neonatal foreskin epidermal keratinocytes in a frozen state were melted, and then the cells were seeded in a 75-$cm^2$ flask or a 25-$cm^2$ flask at a density of 2500 cells/$cm^2$. The cells were cultured in a serum-free medium for human keratinocyte culture (Defined Keratinocyte-SFM, manufactured by Invitrogen, Inc.) containing added supplements, under the conditions of 37° C. and a $CO_2$ concentration of 50. The cells were subcultured at the time point at which the cells reached a sub-confluent state, and the cells were seeded in a 6-well plate at a cell density of 2500 cells/$cm^2$. At the time point at which the cells had reached a sub-confluent state (Day 0), the medium was exchanged to a serum-free medium for human keratinocyte culture containing no supplements, and the cells on Day 1 were used as the cells for screening.

To the medium (serum-free medium for human keratinocyte culture containing no supplements) for the cells for screening prepared as described above, a plant extract was added to a final concentration of 0.1% or 1%, and the cells were cultured for 24 hours under the conditions of 37° C. and a $CO_2$ concentration of 5%. Furthermore, as control, 50% ethanol (control) was similarly added to a final concentration of 0.1% or 1%, and the cells were cultured.

After completion of the culture (Day 2), the medium was removed by suction, the cells were washed two times with PBS (manufactured by Invitrogen, Inc.), and then 1 mL per well of ISOGEN (manufactured by Nippon Gene Co., Ltd.) was added to the cells. The cells were sufficiently lysed and mixed through pipetting, and the solution was collected in a 1.5-mL tube. Total RNA was extracted by the same method as the method described in Example 7, and cDNA for use in the quantification of the amount of gene expression by PCR was obtained. The quantification of the amount of expression of the hair shape susceptibility gene was also carried out by the method described in Example 7.

In regard to the determination criteria for a substance that regulates the amount of expression of a gene, for example, if the amount of gene expression is higher by 10%, preferably 30%, and more preferably 50% or more, as compared with the control, the amount of expression is then said to be significantly high, and the test substance can be selected as an expression promoting agent for the hair shape susceptibility gene. Furthermore, for example, if the amount of gene expression is lower by 10%, preferably 30%, and more preferably 50% or more, as compared with the control, the amount of expression is then said to be significantly low, and the test substance can be selected as an expression suppressing agent for the hair shape susceptibility gene.

Approximately 700 kinds of plant extracts were evaluated by the screening system described above, and a search was made for substances that regulate the amount of expression of the hair shape susceptibility gene. As a result, expression promoting agents and expression suppressing agents for the genes were respectively found as indicated in Table 13.

TABLE 13

Substances that regulate the amounts of expression of the hair shape susceptibility genes

| | Name of plant extract | |
|---|---|---|
| | | Amount of ANXA9 gene expression (relative to control as 1) |
| Expression promoting agent | *Cinchona officinalis* (bark extract) | 6.04 |
| | *Polygonum chinense* var. *thunbergianum* (whole plant extract) | 4.82 |
| | *Ipomoea purpurea* (morning glory) (seed extract) | 2.03 |
| Expression suppressing agent | *Ligusticum sinense* Oliv. (rhizome extract) | 0.38 |
| | *Indigofera tinctoria* (*leaf* extract) | 0.22 |
| | *Anthemis nobilis* (Roman chamomile) (flower extract) | 0.18 |
| | | Amount of IVL gene expression (relative to control as 1) |
| Expression promoting agent | *Sassafras albidum* (bark extract) | 6.00 |
| | *Passiflora caerulea* (blue passion flower) (whole plant extract) | 3.69 |

TABLE 13-continued

| Substances that regulate the amounts of expression of the hair shape susceptibility genes | | |
|---|---|---|
| | Name of plant extract | |
| | *Mitchella repens* (squaw vine) (whole plant extract) | 2.65 |
| Expression suppressing agent | *Eupatorium perfoliatum* (*leaf and* spike extract) | 0.42 |
| | *Citrus unshiu* (pericarp extract) | 0.29 |
| | *Citrus junos* (fruit extract) | 0.18 |
| | | Amount of CRCT1 gene (relative to control as 1) |
| Expression promoting agent | *Ipomoea purpurea* (seed extract) | 7.72 |
| | *Benthamidia florida* (bark extract) | 3.34 |
| | *Artemisia capillaries* (flower extract) | 2.13 |
| Expression suppressing agent | *Allium tuberosum* (seed extract) | 0.38 |
| | *Viola confusa* (whole plant extract) | 0.32 |
| | *Dictamnus albus* (root bark extract) | 0.20 |

Reference Example

Relations Between Hair Shape and Form of Hair Follicle

In general, the hair shape varies with the human races, and the people of the Asian race relatively more frequently have straight hair, while the people of the African race mainly have kinky hair (or curled hair). A large proportion of the people of the Indo-European race have a trait of wavy hair (wave hair) which is intermediate of the two. As a feature related to such variation of hair shape, the form of the hair follicle at the hair root part may be mentioned. That is, if the form of the hair follicle is curved, the hair is curved, and if the form of the hair follicle is straight, the hair is straight (Thibaut, S. et al., Br. J. Dermatol., 152(4), p. 632-638, 2005).

In order to investigate the relations between the hair shape and the form of the hair follicle in more detail, tissue specimens of hair follicle were produced from the human scalp tissues of various races, and the form of the hair follicle was observed. Meanwhile, in regard to the collection of specimens from the test subjects, an approval was granted in advance by the ethics committee, subsequently the person in charge of the implementation of informed consent explained the contents of the study to the objects using a written explanation, and written consent was obtained. The collected hair follicles were frozen after being embedded in Tissue-Tek OCT Compound (manufactured by Miles Laboratories, Inc.), which is an embedding medium for frozen tissue section preparation, and frozen section specimens were produced according to a standard method. Subsequently, the specimens were subjected to HE staining, and were observed with a microscope.

Figure 11:
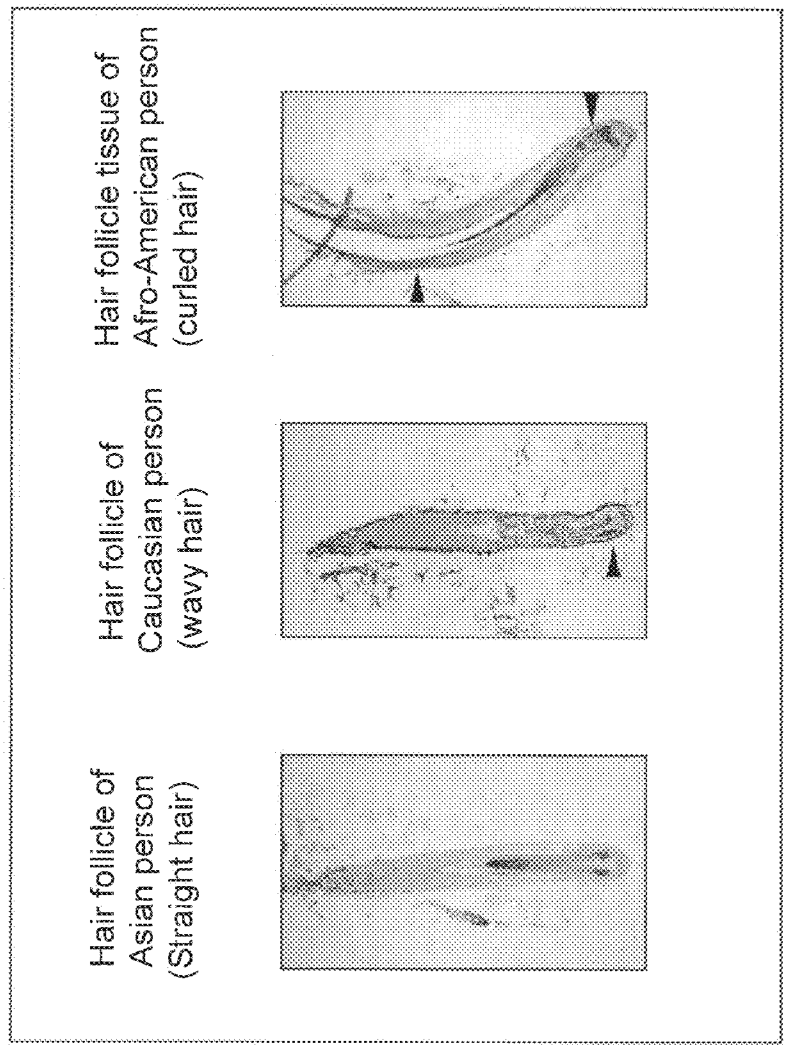
FIG. 11 is a set of photographs showing the images of hair follicle tissue of various human races, while the arrows indicate curved regions.

FIG. 11 presents images of the hair follicle tissue of various human races. As can be seen from the results shown in FIG. 11, the hair follicle of an Asian person having straight hair was straight, while the hair follicle of a Caucasian person having wavy hair was bent only at the lowermost part of the hair root. Furthermore, in the case of an Afro-American having curled hair, it was found that the entire hair follicle tissue was curved. Therefore, it could be confirmed that the hair shape and the form of the hair follicle were closely related to each other.

Example 9

Evaluation of Form of Hair Follicle Through Culture of Human Hair Follicle Organ As a method for evaluating the hair shape and the form of the hair follicle, an investigation was conducted on an evaluation method based on the culture of the human hair follicle organ. The scalp tissues of the temporal region or the occipital region of men and women in the age of 30's to 80's, which had been excised by cosmetic plastic surgery and became unnecessary, were obtained and used in the experiment. Meanwhile, in regard to the collection of specimens, an approval was granted in advance by the ethics committee, subsequently the surgeon explained the contents of the study to the objects using a written explanation, and written consent was obtained.

The human scalp tissue thus obtained was recovered in a petri dish filled with Williams' E medium (manufactured by Sigma-Aldrich Company) containing 1% of antibiotic/antifungal agents (manufactured by Invitrogen, Inc.). The hair follicles were aseptically isolated one by one under a stereoscopic microscope and using forceps and a scalpel or a needle teeth. The isolated hair follicles were separated from the epidermal tissue at the position of the lower part of the sebaceous gland, and any extra connective tissue, adipocytes and the like attached to the lower part of the hair follicle, were removed as much as possible. The isolated hair follicles thus prepared were transferred, one hair follicle per well, onto a 24-well plate to which Williams' E medium (manufactured by Sigma-Aldrich Company) containing 400 μL of 10 μg/mL insulin (manufactured by Invitrogen, Inc.), 40 ng/mL of hydrocortisone (manufactured by Sigma-Aldrich Company), 2 mM L-glutamine (manufactured by Invitrogen, Inc.), and 1% antibiotic/antifungal agents (manufactured by Invitrogen, Inc.) had been added, and culture was initiated. The culture was carried out in the manner of suspension culture, under the conditions of 37° C. and a $CO_2$ concentration of 5%. Thereafter, the medium was exchanged at an interval of 2 to 3 days, and at the same time, photographs of the hair follicles were taken.

Figure 12:
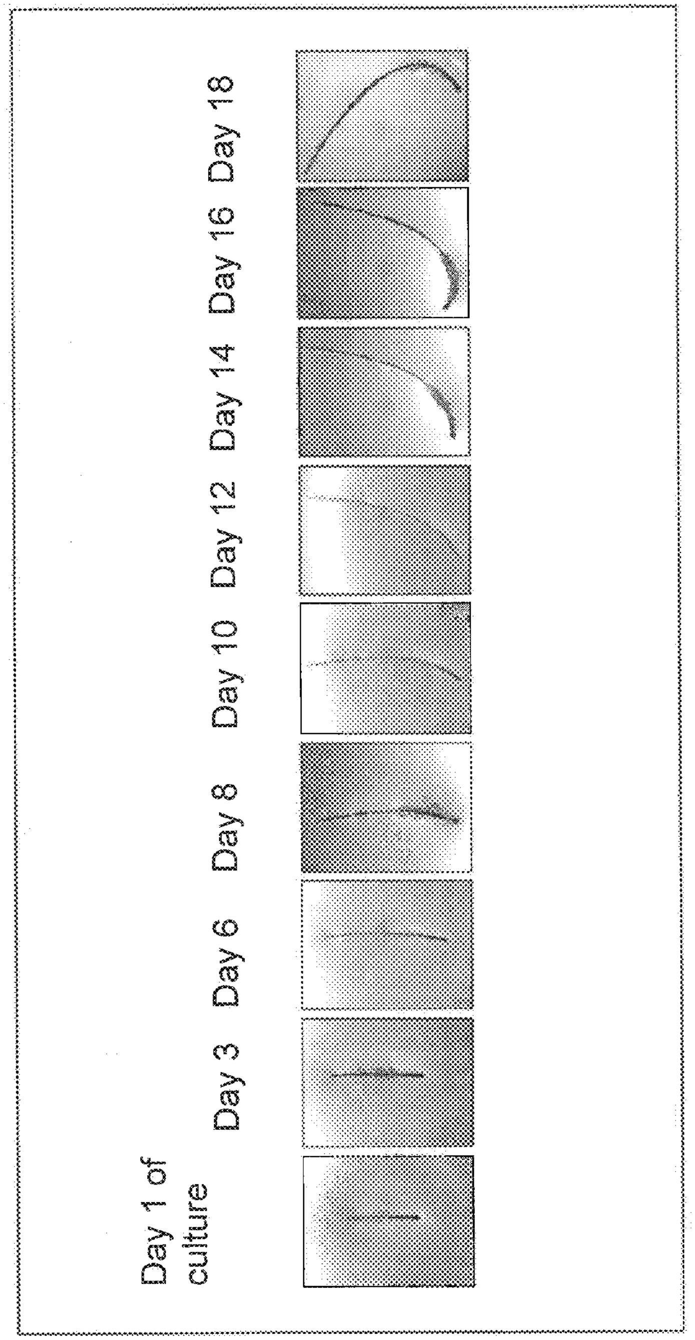
FIG. 12 is a set of photographs showing the changes in the shape of a hair follicle during culturing in a human hair follicle organ culture system.

The photographs of the change in the form of the hair follicle during culturing days are presented in FIG. 12. The hair shaft in the hair follicle grew with the progress of the culture, and thereby elongated. Furthermore, along with the progress of the culture, it was observed that the hair follicle was straight (straight hair) after one day from the initiation of culture (Day 1), but the hair follicle (hair shaft) was gradually curved with the culturing days.

In order to quantify the degree of curvature of the hair follicle (hair shaft), the ratio of end-to-end distance was calculated. The ratio of end-to-end distance is one of the indices representing the degree of curl, and can be determined by the following calculation (Hrdy, D., Am. J. Phys. Anthropol., 39(1), p. 7-17, 1973).

Straight length between the ends of the object (hair or hair follicle)/curve length along the axis of the object (hair or hair follicle)

That is, according to the formula shown above, the ratio of end-to-end distance represents a value between 0 and 1, so that a straight object gives a value close to 1, and an object with a large degree of curvature gives a value close to zero (0).

The photographs of the hair follicles shown in FIG. 11 were analyzed using an image analyzing software (Nexus NewQube Ver. 4.23, manufactured by IMAX Systems, Inc.), and the length of the hair follicle (hair shaft) and the ratio of end-to-end distance were determined (Table 14).

As a result, it could be confirmed that the hair follicle (hair shaft) elongated with the culturing days, and at the same time, the hair follicle was gradually being curved. Therefore, it was found that when this evaluation system is used, search for an agent for curling of hair, or a curly hair ameliorating agent (hair straightening agent) can be conducted. That is, a test substance is added to the evaluation system of human hair follicle organ culture, the hair follicle organ is cultured, and the ratio of end-to-end distance of the hair follicle (hair shaft) which has elongated to a certain length is measured. When the hair follicle is cultured in the presence of a test substance, if the ratio of end-to-end distance becomes smaller as compared with a control cultured without adding the test substance, the test substance can be selected as a hair curling agent. When the hair follicle is cultured in the presence of a test substance, if the ratio of end-to-end distance becomes larger as compared with a control cultured without adding the test substance, the test substance can be selected as a curly hair ameliorating agent (hair straightening agent).

TABLE 14

Changes in the length of hair follicle (hair shaft) and the ratio of end-to-end distance in the hair follicle during culturing

| Culturing days (day) | Length of hair follicle (mm) | Ratio of end-to-end distance |
|---|---|---|
| 1 | 3.465 | 1.005 |
| 3 | 4.419 | 1.002 |
| 6 | 5.732 | 0.997 |
| 8 | 6.748 | 0.998 |
| 10 | 7.571 | 0.973 |
| 12 | 8.131 | 0.958 |
| 14 | 8.758 | 0.901 |
| 16 | 9.433 | 0.825 |
| 18 | 9.720 | 0.818 |

Example 10

Evaluation of an Agent of Regulating the Expression of Hair Shape Susceptibility Genein Human Hair Follicle Organ Culture For the purpose of verifying the effect of an agent of regulating the expression of hair shape susceptibility gene on the form of the hair follicle, an evaluation was conducted using the evaluation system of human hair follicle organ culture.

The human hair follicle was prepared according to Example 9. The isolated hair follicles were divided into two groups, with 12 hair strands per group, so that there was no fluctuation in the size. One of the groups was suspension cultured for 15 days in a medium for organ culture (400 μL) to which a morning glory extract, which is an expression promoting agent for ANXA9 gene and CRCT1 gene as described in Table 13, was added at a final concentration of 0.2%. The other group was suspension cultured for 15 days in a medium for organ culture (400 μL) to which 50% EtOH (a final concentration of 0.83%) was added, as a control. According to the same procedure, a group added with a passion flower extract (final concentration 0.2%), which is an IVL gene expression promoting agent as described in Table 13, and a control group (50% EtOH, final concentration 0.83%) were prepared (n=12 for each group).

After the initiation of culture, the medium was exchanged at an interval of 2 to 3 days, and at the same time, photographs of the hair follicles were taken. From the images of hair follicles thus taken, the degree of elongation and the degree of curvature (ratio of end-to-end distance) of the hair follicles were respectively measured.

Figure 13:
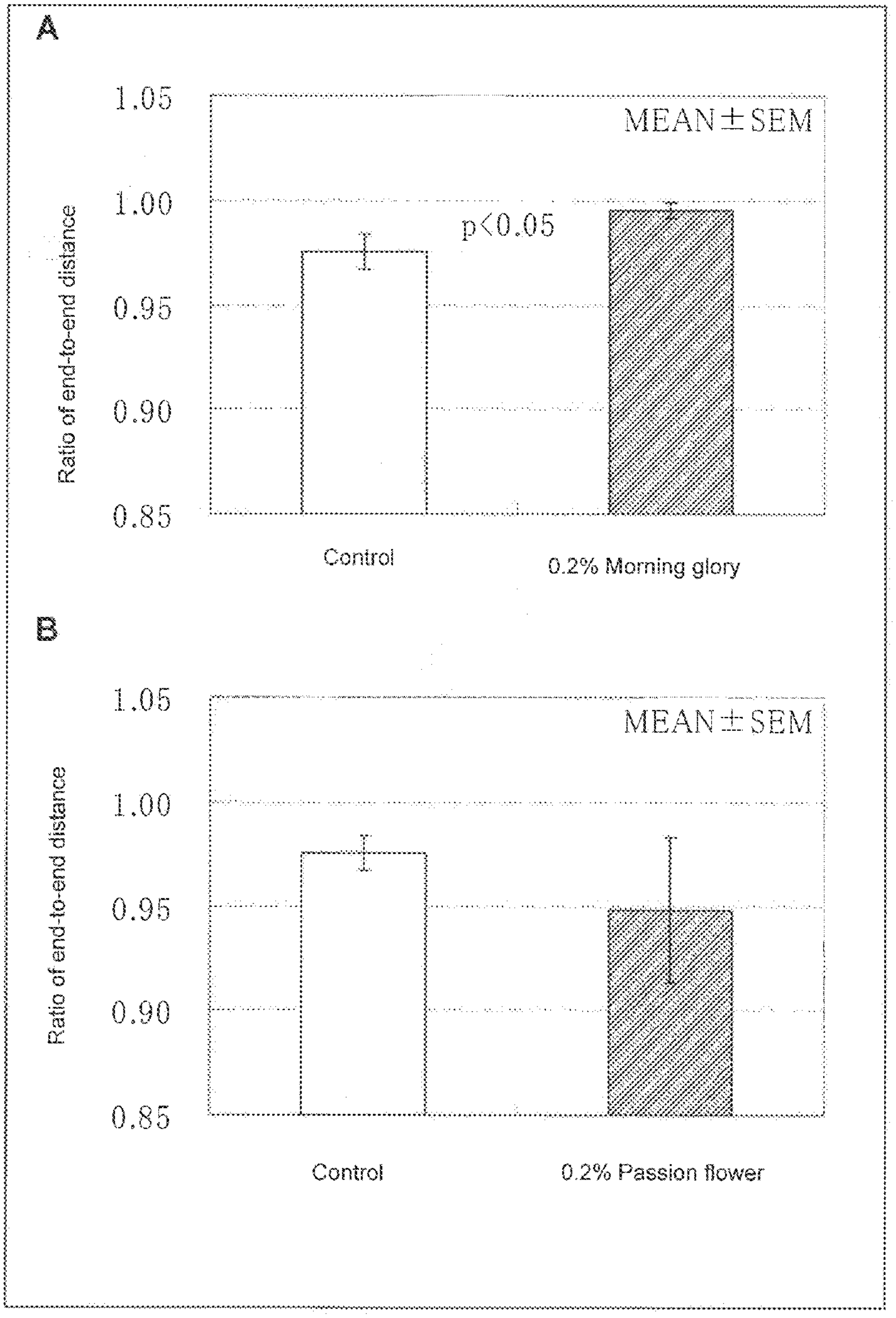
FIG. 13 is a graph showing the effect of a hair shape susceptibility gene expression regulating agent on the hair follicle shape, A: common morning glory, B: passion flower.

At the time point at which the length of the hair follicle (hair shaft) elongated by 1.5 mm or more as compared with the length at the initiation of culture, the ratio of end-to-end distance of the hair follicle (hair shaft) was measured. As a result, it was found that the morning glory extract significantly increases the ratio of end-to-end distance, which indicates the degree of curvature of the hair follicle (hair shaft), as compared with the 50% EtOH-added control, and the passion flower extract decreases the ratio of end-to-end distance as compared with the 50% EtOH-added control (FIG. 13). From these results, it could be seen that an agent of regulating the expression of hair shape susceptibility gene expression can be selected as a curly hair ameliorating agent (hair straightening agent) or a hair curling agent.

The invention claimed is:

1. A method for evaluating or selecting a hair shape regulating agent, comprising the following steps (a) to (e):

(a) culturing cells in the presence of a test substance, wherein the cells are capable of expressing a human IVL gene or a protein encoded by the IVL gene, and wherein the cells are selected from the group consisting of human hair follicle tissue cells and hair root area-derived cells;

(b) measuring the amount of expression of the IVL gene or the IVL protein in the cells that were cultured in the presence of the test substance in step (a);

(c), selecting, based on the results of step (b), a test substance that increases or decreases the amount of expression of the IVL gene or the IVL protein as compared to that in control cells cultured in the absence of the test substance;

(d) culturing a human hair follicle in organ culture in the presence of the test substance that is selected in step (c);

(e) measuring the degree of curl of the hair follicle's hair shaft; and (f) selecting a test substance from step (e) that alters the degree of curl of the hair follicle's hair shaft, as compared to that of a control hair follicle cultured in the absence of the test substance, as a hair shape regulating agent, wherein a test substance that increases the amount of expression of the IVL gene or the IVL protein, and also increases the degree of curl, is selected as a hair curling agent, and a test substance that decreases the amount of expression of the IVL gene or the IVL protein, and also decreases the degree of curl, is selected as a hair straightening agent.

2. The method of claim 1, wherein the test substance increases the amount of expression of the IVL gene or the IVL protein.

3. The method of claim 1, wherein the test substance decreases the amount of expression of the IVL gene or the IVL protein.

4. The method of claim 1, wherein the IVL gene encodes a IVL protein having the amino acid sequence of SEQ ID NO: 51.

5. The method of claim 1, wherein the sequence of the IVL gene is that of SEQ ID NO: 50.

6. The method of claim 1, wherein the cells in step (a) are human hair follicle tissue cells.

7. The method of claim 1, wherein the cells in step (a) are hair root area-derived cells.

8. A method for evaluating or selecting a hair shape regulating agent, comprising the following steps (a) to (g):

(a) introducing a fusion gene to cells, wherein, in the fusion gene, a regulatory region of the human IVL gene is linked to and controls expression of a reporter gene, wherein the cells are capable of expressing an expression product of the reporter gene and are selected from the group consisting of human hair follicle tissue cells and hair root area-derived cells;

(b) culturing the cells that contain the fusion gene of step (a) in the presence of a test substance, (c) measuring the amount of expression of the expression product of the reporter gene in the cells cultured in the presence of the test substance;

(d) selecting, based on the comparison results of step (c), a test substance that increases or decreases the amount of the expression product of the reporter gene as compared to that in control cells cultured in the absence of the test substance;

(e) culturing a human hair follicle in organ culture in the presence of the test substance that is selected in step (d);

(f) measuring the degree of curl of the hair follicle's hair shaft; and (g) selecting a test substance from step (f) that alters the degree of curl of the hair follicle's hair shaft, as compared to that of a control hair follicle cultured in the absence of the test substance, as a hair shape regulating agent, wherein a test substance that increases the amount of expression of the reporter gene or the reporter protein, and also increases the degree of curl, is selected as a hair curling agent; and a test substance that decreases the amount of expression of the reporter gene or the reporter protein, and also decreases the degree of curl, is selected as a hair straightening agent.

9. The method of claim 8, wherein the test substance increases the amount of expression of the reporter gene.

10. The method of claim 8, wherein the test substance decreases the amount of expression of the reporter gene.

11. The method of claim 8, wherein the sequence of the regulatory region of the IVL gene is that of SEQ ID NO. 57.

12. The method of claim 8, wherein the cells in step (a) are human hair follicle tissue cells.

13. The method of claim 8, wherein the cells in step (a) are hair root area-derived cells.

* * * * *

SEQUENCE LISTING

```
<160> NUMBER OF SEQ ID NOS: 58

<210> SEQ ID NO 1
<211> LENGTH: 23252
<212> TYPE: DNA
<213> ORGANISM: Homo sapiens

<400> SEQUENCE: 1

gagggccagg gggaccccgg ctgcggagct gcagtaccgt gtttacccag cctaactgcg      60

gtcacccagt ctcctgcatg tgtctgaggt cagcctcggg ggctcccctg agtaggtatc     120

tacctgaggc tcttcccctg atgctacctg cataccaatt ccacccagga acctggcgtc     180

ctcaggaggc tgcacttccc aagtgggctg agacagcccc ttaatatgtg gggctggagc     240

cagagacctc aaggggccac tagggggctc gagactctca gtggctgctg acgccctctt     300

gtggccattt tggggattgg ccagaaaagt ttcagaagcg agccaagatc ggaattctta     360
```

```
aggaggtaag taataacaac agtaacagtt accatataac aatacttatc gttatatatt    420
tgataacatt gtgacatttc tacttaacag cgctgtgccc agaactcttc taagtgcttt    480
atatgcactg tagttattta attctcacaa caacctataa cataaacact attacttgtc    540
tgttgatgat gaggaaactg agcacagaat agttgcccaa ggtcacacag aagaccagaa    600
tcccgactct gagaagtctg gctccagaag ctttgctttt agccaccacg ctgagactga    660
gttccatttt ggggttgtca ggtgaaatac aggacacact gttaaactat aatttcagat    720
aaacaaaaaa taataattac aggcggtggc tcacgcctgt aatcccagca ctttgggagt    780
ccaaggcagg tggatcacga ggtcaggagt tcgagaccag cctggccaac atggtgaaac    840
cctatctcta ctaagaatac aaaaaattag ccaggcatga tggcaggcgc ctataatccc    900
agctactcgg gaggcggagg caggagaatc gcttgaaccc gggaggtgga gcttgcagtg    960
agccaacata atgccactgc actccagcct gggcaacaga gagagactcc gcctcaaaaa   1020
aaaaaatgtt agtatattta atgaaatatt tgggtcatac ttgtaccaac aaatgattcc   1080
tcatttacgt gaaattctga ttaagctgca tgtcctgtat atttatttat ttaatctaat   1140
acccctactt tacagggcac ttttctctgc cacatgcaat tacacagatt actttttttt   1200
tttttttttt tttttgagac ggagtctcac tctgtcgccc aggctgtgga gtgcagtggc   1260
gccatctcag ctcactgcaa cctctgcctc ccaggttcaa gtgattctcc tgcctcagcc   1320
tcccgagtag ctgggattac aggcatgcgc cgccatgccc ggctaatttt ttgtattttt   1380
agtagagacg gggtttcact gtgtaagcca aggctggtct cgatctcctg cctcatgatc   1440
cacccgcctc ggcctcacaa agtgctggga ttacaggcat gagccaccgt gcctggccac   1500
attaccttat ttatttattt atttatttat ttatttttat gagttcaata gtttttgggg   1560
acaaggtggt gtttggttac atggataagt tctttagtgg acacattact tcatttaatc   1620
atcccaggaa acctgtcctc ggaggcccca gcatgtccca cagcctccgt ctctctcaat   1680
cctcccattt agagagctga aaggactagc gaagcttaca gaacataggt ggcagagctg   1740
gatattgaac cctcattctc cagttctgac acaggtgcat gttttccttt taacaggaga   1800
gaaaagtgag gagcagtgat taccgccaca gaaatatcct ttcatggcgt gtcctccggc   1860
atggtctact cagtgtggtg gagccactgc aggtccctcc tccagggatg taggaatgcc   1920
agtgaaggcc ttcctgagtt gggagagagg cagaggagtg agtggaggca gggctgtagc   1980
ttctgtgccc cgcccctacc caggctctcc agggaggcag gaaagaggct gtgtttagac   2040
ctgagggagc cagctgtgag gctggagcag ttgctgcatg gcggggcggg ggctccacag   2100
ggctgttcac ctgctgctct gtgcagagac agcctcaagt ccagctgctg gggttgcatc   2160
acctgcagct aaaacagcca cagggcccag gctgccaaaa ggcaacagaa gcaatctaag   2220
aaaccaggca agggagcctc ccccatctcc ctgttgcctt ttgggagcat agagcttccc   2280
tctgaaggta acaccctttg catttttctc tcttgactct gttcatcaac ttccactccc   2340
aaatacttgt gcccttcctt ctccacagat atacacaatc cctgggcact ctccacctag   2400
gtcagctggc tctagtaagg cagcagtcaa gggagtttct gggctgggac cccctctggg   2460
gtgcaggctg gggtgccctg ctggtatgtg ccccaacagg tttttcccta tcagccttga   2520
aatcagcctg cagcctgtct gacctgcccc ccagggagct ggagccagag gcagagccag   2580
gtcagaagct ggggcagagc caggtcagaa gctggacttt gagactaggt ctctgtggtc   2640
ccacctggac ccacagggaa ggcagtgcat aaaagcctcc tgtgtttgag gctgagccgc   2700
tgagaggctg agtggagttc actcacatgg attgaggccc agttcctggg agaagagatg   2760
```

-continued

```
ctgggcagga aggtgtctgc atgtgggact ctgtacagcc cggtcctctc ccacgtctgg   2820
gaggggccag agtcagacaa ctgctgggtt cgtccctaag agaggtcatc tgactggctg   2880
ttcagcctag gctgcacaca cccccacttt cctctaccag gccacaccgg aggcagtgct   2940
cacacaggca agctaccagg ccacaacaac gacacccacc tcacctctgg cacctctgag   3000
taagtactgg gcccacggcc ccatgccagg agggcttgtt gattgcttgg gggagggaaa   3060
aatgagtttt ccttttccaa catgagagtg cctcctttct gtccaggcat ccacgtactt   3120
gcaagaactc ttgctcacat cagctaagag attgcacctg ctgacctaga gattccggcc   3180
tgtgctcctg tgctgctgag caggtaggca gctgtacagg caggaattga gggttgcttg   3240
tcagctgggg ctgccggtgg gggaagatgc tatttcgagt tgtcttccac tctgcgtggt   3300
taatcctgcc acctcacctc agctcccctg cactgcccag gagaccccag ccaggcccag   3360
gaaggagggc catagacctc agaagggagg catctaccgc ggaccaaggc ctgaggagct   3420
ttggtgctga ccctggcatc agggagggtt ggcgcctggt ccaggagcat tccgcatcaa   3480
tccccacttc ctaaaggagt ggggagaggt ggggaaggtg ggggctcccc tcttacctca   3540
ccatttcagc tccatttctg gctccaagcc taagcaggtt gatctttttt tctgcagcaa   3600
ggaaaggaac aggtgactgg aacccagggt ccagggtctc ggggggtca taaggagtcc   3660
ctgaagggcc aggaaattca gctctgtggg ctcctgtttc cttccccagg gcaaccagta   3720
gcaccatgtc tgtgactggc gggaagatgg caccgtccct cacccaggag atcctcagcc   3780
acctgggcct ggccagcaag gtaggggctg ttgggatttt agagatcact tttagtatct   3840
cagctcgggc tgtgagagga tgggaggcag gaaagtggag gacaggccct gaggttatgc   3900
tgaggaggtg taggcagcct ggccctggcc cttgccaact accctgtgct cccacagact   3960
gcagcgtggg ggaccctggg caccctcagg accttcttga acttcagcgt ggacaaggat   4020
gcgcagaggc tactgagggc cattactggc caaggtgagc ccctttcccc cggcacttga   4080
gactgccttt tagagccaat ctgtagacca aggaggagcc aggaaggagg aactagtgat   4140
gttggagaaa tgtttgtgga atgccttcat tcttgtatgt caggcgccac agtaggtgtg   4200
tcaaacccat tctcacaaca cccctgtgag gcaaggctta ttatttccat tttccagatg   4260
aggaaactgg ggctcaggga gattaagagg cttgcccaag gtcactcagc tcatgacgga   4320
ggtggtattc tcatctaggt cagccgatcc ccccaagtcg tatttttttt taaccaccac   4380
accaggccac ctttgccttg gtctgggtca gatttgcatg ctgttttgac attttatttg   4440
caacttcttt tgagataaaa tggaagtggg ggtgatatag cccctgctcc tttccttccc   4500
agccctctcc tggagcgcct tccctcctcc aaggagtagg aacatcccac tatgtaaaga   4560
ccctgctcac agcacagccc tcatctcggt tcaggcgtgg accgcagtgc cattgtggac   4620
gtgctgacca accggagcag agagcaaagg cagctcatct cacgaaactt ccaggagcgc   4680
acccaacagg tgaggccatg ctgacctccc acagcagtgg actggggtga gaaacccccct   4740
ggaggactcg agagacagca acagccgctg aggccagccc ctgcttcctg gctaaacagg   4800
gcctgagatg aaaaccagcc aaatcttccc aaacctcccc acacttctgg ggcccttccc   4860
ctcacccccg tccctctgct gtgaggacca tttattgtag gacctgatga agtctctaca   4920
ggcagcactt tccggcaacc tggagaggat tgtgatggct ctgctgcagc ccacagccca   4980
gtttgacgcc caggaattga ggacagctct gaaggtagca ggaggggaga cttgctgggg   5040
tgtctgggga agggagaagg ctgtcagcct tgcttttgca agacgagagt cccctctcg    5100
```

-continued tcgtcccata ttgtttctta gaaggagaag cagccagcgt ctgcccctct gtctgccatc 5160
ctaatgacac ggccagtctg agagtagact cccaatttct tgtaggcctc agattctgct 5220
gtggacgtgg ccattgaaat tcttgccact cgaaccccac cccagctgca ggagtgcctg 5280
gcagtctaca aacacagtaa gaatatagag ggaggggtcc cagatgctgg agaaggggct 5340
gtaggacagg ccactcctct cctgtactcc ccataggtga gctatctggc aacctggctg 5400
cctaagttct attcccttgg ggtctttcct cttgcccca ccagtgcctc agtctctcag 5460
gggagagacc cagatgtgat cattaaaaaa agagaagcag gccaggtacg gtgactcatg 5520
cctgtcaccc caacactttg ggaggctgag gtgggcaggt cacttgagcc caggagttca 5580
agaccagtca caggcaataa aggaaaacct catctgtgct aaaaattcaa aaaaaccagc 5640
tggtcatggt ggtgtgcgcc tgtggtccca gctactcagg agtttgaggt gggaggatca 5700
ccccagcttg ggaagttgag gctgcagtga gctgagatcg tgccactgcc actgcacacc 5760
agcctgggtg acaggagtga gagcatgtct ctctctctct ctctctctct cacacacaca 5820
cacacacaca cacacacaca aataaagaga gagaagcaat gattaaccat cttaatctgg 5880
agctccaagg cagattccaa agtgacagtc ccaaaggtac tcatgtcacc ttcccagccc 5940
cttgccatcc ctgccatcac accacattcc aagctgaacc cagccatgct gcagcctgag 6000
gaaaaggtgg gaatctgccc tctgagtcat gggtgtcacc tttcatgtcc ctgatggctg 6060
gccttgcttg gctacaagtg tctcacccac taatttgtgg ctttttccca tcctcatctt 6120
accacccctt ccccccaccc ctacctcttt ttcttgcttt ccccaatttt cctttgatgt 6180
ctaatcttgg cctatgttct tcttttgaga caaggtcttg ccctgtagcc taggctgtgc 6240
agtgatgtca tcatggctca ctgcagcctt gacccttctg ggctcaatca gtcctcccac 6300
ctcagcctcc taagtagctg ggactacagg tgtgccacca ccatgcccag ctaaattttg 6360
tattttttgt agagatgggg tttcgctgtg ttgtccaggc tggtctcgaa cttctgggct 6420
caagccatct cctgcctcag cctctgaaag tgctgggatt acaagcatga gccaccgccc 6480
tggccgtggc ctatgttctt aatccctctc ctaccttcct tccttcttgc atctgtttcc 6540
cttttctctt tctttttctc cctttcctgc tcttttcctt cctcatatcc cacctctcat 6600 atcattttc cttacctcca atgagggtgc caggtcctaa ccatcttgtg ttataatacg 6660
ggtttcccta gctcttcttc actgcctggc cccaactcta ataatggttg cctcctgccc 6720
agcaggttgg tgcttggtga tgaagccact gcacacctca caacttagag atgtttttag 6780
agtggccgtg atggtacttg tgccttacat cctgggaatt agcagccatc aagctactcc 6840
aagcaggggc tagcagggct ggcagggtat agcgggtcag gcatttggca ggtcctgggg 6900
atatctacac taggaaaact caggaggatt cagagagctc ctcaccccac cccagatttc 6960
caggtggagg ctgtggatga catcacatct gagaccagtg gcatcttgca ggacctgctg 7020
ttggccctgg ccaaggtgag gaggactgac ctgcaaggaa gggagtcacg ttcaccaggc 7080
aaggagacac gctggagcag ggagcattgc tgtcctgtaa tggacaagag agggctttag 7140
gggagaccag ccttcgcttg ttggtctgaa gataaaaagg tgcccttcaa agagccctct 7200
aagaacagtt tctcctccta ggggggccgt gacagctact ctggaatcat tgactataat 7260
ctggcagaac aagatgtcca ggtgagcagg gggtttagga gtgtgcacag ccgccatgca 7320
cataagatgc cttcctccac catatcttag agccggtgac ctacgtgccc atttttcccg 7380
caaacccatc cctgccttgg agagggagtt ctcagttatg tggtaggggc aggaggtgtc 7440
aggtagcgtc atagctgaag ccttttcact catctagcct ctgactcctg agctcatcaa 7500

```
ctgacatatt ctcctctcat gagcgtttgg gggcagaaag cctcctcaga ccttttgggg   7560
attatttaat cctcgggtac caggattttt ccaaatcagt gaatagagct gtgaggctgt   7620
aagggcagag ccctctctta gccctatttc tttcttaaaa aataaaaaac ataagataaa   7680
aaaacataaa taaaaacaac tagtaggcca ggcatggtgg cttatacctg taatcccagc   7740
actttgggag gctgaaacaa gaggatcact tgagcccagg agtccaagac cagcctaggc   7800
aacatagtga gactctatct ccacaaaata tttttaaaaa ttagctgcac ctgtagttcc   7860
agctagctag gaggctgagg tgggaggatc gcttgagcct gggaagttga ggctgaggta   7920
agccctggtc atgccactgc actccagcct gggtgacaga gagagacccc atctctctcg   7980
ctctctctct ctctctctct cacacacaca cacacacaca cacgcacaca cacaaaccta   8040
gtttacgggt taaaataaac tttctggctg gtcgtggtgg ctcacaccta taatcccaac   8100
aatttgggag gccgagacag gtggatcact tgaggtcagg agttcgaaac cagcctagcc   8160
aacatggtga aaccccgtct ctactaaaaa tacaaaaatt agccaggcat gatggtgagt   8220
gcctgtaatc ccagctactc aggaggctga gcctggagaa tcacttgaac ctgggaggca   8280
gaggttgtgg tgagctggga tcacaccatt gcactccagc ctgggtgaca gaatgagagt   8340
ccttctcaaa aaaaaaaaaa aaaatccttt tccaccctca atcccatttc catcatgatg   8400
atgatagatt ctggaacgtc atacccatgg ctccctaggc cccaaccaat gatcctgatt   8460
gactcctccc tgactcattc ctccctccta ggcactgcag cgggcagaag gacctagcag   8520
agaggaaaca tgggtcccag tcttcaccca gcgaaatcct gaacacctca tccgaggtac   8580
acacaagcct tcttgtcccc ctagcttgct ctaatgatca gtttgggctg aggaaggtgg   8640
ggagggccca tcctttccag agataattaa tcccccatcc atctttctaa ctgcctccta   8700
cacacacaag tgtttgatca gtaccagcgg agcactgggc aagagctgga ggaggctgtc   8760
cagaaccgtt tccatggaga tgctcaggtg gctctgctcg gcctaggtag gggcctgctc   8820
aggatttgtg aagtaagtct ctcttgggat gggagattgt ggtcctagtt gtgaacctcc   8880
atccttccat ctttgtttcc agcttcggtg atcaagaaca caccgctgta ctttgctgac   8940
aaacttcatc aagccctcca ggtgagaggg gcactccttt ccctccccag aacagaaact   9000
ggggaggaga gaggaagtct cagcttgctg cttatgtaac catcctatat acaccgtcta   9060
aacctcaagc cgctctcctt cccagggctt acacaccagg gcttacacag gggtggagga   9120
atgagctgtg gtgagaacta acttagttgg ctcccagggg ccctgaaact aacattttgg   9180
ccttgttaat gtctaggtgg ccaaatagag atatgaatct gctctgtaag acagtgcctt   9240
gtgcaggctt agttgttgcc agagtgatgg tgataacact agcaagaata atgacaaggg   9300
ctggcatttt gcaggtgctg attgtgtgcc acagcctatc ctgagcaggg cacacatatt   9360
tcaattaatc ctcacaacca tatccatccg tatcttatag atgaaaaaac tgaagcccag   9420
agaagttaag taccttgctt gaggtcacgt agctagtaag ttatacagtc tccctacaca   9480
acacttcacg atgtaagata ttgaccatcc ttgtcagcta tacgataagt gctcttagca   9540
cccaaggccc cctttctcca cgctggtcag attttgttcc acattatcca tacttttttt   9600
tttttttttg agatggagtt tcactcttgt tgcccaggct ggaggctgga gtgcagtggc   9660
acaatctcgg ctcatggcaa cctccgcctc ctggattcaa gcgattttcc tgcctcagcc   9720
tcccaaatag ctgggattac aggcgcccgc caccacatta tcctaatttt ttgtattttt   9780
agcagatgcg gtttcaccat gttggtcagg ctggtctcaa actcctgacc tcaggtcatc   9840
```

-continued

```
aacctgtctc ggcctcccga agtgctagga ttacaggcgt gagccactgc gcccagccca   9900
tattatccgt acttaaactg ctgactgtgg cttgagtgct tccaccaata gaatccagtt   9960
attctgttga ttgaattagg tctcctatta gtagaactgt cccccaaaat ctataaataa  10020
aaagttcagg aagggcgcag tggctcacgc ctataatccc agcactttgg gaggccaagg  10080
tggatggatc acttgaggtc aggagttcga gaccagcctg gccaacgtgg tgaaaccctg  10140
tctctactaa aaatacaaaa attagccagg catggtggca ggcacctgta attccagcta  10200
cttgggagtc tgaggcagga gaattgcttg aacctgggag gcggaggttg tagtgaacca  10260
agatcacgcc actgcactcc agcctgggtg acacagtcag actaaaaaag tagttatcat  10320
tttggcagat ggaatagctt tctgtagact ggttgagaag ccatcatgcc atgttgatga  10380
ttgcccaaaa gttagtaaat ataagcaatt gttctgtcat ctagagattt ctatcttgac  10440
agtagattat tatacttgcc caataaagcc tgtatgatta taatgagtca acactaagat  10500
tcatttgaag agttgtactt atctgtccaa attcctgtca taaatacaaa ctatcccagc  10560
agtagatgat tttgtagtgt atttggatta caagacccac actcttgagt gtagataaaa  10620
gatttatctt agaagtagta gtcaggggcc aagcatggtg gctcacacct gtaatcctag  10680
cactttggga agctaaggtg ggaggatcgc ttgaggtcag gagttcaaga ccaacttagg  10740
cgacatagca agaactcgtc tctacaaaaa taagaagaaa atttgccagg catggtggca  10800
cctgcctcta gtcccaacta ctcaggagga tgtggtggga ggattgcttg agcccatgaa  10860
ttagaagtta cagtgagctg tgattactcc actgcacttc agcctgggta acagagcaag  10920
accctgtctc aaaaaaagaa aaaaagaagt ggtagtcaga aaataacata ggcccatttt  10980
tctgaaaaaa aaaatttttt ttttgagata gagtctggct ctgttgccta ggctggagtg  11040
cagtggcgtg atctcagctc actgcagcct tcaccttctg ggttcaagtg attctctggc  11100
ctctgtgtct taagtagctg ggattacagg cgtaggccac catatctggc taattctgaa  11160
ttgtttctaa aaaggaaaaa ctcgggctgg gcgctgtggc gcatgcctgt aatcccagga  11220
ctttggtagg ctgaggcggg tggattattt gaggccagga gttcaagacc agcctggcca  11280
acatggtgaa accccatctc tactaaaaat acaaaaatta gccagggggt agtggtgagc  11340
gcctgtaatc tcagctactt gggaggctga agcaggagaa tctcgagcct gggaagcaga  11400
ggttgcggtc agccgaggtg acgccactgc gctccagtct gggtgacaaa gtgagacctg  11460
cctcaaaaaa aataaataaa caggccaggc gcggtggctc atgcctgtaa tctcagcact  11520
ttgggaggcc aaggcgggcg gatcacgagg tcaggagatc gagaccatcc tggctaacaa  11580
ggtaaaaccc tgtctctact gaaaatacag aaattagcca ggcgtggtag cgggcgcctg  11640
tagtcccagc tacgctggag gctaaggcag gagaatggct tgaacccagg aggcggagct  11700
tgcagtgagc cgagatcgcg ccactgcact ccagcctggg caacagagtg atgctccatc  11760
tctaaaaaaa aaataataat aataaataaa taaacaaata taaaataaat aaataaggaa  11820
aaaatcatga tacatctgta ttattctttt tatttatttt tatttttatt tttttagatc  11880
gagtctcact ctgtcgacca ggctggagtg cagtggcgcg atctcggctc attgcaacct  11940
ccgcctcccg agttcaagcg attcttctgc ctcagcctcc cgagtagctg ggattacagg  12000
cgctcaccac catgcctggc taatttttgt gtttttagta gagacggagt ttcaccatgt  12060
tggtcaggct ggtccttaac tcctgatctc gtgatccaca cgcctcagcc tcccaaagtg  12120
ctgggattac aggcctgagc caaggtgccc ggccttcttc ttcttctttt tttttccttt  12180
gagatggagt ctcactctgt cgctaggctg gagtgcagtg gcacgatctt ggctcactgc  12240
```

aacctccacc tcctgggttc aagcaattct cctgcctcac cctcccaagt agctggaact 12300
atagttgccc gccaccacat ccggctaatt tttttgtttt tagtagaaac agggtttcac 12360
cacgttggcc acgctggtgg caaacttttt ttttttttctt ttttaagatg gaggcttgct 12420
ctgtcaccca ggctggagtg caatggcgcg atcttggctc actgcaacct ctgcctcctg 12480
ggttccagca attctcctgc ctcagcctcc tgagtagctg agattacagg cgcccgccac 12540
cacgcccggc taatttttgt atttttagta gagacagggt ttcaccatgt tgaccaggct 12600
ggtctcaaac tcctggcctc aggtgatcca ccagcctcag tcttccaaag tgctgggatt 12660
acaggcgtga gccaccgtgt ccagcctgta ttattctttt atgagagata tgtagatata 12720
tgaaaacata aattgtgaag aatatttatt cagaaaaaca accttcagaa aatcagcaat 12780
ggctgattca ggacaaattt ccaccaatct gtagtaaaaa ttaatgttcc tggtgaagat 12840
cctagggcca tatgcaatgc caggtatacg attaagtatt ataattaggc caggcatggt 12900
ggctcatgcc tgtaatccca gcactttggg aggccaaggc aggtgaatca cccgaggtca 12960
ggagttcgag accagactga ccaacatggt gaaaccccgt ctctactaaa tatacaaaat 13020
tagctaggtg tggtggtgtg cacctgtatt tccagctact tgggaggctg agataggaga 13080
attgcttgaa cctgggaggc agaggttaca gtgacctgag atcgcaccac tgcaccccag 13140
cctgggtaac agagtgagac tccatctaaa caaacaaacc atatatatat atgctgaagc 13200
gagcagatca cttgaggtca ggagtttgag accagcctgg ccaacatggt aaaaccccac 13260
ctgtactaaa aataaaaaaa ttagctgggc gtttggcaca tgctatagtc ccagctgctt 13320
gggaggctga ggcaggagac ttgcttgaac ctgggaggcg gaggttgcag tgagctgaat 13380
tcacgccact gcattccact ctgggtgaca gagcaagaaa aaagaatact tgtacaacaa 13440
tgagagtatt cagttaatga gtgactcttg cccaattctg taactttaga gtaacaagcg 13500
ttggaagaag agaagaatgg atactgggga gcaattggca atctttatga caatacaaaa 13560
ctaatgatgc ataaaagtta aaatgaagta gacattaggt ccactgacaa ttaggtaatg 13620
agtctaaatg aattggagca tcctgtttta cttcattttc ttttgttttg tcaaaggagt 13680
ttatgatcta ttgggatgcc ctaagtatgt gttgtaggca gttctgggaa gagtcttgtg 13740
agtaaagtga ctcaggaaac tctgaaaatg aggatattag gaattgatga caacactggt 13800
gcacagaaaa aaaaaaacac aggaatttta caattaaaag tttttattta aaaatctctc 13860
ataacaacac attacttagt ataatcaatt ataattcagg attttgatga cttgtacctg 13920
tgttatttct tttcttttct ttttttttga gacggagtct tgctctgtcc caggctggag 13980
tgcagtggtg tgatctcagc ttactgcaac gtccgcctcc caggttcaag caattctcct 14040
acctcaccct cctcagtagc tgggattata ggcgcctacc accacacctg gctaattttt 14100
gtagttttaa tagagacggg ggtttcacca tgttggccag gctggtctcg aactcctgac 14160
cataaatgat ctgcttgcct tggcctccca aaattctggg attacaggca tgagccacca 14220
cacctggcct gttatttctt ttttctttct ttcttttttt tttttttttt tgagacggag 14280
ttttgctctt cttgcccagg ttggagtgca gtggcgcgat ctcagctcac tgcaacctcc 14340
gcctcctggg ttcaagcaat tctcctgcct cagccttcca agtagctggg attgcaggca 14400
cccaccacca tgcctggctt atttttgtat ttttagtaga gacggggttt caccattttg 14460
gtcaggctgg tctcgaactc ctacctcaga tgatccacgc gcctcatcct cccaaagtgc 14520
tgggattaca ggcatgagcc actgtgcctg gcctgttatt tctaaactga acctttcatt 14580
actttcttta gccaaaaaac aggcctgctg catgtacagg aggaagatag caatgtttca 14640
gcctaagggt ccaaccggag aaactaatat gcagagatgg ggctgtgaga tggccctatt 14700
gggttggaat cagaactaga agtcacacaa ccttgaaccc tatcagagcc tcatcagctc 14760
agtttaggga tagggcaggt atatcctcct tggatattca ctaacttgaa agttaaaagc 14820
agttttcctg gttttcatgc tggcagtctt tatatgcacc aaatcttttc tagccttcct 14880
ggtgtaccta tctttggagc tgctcaccac caaattctgg aggtacacag ctctaagcta 14940
atggtagggg caggaaagac atgtggaaag aaataaatac tcaagctgcc cccacagaga 15000
ctgatctttc ctgctgtgtc atcttccttg aggatggaca aacataactt ttgtcccgag 15060
ataatgtata atgtacactc ttatcccttg actcccacct tgcctcccct tcctacaata 15120
accctccaag ccattcaacc cctactctca gtgagactct cactaactac cccccatctc 15180
tttcttcccc tactaggaaa ctgagcccaa ttaccaagtc ctgattcgca tccttatctc 15240
tcgatgtgag actgaccttc tgagtatcag agctgagttc aggaagaaat ttgggaagtc 15300
cctctactct tctctccagg tgaaacttgg ctacttctta gcctggagcc tcaggccttc 15360
actcctcacc tccaccctca ctccctgcac acagctgagc atattcttgc cccatagaaa 15420
acccagtagt tagccaggca cagtggctca cgcctgtaat cccagcactt tgagaggctg 15480
aggtgggcgg atcacgaggt caggagttca agaccaccct gaccaacatg gtgaaacccc 15540
gtctctacta aaaatacaaa aattagccag gcatggtggc gtgcacctgt aatcccagct 15600
actcaggagg ctgaggcagg agagtcgctt gaacccagaa ggcagaggtt gcagtgagcc 15660
aagatcgtgc cactgcactc ccacctgggt gacagggcaa gactccatct taaaaaagaa 15720
aacccaggag tctttggtta atgtagtgca ggactctgag ctcccgggag gacccttccc 15780
tcccagatga actgtgatgg accagcccaa aggaggggag agagcacttg ggccatagtg 15840
gtggtggatc tttctaacac tgaattccct tgtctgcagg atgcagtgaa aggggattgc 15900
cagtcagccc tcctggcctt gtgcagggct gaagacatgt gagacttccc tgccccaccc 15960
cacatgacat ccgaggatct gagatttccg tgtttggctg aacctgggag accagctggg 16020
cctccaagta ggataacccc tcactgagca ccacattctc tagcttcttg ttgaggctgg 16080
aactgtttct ttaaaatccc ttaattttcc catctcaaaa ttatatctgt acctgggtca 16140
tccagctcct tcttgggtgt ggggaaatga gttttctttg atagtttctg cctcactcat 16200
ccctcctgta ccctggccag aacatctcac tgatactcga attcttttgg caaacttcgc 16260
tgttgtttgt gttccctgat tgaaggttgg gtggagcagg acatggaccg ggaagaggca 16320
ctggagttgg aagtgccttt gatgtgcact tggctattcc gcaggaatcc tgttttgcct 16380
tagtgctaca gtaatccaca cccaggtctc ccactccagg tctcccctca ccctcattct 16440
ccaggaaact tcaggcaaaa taattgagaa acaggcatta gaacaaggtg agaaatagag 16500
ggagcaaagg accatctgta tgaactggga agcaagcgga gggccaagct accctcccca 16560
gcatgggaat tcttgggtta gtggagagca caaccctcaa attcatgtgt ccaagcagag 16620
atttggaaac ccacctccca ggagagcact atttcccata gaaaacaaaa acaaaaacag 16680
aaacaaaaac aaaaagtcag gctttggttc cccctgcagg ctatattaga aatgacaggt 16740
agctgggcgc agtggctcac gcctgtaatt ccagcacttc gggaggccaa ggcaggcgga 16800
ttacttgagg tcaggaattc aagactagcc tgaccaaagt ggcgaaaccg tctctactaa 16860
aaatacaaaa attagctggg cgcagtggcg catgcctgta gtcccagcta ctcaggaggc 16920
tgaggtagga gaatcgcttg aatccgggag gcggaggttg cagtgagctc agattgcacc 16980

-continued

```
actgcactcc agcctgggca atacagcgag gctccatctc aaaaaaaaaa aaaaaagaaa  17040
aaaagaaatg acaggtaacc accttcctgc ctctgaccca cctcccgctt tttgcattct  17100
tcaattgggt caaatactta accctattgc ttcagggtaa ggcaaacaac agatctcagg  17160
aaagaaggtt tttttttttt ttagacagtt ttgctcttgt cgcccaggct ggagtgcaat  17220
ggtgcgatct cggctcactg caactttcac ctcccaggtt caagtgattc tcctgcctca  17280
gcctcccgag tagctgggat tacaggcgcc caccatgacg cccagctaat ttcttgtatt  17340
tttagtagag acggggtttc accttttttgg gcaggctggt ctcgaactcc taacctcagg  17400
tgatccgccc accttggcct ctcaaattgt tgagattaca ggagtgagcc accgtgcccg  17460
gccagaagtt ttatttccaa accccaggaa ggcattacaa ataagagata gaaacccaaa  17520
ttaagctctg aaacaactgg agacaggcct gcctaggtga tcaggagcat ccaggcagca  17580
gggatgggaa gcagaagaga tgcattctgg atagggacct caccccagag cctcagtctg  17640
tacatacgtg tgactattca gggaccggga gttgagaacc agaaacccac caatcctagt  17700
gttgccctgg atgggaggca gagaaggcag cagcacgtga ggtcaaggac attaccaagt  17760
ctgaccttgg catttgttgc ctgctctcat ccccaacagt ccataaataa gttatccagc  17820
acatctcagg ggtggaggcg ggggagcaag ccaactagcc atagcctctg gaagaagggg  17880
caggccagcc tggcactggg gcagagctac agcagaatgc agtctgactc gtgcttcggc  17940
ctctgccgac gctccccggc tgggcgtcca gatgtggctc ctctcccctg tatcggattt  18000
aacaattggt cactgaactt ccttggaaga gcacaagaag agattctaga agaaggggtg  18060
tcaggattgg gacagagagt agggagagga agacaggaag gggctccagg ggagagggac  18120
aggcagggga aggactctga gagaagaaac cttgaagaga ccagtgcagg aataacaggt  18180
gttctggacc cggcaaagca tgaggtggaa accgggagtg tgggcgccca ggcagcagcc  18240
cacctgcagt gacaggaccc gcgtccgcat ccgcactggc tgcgctgcct gctgctgttg  18300
atactcctct tgctgaagct gctgggccag ctccaagtcg gtaagcccca gcgggcctcg  18360
tggctgttgc tgctgcaggg acagagcaat caggtagtcc tggggagaac aagagttgtg  18420
cagtgggctg aggcccagag ccgtggctat tcaggcaagg tttccaaatc agttttccca  18480
catccctcaa attctctagc tctttctccc cacagagcag cacacacagc caaatgcatt  18540
atctgtggtg ccagagaata cacaccaagt gaggagacgg tctgaggtaa cccagagaga  18600
gaggcatggg ttcacatggc ctctagcagt taaaatgtat gcagtaaaaa gctctctgag  18660
gcacatgtgc tctctgcact tttcctaagt gccctacaca cctggtctac ctgcagctgc  18720
gtttctgggg agccactccc accttctgct ccaggcccct tgcccaggga atgactcagg  18780
tgaaagtcag agtcacaaaa gcagctgtct ccatccacat tgtgcaggct ctcccatacg  18840
acttgctcct cctgtagaaa gccctggtca gtgaccagta ggtataagtg actctacaaa  18900
gaaaagaaca gagctcattg gggggacagt tgatacggag gcagttcact gccagaaatc  18960
tcggtatgag catgtggact tttttttct tggagatgga gtctcgctct gtcatccagg  19020
ctggagtgca gtggcacaat ctctgctcac cgcaagctct gcctcccagg ttcacaccat  19080
tctcctgcct cagcctccca agtagctggg actacaggca cccgccacca tgcctggcta  19140
atgtttggta tttttttagt agagacgggg tttcaccgtg ttagccagga tggcctcgat  19200
ctcctgacct catgatctgc ccgcctcggc ctcccaaagt gctgggatta caggcatgag  19260
ccaccgcacc cggaccctga gcatgcggac cttttacaaa tatgtgtggc cttgggggga  19320
```

agaaagggat gtctgagtgt atgtccagtt gggtgtgagc acggtggtca ttctggctaa 19380
gcgtggcatg gagtcgttgg ggctgagatg ccacataaga ccctgctccc cccatttccc 19440
attgttctct gggcttgcct gatggctctt aggataaatc ctttgagaac cagagacccc 19500
tccctctgct gctcaaatcc tagagagctt tggcagtttc taacttttga agaccagcat 19560
tgtttaaaaa ttccactgcc ccctcctagg ggaggatcat actttcctgt cccatcgacg 19620
gcaggcttat cccttatggc ttgctctggc cagaagatgt gagcagaaat gacatgtgtc 19680
atttccaaac agaagctcta agcatgagtg cacagtgccc ctctctctct ctgttcccac 19740
atatattcca gataaaggat cttttgtcag ctgggtccca gagtgaagat ggtgtgggac 19800
agaaccgtag ccagtccaca gtggacacgc accaggagcg ggaaatgaac ctttgttgtg 19860
gtaaaccaca gggatttgag gggtcacttg ctaccacggc ttaatctagc tgatcccagc 19920
tggacccacg agaaaaaggc accaggaaat gacagcaccg cagcacgcca cccccaaact 19980
cgcattacct tatgcttagt catggtgcta aagtggttgt ttcggaaaaa gacgctaagt 20040
tcaccctcct tagcagctgc tgtcagctca cacagtccgt ggtaggtcag ctgggccgcg 20100
gtggtctcca ggaactgctc tgcaatcagg cctgccagaa agggacgagt cgggggaaac 20160
ttggcttaaa ttcaaggtcc acaacaggaa ggaccatcca gagagcccct gtcaaaagcc 20220
ccggggggtc agtcccacct tctgacgtcc ctttcttgaa acctggctgt attcattcac 20280
ttaacaaata cttataatag agcagctacc ttgtgccagg cactggggat acctcaatga 20340
actaaacaga aattccccaa gctccttctt gtgaagctta tatctagtgg gatgtggtag 20400
gagatgacac ccaataaaaa ataagcctaa gtagctgtca ttccctccac atactatcca 20460
tgagaagggg aggaatgtca ccttctgtca cgaggttggt gtcactggag tgtttgcagg 20520
tgatgatcct ctccaccagc tggttgtaac tcagtttccc aactgcacgc acagcctcag 20580
gactctgctt gggtagtggg atgtgggata ccaaaaaaat tgggattttt ttttcttttt 20640
taaggaagga aatgaacaaa gctcacaagg actacaaccc tgtgatgaat ggttcctaaa 20700
cacttttttt ttttggtctc tcaaaaaaga aaaaaatttc aggaaccatt catcataggg 20760
ttgctatgtt gcccagactg gcctcgaact cctcccaagt agctgggaat acaggcatgt 20820
gccaccaaac ccatctgctt cctgaatttt tgatgtctaa agaactgacc tatttgcatg 20880
tagtttgctt gtatttgcat gttacccccca aaatagatta aaattcaagg aattctgtac 20940
tgggtccagt ctctaaacac tatttccctc ccaagccaat ctaaccccta actccctaac 21000
ctctacccga caaaaatttg cctctctcat gtcagcttga gctggataag gtcccagtgg 21060
gccctcccac cctcacctgt ggatcaacaa gccagccatg gtacagaggt atgcctagca 21120
ggtcaaagac actgcactcg ggtgtatact caaaatcaga gacgcctgtg aatcgcacat 21180
tgacatccag acctgtggcc agtttaggca gcactgtcat tgcatcatcc acattctggg 21240
ggtagaaaaa aaaatgatgg agattctagc cttctctccc accactccac tcccacctgc 21300
agaaattaaa aattaacctt gctgctcttc ttccctgatt ctcttacaag ccactccatt 21360
tctcccttgc ctcaaccctt ctctatctta tataaatgaa cattgttttt ctttgagagt 21420
ctaagtctaa ttctttcatc caggctggag tgcagtggtg tgatcctagc tcactgcagc 21480
ctcaaactct tggtttcaag tgaccctccc acctcagcct cctgagtagc tgggactaca 21540
ggcacgcacc gccatacctg gctaattctt gaaaaaaaaa atggtttttt ttagagacag 21600
gggtattatt atgttgccca ggctggcctc gaactcctgg cctcaagtga tcctcccgct 21660
ttggcatctc aaagtgctgg gattacaggt gtgagcaccc ggccaatgaa catatttttct 21720 aggacaaaga taaactctcc tctgactcct gcagaatgaa atcatggttc aaggaaacct 21780
ctgaagaagc aacaaaagct tatcttagta ttacaagatg tccccttaca aacctgcaaa 21840
cccctatgcc tgcagacctt ttgcctcacc tgctgaaaat taagctgaag tccctctgac 21900
ttctcctggg gcttgatgga caggaggcag tttcctacaa gacagggccc cttatcagct 21960
taccccacca atcatcccaa aagctaagtt tcctcttctc ctggagaatg cgggtaatgt 22020
cacagaacac agattttcag agctggaaaa tacttagagt ctaatccaga ctcttcattt 22080
ctcagaggag gcgacagcct cataaaggtg aacggcccac ccagggtcag atacaaaagc 22140
taagggcaga attggtgtta caacccagga ctcccgacgc ctttgctttt cattctccag 22200
ccttgcagag aagccccata gacccttacc ctccctgctg tatcagaacc cccaaatgga 22260
gatccctgaa tagtctggat ttctggctga gtggatagct ctggagcccc ttgggtaatt 22320
cctcttcaac gcccagtcac tcaccaagat gggccatgag ctcatccgat gtgatcactt 22380
ccttctgcgg ggggagcttc acctggaggc agaaggggtg atcacgtgtg tgctttcctc 22440
caaagagcac tgaaggaaga acccatggaa aggcaagggg gagctccagt agtagggtgg 22500
ggtaggaaaa aaggcttgca actggcacaa gggaatgaat gtgaaatctt gcaaggcatg 22560
tgcatttgct agggagtagg agatacaggg gtaggacaga tcttcctctt ttttttttt 22620 ctttgttttt aggaacatct tatctcattt gctcaagctg gagaaatagg gagaacaatc 22680
tgaaaagttt tgactagttt gaggacatca ggatgatcaa ggaagtaagt cagggaagag 22740
tactccctga tattttttgc acccctaact gcatgttctc ttaccttcca ctgaagaaag 22800
aggatgttca tgatggcaag gagagggcaa gggccgttag tgctctgggt gatgatgggt 22860
gtctgttctc ctttccaagg gatccacttg acacagtaga aatctggctc aggctgtcgg 22920
gtcctggggg actgaggaag ctcctggggc atggagcatg cccttattgt ctctacttca 22980
ggcagtgtcc caagggttgg ccccggtgga gctgagctag cttcaggcag aggggactca 23040
aggttgtccc cacactggct aggcagcaaa gcttggtctg ctggctcccg ttctctagcc 23100
tccccatcag catctcttgc atctgtgtcc tgagggtgct catctgggcc tgccagaacc 23160
tcatggtttt cagggatgac tgcttctgca gtcccggcct taccaggggc tggatcctca 23220
ggctgatggt attccatggt caaaagggac tt 23252

<210> SEQ ID NO 2
<211> LENGTH: 56552
<212> TYPE: DNA
<213> ORGANISM: Homo sapiens

<400> SEQUENCE: 2
ttttgaattc catctctgct cccaactctc catgtgatcc agggaaagcc tttttccatc 60
tctaagtctc aggttccttt tctgtcaaac aaggggcatg atctaaatca gcaattatca 120
atcccagtgg tgcagcagag ccacttgatg gacgtctgga gaatgtcaaa gcctagatct 180
caccggggtt gagaaccacc ggctctgaat gatggccaag gtcctttcca caactattct 240
atcatcccat gaaatgtcta gaatttgtta atgaaaatct gggtttggat ttgtttgagg 300
cattcatctt gcttgctgaa tagtaaattc aactgaacaa ggaaatgaaa actgagcacc 360
tgctgcctac aaggcactaa attagacccc ttagggattc ctgcactaaa gaccttacca 420
tgtggtcaga taggtgggtc gtgtgcccaa acaattataa ctaaaagggg atggacattg 480
ttccttttag aattcaccaa acccatgttt taaatgggta attcctttaa ttttactggg 540

-continued attccctttc cagaaattca gagcctgtgt tctaccttct tgcttatact tctccacaag 600
gagggcagag acagatccga cgccccaacc ctgtggtctt tatctaggcc tgccctgagt 660
gctggaattt agaagtgaca cagcatcagt tttcatttta aacatttatt gaatgcttac 720
tatatgccgg gcacttttac aagagtttta ggtatgttaa ctcaatttaa tggccccatg 780
agataaacac tactttttg accatttcac aggcgaggac agtgaggtgg aaagctcata 840
tcacttgttc aaagtcacac cactggtaag tggggagttg ggattcaaac ccagagactg 900
gatttagaac tcacgctccc agccgggcac ggtggctcac acttgtaatc ccagcacttt 960
gggaggccga ggtgggtgga tcacgaggtc aggagatcaa gaccatcctg gctaacacag 1020
tgaaaccccg tctctactaa aaatacaaaa agttagccgg gcgtgcgtgg tggcaggtgc 1080
ctgtagtccc agctacttgg gaggctgagg cagaagaatg gcgtgtatcc aggtggcaga 1140
gcttgcagtg agcagagatc gatcgcacca ctgcactcga gcctgggtga cagagcaaga 1200
ctcagtctca aaaaaaaaaa aaaagaactc acgctcccaa ccacttataa atagattctg 1260
tgcccttcat gaaatgttct tatggctacc aaaaataatg cttccaaaca acgaataaca 1320
tgggaaatgt tgatgttaaa atgttaagtg aaaagttagt aaagtaaact catgtaagta 1380
ctatgagaaa gactatgtaa aatacaaaca aaactcaaat aacaacaaca acaacaaaac 1440
cactatatat agaaaaaaat gacgggaagg aaaatagcaa aatagtaacc atattttagg 1500
gatgggatta taggtgattt taaaattctt cctatttttt ggtgttttta aataatgagt 1560
atgctttctt tataatctca ttccctagtg acaagcaaat actcttaata ttttgctgta 1620
agaaaacatc gagtctaagt tctgatatca taaaaattag ttttggtttc aaaattggca 1680
ggtcagtaat ttgaaattta gcatatattt tctcatggaa ataaggatag ccatagtgat 1740 tagtttttc tttttaaac ttgcagttct aggaactgtg ctaagaactt catctgtatt 1800
tctttattca gtggattagg aatgttttca gcccccttt ccagtgatgg ttaagtaact 1860
tgccagaggt tgcacaggtg gagagagcaa gggtgggaac tgatgctgga tgtccctctc 1920
cagggtctgt gttataactg ggctgatgct tctcactgca gcccatttca aagagcatgg 1980
agctaaggta ctgccttttt ctcccagtct tattttctct cactgcagct ttcattgtga 2040
atatgccata ttttggccac cctttccagc taagtcaatt ttgataacta tcctggggac 2100
ccaactttcc ctcagaatat tgtttgctga gaaaatgttt tggatcccac catgggcttt 2160
taaaacctat atactcctcc tcttcacctc tccatccaaa gattaatctt ctcctgaggt 2220
ccttcccagg ttggatgctc ttctcttatg aatgaccaga actggtgcct cacttctgga 2280
aacctccaga tgagtggaga gcttttgctc caccctcagt atacacctgg tctttgctgc 2340
ctcacctcga gctggccaag ggcaccttct ttaacacgag taaataagcc attcctagac 2400
ttctgccctt ttaaaggcat tgttagtgct gaatcggtac tgtttgtgag cagttttgga 2460
gcatcaaatt caggcaagga gagaagccca accacccaca ctgtcagcat tagatctgcc 2520
taaaataaca tcactgagat atcaaacctt ccttgttctg gttatggcat catctagaaa 2580
tgaaaaaaaa atcatgttag attatttgct tgggcctaca attttatttt ggatctctat 2640
tattattcta aaaagggcca tttaatttcc atcttgggaa ttttctcctt cagttcctat 2700
accaaagaga aaacagaact tctgttcatt ccagaggtgt agagccgtat tggcccagct 2760
cagaaaatag aaggcatagc agagctgcct gtgagataga taggtgccat gtgcaattca 2820
cagagctccc tcaccatcct agaggcctgc agttctcagg ggatcttcct gtgggttaat 2880
acttgagatg cttatgcagg gaggaactgg gtccctggga tgcgaggggga gggagtcacc 2940

-continued catgccttta tgaaagatgc ttctagcgtc ccgcacatgg tctgcacctc ctgatgctag 3000
gtcaggactg aattgtataa aaggcagaag cttctgacag cacctcagtc tacctgtctc 3060
ctgagtgatc tgctgcagtg cctgaaccag gtagagtgct tctcaggacc aggatgaact 3120
cttggtgctg gtgttttggg cagaaagagc ccctgggtgg aggttgaggc cattcttgaa 3180
gaaagacaag gataaagaag gattttggag gggaaggttc ttctggaagg ggagggtgga 3240
aggtaggtaa aaggaatgaa ggactgatgc ctttctgaag ttccaagtta ttcatttgaa 3300
aatatggagt tactaggtgg aaatcatttg tatcattctt gttactggtc ttgggagact 3360
gggtttttaa aatctggttc atcttaggcc aggagtagtg gctcatgcct gtaatcccag 3420
cactttggga ggctgaggtg ggcgggtcaa gaggtcagga gttcgagact gaccaacatg 3480
ctgaaatccc gtctctacta aaaacacaaa aattagctgg gtgtggtggt gcacacctgt 3540
ctgaggcagg agaatcactt gaatccggga ggtggaggtt gcagtgagcc gagatagcac 3600
cactgcactc cagcctgagt gacagagtga gactccatcc caaataataa taataatcat 3660
aataataaat tctggtcatc ttagagataa aatcttgtga aattatagtt caattttaag 3720
ggcaaggaag tgaccttggg cttgtattgt ctttcagctt tattcagctt ctacagagat 3780
gtcctgccag cagagccagc agcagtgcca gcctcctccc aaatgtaccc ctaaatgccc 3840
tcccaagtgt actcctaagt gtcctcccaa gtgtccccca aaatgccctc cccagtgttc 3900
agccccatgc ccacctccag tctcttcctg ctgtggttcc agctctgggg gctgctgcag 3960
ctctgagggt ggtggctgct gcctgagcca ccacaggccc cgccagtccc tccgacgccg 4020
acctcagagt tccagctgct gtggcagtgg cagtggccag cagtctgggg gctccagctg 4080
ctgccacagc tctgggggct ctggctgctg ccacagctct ggaggctgct gctgacctgg 4140
gccatgagga gcacggagga gaaggactgg cagatcccag gtgctgaaga tgtgtgtcag 4200
cctgaggctt cttttctctc atttcccatg gaaggacttc ggaaatgcct taagttcccc 4260
tctttatcct gcccatgttc actccattgt agggttgaag tctagcttgt gatattttct 4320
ggcctggctt tccctctcag acatagctct ttggagaact aggtgttgta attcagttat 4380
gaagctattt tctctgtaac aataaagctt tttattcctg atatcactgc ctcctgattt 4440
cattgtttgc ctctcccact ccctacctgc tgcatcaagc catcttccct tcccttctct 4500
taaatgcaag cgaacacttt acaaacttgt ttaggaagca cattttggca gtgaagctac 4560
ttaggcctct ggaaaacaat atttccttct atgcactgga ttctggaact ttaagcttga 4620
aggaaagaat aatgtctgag accattacgc cagacacaag attgtatgag gagagccagg 4680
aatgggtttg aagagaagag gatggttgta ctcaaaaggt tcaggttctg agagggtttc 4740
cttcaagcat gggtcacagt ttgaaaaatt gcttgtcccc attcatgggg aataagattg 4800
cctgaagtgc tcatcctggg ctctaataaa tggacactct ttacttttct gattattata 4860
agctcaggtg tttccatcag ttggctagag ggagagctgg gtgggcagtg agtgagtttt 4920
ggaggcagat atgaaacgtc tgagcacatt ttccctgcat gctgaaatcc tggatttgaa 4980
tctgggtaaa gaactgagaa agacaccctt ctttgcaaag actgtctcta tgtggttggg 5040
acgtacgtgt gtgtgtgtgt gtgtgtgtgt gtgtgtgtgt gtgcagtgag aggtataaga 5100
gtacaggggt tttggtccct gtgttgggtt ttccaagcaa catttcttta ggaatgggct 5160
ggttccttca ggagacactc ataatgtacc tagaaaagat aactagaaaa gttaattcca 5220
aatcagcctt taatataaaa gataaacaat tgatgcctcc tttgataaga gttaatagcg 5280

```
ataaataaag taagctggtt tatgagatca taggatgccc acagaatgag taggcacttg   5340
cccagattat ctccttatac tgattcctac caaacgttct tcattctttt ttttttttt    5400
taaaagaact ttgcccattt tcccagagga gatcctgcct ctgtcttgtt atttcattac   5460
ttccttctct gttctaatat tgactttact ttttggaatg tctcacctat actcaccaac   5520
aggtgctcta ggaactggca acctgttaat caggctctaa atccatgtta aatgaaactg   5580
gtatcttttg tgacttatct ttcctcgcct agtcccttga gccactccca gctcactcgc   5640
ccccaaacct gtctctcatc cttaattcct gaattcttag tcttggactt ctgttatagt   5700
tcacattcac agttgtgggc aatttgatta agaagcagtt ctgaagttga ctgccaaagt   5760
atcctccaat tcttaaaaat tagttattct gaaaacacta tctatcatga acactttgga   5820
cctttggaaa gaactttctt tctttctttc tcttttttt cttctttccc tccctccctt    5880
cttcctttcc cattttcttt tgcactgggc agtggcccta gggagaactt atcttcaaag   5940
gcagattggt ggttgggggt gggataagaa gcaggagtcc cacaggctga ctagcctttt   6000
tgcaattggg ccactgtcct gcacacattt ttctctttgt cataccatgc tgtattatgg   6060
ggatatggca acctgactac attcacaact tttctggtct tatggttcct taactttgcc   6120
taggtttttc ttcctgtctc cagtgacaga gagaaatcac ccctggggtt cccaaaggtg   6180
catccccgtc atcatcttca ctcactgcat cttgaagcat atggatgaaa cccagcaggc   6240
ttatcgcata gcttgtggtc tgccctgggg agccaaggac caagagccag agagatgaga   6300
atcaagataa aaataggtga actaccacct accaagtaga tgactacata ggaatggatg   6360
tgtgggcaag tggagccgtc tgtgtgtgtg tgtgtgtgtg tgtgtgtgtg tgtgtgtgtg   6420
tgtattgaag acaagggcag gggttccaga cctccctgca tttgagcccc atgccctctc   6480
ttagcataca cacagcctcc caggtacaaa cagtgccctg tttggaaagt aaacatgcca   6540
tagcaatcct ggcacctctg tgaagtgact tagatgccca catgcaccac ctacaatgct   6600
acctgagtga tgaatgtctc tgggatgtga gtgtcagctg agcacgtctg ttgggaaatg   6660
ggcccctccc aagagcctga acctgaatac ttcttataaa aaggttctct ggctggacgc   6720
tgctcaatcc actgcctagc aggtggccca ttccagttgg agaacgtagt gagtctttca   6780
gtggagccag ggtctggtaa gtctcctagc agggtctggg ggagagggtg ggatgagttg   6840
agggcacagg ggaggagcaa acagaacaca ggcagcagat agatgtggaa ggggtgtccc   6900
gcaaggcacc tacgcttcta gtgagccaac ctcttaaggt actaatgagg acataaaggc   6960
aacataggag gtggtttttg caagggtaca cagcaagtcc gcagaagagc tgtgactaga   7020
acccaggtct ttcagctccc tggatggggt tatttatatt ggcacaactc tcctttccca   7080
catggttgtg gggcatgaga ggcgtaggca agaaaagaatg atcaggacat gcttctggcc  7140
tgtggattat ttagacccag caggtgggac cgcctgttgg acttgggtgt tttctaactg   7200
atgggggtgt agtaactagg aagatacagt cgaaggtcgg taggaaagta aaatgaggga   7260
caagaaaaaa gccaagtgga gattttggac tggatcatac agataagttg ccgcagtgtg   7320
ctgtttattt tccactgtgg agaacttgag cagtcttctt ctagtcagag aaaatggaaa   7380
tgcattgatt cattgcatgg attgtgtcct gctctgagca tgtttaactc actggaaaca   7440
cctgcttgga tttgcttctt tgcgtccgct ctttctgggt gcttttccct ccttgtccca   7500
ggccaggctg acttgtacac taagccgaat ctcaaaagcc cagacagagt tccattggtg   7560
gaaagaaaaa gccggctcgc ctttgaaagg ctgccttct tccaggtttg tcgtgaggag    7620
ctccgcgatg tcctctcaac agagcgccgt ttccgccaaa ggcttttcca aggggtcgtc   7680
```

ccagggcccc gctccgtgtc ccgccccggc gcccaccccg gcgcccgcct cctcctcctc 7740
ctgctgcggc tccggcaggg gctgctgcgg cgactcaggc tgctgcggct ccagctccac 7800
cagttgctgc tgcttcccaa ggagacgccg ccgacagcgg agtagtggtt gctgctgctg 7860
cgggggcggc agccagaggt cccagcgctc caacaaccgg agctcaggat gctgctccgg 7920
ctgctgagag gcccgcaacc cccagcgctg cgctagagaa acccgcccag cccagagcgg 7980
gcccgccccg ctgcggctcc cacgcggggc tgggcctcgg agtttgcccc gtaaagcgaa 8040
ttgcactttg atgttcagaa acccactttg ttctcagcca cgcaaaactc cctgaccccg 8100
atgtgatttt tctccccggg gattcgagag ccatgcgtgg gacactggac cctactgtct 8160
acacgggctt gcacacagca ggtgctcagc aaatgtctat tgatttgatt gtcttttgaa 8220
gatgtcataa taaagcttct acctcctgag aacacctttt atttgttctt cattcgtttc 8280
tccacccagg tagaaaggct tgaaatgttt gtgaaaggca gaatactata attcatgcct 8340
gaacaagaag gtggctttct gatagttaat tatgatagca gcgatcacat atcgactgtt 8400
tcgagtattt taaggatttt atgcgacaaa gtccttgaat attctcagga ctttatgtgg 8460
cacaatctga ttctcataat gacttgcgta ggagagtgca attataccca ttttacagaa 8520
gagaaactga ggttaagtaa tttgttcaaa gtcacccagc tggcgcatga taaagaagac 8580
aggacatctg attcaagggc ttcattgctc tgctgagttc tcacctgggc ttcccaagcc 8640
ttaccactga ggtgctcctc ccgaccacca ggtccaggca gctgtgtggt aaaagtttgt 8700
tttggcaact ctttggggct ttggaatcaa gccagctgtc ttcttttttt ttttttttag 8760
ttttatgtct tattttattt tttatttttg gcatggaagt tcattgacct actgctttgc 8820
ttgctgggga ggaaattttt cctaagatga gccttccagg aaactgggag ctgccctctc 8880
caggtctcat ttgtgcagct gaagcaggac caacagccat gggtttctgg gagtctctgt 8940
ggtgcagcat gtgtgctcgg aaacatgggg atctcattct ttagagatgg tggctgtggc 9000
agtggcaatg gatgggtcat cttgcatagg tcagaaacct atccctgtgg gcacagattt 9060
tatccactca tttcaggcac gaggaaacag gagaacaata tcctctgcat ggtgtctgct 9120
gggttcagaa ggaagagata atcatggtaa taataatagt aacactagtt accatttatt 9180
tggcactata tttcaggcac aagtcaaggc actttaccta tattatctca cttaatcctc 9240
acagtaatct aaaaatatag acattcactt ccccactttt tatacgtgag cacatgggtt 9300
tagacagttc cagtggtttg gctgaaatca cagagctagt gaatgtcccc ttgagtgagg 9360
gagatgagat tgaaactgga acctgtgtga ctccaaagtc atgccctcac actcaaagag 9420
tcatgctcta ctgtcttaga aatcaccacc acacagggaa gagacactcg ggtctctgga 9480
cacacccagg ctctcagaaa attgcagctc ggcttcttgg ctgctgctcc cttggtgacc 9540
caatgagtgg ggagctctgt catggcatcc acccagcagc tggcggctga gggtgtctgc 9600
tcaaaggtga ggtcggaaat gctctactga ttcatccagg atgtttgacc ttgcggccaa 9660
atgacccctt gccagggagg ctctggaggg cagtcctgct ctgcctggga gtggcccttc 9720
cttccatgtc tgagattctg tgatttccag tgggaggtga tttgtggaag ctgtttacaa 9780
acagatgata tcacccgtgg acctgcctcc ccacactagt aatgtgtgct gaaacagcaa 9840
gccctgggac ttggtgggca gtgggtggga aggaagaact gcctgactca gaacagacac 9900
actacgcagc taatctgagg gtgagggctc aacctggagc aggaagctga ggcctgagct 9960
ctgggaaaga gaggtggtga ctcacggaga gatattagag tccaaatagg agcacatgcc 10020

-continued

```
ctgtacacca ggcatttggg tctcatgtca aatggctggc cctgatggtg gtggtacctc  10080
caggcccaca tgctgctgaa acccagcagg tcagcacaca tggactttga tgagagacat  10140
ttgagtattt taagaatagt ttcattttag aaatctagca agcgactttg gaaggtctag  10200
agctctctgc tcatggtcct tcaggctttt ctgatttcca gcagtaggta aagctgtatg  10260
tgtggcccag gcactctctg tgaggtgatg gtggtggatg ctgagcctgt gggaaatttg  10320
gcaaagtgaa gtcctactca gaggttgtca cctggtacac gtgacaggca gaatcaggtt  10380
tcgtattatc tctggaataa atggacatta ttgttaaata tattttattc atgatggctc  10440
caatttcagc ttaaattata ttattatact ggtaataata acaactgata cttatgtagc  10500
atttagtgtt tatgaggcgt ttccacatat attatctctt tcataattct gtaacataag  10560
tattaccatc tctgtttaac agatcaggga gggactccta cagtttaaac aacccacctg  10620
aggttatcca gctgatacgt gtggtctctg tctggaccag gccttctaat gccctctaag  10680
aaggccaaca gccacttctg aatattcact gaaataattg aataatggca cccagttgat  10740
tacttagaga cagtgctgta ttcactattg catccctagt atcatgccag gtacatatta  10800
aaggtctata aataaatgat tgtttattag tgcataatgt gtaaggcatt gtgctaaaga  10860
attccacaga gatatacaaa gcatttctgg acctcaagga gtttatagtc tgattcagaa  10920
actatggtaa ataaaaatac aagatataaa tgataactca gatctgaaat gcaaaaaatg  10980
tcacaagcag aacatggcat aggcaactgc tctagggatt caactgagtt tagatgaggc  11040
attgtgatac gactttgaat gagggcaagt tactgtggac tggattattt ataagccttc  11100
atgggaggaa ggatctgggc tgggtgtgaa ggatggaaac acatcagacg ggcagagatt  11160
cattcattta tgtatctgtt caactccatc agacactgtt tatggttctg ggacagaacc  11220
agaaataaga ccaaggccct gctggcatgg acctcaattt ctggagtgaa gacagacaag  11280
aaagtgagca aggaagtcag attatttcac accgtgaaaa gtgttgtgat gaaaacaaag  11340
aaaataaagg tataaacatt aactagaggt gtatggggat tttagatgga gctaggccag  11400
gcctctctga agacatgtta tttgagcagg agaaatagga gttatgacac agagcaggga  11460
agcccatggt tacagggttc ctgcatccat ggcagcctag ggctgcaggt gtttgaggtg  11520
tgttttcagt tatgttgcct ccaccagaca gtttcactac taggaaagta acttggaatt  11580
ccagtttctt ggcagacaga tttgctagtg tgattgatcg tgtgccatga ggttggcatt  11640
atttcattgg atcctcacaa ctctcctaca agacaagttt tccccacatt ttgttaagaa  11700
aactgaaaga tagagctgtt aggtagccat cctaggattt cccagcttgt aataggaaga  11760
acaaggtttt gtactggaga cattttcctc tgaagtcaat gttctgaaca ttgtgctaca  11820
gtctgcattt ctgggaaaga ggggagtagt ctcaagcttg gactagggga ggagaaaggg  11880
gtctcaaggg agtggtgttg atattgaaag accctgagga cacatcttca gagaaggaga  11940
taggaggcca gatcatggat ggtttggagt gccaaatcaa ggagtttcaa ctatctcata  12000
tttgtggagt atggtggtag gaaaatggct ttgaaagaag tacattagag agataaaagt  12060
tggtttatat aacatctaga gtactctctg acatgaccct aagattaatt aggcagcaat  12120
gattaaggtg ctccagaaga ggaagttaat ggagagatta cctctgtgag caggtgcaat  12180
ggcccaggca tgaaatgaag atctgaacct ggcacatggc agtcattaca aaaaggaaat  12240
gactgttgtg aaaagcattt gtccagaagg aagagggata gaatcaggtg atgtattggg  12300
gttgagaaag aggaagcaac tggggtgtct ctgaggtttt gtgccttgtg cctgggaaat  12360
gatgacagca ttgacaaaat agagaagtca ggagaaagaa caagtgtgag gaggagaggt  12420
```

```
aagtttggtc caagatgtgt tgggtttgac gtgctggcag gacatgacca tgtgacagtg  12480
atgtggggct ggaacttcag actcagaatc cttgaacatt gacataaaca caattaagat  12540
aaatggtaat aagccttatg cagcttggag tcaaatcttt gggaatgaat gcagtcctat  12600
ttctgcagtg aaggttatga gaaaatagac ttggtctgtc ttgttcattg cagcaacctc  12660
agtgcaaaga acagagacct aggcaagtaa aggcactcag tgaatatgtg ttgagtaagt  12720
caataaataa aacagcaaga cagagtgccc aagacttgag ttgagggaga aacgaagcag  12780
aaaggaggaa gttgaattcc gatcgaaggg ggcaaagatg atgaagtcag agaaattact  12840
cagatatttg gcctcaacaa ttcatataag gttactttaa agtcttatgt tctaggaatc  12900
tgggcagaag ggaaccagca cgatgcaaga atgcagaagc taaagaatgt caaccagtca  12960
gggtcttcct tcccactgcg cgatctatct ttggcatctt taaaccattg aacagttata  13020
gtaggaaatt ccatctgaag ggatagcagt ttcatcctaa ctaggtagaa cgggttgaac  13080
aggaaaactg gcattcacat tgagtaaaaa aaaaaaaatc ctctcttcca tggatgacac  13140
tgcagcaggt cagaatgatt tggccatgat aaatctgaaa catattatct tggctcaggt  13200
tgagtaatag tcaaccctag aaaagcaagc atctcttctt ctcttataaa cattgcatca  13260
gggcaagagt gaggggtatt aagccatctt atttaatgat atatctcatc cttaaggatt  13320
tattagttcc attgccaata atgtagctat atcagctctg catgtttgga aacttaattt  13380
gcaattaagt tcaaaggcca tttttccatg gtatgaaata ggattatatg tacttgaaag  13440
tcagaaatta accatttccc actacccaaa ataattttct gttcattaat tactgcaatc  13500
ttccattcat aaacatttat tgtgtactta ctatatttta ggcactttgt gatacaaaca  13560
actcttctcc aatagtttag tgggaaagag tcaaatatca taatactgtg taatttgata  13620
aacgctttaa gtcagcaata cagagaggtg atggctcatt cggctgaggg actggcaaaa  13680
ggtattgttt gaagttagtc cagaatgatg tgtaggaatt gctctggctg agaacgtaga  13740
aaagatattt aatttaaagt agacaacagc aagtgcaaag gttggaaagg tgatcatgta  13800
ttttatagaa agcaatattg cacggctgaa gatcatggaa gccagagtag gtgagattat  13860
atagctagtc ggggaataaa taaagcaggg tcttgtatga ctcttgaaaa ctcctggaac  13920
cttatcttgg aggcgacgtg gaccatggca tttttgtggc ttgataggtc tctctcttgt  13980
gtttttaatt atactgaagt taccttagct taaaaaaatg agggcattag catcatttct  14040
agccaccatg ctcacctatc ttcttttctt agtgtcttcc ccaaatttca aaaagtgctc  14100
ttcatagttt tatattttac ttgaatcttc cttaacctca ttgaataatg cttgtcccac  14160
tagccattct gcttgatcat ttcatcccag tcaccatgtc atctcctaag ttctgtgctc  14220
aacagtcttt ctttacttcc cagggtccca gccctctgga aagcattgcc cactcttggt  14280
cagctcctgc ccctctattc tggacactgc actgctgtca gtgttttata attcactggg  14340
attctccccc gtctcttctc tgctagtatt tctgctagtt ccaattctaa atctgtgcat  14400
aataactaag gtttagccct tagctgtctg actttttctt tctacagaaa aatctcattc  14460
attcattcat ttactaattc ctcacacttt tattgagaac ctaatatgtg ctaggctctt  14520
cattaggagt tcagatagaa atatgtatct gagatattgc tttatgtgtc tgtctctaaa  14580
atttctatct ttaataatga tacttcctga aaattaaggt taaaaacctc tgattctcat  14640
aaaatggttt tatttcacta attcagacgc atctcacatg aaacatcact acctctcaaa  14700
ctagtgttgt tatatttttc tttagatttc tctactttag aggatgggga tactgtcacc  14760
```

-continued

```
aattacacta aaaactgcag tgaaatcttc gactcttccc tttcttttga ttttgcatct  14820
aatcatttgc caaagtgtat ttcttttttct ttgctccctt tccccctata tctactacca  14880
tcatctttta atcctctaaa agaaaatggg cacagaactt ggaagtaaag gatccaggca  14940
aggcatttgc catgtggtac cagacgaggc tcaagttgga aatcttaatc tatgcctaca  15000
tatggtggca acaagctatc tctgatgagg tcagaccaca tatgatggac agctgcttat  15060
atttcccatg ctctggagca gtataacatg ttagagcact ttaactataa acatatactt  15120
cttgcctttc attttatttt tgtctaatat tgtagtttca tcttaacacc ctgaaactac  15180
ttctactatt ttatattgtc aatgcttgtt tatttttatc cacattttca tatttttctc  15240
tgccccctta ccattgccta ctttagatta ttctctcctt atggattcaa ttttcttctt  15300
cctggagtaa atccttggta gttcttttag ccactattag tagcaagatt aatcttcatc  15360
tgaaaatacc ttaattgcgc ccttacgctt aaataatatt ttagctagat atagaattcc  15420
aggttggcaa atattgtctc aaatcacttt gaagatatta ttccactatt ttctgacact  15480
aatggttgag aaaggtgcta tcagcctttt tttttctggg gaggtaatct gtttcatatt  15540
ccgatacttt ttacaatttt cccttcagat ttgtgtttgt gagaattcat gtctttcatt  15600
catttctaaa aatttagagc caatacctct tcaaatattg ctacttattc attatttctt  15660
atattccttc tggaaatctc attagatgca tttaggactt ttgcattctg taatatggaa  15720
atcactgcat tctaagtcat ttcaacatat ctctcagttc ataatttctc ttttcaacta  15780
ttttaaatat attattgttt gccacttaag tgttaattta cctcaatatc tatgtaacct  15840
tcctttcaca ttaataaaac ttctaagttt taattgggtc tatgacttcc aagaataaac  15900
attccaggat cccttgcagc taagcatcgc catatgactc gttctgggca ataggatgtc  15960
aatgggagta tcttcaagac acgttttcaa aagataaacc cacatccttt ttttcctttc  16020
cttcttcatt ccttcctctg cttagaatgt atactgatgg ctggaactgc gtattgagcc  16080
aaaataacaa gtgtcaccca ctaggagttg aaatagaaat gtagaagaat aatcagttcc  16140
agatggctat ggcgccttaa tgccaatgct gaacagtcaa gatctgggat ttttatgtga  16200
gaaacaaatt aattttatgt gagaaacttc taacttctta atctatcttt ttttggcttt  16260
tattctcagg cacatctaat tttaacctat accatttatt tattgatttt caaatgacaa  16320
tgaatatact tttaatttct tatggttcta tttggttctt tttttataga gtcgatatat  16380
tttcttatgt cttaaattct tatttgtgtt taatcatttt aaacatactt ttaaagattt  16440
aattttttag agcagtttta ggtttacagc aaaattgaga ggaaggcatg gaaatctccc  16500
atacaccttc tgccccaaga tatgcataga ctccttgatc accaatatcc cccaccagag  16560
tggtacattt gttacaattg ccgagcctac actgatactt cataatcacc caaatttaca  16620
atatttatct gataattctt ttatctgaaa tttcttggtg gtctaattct actgcttata  16680
gtattcattg attctccctg aagatgaaat cacaattcaa aattagaaaa catacaagaa  16740
aacaagccac aagagttcat cttcagtgag actttatgtg tgggcatcct aaggggatta  16800
tgttgaagac aaatccctct agattgattt tgaatttatt tctgccaggt atctcaggta  16860
tctgtcatct gcctggaacc aatttttatg taattatcta gtttaggtat tctcagatcc  16920
catgtgtagt gtcctttgga aagagtggca aatatatatg aggcacagac ccttggttat  16980
acattttaag ggcttatttt ctcccctcct tataaaccca agctaaggca gacaagcttc  17040
tttgtgtctt gtggtgttgc ttctgtaatc cacctttttcc agtgaggatg tttcctttat  17100
tgctcccaat cttgtctcct tctcttcaag acctgagatt ccaaaacctt agaaaataac  17160
```

```
attttctact ttcagacagc tgccacatca acctatgggc cttttatttt ggttttggtt  17220
ctcaattctc tattcaatta tggaacttgg gaattttttt aactttcatg caagtttaga  17280
tacacattaa aaatatattt attacattgt atctaacaca tgagatggta atagtataaa  17340
gatttaaaag ttttctaata agcaatactg tcagaattgg tgttagttct tagaaagttc  17400
cagatgatca cagctgtgct aaggaaaacg aagggaaaac atttctgcta ttcttagggg  17460
caagtatgcc ctggagactg ctgaatcagt gatatttgat gtgagagaac cttaaaaaaa  17520
aggcaaaatc caggagcagg ttgttgattc tcagcccatt gctaaatatg gcaaattttg  17580
tcatacaact gctggactct atgctccttg aggacagtgt catgtcccat acatcttact  17640
atttctctgt ctacttggca ctgcagtttg tatatggaag ttgctcaaca caactgatga  17700
ttgattgttg acagtacaaa tccttgcttt gaactttgta ctcatcagaa aattacatca  17760
aggtgtggtg catttcagtg taaagtacca tattaactgt gcactccacc cagtgtagaa  17820
acatacaaaa aaatgccagg gctcattttt gacattattt ccattccata actaatatta  17880
tagtcaataa taaagtagag atgattgatg tattcctgct tagttcaaaa tagattctaa  17940
aaaactttc agggtaaaca gtcgaaagtt cacgacatat ttataatttg agaaggttat  18000
tagagactat gtagtcagat cactcattaa atgcagaaaa atgtccttct gtaataacct  18060
gattagtgct aaacacagct agatacagga tgttagctca ctgcctcaca taatcattta  18120
tctcattttg aaaaatttaa tcttttcaat aaatttattg cacttctaga aaactttact  18180
taaaaaatct ttgtattagg tttttgattt taaaatatac ttttctctta ttattgaata  18240
attctagaat gttcagggca taacattttt atatattcag gaaagagact atgatgacct  18300
ccattataga ggaaggagca ctgccctgtt taaacccagg gcatataaaa ctgaattgta  18360
gagaaataca aatatacata aacaaaaaaa taaaacaact tataattcta ttgtctacag  18420
ataatcattt ttacacctaa ttgtgcattc ctccagatct ttatgcaaac tttttttct  18480
tttaacaaaa ttgtcttcag gttttgaacg ctattttttc atctgaactt gtcacccaat  18540
tatgtatcat agcatctttg catgacaata cacattcatc catagcaaac tttttatgcc  18600
ttaatcattt tctattttat ggatagtcca ctatttattt aagcaactcc ttattgttgg  18660
gcattgtctt gcctccaatt ctttactata attaaatatg ctgtaatgca tttattcatt  18720
cagcaaatat ttgtcaggca ccttaactct gcctgcacca ttcagcatgg gaaacgaagt  18780
tcctgtcttc agtgttaact tctgaagggg gagatggaga ttgaaaataa acaaataatc  18840
agagcacaaa tatcagataa tcacaaagag tgataattgc catgaaaaaa ataagatggg  18900
ttaatgagat agtgacaagg ctcagtctgt aatttaggag gggaaataac gttgtgtcac  18960
atatccatag gataaacctt agatgaacct gtagaattgg aattgctgca ttttctatta  19020
agctatcctc ccactgtggt ggagaaggcc tgcttcttgg agtgcttacc aacactgtct  19080
tgcaccttgc tcccactctg ggccctagtc ctgccctctg caccacctca gcaccatttc  19140
ttctctattt gcctcataaa aatattgtcc ctcacatgta taggacttta tactttacaa  19200
acaagtttca catgctaact taatgcatta attattttgt ttctatattt tattacgtaa  19260
atgttcaaat ctgcaccaaa agagagggta ggataatgat ccctcaattc ctcagcaccc  19320
agatgaaaaa gaaatcagca ttgttcccat attgtttcat ttgttctctg gccccctatt  19380
cttttttct ggactatttt aaagcaaagc ccacatataa cattttcccc cacccactaa  19440
tactggagta catgtctgta attgacatag acatttttct ttcttgcata tcttcaatgc  19500
```

-continued

```
cattaccatt tcttttttttg tttgttaaac ttttaggttc aggggtacat gtgccggttt  19560
gttatataag taaactcatg tcatgggggt ttgttgtgca gattattttt cacccaggta  19620
ctaagcctag tacccaatag ttactttttc tgctcctttc cttcctccca ccctcggccc  19680
tcaagtaggc cccaatgttg gttggtccct tctttgtgtc catgagttct catcgtttag  19740
ctcccactta taagtgagaa catgtggaat ttggttttct gttcctgcat tagtttgctg  19800
aggataatgg ccaccagctc catccatgtt ctgtaaaaga cataatctca ttcttttta  19860
tggctgcata gtattccatg gtgtacatgt accacatttt ctttatccag tctatcattg  19920
atgggcattt aggttgattc catgtctttg ctattgtgaa tagtgctgca atgaatatgt  19980
gtgcatgtgt ctttatcata gaattacata tattcttctg ggtacttacc cagtaatggc  20040
aaatggcagt tccgatttta ggtctttgag taatcatcac attattttcc acaatggttg  20100
aactaattta catgcccacc aagggtatat aagtattccc ttttctctgc agccttacca  20160
gcatctgtta tggttttgac tttttaatga tagccattct gtctggtgta agatggtatc  20220
tcattgcggt tttgcatttc tccaatgatc agtgatactg aactttcttt catatgcttg  20280
ttggccacat gtatgtcttc ttttgaaaag tgtctgttca tgtcctttgc ccacttttta  20340
atggggtgtt tgcttttttc ttgtaaattt atttaagttc cttatagatg ctggatttta  20400
gacctttgtc aggtggacag tttgcaaata ttctctccca ttctgtaggt tatctgttta  20460
ctctgttgat agtttctttt gctatgcaga agctctttag tttaatcaga tcccatttat  20520
caatttttgc ttttgttgaa attgcttttg gcatcatgaa atctttgcct gtttctacgt  20580
cctgaatggt attgcctagg ttgtcttctg ggtttttat agtttagggt tttacattta  20640
aatctttaat ccatcttgaa ttgagttttg tatatggtga gaggaagggg tcccatttta  20700
atcttttgca tatgggtaac cgtttactga atagagagtc ctttccccat tgcttgtttt  20760
tgtcagcttt gtcaaagatc agatgatcat aggtttgtgg ccttatttct tggctcccta  20820
ttctgtttca ttggtctatg tgtctgtttt tgtaccagta ctgtgctgtt ttggttactg  20880
tagccctgta gtgtagtttg aagtcaggta acatgatgcc tccagctttg ttcttttgc  20940
ttaggcttgc tttggctatt tgggctccat atgaatttta aaatagttct ttctggttct  21000
gtgaaaaatg ccattggtag tttgatagga atagcattga atctgtaaat ttctttggga  21060
agtatggaca ttctaatgac attgattctt tctatccatg agcatggaat ttttttttaa  21120
tttgtttgtg taacctctga tttctctgag aagtgttttg taactcttct tgtagagctc  21180
tttcacctcc gtggttagct gtattcctag atattttact ctttgtgtgg tagttgtgaa  21240
tgggattgtg ttcctgattt ggctcttggc ttgactgttg ttggtgtata gtagtgctag  21300
tgatttttgt acattgattt tgtatcctga aactttgctg acattgttta tcagctgaag  21360
gagcttttga gccaagacca tgggattttc cagatatgga atcacgtaat ctgtaaacag  21420
ggatagtttg acttcctctc ttcctatttt gatgcccctt atttctttat cttccctgat  21480
tgctctggcc aggacttcac atactgtgtt gaatagggat ggtgagagag ggcatccttg  21540
acttgtgcca cttttaaggg gagtgcttcc atcttttccc aattcagtat gatgttggct  21600
atgagtttgt catagatggg tcttgttatt ttgacatatg ttccttccat atctagttta  21660
ttgagagttt ttaacatgaa ggaatgttgc actttatcaa aagcctttgc tacatttatt  21720
gagataatca tgtgtttttt gcctttagtt ctgtttatgt gatgaatcac atttattgtt  21780
ttgtgtatgt tgaaccaacc ttgcatccta gggatgaagc ctgcttgatc atggtggatt  21840
agctttttga tgtgctgctg gattcagttt gcaaatgttt tgttgatttt tgcatcaatt  21900
```

ttcatcaagg attttggcct gcagttttct ttttttgttg tgtctctggc aggttttggc 21960
atcaggatga tgctagcctc atagaatgag ttgggaggaa tccctcctcc ttgaattttt 22020
gcgaatagtt ttagtaaaag tagcactagt tcttattttt acatctggta gaattcagct 22080
gtgaatctat ctggtcctgg gctttttttga ttggcatgct atttgttact ggttcaattt 22140
ttgagctcaa tattggtctg cttagggcat caatttcttt cttcaattca gtcttgagag 22200
tgtgtgtgtc caggagttta cccatctcat ctaggctttc tagttcatgt gcacagaggt 22260
gttcatagta gtttccagtg gttattttta tttctttggg gtcagtggta acatcccctt 22320
tgtcatttct aattgtgttt acttggctcc ctctcttttc ttctttatta atctagttag 22380
tggcctattt atcttattaa ctttttcaaa aaaccacctc ctggatttgt tgatcttttg 22440
aatggctttt catgtcttga tttccttcag ttcagctctg attttggtaa tgtcttgtct 22500
tctgctagct ttgggttggt ttgctcctgc ttctctaatt ctttcagttg tgacgttagg 22560
ttgttcattt gagatctttt taactttttg atgtgggcat ttagtgctct taatttccct 22620
gttaacactg ccttcattat gttccagggg ttctggtatg ttgtaacttt gttttcatta 22680
atttcaaaga tcttcttgat ttctgcctta atttcattat ttactcaaaa gtcattcagg 22740
agcacgttgt ttaatttcca tgtaattgca tggttttgag agttttttta gtcttctatt 22800
tttaatgcgc tgtggtctga gagtgtgttt ggtataattt caattatatg atcagcttta 22860
gagtatgtac catgtggcaa tgaaaaaaat gtatattctg ttgttttgtg gtggagagtt 22920
ctgtagaggt ctattatatc tatttggtgc aattttgagt tcagatcctg aatatcttca 22980
ttaattttct tcctcggtta tccatctaat aatgtcagtg gagtgttgaa gtctcccact 23040
attattttgt gggagtctaa gtctctttgt aggtctctaa gagcttgctt tatgaatctg 23100
ggtgctcctg tgttgggtgc atatatattt aggacagtta ggtcttcttg ttgaattgaa 23160
ccctttaccg ttatgcaatg cccttgtctt ttttcatctt tgttggttta cagtctcttt 23220
tgtctgaaat taggattgca acttctgctt gttatgattt ccatttgctt cgtaaatttc 23280
ctccatccct ttattttgag cctagggatg tcattacatg tgagacgagt ctctaaagac 23340
agcattccat tgagtcttgc ttttttattc agcttgctat tctgtgcctt ttaagtggag 23400
catttagcaa atttatattc aaggttagta ttgatatgtg tagatttgat cctgtcattg 23460
tcttgttagt tggttattac gctggcttgt tgtgtggttg ctttatagtg ttactcatct 23520
gtgtatttaa atgtgcatta ccatttctaa ccgacctaac agtacttctt taatatcaca 23580
taacacatag ttcttgttta catttccaca attatctcaa aaatgcagct tttgttgggg 23640
cgatcagacc caacaccagg tcgtgggggt gatgaagtcc ggcggagtca aaggaattag 23700
aaaaagacag tttgagaggg aaagtgggac caggggggcca ttgcaagtgt agaggctgcg 23760
aaggccctga gctctgggag cccatacaat ttattggtgt tcaaacaaaa aaacaggtgg 23820
tgaggatggg ggttgaaatg aaacagtgta tcaagtgaat aagaaacata tggctgcttg 23880
agataacggc agtgctagaa acaaggagcc agcaagtctg gcagacatgc tagccctgcc 23940
tcagcttctc tcccaacact cagctttact cccaacagct ttcaagttga tttctttgag 24000
ttaggatgca aacgaaatcc acacatttag ttggtttgtc tcttaagttt cttctaatct 24060
gtagcaaccc ctgtactctt tcacatcatt tactttttaa ataaataggt tgtgcatcct 24120
gaaaaatttc tcacattttg agtttggctg attgcttctt tcttgtgtca cttgactttc 24180
ttgttatgtt tctatattcc ccagtatttc ttataaattg gcaattagat ttagaagctt 24240

```
aaactaaatt caagttcaat ttttttgtg ataagcataa atcggatgtg atgtgcactt  24300
cttattatac catagaggag gcacatactg tctaggactt ctaagtttag tgatgttaag  24360
attcaactgc agatttaggt gtcagcacca tccatttatc cattttaagg ttctccacaa  24420
tcctttcacc caatgatata agcacctctt ggttattgtt tctagaccca cttttttttc  24480
attatgggtt aataaacagt aactttctct ccctcgtctt catttattaa ctggattttt  24540
taataaaaaa taactttcct catcaattat ctggtaatcc aaattacagt tttataggaa  24600
atatagagta aatgcaaaac tcctcctctt gccagttttc agaataataa gttggtggcc  24660
caacaatttc caaagataac tctttttatt tttttaaaat agtatcatta tagattcatg  24720
ggtttctctt tttctttaat gcatcttgat caattgcaat gattatttct ctcatttttt  24780
agacactggg agttctttaa aattgcctcc tgtgtttttt ttttttttgac acaaccccca  24840
gagtctacca tagtttgctt gctttctggt acaataagat atcctgggct aattctgtat  24900
attacctgcc tcagatctag acccaggtat ttctccagtg gtttcttgcc tttttttttt  24960
attttttttt tttagtggta aatggtatgt agagacctta ctctagacac tatggagaca  25020
aaatgtgact gcgtttttat tgttgcgaga ttttttttgt gagcagttag aaaacacatt  25080
ttaaaagaat gaattaataa ccaattcaaa tttaacattt cagaataagc acttaacctc  25140
tttggttcta tacttgcatt tttttttctt atgctgaaaa ttttgttttc tctttgtttt  25200
atcctacaat atggctatgt tttcttccaa gtgataatgc gaacattatt attatcagta  25260
agatcattca atgctattta cattttcttt gagactcatt tgtccttgga atagaaatgt  25320
ggagtaaaaa tgtgctttag aattacttgc agtaattctt ttctgtatat agttatgcca  25380
ccaaccctga tatgcatttg gacttatttt ggtttgtttt tactgtttgt agatttttat  25440
ttaataattt tgtttttaat tatgtatata acatttacat taatccaaag tcaaaactat  25500
caaacaagat gtattcaaca aagtctagct tacatctttg tccccccttct tcctcccttc  25560
tgttccataa gtaatcattt gtattagttt ttatgtttag cccacatttt ctttaaggca  25620
ttatctctta actgtatttt ttaacacttt tatgtaggca agagggatga tgcttaccta  25680
catcataaag gaagtagcac tgtcctattt aaaccccccgc cccaggaatc caaatcctgt  25740
gctccttcct ctgtcccatg ctgccctcta cagacacctc ggggaatttc aaggagaggc  25800
agctgtcagt tcttcctgag gttagatgtc caaattaagc agactctttg tgcttcagtg  25860
atactacctt ctactctaga attttgtaaa aatacgtatg cgaacctttt tggggctcca  25920
ggcagtgctt ggtgtccagg cgaaaatgtg tgaataagca agcactcgtg tgtgttggga  25980
aaacaaatta tccctaaatg ctgtcatttt ctcttaacac cagctgcgat gatgtggaat  26040
tgaggtacaa ttaaaaccca tgaaatgttc tgcaagttta aaatgaccat aggtttaaat  26100
attttttttt tctatctaat tcaatgtaat tttaaattgt cttgacaact aggcagaaaa  26160
tagaaactac aactttccta aagaaaattc ctggccgggt gcagtggctc acgcctgtaa  26220
tcccagcact ttgggaggct gaggcaggcg gatcacctga agtcaggagt ttgagaccag  26280
cctggccaac atggcgaaac cccgtctcta ctgaagtaca caaagtagcc ggcgtggtgg  26340
ctggtgcctg taatcccagc tactcaggaa gttgaggcag gagaattgct tgaacccggg  26400
aggcggaggt tgcagtgagc cgagactggg ccactgcact ccagcctggg cgacaagaga  26460
ctctgtctca aaaaaaaaaa aaaaaaaaaa aaaaaaaaga aaaaaaagaa agaaaattcc  26520
taactgggcg agtgcataag taagacagag ttaaaatcct acggtactgg gtattgttta  26580
ctcccaaagg gtttcttcca agtcttctcc gctcccgtcg ggcctcctgc cggggcggca  26640
```

ggagcaaagg tggcgccgtt ctgtacacag acatgttcta gcgttctagc gtccccagtc 26700
tcttccctct tcgttctgct ccctgaggca cctagaagca aaagaaggtt ttgttgttgt 26760
tgttttgttt ttgtttgttt tgttttttga gaaaggggcg cgaagcaggg tgcgaatgga 26820
tccctaaatt caggtcgtgg ctggctttcc cagcatccag tttctgctta gcaaagatcc 26880
aagagagctt ccccgtaact tttggatttt tgtctgagat aagggttcaa aagcagagca 26940
ttttaatgtc atagatagtt cagatggata cattagaatt aagttatttg aaaaacaaac 27000
aaatgataca ggagctataa agaaattatt taggcagtta gtgagtgtaa gagagtcctc 27060
cgtaaggctt ccccttttaac aaaaagcagc ctccaaataa tttcttttcc agcaaagaac 27120
agcttgtaaa actgagctgc agacctaaac aagcaagctg gaagcttgca tagttagatg 27180
ctgttagctg tgctgataga aaaaaggcta cctgggggcc aggcatgttc aacatggagg 27240
atccctcttc tcttttcttt gtcgccactt gggcagtaaa aaggcaggca acatggtccg 27300
gactggtaga gaccccatct gcataataaa atattagcgg gggatggcca gcttcttcac 27360
actctataca aacagcacac ctggtccgag caatctctca ggccgtatgt taatcagaca 27420
ctgcctcctc aagcttgtct ataaaaccct gtgcgtttca ccaggaaacc cgaagaccca 27480
cttgggcacc cgtctctctc tgcaggagac agagctattc tcttttctct ttctttcacc 27540
tattaaacct ccactcttaa actcacttct tgtgtgtccg catcctcgat ttccctagca 27600
tgagacaatg aacctctggt atttacccta gactatgagg cctcttcaca aacaaacaaa 27660
cagaaaaacc aataacaaca gtaaaagtgc taaaatgcca gtaggaagtg gtgaaagcgg 27720
tgctgcaagt gggtggggac cagaaacatc aactttgaga tgagggcagg cagggtagct 27780
ttaatttgtt cccagtggag caggcccctc caggaggagc tgccaccggt ttggggagcc 27840
cacaggtcct cctcccaggt ctggggcagg acccaggcag gttgcgcacc tgagcgacgg 27900
cccttgtcct cttatttct gggtaagggg ctgccctttt cccgcacaac agtggtcagg 27960
agaggcagtc actgacttga ggtgaccagg gaagagcagg gccatccgtt tcttcggaaa 28020
aaaaaaatca gagttttaaa atcagagaca tgcccagggc tgaagcctga agctgtttct 28080
tcctctgtgc cagataacct caggatccat aattctttgg aatctcaccc tgccgaatta 28140
ctttctttca aaaataaaat tattttctga taattacggt aatgtacatt ccctaaattt 28200
ttgaaaacca tggaaacatg aaaaaggtgt gtgtgtacac acaatggaga cacactttac 28260
attctgtaaa tgctgctttt tcacatcaca tgatgacagt ttgtccactt ttaaaagtgg 28320
ttgtaatgac tgaacaatat tttacccatt ttagggatgc acagttcttt agttaactat 28380
tcccttcgtg ttgaacatta aggcagttct acttcattgc tcctgtaaag aatgctcctt 28440
cacagaatac cctgggtctc agcttccaca ctggaggaga ggaagttgct gggaacatca 28500
gactgggaca ggtcacccat cctttgtttc ttccagtatt gctcctctgc aaaccttagg 28560
gccaccatca gcagcagcct ccaaaccagt attgtggggt agggtggtca ctacataagg 28620
atatctggcc tatggggaaa gtggggactg taatccagct tgaatgttgc tggcctacct 28680
gtgtgtaagc ataagtctgt gtccattctt ctaattcact caaaggtgcc acatggatta 28740
gacgaacgag tggtcctggt agcaactggg gcctgagggg gtgcatacat agaaatggaa 28800
tactacgatg tcgttttgat tttttagttt tattttagga atatcctggc ttagatttgg 28860
ctatgatttg tgctttactc tcatttcaac actttaccat cagtgggaaa tatcactgtt 28920
gctttatgtg caaagtgatg gttttaataa ggggtaaaga ggcatagtta gttgaccact 28980

-continued

```
gcactttcat ctgggacagc acctttctta cccaaacagg atcatattga agctatgact  29040
tacatggttt gggatcttag ttgtatacat ttcaaaaagc gatgttaaac acattgagct  29100
aggctgaaaa aagtaattta gaaagaattt tacttcctgg ttcgaagtaa atcagtatag  29160
catggtggtt gtgttcatgg tctctgcatc cagactgctg tatgaccttg gcaagtgaag  29220
gcaacatgtg atgattatgt ttccataact gtaacatgaa agactaagag tacctacccc  29280
aaagggttgt tgggaagatt aattgagaaa ctgtaggtaa gacacgtaga acaatgcctg  29340
gctcatcata agtgctaagt aaatgttaga ttttatgatt atatccattt ataaaaccag  29400
cagcatttct catttccact tttttcttct ttccagtctt cttacataag atacttgttc  29460
atagaatccc agtctcattt ttctccctgc atccacaacc tcttcatgtt taactctccc  29520
taaggcactc cagatattta ctgaaaaaat tgagttaata gttattcctg ggttcttcct  29580
ttcccaccct ggtctctcag caacttttct tctagttttt ggattctttg cctccccatt  29640
ctctgtctta taggtgggga tcctggaata tctttcataa cctgatggta gcagttgcct  29700
tcaaccagag cctgggcact acattacagg ggaaaatcag gcctcattgc tgtggctatg  29760
aactggtacc cctcctcttc ctgccccaac gtaatcgtcc tacaggcccc ttcagagatg  29820
ttagaacttc tacttttctg gtctggagtt gagctctgtt tcttgtgcca ggcagtgctg  29880
gctggagtag cagaggggag gagacactca cagagcagcc tgggctgtag caaaggcaga  29940
gagtaccacg tggtgctgat aaaacaaagg ctttattttt tcatagggtc agacacaggt  30000
gatgacaact ggctgtgcag atattgcaca cactggcaga taccagggtt gatatcctgt  30060
gggatcctgg agaatggaca ggaagagcca ctagggatac ctcagagctc tctgcggggg  30120
aacttctcag tgctgaccaa aggaaaggag atttgagtat gagagagcaa agcagaccag  30180
gatgctcctt ggactttctt tcctctaaag ttgcttattt cagcataaag atccaggtca  30240
gtggcagcct gagcccccac cttgctgacc actgcccctg ccacagaagt tggagctgtg  30300
gcacttgcat tggcgggacc tgtggcacct gtggtggctc agggagcaca gacactttgt  30360
gtcccctcaa agtgctcctg tcactcactc tcctcctcct gagatcaggt gtccacagtc  30420
ctcacacaca caggatttgt ctgtgatgtc ccctcaaaga ggggacacaa agtgttggaa  30480
aacacagtgc tattttcccc agttttgctg gtgatggagg ccaagagaat gtcagctggg  30540
cagaaagtca gtctaatgaa gctgtgtcat tgtggggctc tgggccttct aaagggtcca  30600
cctcagtccc tagtccatgg ctgtagatgg agacaccacc ttctgtgttt ctttatcatt  30660
tggcttcagc ctcctcccct tcctaatggc cagcaccagc cctcctcact ccatgaaatt  30720
cctcctactt caagtccttc attcccatat tccttcatta ataaatttct attgagactt  30780
agcaatgttt cccatccaaa gagcaccaga aaagtaacta tagtagaatg actttatgtt  30840
tgttgacttg ttgcaatgat ggagatagga catgatatgg aagcattaag aggtgctcac  30900
tgtaggattt gggcttgtgt gttaggtagt ttgggggagt gttgacggaa ttaaagtttg  30960
ttctggattt gatgctgtca gaaagcaagg acacttcaat aagcaggtat cttaattttt  31020
aactaggaag ttggagcaat gaggcaaggt taaagctata actagtaaaa aggtagaagt  31080
cattcatatg agctgagaca agtgaatgtt tggtcatttt tgtggtttgg gcaatgcttt  31140
tgcttcattg atgctcagag tggtcttgtt tttgtcttgc tccctcgagg tcacagagtt  31200
agcttatcta aggttagagt tctgtaaaag tatttatatt caacaggaga acatcagatc  31260
cttgctacta gagcgaggcc agcttgctgc cagaaatctg ggctactcct tcttttctca  31320
gcatcaatta tgggccaggc atcatggtca gtagtagtga tagggtaggt aagagaaaat  31380
```

catggcatct gtcttcaatg agcttaaagt ctagcagatc taacaaacat aaaagagtaa 31440
attgttaggg ataatggacc ccagaaggag ttccatgtgc tatgggcatg tagagaaaag 31500
gtattgaagt ctatactttg ttgcaaactg aatatttatt ttttcatatc ttgcagttat 31560
cataagcaag ccttatcctc cagacagggc aaacatggca gccattttcc tccatggcag 31620
ccattttcct ccatagattg caaccctgag ccgttggcag caggggaggc aagaggtagg 31680
agccagaatt aaaaaggaaa ataaatcaca cattttgggc aagtttcaaa gaatcaaaat 31740
atcttttcca atgactttca gtacatcgtg ttacctctgt tttatgaaac acagtggatg 31800
actattaggc tttcttccag ccccattctt gactacctgt cttgaaagcc tccccacaag 31860
acctggagag ctcattaatc tcctttctac cttagtgatt gcccttgtca ctcactctcc 31920
tcctcctgag atcaggagtc cacagtcctc atatgcacag gatttgtcct gtgatgacac 31980
atggtagcta taagaccatg atctggtcac ttcccttaca gcacaagggc acctccctga 32040
gagtcactag tcccaggagc cccatcctga ggagacttgg cttcctgtgg tccccagata 32100
tcaaggaaat acagagactg ctctggctgg atgaatccag gaaaaatttc atgacttagt 32160
cattccaatt ggtactatag gaacaggcac tgcaggacct caggtttagc tctttggagt 32220
acattttgga cattccacat cagcaatcaa agatgagtaa acaaacagaa ttcttctccc 32280
tttgcttaca actcacagtt ccttctccat tctgttcctg ccatgactgt gacagtcaca 32340
ttccatggca agcagctgag tcattcttaa ggaaaatggg actcggtagc cagaaagtgc 32400 catataccttcaatgtgcct aagtttctta tatggattct aattttcccc tcaggttaag 32460
tagtattttg agctatttat acctctttag tctcctgaga aagttctggt tggacccagt 32520
gtgtaaaaga atgttggact cgaatttttt tcttgtgttg ggatgttggc tggagttgaa 32580
agataaaaat aatatgtgcc ccttatcccc ttatactaaa gtaacctcag gataagctgc 32640
tgaaaatctc tgcaggactt gctaagaaaa aacataactc tatttctctg gtccagttat 32700
atatctggaa gtttgagttt tgataaaaat tttttaggta ggagagttat tgtcctagaa 32760
gacagtacta tggtttcacc cttatcttgt ataggaaggg aactggttgc tctcttgtaa 32820
cagagatcaa tggaaagggg aggactcatg attcgaaatt gtagatgtta gaggtccctt 32880
caaaaaagga agacaggatt ttcatccagc agcagaagtt ctgctgcagt agtagatttg 32940
attgtttaac ttctgagcct attgtttaat aaagaaaagg aattaaagag atagagcagg 33000
atgttgagac ataatagtag acaacatctg ggaaggaaga ccagcttgca cattcttcct 33060
agtgttgtgt ttagaacggt tttctgttga gcagtgagac ctcatcatca agaagctgtg 33120
gctggtgtca atgaaggtgg gaacttaagg agtatctgaa gggttaaatc tgactgctca 33180
tcccatgtct gggagtagcg ctgtggggag aacccttgca gatgctccag aaggactcac 33240
aaaaacaccc tataagacag ccctcctgca gagcctgcca cacacaggga gcaagcaacc 33300
aacagaggag gctagtggta cagtcacatg tgtaatgatt tcccctcccc ttttccatct 33360
cccaatacaa tggaggagga agtgttattc aggaagaagg tggagaggtg gtagtgaatg 33420
agacaaagag ccatacatgt tccctcccaa ctccagtctc ttgggagagc catgggcagt 33480
gctcactggg aagggtgaat ttgagtttga agatgcgtac cgaattaaat tcagctggtc 33540
tggactttaa tatccataaa attcactcca gaaatgtgga atttccctga gatattttca 33600
ggagagattc aacacagcat aggagaagat aatgatggga taagacaatg cttcttgttt 33660
ttatgagacc aagtttataa ggtttaatat actattttta aggttctaac aatgtcttta 33720

-continued taacaaggga tcatctttgg gattctccac cttttctaac atcaatgaaa tcaataaatg 33780
ccaagattcc atgtcacaaa ggacaaaaaa aagcaggttc agggatgttg gttgagggct 33840
tcaaaatgac cacatgtggg taatgcaaag gcaataggaa gtagaaactg ggaagttctt 33900
gagggtggga gacatgttgg gattttgggg gccagatagg aagtcttcta gggagaggaa 33960
tatcttaggt caagaggtgg aggagaggaa gttgggtgct ggatggtgag aatactgtgt 34020
gctactcacc tgtagtccat ggggagaaag aataaaggaa aacttttggg gagtcagtag 34080
aagaccctga tcaatctgac ccttgccaag ttccttttat tcaacatctg ccatcttctt 34140
ccccaattct tggctacaat tcttttcttg taccatgttt tctcccaaca ttctgtctat 34200
cctgaatgta aggagaggag tgaatgtact gagacataaa agatctgtgc tagatcccag 34260
gcaggtgtat cacgttagtg actgatactt ggtactcaag aaataaactt tggctctgac 34320
agagttctcc tctccagggg gcatggaata ggtttattta ttgtggaatg gatagatgca 34380
gggtagttgg aagagaaaat aaatgggagc attgaaagaa cccaagaaca tttgacagaa 34440
tctggagtgg gcaccacaat attgtgttgg ctggcattac acctgggcaa tctgctgagt 34500
cagagtcttt ctggaaatta ggccaaagat ggggttatta ataccagcac acactgagtg 34560
ctggaatcca gatatttatc aatgcaagtt tttatttaaa gattaggatt tatggtttat 34620
atgtgatttc caacttaaat ggtaaattct gtaagggaat ccccacctct accatcttcc 34680
ctaatgttcc atggaacttc tccacccagg agatacagag gtgatggagg aggaaaagca 34740
tcacactgga gagaggcttc tcttttgctt cactggatca tccagccctg ctcctctgtg 34800
gttttcagag ccctggttgc tgcatgagtg acagcaccca gaactctgat gctgtgctta 34860
gttggaggtg tgaagcttgt gatggctcag gcaggagcgt tctccagagc tgaggctatg 34920
gcagccccta gagctggggc tccatgggaa gagactgcag tgggcactga agaccatgtt 34980
tgggtggtca ctttgccccc aaagtcattt gggagaggct tgaaactctt cctcgtttta 35040
cttccaggac accttagggg aagtttagtg actctagaaa aagtaaaaag gggaataatg 35100
gcatgtaatt gtatcagttt taaaaattgg ctattttctt atttacttca gagaatgtgg 35160
ctttgaatcc acaacttagg gaaaattcct gagcagatga gagtgggaaa tggaaagtta 35220
acttgggtaa aagggtcttc atccagtgag gactgactat accttggagc tgttttctta 35280
ttttgttttg caggcaagaa atgagtggtg ggattgggag gggtgggagt gatgagtctt 35340
gtttaggagt cagcttcttc ccttctgtag ccccaagccc tctgcatctc catggcaggt 35400
gtcaggagtt atgaggagag cagggatcca agaaactcca atatccaaga tattcatata 35460
tttctgcctc aatctttctg taggtcttta gctctttatt tttcatttgt tatcatcatc 35520
cgttatttaa acaatttata ttgagatgat ggtgatacga gaggcgggca gggaagtgct 35580
gggtagagaa gagtggggtc cctggtgagg gctccaccct caggcctatg cccatggacc 35640
taagtgagga caggcactcc tggttttgca cccaaatgtt gcattttcta agcccactct 35700
gacccaccat gccccacatc ctgggcccat aaaatcttca agaccctagt gggcatggac 35760
acaagtggct ggacgtggag aggagcagaa gagcacactg actgatacca gcagacgcca 35820
gcaggccatc aacagcagga cctcatggaa ttcagtgggg gcagttggag gccagctggc 35880
cactgggtgg tccgactcca gctgaagcct atcttcccac cccatcccct tgctggcccc 35940
cccatccatc tcactgagag ctacttccac cactcaataa aaccttgcag tcattctcca 36000
agcccacatg taatctgatt tttccagtac actagagcct acagaatatg ggatacagaa 36060
agctctctgt ccttgtgata agtcagaggg tctaactgag ctgattaaca caagctgcct 36120
gcagaccgca aagctgaaag agcacactgt aacacatgcc tactggggct ttgggagctg 36180
taaacactca accctagaca ctgccatggg gtcacagccc aaaaatgctc ccaggacctg 36240
cccatttgca tgctccccct agcggttcga gcagcaggac atcaaagaag cgagtcacac 36300
ccctgttgca tgccctgcaa atgggataag ggaactcctc ccatttcaat ggcacactct 36360
gtgctgggca aggcatattc aagagtaaag atactatccc taccccttagg ctgatgaggt 36420
agtggggctg agagataagt aggaaactaa gtctgagcca agtgagggtg ctgagataca 36480
cgtgtgtggg agtcctcagg cctgaggtca gagttgttgg aggttagtcc cttgttgctc 36540
tgcagtgact tgtagtgaat gatgaataca gatggtgtca cctgctgtca cttgggatgg 36600
ttgacggggt gagtaagatg tggatcctgt gtccgtccaa ggacagtaaa ctcaggcatg 36660
gcaactaaga ggaacttgtg gacccaagaa gcatgaaggg ggtgatgagg aggaagagat 36720
aatggtgggg tgaggaagga tggggctgac agaaacattg ggacatctac aatcttgagg 36780
acaagatgat atgctcattc agagcatctg gtttggagac aggaacttcc tagtttaatc 36840
tttggccact tctcctaata gctgtgtcaa ggtagagatg cccaaggcag aaaaatctat 36900
atggagacaa gatgatccag ggatgtccca ggtaaaacca gagacaggga taagaaatct 36960
aaaatggctg tgatggtaat gtgtcacaga ttaacataca tttaagacat tatgtcagga 37020
tcttagtgac tatagtattg attctaagag agccaggaaa gagagtgatt caaatggctg 37080
ggatggctaa gagagattag tccaacgatt aatggtaatt aatgggtgtg ttataatgag 37140
gttgatggga taaacgtgaa cacctgacat aaagtagact aagtttgcag agacagacct 37200
aaactctata ctattttcca tactatttat tttatatata tatacacaca catatatatg 37260
tatacacaca cacacacaca cacacacaca tttcatcctg aatcatgata tattaaaaat 37320
aagtaaaaat gaggccagga ttggtggctc acatctgtga ttcctgtgct ttgggaggct 37380
gaggtaggag gatcccttga gtctgggagt ttgaggccag cctgggcaac acaggaagac 37440
ctcatctcta ccaaaaaaaa aggaaaaaag aaagtaagaa aaatatttaa acttcaaata 37500
tatgctcaaa tcgcaagatt ttgataaaat attcttattt attttggttt aaaatggttg 37560
actagaagca gctagtgtgc actgctctta tggagaggat acaaagcagt gactaaatac 37620
tagctcttca agtgaattgt caaagagatc atattgggat ttaccaagga attgacagga 37680
cccacagaga gcagagagga gcaaagctgg gcagccattc atctgagact ggcacagagc 37740
tgggggaagc tccctaaagc agagaaagag tgagtgagag ttcccgggga ctcacacttc 37800
tgccatgaac ctttgcaata ctaggcatag gagagcccct ctgactcctt gagcctccag 37860
accaacacag agagcctgtg cagaggcacc agttaagtcc acttggagcc ccataggcct 37920
tgtatcccta acagccagtg ccagctgctt taggccagcc aaaagggggc ctgggctctt 37980
ttgcacaccc ctgggataac tgctgctgct gcatggctga ggagtggcca ggattcagac 38040
tccatcccct gctgctactt aacagataag gcctgcatgc ctgggctccc cgagcagtgg 38100
cctcaccccc acctgaacag tgcagttagt catggtccta tactcctctg cagcaaaact 38160
cccagagtaa cagacaaggc ttggcacttt tgcatacccc caaccacaaa atccagtggc 38220
agcaatggag actggtggct atgggggcac atagcatgct gaaaatgggt ccccagtctc 38280
ttccagcttg taaggtttct gatgagtagt ccactgttag cctgatgggc ttccctttgt 38340
acgtgatttg accttttttct ctaggagcct ttaagtctga ctatatgcct gggtgatgtt 38400
catttgtata tgcatcactt ggtgggagag aagtgtgagc atgccatgtg cccccatagc 38460
caccagtctc cattgccacc acggagaggc cctgccctcc ccagtgaaag gcccacagca 38520
cagccacctg ccctgcctga acatttcagc tacagcccag agcccttcta aaaactgaac 38580
cctcacaggc ctataatact tcctaaggct cttaccaccc taagcattct gtctgccact 38640
gcctaagagt ttggcccatg acccagccca gcccttccca tcacagccaa cacctgaact 38700
gggctagcct gacccttgtc caaccccttt aggactcata cgcactgtcc agggggccat 38760
gtaggaactg gggaactccc caccccatta caactctgct ggcacctgac tacttgcctc 38820
atggcctgaa gttgggctga cctaaccaac caacaccacc acaaccagta cccactcaca 38880
cagccccggt gatgtagccc ctctacttat aagaagtggc tgtattgcct cattagagaa 38940
caggtgagca ataaagctat ctgttttagg ctgagtgaca acattatgct ctgaaaacac 39000
tcccatggag tatcacaaaa catgcatttc ccatggctgt caaccacatt gtggtcaaga 39060
gacagactac agtgtgcttc tgaactagga gtcatgagtt ctgggtcaag ggtatgatag 39120
ggaaacagat caacttcctg cctacctaag atgaggaagc agtgcagctt ccttgtctcc 39180
ccacggagac ttcagtgtgc ttcaccagaa gttcctgtca gccacccttt tcagggcttg 39240
tgcctgtgct tgccattgga gtattcatgg gcaagccagg gactccagtt ctgcccagtg 39300
gtgtgcccct ccccctgtgg agcaggaagc tcagggccct gggtgctcca ctgtccatcc 39360
tgtcacctga aataacaaag agcccttcac agtaaacaaa aattataccc acctgcttgt 39420
gctgcagctg gatcttacct gcaagcccta tctgctggcc tgtaggttga actgcacagc 39480
ccaatataaa acctactaac ataagtgcac agagctataa aaacaaagcc aaaagacttt 39540
ttccaatata ctttccagtc ataccctaaa gggaaagaaa gaatatatag gaaaagagaa 39600
aaaaagtcta ttttcatgaa aataattaca ataattagaa gtgccagcct ttctagatga 39660
gaacaaactg gtataggatc tggcaccatg aaaaatctga atgttgacac accaccaaag 39720
tatcacacta gttctacagc aatggtccct aaccaaatgg aaaaacagaa atgacagatt 39780
aagaattcaa aacatggatt tcaaggaagt tcaacaatat ctaagatgat gttgaaaaac 39840
aacacaaaga aaattctaaa gcaatgcagg aaacaaagga agagataaac atcttaaaaa 39900
taaatcaatt ggaggtaatg aaatggaaaa actcacttag gaatttcaaa ataaagttga 39960
aagctttatc aacagactca accaaacaga ataaataatt taatagcttg aagactggtc 40020
tttctttttt gttttttaa ttatacttta agttttaggg tacatgtgca caacgtgcag 40080
gtttgtgaca tatatatata tacatatgcc atgttggtgt gctgcaccca ttaactcgtc 40140
atgtaacatt gggtatatct ccgagtgcta tccctccccc gtcccccac cccacaacag 40200 gtccccgtgt gtgatgttcc ccttcctgtg tccatgtgtt ctcattgttc aattcccacc 40260
tatgagtgag aacatgcggt gtttcgtttt ttgtccttgc aatagtttgc tgagaatgat 40320
ggtttccagc ttcatccatg tccctacaaa cgacatgaac tcatcatttt ttacggctgc 40380
gtagtattcc atggtgtata tgtgccacat tttcttaatc cagtctatca ttgttggaca 40440
tttggcttgg ttccaagtct ttgctattgt gaatagtgct gcaataaaca tacgtgtgcg 40500
tgtgtcttta tagcagcatg cttaataaac ctttgggtat atacccagta atgggatggc 40560
tgggtcaaat ggtatttcta gttctagatc cctgaggaat cgccacactg acttccacaa 40620
tggttgaact agtttacagt cccaccaacg gtgtaaaagt ggtcctattt ctccacatcc 40680
tctccagcac ctgttgtttc ctgacttttt aatgattgcc attctaactg gtgtgagatg 40740
gtatctcatt gtggttttga tttgcatttc tctgatggcc agtgatgatg agcatttcct 40800
catgtgtttt ttagctgcat aaatgtcttc ttttgagaag tgtctgttca tatcctttgc 40860

```
ccacttgttg atggggttgt ttgttttttt cttgtaaatt tatttgagct cattgtagat  40920
tctggatatc agccctttgt cagatgagta gattggaaac attttctccc atcctatagg  40980
ttgcctgttc actctgatag tagtttcttt tgctgtgcag aagctcttaa gtttaattag  41040
atcccatttg tcaattttgg cttttgttgc cattgctttt ggtgttttag acatgaagac  41100
cttgcccatg cctatgtcct gaatggtaat gcctaggttt tcttctaggg tttttatggt  41160
tgtacatcta acatttaaat ctttaatcca tcttgaattg ctttttgtat aaggtgtaag  41220
gaagggatcc agtttcagct ttctacatat ggctagccag ttttcccagc accatttatt  41280
aaatagagaa tcctttcccc attgcttgtt tttctcaggt ttgtcaaaga tcagatagtt  41340
gtagatatgc ggcattattt ctgagggctc tgttctgttc cattgatcta tatctctgtt  41400
ttggtaccag taccatgctg ttttggttac tgtagccttg tagtagagtt tgaagtcagt  41460
tagcgtgatg cctccagctt tgttcttttg gcttaggatt gacttggcaa tgagggctct  41520
tttttggttc catatgaact ttaaagtagt ttttttccaa ttctgtgaag aaagtcattg  41580
gtagcttgat ggggatggca ttgaatgtat aaattacctt gggcagtatg gccattttca  41640
tgatattgat tcttcctgtc catgaatgtg gaatgttctt tcatttgttt gtatcctctt  41700
ttatttcatt gagcagtggt ttgtagttct ccttgaagaa gtccttcaca tcccttgtga  41760
gttggattcc taggtatttt attctctttg aagcaattgt gaatgggagt tcactcatga  41820
tttggctctg tgtttgtctg ttattggtgt ataagaatgc ttgtgatttt tgcacattga  41880
ttttgtatcc tgagactttg ctgaagctgc ctatcagctt aaggagattt tgggctgaga  41940
cattggggtt ttctagatat acaatcatgt catctgtaaa cagggacaat ttgccttcct  42000
cttttcctaa ctgaataccc tttatttcct tctcctgcct gattaccctg gccagaactt  42060
ccaacactat gttgaatagg agtggtgaga gagggcatcc ctgtcttgtg ccagttttca  42120
aagggaatgc ttccagtttt tgtccattca gtatgatatt ggctgtgggt ttgtcataaa  42180
taactcttat tattttgaga tacgtcccat caatacctaa tttattgaga gtttttatca  42240
tgaagggctg ttgaattttg tcaaaggcct tttctgcatc tattgagata atcatatggt  42300
ttttgttgtt ggttctgttt atatgctgga ttacgtttat tgatttgtgt atgttgaacc  42360
agccttgcat cccagggatg aagcccactt gatcatggtg gataaacttt ttgacgtgct  42420
gctggattcg gtttgccagt atcttactga ggatttttgc attgatgttc gtcagggata  42480
ttagtctaaa attctttttt tgtgtgtgtg tctctgccaa gctttggtat caggatgatg  42540
ctggcctcat aaaatgagtt agggaggatt ccctcttttt ctattgattg gaatagtttc  42600
agaaggaatg gtaccagctc ctccttgtac ctctggtaga attcggctgt gaatccatct  42660
ggtcctggac tttttgggt tggtaagcta ttaatttttg cctcaatttc agagtctgtt  42720
attggtctat tcagagattc aacttcttcc tggtttagtc ttgggagggt gtatgtgttg  42780
aggaatttat ccatttcttc cagattttct agtttatttg catagaggtg tttatagtat  42840
tctctgatgg tagtttgtat ttctgtggga tcggtggtga tatcccttt atcatttttt  42900
attgtgtcta ttttattctt ctctcttttc ttctttatta ctcttgctag tggtttatca  42960
attttgttga tcttttcaaa aaaccagctc ctggattcat tgattttttg aagggttttt  43020
tgtgtctcta tttccttcag ttctgctctg atcttcgtta tttcttgcct tctgctagct  43080
tttgaatgtg tttgctcttg cttctctagt tcttttaatt gtgatgttag ggtgtcaatt  43140
ttagatcttt cctgctttct cttgtgggca tttagtgcta taaatttccc tccacacact  43200
```

```
gctttgaatg tgtcccagag attctggtat gttgtgtctt tgctctcatt ggtttcaaag  43260
aacatcttta tttctgcctt catttcgtta tgtacccagt agtcattcat gagcaggttg  43320
ttcagtttcc atgtagttga gcggtttcga gtgagtttct taatcctgag ttctagtttg  43380
attgcactgt ggtctgagag acagtttatt ataatttctg ttcttttaca tttgctgggg  43440
agtgctttac ttccaaccat gtggtcaatt ttggaatagg tgtggtgtga tgctgagaag  43500
aatatatatt ctgttgattt ggggtggaga gttctgtaga tgtctattag gtccacttgg  43560
tgcagagctg agttcaattc ctggatatcc ttgttaattt tgtctcgttg atctgtctaa  43620
tgttgacagt ggggtgttaa agtctcccac tattattttg tgggagtcta tgtctctttg  43680
taggtctctg aggacttgct ttatgaatct gggtgctcct gtattgggtg catatatatt  43740
taggatagtt agcttttctt gttgaattga tccctttacc attatataat ggccttcttt  43800
gtctcttttg ttctttgttg gtttaaagtc tgttttatca gagactagga ttgcaacccc  43860
tgcctttttt tgttttccat ttgcttggta gatcttcctc tatccctctt ttttgagggt  43920
atgtgtgtct ctgcacgtga gatgggtttc ctgaatacag cacactgatg gttcttgact  43980
ctttatccaa tttgccagtc tgtgtctttt aattggagca tttagcccat atacatttaa  44040
gattaatatt gttatgtgtg aatttgatcc tgtcgttatg atgttagctg gttattttgc  44100
tcgttagttg atgcagtttc ttcctagcat cgatggcctt tacaatttgg catgtttttg  44160
cagtggctgg taccggttgt tcctttctat gtttagtgct tccttcagga gctcttttag  44220
ggcaggcctg ttgttgacaa aatctctcag catttgctcg tctgtaaagg attttatttc  44280
tccttcactt atgaagctta gtttggctgg atatgaaatt ctgggttgaa aattcttttc  44340
ttaagaatgt tgaatgttgg tcttcagtct cttctggctt gcagagtttc tgctgagaga  44400
tcagctgcta gtctgatggg cttccctttg cgggtaaccc gacctttctc tctggctgca  44460
cttaacattt tttcgttcat ttcaactttg gtgaatctga caattatgtg tcttggagct  44520
gctcttctca aggagtatct ttgtggggtt ctctgtattt cctgaatctg aatgtcagcc  44580
tgccttgcta gattggggaa gttctcctgg atgatatcct gcagagtgtt ttccaacttg  44640
gttccattct ccctgtcact ttcaggtaca ccaatcagat atagatttgg tcttttcaca  44700
tagtcccata tttcttggag gctttgttca tttcctttta ttcttttttc tctaaacttc  44760
tcttctcact tcatttcatt catttgatct tccatcactg atacccttc ttccagttga  44820
tccaattggc tactgaggct tgtgcattca tcatgtagtt cttgtgccat ggttttcagc  44880
tccatcacat ccttttagga cttctgtgca ttggttattc tagttagcca ttcgtctaat  44940
ttttttcaag gtttttaact tctttgccat gggttcaaac ttcctccttt agcttggagt  45000
agtttgatca tctgaagcct tcttctctca gctcttcaaa gtcattctcc atccagcttt  45060
gttctgttgc tggtgaggag ctgcattcct ttggaggagg agaggtgctt tgatttttag  45120
atttttcagt ttttctgctg ttttttcccc aactttgtgg ttttatctac ctgtggtctt  45180
tgatgatggt gacgtacaga tggggttttg gtgtggatgt tctttctgtt tgttggtttt  45240
ccttctaaca gtcaggaccc tcagctgcag gtctcttgga gtttgccgga ggtccactcc  45300
agaccctgct tgcctgggta tcagcagtgg aggctgcaga acagtggata ttggtgagca  45360
gcaaatgttg ctgcctgatc gttcctctgg aagttttgtc tcagaggagt acctggccat  45420
gtgaggtgtc agtctgcccc tactgggggg tgcctcccag ttaggctact cgggggtcag  45480
ggacccactt gaggaggcag tctgtctgtt ctcagatctc aagctgcatg ctgggagaac  45540
cactactgtc ttccaagctg tcagacaggg acagttaagt ctgcagaggt ttctgctgcc  45600
```

```
ttttatttgg ctatgccctg cccccagagg tggagtctac agaggcaggt aggcctcctt  45660
gagctgtggt gggctccacc cagttcgagc ttcccagctg ctttgtttat ctattcaagc  45720
ctcaacaatg gcaggcgccc ctccccaagc ctcgttgctg ccttgcagtt tgatcttaga  45780
ctgctgtgct agcaatagtg aggctctgtg ggcgtaggac cttctgagcc atgcacggga  45840
tataatctcc tggtgtgcct tttgcttaga ccatcagaaa agtgcagtat tagggtggga  45900
gtgacctgat tttccaggtg ccgtccatca cccctaggaa agggcattcc ccgacccctt  45960
gcacttcccg catgaggtga tgcctcgccc tgcttcagct caggcttggt gcactgcacc  46020
cactatcctg cacccactgc ccaacaatcc ccagtgagat gcacccgata cctcagttgg  46080
aaatgcagaa atcattcatc ttctgcattg ctcacactgg gagctgtaga ctggagctgt  46140
tcctgttcag ccatcttggc tcaaactaac ccactcagac tgtgttagtc tgaatgaaga  46200
atatgaagaa aaagaattta agaaattaac aaagtttttg agaaatatgg aattttgtaa  46260
agtgatcaaa cctatgaatt attggcattt ctgagagaga aggagaagga ctcaacaatt  46320
tggaaaatat atatgaggga ttaattcaag aaaattttct taatcttgct agagggatag  46380
acatccagat ataggaaaac cagagaacac ttcgcagata ctgtacaaaa tgaacatcac  46440
caaggcatat agccacagac tgtcaaaggt caatgctaaa gaaaaaaatc ttaaagccag  46500
ttagagaaaa aggtcaaacc atgtacaaag ggaagcccat caggctaaca gaggattact  46560
catgagaaac cttacaagcc agaagaaatt gggggcacat ttacagcatt cctaaaggaa  46620
agaaattcca tgcaagaatt ttatatccca tcgaactgaa cttcataagc aaaggagaaa  46680
cgaaaacttt tccaaacaag caatcactaa tttgttacca ctagaccagc cttaaaaaag  46740
atccttaaga gatttataaa catagaaacg aaagaacaac atgtgcaacc acaaaatcac  46800
atgtaaatac atagtccaca gtccctatac agcaaccatg caatggaaac aacaaagcca  46860
tcagccatca acttcacaag aggattaaaa cttcacatat caatattaac cttgaatgta  46920
aatgatctaa tgccccacat aaatagcaca aagctgcaaa ttggaaaaaa aaaacaagac  46980
ccatttgtat actgtcttca agagactaat ttcatatgta atgacaccta tagtctcaaa  47040
gtaaatgggt tagagaaaga tctatcacgt aaactaaaaa caaaaaagaa cagggatata  47100
tatatatata tatatatata tatatatata tatatacgca tatcagataa aacagacttt  47160
aaatcaacaa gtaaagaagg gcaaagaagg gcactacata aactatagtt caacatgaag  47220
atttaactat cctagatata tatgcatcca acattggaac acttaaattt ataaaacaag  47280
tacttctaga cctattaaaa gacttagata gccatacaat aatagtgggg gacttcaata  47340
ccccactgac agcattagac agagcatcaa ggtagaaaac tagcaattct ggacttaaaa  47400
tcaacatttg accaattgga cccaatagac atctacagat ccctccaccc atcaacaaca  47460
gaatacatct tcttatttgc gtgtagaaca tactctagga ttgaatacat gcttggccat  47520
aaagcaagtc tcaatatgtt caaaatcatt aaaattatgc caatcatact ttctgatcat  47580
agtggaataa aatggaaatc aatataaaaa gatttcttaa aaactacaac atgagttgga  47640
aattaaacaa cttgttccca aatgactttt gggtgaacag taaaattaaa gcataagtca  47700
aacaattctt tgaaataaat gaaaacagac acacaacata ccaaaatatc tggcatgcag  47760
caaaagcagt ggtaagagga aagtttatag cactaaatgt ctacataaag aagttagaaa  47820
gatctcaaat taacaatcta acttcatccc taaaggaacc aggaagcagg aaaaactagc  47880
cccaaagcta ggagaagaaa ataaatactt aaaatcagag caaaatcaaa tagaagagac  47940
```

-continued

```
ctaaaaattc atccaaagga tcaataaaac caaaagcttg ttgtttgaaa ggataaacaa  48000
gatcaataga ctgctagcta gattagcaaa gaaagaaaag tacaattaca aatgacaaag  48060
ctgacattat gacccagccc atagaaaaat aaaagatcct cagatactat tatgaccacc  48120
tctatgcaca caagctagat aaactagaga aaatgaatac attcctagaa acacacaacc  48180
ccctaagact gaatcaggaa caaaccaaaa ccctgaacag accaatattg agttccagaa  48240
ttgaatcaat aacaaaaaaa cttaccaacc aaaatgagcc caggaccaga gggattcaca  48300
gccaaattat actaaaggta cagagaagag ctggtaccaa tcccactgaa actattacaa  48360
aaaaaacgag gatgaggggc tcctctcaac ctcattctac aaacccagta tcattttgat  48420
accaaaatct ggaaaagaga caatgaaaag gaaaactatt gcaaatatcc ctgatgaaac  48480
agatgcaaaa atccttaaca aacaaactga atgcagcagt agctcaaaaa gctaatgcac  48540
catgatcaag tttgtaggct ttattcctgg aatgcagagt tggttcaaca aaaagcaaat  48600
caataaatgt gattcaccag ctaaatggaa ttaaaaacaa aaaccatatg ataatctcaa  48660
tagatacaga aaaaactttt gatgtaatcc atcattgttt cataataaaa atcctcaaca  48720
aactaggtat tcaaggaaca tacctcaaaa taatgagagc cgtctatgac aaacccacag  48780
ccaacatcat actgaagggg caaaagctgg aaacatcccc ttaagaacag gaacaagaca  48840
ttaattctca ctcttaccac acctattcaa catagtgcta gaagtcctag tcagtgcaat  48900
cagccaagag aaagaataca aggcatccaa ataggaaaag aggatgccaa attctctctg  48960
tttgctgaat gtaaaataaa agttgaaata atataataaa atcattattc aaaaaattat  49020
taataggtat tttaaaaaca ctattattac attaaacatg tctgagtatc ctgatacagg  49080
gaagtctgta ggtgtggcca tctttttttat ttgctcacat acattatagc caagtaggaa  49140
acaaaagcac tttcaagaca cttgggtgaa tggggttgtt ccctgagaat gagactggga  49200
aaggacgagg actttcaac tttcaaacaa acatttcatg gttggaataa ccacctattc  49260
cttgcctcac taaactctta ccttgggtgt ggaagcaagc agatattaga tgtccttttt  49320
gtatccacta agacaatgat atccaatgtc aaaagtttgc ccatgatggg tgccttcact  49380
gggtttagct actctttacc agcatctgtc aagtgcccca gagtgggaat ccaattgaat  49440
atagagccac ctttgtctaa atctgctgcc aagcaaggaa gccagaagat gcctccaatg  49500
ggcccctgga acataagctc cctgagaggg gactttgtct tgtttcaaac tgatccaagt  49560
acctagacca gtgccaaata agtatgtagt gaatgaataa atttttgaat gaatgaggct  49620
tggcctagaa gtcccctgat gaggactgaa aagtctgtct tcacacttac tgagacctca  49680
cttgtaggaa tcagcttcca gtggcgggtc accactgcca taacttctgg ctcccatgaa  49740
ctgtactaat gtctcaaccc aaactttctt agttgattct ggtgccacct ttctacatct  49800
tggggtaatt cactgacagc aggagttctg gtggtacttt ggagcacaga tctgactcca  49860
caggcacagc taggtctctg tgcccaggtc tagggatcct tttttttttt tttcatattt  49920
cttaaaacat tttagaggaa ttcagggtac catggtggtc aggagcatgt ggtcagtgaa  49980
actgtctggg tttgcacggc agcttctggg agaccttggg cacccattct acattgattc  50040
ccctctgtaa aatgggagaa ggctagtatc taactcaaag gactgcagtg aggattaagt  50100
tatttactgt atgtcaagcc actggtacat tatgagtcct atataaatta tagatcctat  50160
gaatacatat ccaatttgca actcctgaaa tgatctcatt ttttcccctt tccctaagtt  50220
cctctcagta tatgcccttg caaacacctc catttctctc tttgcacctg tcacctaatt  50280
agctttcaag gatcccttcc taccccgtca acacccagat cttccctata gaaataatat  50340
```

gaatgttttc tctgcagccg tgtgtccttc tgcaacctct ttccagtcct aacacataaa 50400
ctcctcacgg tctccctatg aatggagata agtgacattt ctcattcttc ttgtcctgtg 50460
aggcactcag cctgggagat aagaagggga agagcaatgg agcagctttg ggaggggcaa 50520
aatagaaatg taggtggaga agagaagctt tatttttcac agagtgagac ataagtgctg 50580
ctaagcactg aacagaacat gggtgtggag acaaccatga gggacaccca gggagaccgc 50640
tggagatcac tgacaaccct cttcaggatg aactcaggag ctcagaccat gggcaggagg 50700
ttaggagtgg gtacatcaga ctgaggttaa tcctgggcac tttggtctct ggttccttta 50760
aaattgctca tctcaatgta ctgccaaggt cagcagtaat tctctagcaa tggctggagc 50820
ccctggcagg ctcactcaca gcagtagagg ctgtggtgcc tgtgccagta gaaaagatgg 50880
ggcctttgat aggtcaagca gcagtgcccc actaaagtta aagtgacccc tgaactgggg 50940
ctgcagggaa aggctggagg tgggtatgag gcttagtact ggggtgtgca ctttgaaggc 51000
tttgggggtt atcactgctg ctggttttgc tggagggcat ctcagaagac atcaatagaa 51060
tcagatgtgc ttgtaatgca caaacctctg tcaatatctc ttctgtgatg ggtgtcatag 51120
accccatgct ctcctactga actaagaaat acacggaaga aatgaaaagt tacttggagt 51180
tagtttacct tggaaaaatg cgtttttctc tggtctccta ctagaaaagg atgctgagtc 51240
ttttctaact gggcccctca ggtatcttat ctccatgtaa tcacagagga gaataagcct 51300
gtttgggtaa accttccttg atgatgtctg gtgagatcag tgcatctcgc agaacaaatg 51360
taggaagaag atgagggtgt gctgaaaacc cattaccttc acagtcacag gacacctgaa 51420
acatcctgag agggtgccca ttaaccccac actcttcctg gtgcctccat cccagacct 51480
ctgcttcctt ctcccctgat ggaagcctgg gcttgtcttc ctaggtcttc cagctcaggt 51540
cctgtctcca gctagacatc catctgattt catagaagcc agagaatgct gattttgaga 51600
agtcagtgga ctggggagcc caggacagga gctcctagca tgtgaggggc agcatgagtg 51660
ggctgctggg ggagttgaca gcactaagta ccccagccca gcttcaggac ttatccacct 51720
tccctggaac aggatggcat gtttgaccac aaagagcctg gtcctcactt gtgcatcttc 51780
cacccaggcc tacatgtgtc cttaaaagag gctgtgccct gtgctttgtg gtgaaaggta 51840
gagttcaata tgacatgtca cctgacctat agaaattaat tgtctaattg cacagacaaa 51900
caagtaaata gggagcctgc ttccatgaga aaattgctat aatgtaagtc actatgcaca 51960
aagtttgcag gtctttgtcc atatacttct ttctagcatg ttcccttagg aaaaccaaac 52020
acccagatgt ggtgttgggg tggtgacttg ctgttggggc ggtgactgag ctaaggacgc 52080
tggacattca gtatgggctg tgtgtaaaac agatggaagc ctaaagtcag gggaggtgag 52140
ggtccctgaa agagcccccg ggcaggagag gaggggagtc aaatgagtac ccgattgaag 52200
ggcaaatgta gagaaggaaa gtacaatagt tgcagtaata agagtcacaa ctgacgcatt 52260
ataaaaaagc atgaccttcc atcaaaatcc aaggaatgcg tgctctttat ttgaagacga 52320
tgaaaacact gagggaggag tcgttcatct gcttggactc ggtaaggaag ttgtgcaaat 52380
gtgcatgata atggatggcc ttgatgaaga tggctttgct gtacgtgttg ctgcttatga 52440
ggttgatggt agtgctgggt gcatctcttg taatgaagct gacctgatgg tgtctatgtt 52500
tgggtatgcc gaattggtgc aaactgaatg ctatttcctt gttaatttca ttttaatttt 52560
aaatgaattt atcattcaat taatctctaa tattaaaaga ccttttgcta gatatttttc 52620
aagataaatc acagtcaggt ctataaccaa actttagcca tattaaaatt ataattttca 52680

-continued

```
aagaaaatta aattatgttc attatcagtg ggtgtaattt ttctcttact ctgcctaaga  52740
gtttgcccct ttaagtacat agtgatgcct gtaggagcat aaatgcaccg ggctgtaagg  52800
aggacagtgg ctctgtgtgg atgggtagag ggtgggtgca gattttgata tcctcagcag  52860
ccttttcctg cctccagccc atggtacctg cctctggttg aaaggtattt tcagaatcat  52920
ttccagaact actcctgagt ggccgttttt ctcatattgt ttagggtttc ttcagtagac  52980
cctggcctgc aaaaaggcac ttaagaaaaa tggaccaagt actttctcat ggtacctaga  53040
ttgtgaagct gaacaaagct gggtggccac ttttgcttct taggtgtaga atctctagta  53100
tttgggatac aacaacagag gagtaagttc taaagtttca aaacacccca gaactgtagt  53160
gggggccctc cttctgtctc atggaatgca gcagatgtgt gcatatgggc ctctccacag  53220
cccctccccc gatgcctggc ttgggaggct ccatacttgt cctggtgagg atgcccacca  53280
aactttcttc ccctccacga ggaactccca ctttttggcc cctctgtttg ttatcagagc  53340
aggagctctg taggttcaag gctgagcagg tgtcctggga tgacagaggc ttggctggag  53400
gaccactgcc ctgccactta cccagagcat gacatcagct ctctgagggt aatctctacc  53460
aggagtacca cccttagatc tctggctttc taaggttctg tgaggtcagg tgacaagaga  53520
acctggcctg gctggatata tctggataat ttcatgactt agtagtgcca atgggaatga  53580
tgggcacagg tggtatagtg gctcaggttt ggctctttgg agtgcatttt aatcaggtca  53640
tataaaatac acgtaaatga ctatctaaat aacaaaaaga tctttttcat tccctgcaga  53700
acacagcttc ctttcagttt aggaccttcc catccccaaa ccattagcat gaccatggca  53760
agcagctgag acaatctggg ttctcaatgt tatccttgtg tccctagtgg agacacaggt  53820
accacagaga gatgtgaagc cctccatgtg gtggttggga gtaaaagggg aatggaagag  53880
agccttacta atggaaaaga tccaggaatc ccccaaactg tccaaatatc tgttctttaa  53940
atcttctgta ggcctaccat ctcttatttt tctttttgtc cttcctcccc tcatcccttc  54000
tcttcttcct tcctgccctc ctgcccttct ctttcccttc ctgccccctc cctctctatt  54060
ccttccccat tccctttccc tttccctacc tttccctcct tctgtcattc tttccttctt  54120
tactttggaa tatgttgagc tgaacaactg taatctctat tactacgccc tctatatctt  54180
cttgggcaga tgctaagagt ttttttgtga ggaaagtcac aggactcttg aaattcctgg  54240
ggcccagcct tcctgtaggc ctgtcacttt aattttttct ttcattcagt catccattta  54300
ttcaattatt caagtgagat gtgttgtgct gatatggcac accaggcatt ttgctataca  54360
caggagagtt ataaatgaat aagatttgtt ctctgttctt gagtagctca cagtgcagtg  54420
gggcagacag acaaataaca aaataagcat gatccaatgt ggcaagtaca ggaatgcagg  54480
tgtgtggaat gtccttgggc tcaagttcag accctttggg tttcaaaccc cttttacttg  54540
gagtgactct gtgggggaaa atgtgtctag atgttgccac atgctatcat ttgaggatga  54600
gatcactggc ctttgacaat agtatctgtg caagtagcag gagcagaggt ataaatcctt  54660
gatctgtctg tgggcagcca gccaagatgg tgataccaag aggagctaat ggaacccagc  54720
tcatggaacc tcaccaggag gaagagataa tgctgttgct aaggagaaga gagctgaggg  54780
ggaccctgag ggatctaaga caaagtggag ggggcaggat aatgggcttg ttcagagcat  54840
tcattttgga ctcagacatt cctgagtttg aatcctgctt ccccaggtag cagctggtat  54900
caaggtggga agctataaag tgataagagg cacaatggac caaagatgtg aggggcaaaa  54960
tcagagaaag agacaggaag tctatagagg ctgtgaggac atggtttaca aattaaagta  55020
catctgaggg ccattgtatc agtatcttag tgactgtggt atttactcta agagctccag  55080
```

agtagtttca gggagggagt gatccacctt agttggggtg gctaagggaa attagctgag 55140
ctgtgaataa tacttcatgg atgtagtgat gatgaggcca acagtgggga agcttgtgaa 55200
cactgaatgg gcagtgattg aacaggattt agcaaattgc aattacataa gctatgtagt 55260
attttttcca ttgcatttta tataacatta gagatgcatt gcctctgaaa caccaccttt 55320
aaaaatggga caaatctttt aaatcaaaaa cacgaattaa aatgatcaca aaatgttact 55380
gtcttttata aacgttgatg aaaattttgt gtctggttat cctgttacag ggaggcgtat 55440
aagtgatgaa atctccatta gatgatgaaa tagttaatat ttgtgggatg aaaagtgacc 55500
ctgtgagaag aggtttattc acagggctgt ggagagaggg agggagatgg ggaagggcat 55560
gaggagagag gcctgcttgt gcaataactt tgtccccttg gtagtcatga tttatccttt 55620
cttctttctt ggctgttgtc ttttgatgtg gaagctagaa aacacttgat gccctttcct 55680
tttgtcacca ccaaagccac tgtctcagag cctcaatatt ttgcctaggc tgagtgtctt 55740
ctctgggttt attaaataaa caccagtgtc cactcacctc cagaggctga gaggccaact 55800
gaggagaagg ccactgtgat tcactctgcg atgcatgcaa aatcgggaac tgtctccttt 55860
ggaccagttt tgaatgtgag gtcccaaaag acagaaattt gtctctctga ttccttattg 55920
tgtccctagt gcctacaatc aagcacataa tcaatgctca ataaaaatgt gtcaagtgaa 55980
taaatgggtc cagggctcag gacttggtat tgcccagatg cagtttggga ctttgttttt 56040
ctctgctgct ggaaactccc ttattgggct ccatttttga gaggtccttt tatacttctt 56100
tatagattcc caggatctca ttgatttgcc agcaatgttg actctgctcc attttctctc 56160
cactcagatt cgatccaacc atagccagaa ccccgtcatt cttcagtgta gtggaatgag 56220
gtgttctggg cctccaacct tgttctgcag cccctgacag gaggcaggct ctaattctcc 56280
agttttgtcc agcctgtgtc atgctgcttc caggtctgca cagagatgct gggtctgcat 56340
gtgggtatca ctcacattcc aagtgtggag ctttgcaggc tgtatcagcc atggcacact 56400
cttccctggg ggcaggcctt tcaccccctt cactgtccct gggtgagagc tctctagtga 56460
tttcaaaccg aacttaaacc aatggcccaa agctgtgcct cctgcttcaa tttcaacaaa 56520
tttctctctt tttttaaata cctattggtg cg 56552

<210> SEQ ID NO 3
<211> LENGTH: 23382
<212> TYPE: DNA
<213> ORGANISM: Homo sapiens

<400> SEQUENCE: 3
tcctgatccc aatagagcct cttacctgag ctttcctaaa gtcccaacaa tttcctaaat 60
ctcactggct gcttgtatgt acagaaggga tagagaagta taaattttga tatctggaca 120
tggtgtggtt ctggacaaaa tttaaagatg taagttaaga atgaagtgga gcacgcacat 180
tgcgtacaca tccaatcaag tagttcttga tatagttcaa cctgctgagt aaagacagct 240
ggattgctgg tttctggaaa tagcgacaca gactctctgg gtacacttca cttacctctt 300
aatgcaacat tcaggaacgt cctgcccacg tttccacctt tatggtctct gctgtatgca 360
ctgaggcaaa tctgcctgga aggttgatta ggcaggggaa ttcactgcct gcagctgagg 420
tctggagtgc tctgggggc tccctggaga caggcacaag acctggctta tggaagcctg 480
gcggaggctc caggttactt ctgcctcctg tctccccacc tctaatccac ccatcaccca 540
gaagtgggcc aaggatcagg ggtctggatc atctctcaag ggcaggagga gggtgaggct 600

-continued

```
ctgagaagaa gtgtgctgtc caatcagaaa ccatacttgg tgttatggct gcatctcttt    660
caaaggtatc tagagtggga gggtgacaga tgattaactc tgggttatct gaaatatgac    720
ccaagtgagg agagtcaaca gtaaccagaa cacattgtga aaaggaaaag gtggatagat    780
tgtcacctgg gccagaatcc ccagagagca ctttcacctc cacatcgaat gaaaaattct    840
acctggtcac cctcttgagt ccccagaggg tcagcccagg aatagggtag agtagaaagg    900
agttttgggc caggatggat gcttgtgtgt gtggttatct caactcggac cctctgagat    960
ccacagcagt gcccgagagc tgcgacgctg ctctctcact gactctccag gctctgtcgc   1020
tgctgctgca acagctctgc agccaaggtc tgctgactgt gttttgcctg tgctaactcc   1080
aggagcagct gctcccagag caggaccaac actaacccca gtgctaagaa aaactccaga   1140
gcctgaggga ccagcatatt ggccggctct tggagggact cttactgttg ctggctcagt   1200
tggcaggata tcttaacatg agttcagctg gaagtgaatt cagctgaaca gaacacatgt   1260
gtaaactaga ataaggctac ttttcatttt ctaaacaatt ctccttctgc ttgtaaataa   1320
ttggcaaacc cactaatatt cagaaagaaa ttccccatgt taccatttca tggttgctcc   1380
ttgaccttgc taggtcagat ttcaatccta gtccaccccc acgctggttg cattgctcca   1440
tcttcacacc taattcagaa ctatgtacag aaagagtaaa actatgtaat tctaaacttt   1500
tgtgctagtt ataagatatg cactcttata agtgtttcag gtgtaactca accaaaataa   1560
caattaattc acacaatatt gctgttagga aattacagct attttccaca cttcatagat   1620
gaaaagacag atgcacagac aatttcgggc acatttctaa ggctttaagg caagtaactt   1680
gttctcagaa tccaaatcta ggtgatttaa ctacattctg tggtctcaac aagttctctg   1740
gagttaaact gggaaggcat gcactattta ctgtgtgtga aattcaaaca gcttatggta   1800
agttcttctc aacaagctag acttaaaaca gctattccct tcttttcttg cctgatatac   1860
taatgtttct gtgttagttc ccacactgca taaaatgagc ctctatttct catgccctct   1920
tcatccacgt ccctccctcc tttctgaaga atatagtcac agtgggcaga tattatattc   1980
ctttcatatc atgtagtatc cccagagttg gccacatagt caacaatact tgctgagtgt   2040
gtataagagt gaattaataa actctgatta ttgaatttac taatgggaga cagtccaaga   2100
aaatcctcaa attgttttct ctttagagat gttcttttct tttaattcat ctgatcatat   2160
ccttctctca tttactcttg taagaactgc ttaatagtta cctaatttgc tcagcacaga   2220
attcttggaa aagttccttg ctccagggaa tcctaaggca tggatatgca gtgattgcaa   2280
atagaatatt taattaatgt gcactattca tctaacactg acattcttct aattccaatg   2340
attagaaaga aatactggat ataaatggac ataggcagtg agggtgttgg tgtgtgtgtg   2400
tagtgatcat atgtaattaa cataattttc tcccatgata gcctataaat agtgctgtct   2460
gggtcatgaa aaacgatggg ttcagtcttg gttttgatta agaagtaagt gcatagatat   2520
tgcatataag agaggtacac agacaatgtt ggcagggaat tggtatggga gagggattta   2580
gaaagcatag ttataaatta tctggaaaat tcatcccacc aaacaaaata attgacaatc   2640
tggactagac agatggtctg acattgtgtg tgtgagtgtg tgtgtgtgtg tgtgtgtgtg   2700
tgtgtatggt agtgtatcta tgctgtgtgt aaacttgttg tcagaaacct gttgacatta   2760
tactaaaata attgaaattt ttttggttaa attttctgaa ctttattccc agctgtgtga   2820
acttgggcta tttgtttagc tctaggagcc tttgttttct cattagtaca gtgggaatat   2880
taataccacc tacatcacat gattagtatg aggattaaat gagataatgt gtataaaaca   2940
cttaaataat acctagaaaa aaatagatgg tcagtaaaca tcagttatta tattactttc   3000
```

tgttattttt atcattgtac acacatgtat gtatgcatgt atacacacac acacacacac 3060
acacacacac acacacacac ggaggcattt gacccaaaag cacaactcca ctcaacctat 3120
acctcaggga aagatgggga agtaggtaga cctgaattgg ctagggtttt gcagagaaac 3180
agaagagaga gataaattta ttttaagaaa ttggctcatg agatgactgt gtgggctggc 3240
aagtccaaaa tcttggctgg aaattcagat aacagttgat gttgcagcat tgagtctaaa 3300
ttctgcaacg cagtagtctg gaaacaggca gagtttctac attgcagtct tgaggataat 3360
ttattctttg ggaaacctca gtgtccatta ttaaagactg cagctgattg gatgaggctc 3420
atgttaggga agataatctg cttactcagt ctactgatta aatacttaca gagaaacatg 3480
tggattgcta tttgatcaaa caactgggta acacagcata gcctgggcaa aattaaccat 3540
cacagagact gagaggatac atggaggtca ctggagatat gacccaagag acagaagagg 3600
gtcaacagtg acgaggacac actaagaaca tgccatgatg gttttatttt cacttaggat 3660
aaaggcaaat ttctggacag acctttggag aatattggga aaacagaagc ttctacctgg 3720
taaccccatg gtaagcccaa caaagctgtg atgttaggag gactggagaa agggagtgca 3780
gcatgcggct gaggaggccc ttggccttcg cactttggtt tcacagaagt gtagtcagta 3840
cagcacggac aaggctgctg accactgcac agtagctgga gctctgggga ctggtgattg 3900
ctgcagcttc ttcctatgca ggggtcacac aagaagattc ggaggtgaac atgggctgtg 3960
cactggagtg gcactgtgga gggccctttg aaggcattgg cattgctggt ggttttttgg 4020
aaaggtatct gagtttcaga atgaattgaa taataagtca gataaattag agccaggacg 4080
ggcataattt tgccctttta aacctattct tggtgtgctg gcagacagtt tataaaatac 4140
atttgtatcg aattagtacc tatgaagaaa cgtataaccc caagttaaaa gtgttagaac 4200
tgacatgctt aaaaacagaa ttaatgctaa atcaatgtca attctgtctc tcatttcatt 4260
tcatatctac gtacccactt cctacctaca gtatttcatg agctttaaga ggctatcaat 4320
tgtaagggac acccttattt catgcaccac aaggaaagaa aaaaatgctg caaattcaac 4380
aattacgtgc caccaatcat atggtatata ctgatttaag ggctgttaac aagtattaga 4440
agactgtatc atggaattga tgaattaaga taagtataaa accgatccac tttaggtcat 4500
ataaatatgt atgtaaatac tagacgggcc aattcttgct ttgcccagaa cacccctctg 4560
ctgtgctcct ccctatcact atgtctagca ctagacactg ctagacagta ttgacaaaaa 4620
agatcaaaag gcctacaaag atatggtaca ggaaaatttt ggattggtca atctattaaa 4680
taaagggaga caaataaaaa gacatggtaa ggcttttttct tgtactgtag ataaaataaa 4740
gttcccacat ttggtaggga gtatttttct ggaatatatg gagtttaagt tcccagggag 4800
acaaatcaag gagctacttg gagagaccag cctgcaggag agtgacttgc cagatgacat 4860
gaacttcaga tgaaatgttt gaagtcaccc gcagggcatt cttctcatga cacctacatg 4920
ctcgtccatg tggtcctaaa atgatgcact gatcctgcca acactcatgt ggcaattaag 4980
tatgtgggtg gtccctgagg gagcatgggc aatgtgaccc actgggtctc ctggctcaga 5040
gagatcacac atgatgatgt gaagactgtg gagacagaag caagaatatc tatagtcagg 5100
tgtttcttca ctgacttgtg aaccaattcc caccattttt tgagatataa agggaaaaag 5160
tgggcatgtt aaagagctgt ttatctccca gttctggttt cccagagggt cggttcccat 5220
tagtccttcc attgcttatt caaccactca atacagatgc tcatgtatgt gcatgttcat 5280
ttcacctgca cttttatatg aatacagcat acatgcacac agtgcataca tgcacacagt 5340

-continued

```
gcacacatgc acacacacac acaggcttgc ctcccctatt tcctcactta caacattgta   5400
acaaatatct ttgtcaaaga gtatgaggaa gctgagggtg atatcaccat gaagacagtg   5460
gaatgaacta acatctttta aacacattgg gaaatagtga ctcaggaggt tcaggcctca   5520
aacatcatct tctttggtat ccagtttgtc tgcagtcatc ttcaaaaagg ccactaaatt   5580
ctacagtctt tgaggtcatg ggctacttat tgttcacctc tatatcccta tgtttggaca   5640
tacatgctcc aagaatgttg taggctttca aagaatgcct tttgaattca ctgctctaat   5700
cacactgtgg acttagttta tccttgaggt aaaagctctc tgagaacagg actcgggtct   5760
gaaaatagga ctgtgtaaat aggtgaatag aatccctcag gtagaagcag acaatgggaa   5820
actatgcttt ctacctaacc accctccacc accaagtaaa cattaggcaa tgtcaaggca   5880
cggtctgttt ctgttttaat cagaggtgtg aataactatc tttttcaatt ctaatttcaa   5940
catcttcatt gagccataat tcacttatta tacagctcat ttatttaaag tgttaattca   6000
gtgggtttca atatattcat agagttggac aatcaccacc aaattttaga acattttcat   6060
tactccacaa agaaaaccta tatccatttg ttgtaatttt ctaatttctc ccagcctgct   6120
aaagtacctg gaagccactg atatttcctc agaggatgtg cacaaaagta aaaggcgata   6180
cagggaacag aatcttgtcc aggctctggt tcctcagatg ccctaagtca gctcttcagg   6240
cgtccagcct gagagaggct gtaactggct aaagcctcat tccctttcta gttctacaga   6300
tttgcctact ctacacattt catataaata ggatcataag aaatgcagtc ttttgtggtt   6360
ggcttcttcc atttagcgta aggttttcaa agttcatcct ccatatatct gtttaaaata   6420
agtgaataaa tgaatgggta actctgtcta gtgcaaccct gaatcagaac tctgagtaag   6480
tagacccctt tctgaccctc tacttcatga taggaaagga attccctctc cacagaagcc   6540
acaataaatg atgtctactt cctaagggag ttttcaaata aactgtcttg taagggttct   6600
atatggacaa tgaatgccac ataagacctg ggtaagtatc caatacatgg cattagtttt   6660
tcttttaaac acatatttat taagggtcta tcaagcacat agtgtcacac taagctcttt   6720
cttacttctc atttaatatt aaaaacagct cagtgagata agtatacctg gtttataacg   6780
gccattacat atgagaattg atactcattg tgagtatcat agtgacactc tagcaattgt   6840
tgataattgt tgtagcaatt tccagagatc actcagttat catatgcaag ttttctgatt   6900
ccagtagcac attcaataca attcctccga ctaagggcaa tgttttgatt ttagagggaa   6960
ttgtttattc tcaatcatat tctttgctct agaccacaga atcaactcag atttaatcca   7020
ctgaatctgc tggccatggt gagttggagg aaaagcagaa acacagaggc caggaggaag   7080
ggctgagagc ctaggcaagg gagggatgcc tagaaaaagc caaggctgta gaagccccct   7140
gggatggctg gatccacagc aggacatgga agagaaactg ctcagggtgg agggagtcat   7200
aatggaacat ttccacaagg tcagggaaag ctgtggctca gaactgatgt ttcctcagag   7260
gacacgaata caaaagatgc agggaacagg atcttgtcca ggcatgggtc ccttgggtaa   7320
cctaagttaa ctcattaggg ttcccacctg gtggaggctc tgactggcta aagcttctct   7380
agaccgcagc cccagagagg agtcctggaa gctcctgagg cctctttgga ttgcagggac   7440
taggaggcag gagaatgtca ggaatgaccc agcacgtgcc tggttgtgca aaagccacct   7500
cctcctcttt ccagagccaa gcctgggccc tataaaagac acatccagct tcagcacctc   7560
atctgctctg actccccagg gacgtgtctg tgctcctgcg tgtgaccagg gtgagtggca   7620
acctgggata ccagaggggt atgagcaagg cagagggatg gggaggatgg aggtaggctg   7680
gagaaagagt tgtgtgcttg tgttctgcca tactgaggag gaatgggact cagtctgcct   7740
```

cgaatctgtt gaggctgtga ggcctaccgg aggtcgtata ggtggggaaa gctaactgtg 7800
cacatctttt ccaattctgt gttcagtgac ttcatgttgg taacttcaaa actgctgtgt 7860
tgggcatatt tacaccatgg aaactggcaa atacttcaag ccaggctctt ttatctggag 7920
gtttcattgc aaaatctttt tccagaggac ctcctggtgt gtcctgcaac acgcagctgg 7980
tccttagggc ttgtattaag ggaatcggta cttcatggag tgtgaatact ctattcaggc 8040
ttgtgaggat agagtaatct cagcttcccc tgaaaggaag aatacgaagc tcattcggtt 8100
ggttttttaa tgtatgtgct tttatttaga ggaaagattc aagttgtttc tttcaggtta 8160
ctgatgtgac tgtatgatct aaatatcatt cttcttctac acatgcattg attttagaag 8220
aggtataata tgatccttgg tttgaaatat ttaaagagtt tcattattat ctttcaggtt 8280
gactaaactc tgccaggatg tcttgccagc aaaaccagca gcagtgccag ccccctccca 8340
agtgtcctcc caagtgtacc ccaaaatgtc cacctaagtg tccccctaaa tgcctgcccc 8400
agtgcccagc tccatgttcc cctgcagtct cttcttgctg tggtcccatc tctgggggct 8460
gctgtggtcc cagctctggg ggctgctgca actctggggc tggtggctgc tgcctgagcc 8520
accacaggcc ccgtctcttc caccggcgcc ggcaccagag ccccgactgc tgtgagagtg 8580
aaccttctgg gggctctggc tgctgccaca gctctggggg ctgctgctga cctgggctaa 8640
gaagaactct ttggacagaa tgtttaagaa cctcctacag cctgatgctt aaccctttcc 8700
atttcctctc attccattca tgggtggaca gcgaccacaa agactcatgg ggcttccctg 8760
ggagaacttt gcacttgatg gagcacctca attgcaggtt ttgttttcct cctttacctc 8820
atgttataat aaagctctga tttctgactc acaaattgtc ttggtcgttc tcttctcttc 8880
tgagatttca aacgtcgtcc aaaggtcagg gcctcagaga aattctcttc atgggtcaag 8940
gacaggacct gagtaggtga tacatgaaaa gctgctccaa ggaactgatt ccctcaaatg 9000
cagggtggat ggagctcgaa gagggtcacc tctggctatg gcagctttgc ctttctctcc 9060
actaagccag acacatgttc taattttctg tgtattccag acattgggaa ggttgggaag 9120
ctctgtagac ttgttcttct ctagggagaa gaacacatct ctatgaagca aaacttccct 9180
gctgttagaa tcaatagtcg gataaaatgc ttgaaatgca tgttgagacc cttccttctg 9240
caaagtacag cccacagtca ctgaactcct tctcagggag ggtgagtctg gttaagatca 9300
gcccattgac ttgctgcctc agacacctag cttcagttcc tcaaagtgtt agatctgagt 9360
cccaggatgc tgtcctgcca cttggcctat gtgttgggca ggtgagtgat gagtgatgga 9420
gatatttatt agaaaaaaca tggaggtccc actttgaaaa tacaacgaat ttatggtaca 9480
cgacactgta gggaagatta gacgtttcct ccttcaatac taaccttctt tgtccagcca 9540
ccctcagatg tgagggggga gaagtgccag gatggttggg ggatctttag tattaatggg 9600
agaaggggag agaagcaggg aaacagcagg ggaaataagg actagtgctt cttaggttca 9660
ggctgacagg tgtcaacatg aagataatgg attcagcgaa gagagaatct gacagagatg 9720
gagactgtta ttaagatgtt cagctgcctc ctcatccttg cagctgctaa gaaaaacacc 9780
tagctcttta accagtctga gattctgtac tctctgtgtt ttaaattagc ctttgcactg 9840
agtcatttta tttgatgtaa tgctctttat tatttttgcc agtctcattt tattttattt 9900
tttttactta agttctggga tacatgagct gaatgtgcag gtttgttaca taggtatata 9960
tgtgccatgg tagtttgcta tgtctattaa cccgtcatct aagttttaag ctccacatgc 10020
attacgtatt tgtcctaatg ctctccctcc tctcacctcc acccccaata tgccccgatg 10080

-continued

```
tgtgatgttc cctgccctgt gtctatgtct tctcattgct cagctcccac ttattagtga  10140
gaacatgcgg tgtttggttt tctgttcctg tgttagtttg ctgaagatga tggtttccag  10200
cttcatccat gtgcctgtaa aggacctaaa cttattcttt ttatggctgc atagtattcc  10260
atggtgtata tgtgccacat tttctttatc cactctatca ttgatgggca tttgggttgg  10320
ttccaagtct gctattgtaa atagttgtgc tataaacata agtatgcatg tctttatagt  10380
agcataattt ataatccttt gggtatatac ccagaaatgg gattgctggg tcaaatagta  10440
tttctggttc tatatccttg aggaatcacc acactgtctc ccacatgggt gatctaattt  10500
acagtcccac caacagtgta aaagcattcc tatttctccg catcctcttg agcatctgtt  10560
gtttccagac tttttaatga tcgccattct aactggtgtg agatggtatc tcattttggt  10620
tttgatttgc acatctctaa tgaccagtga ttatgagctt tttttcatat gtttgttggc  10680
cgcataaatg tcttcttttg agaagtgtct gttcagatcc tttgcccact ttttgatggg  10740
gttgtttgtt tttctcttga aaatttgttt aagttccttg tagattctgg atattagacc  10800
tttgtcagat ggatagattg caaaaatttt ctcccactct gtaggttgcc tgttgactct  10860
gatgatattg tcttttgaaa agattaacaa aatagataga ccactagcca gactaataaa  10920
gaataaatga gagaagaatc aaatagacac aataaaaaat gataaagcat atatcaccac  10980
tgataacaca gaaatacaaa caaaccacca tcaaagaata atataaacac ctctatgcaa  11040
ataaactaga aaatcttgaa gaaatggata aatttctgga cacagaaacc ctcccaacac  11100
taaactagga agaaattgaa tccttgaata gaccaataac aagttctgaa attgaggcag  11160
taattaatag cctaccaagc aaaaaaaaac cccaggaata gagagattca cagtcgaatt  11220
ttaccagagg tacaaagagg agctgatacc attccttctg aaactattcc aaacaataga  11280
aaaagaggga ctcctcccta actcatttaa tgaggccagc atcatcctga ttttaaaatc  11340
tggcagagac acaacaaaaa aagaaaattt caggccaata tcactgatga acatcaatgc  11400
aaaaatcctc aataaaatac tggcaaactg attccagcag cacatcaaaa agcttatcca  11460
ccacattcaa gtcggcttca tccctgggat gcaaggctgg ttcaacatac acaaatcaat  11520
aaacgtaatc catcacataa acagaactaa tgacaaaaac cacatgatta tctcgatgga  11580
tgcagaaaag gcctttgata aaattcaaca ctgcttcacg ctaaaaactc tcaataaact  11640
aggtattgat ggaacatatc tcaaaataat aagagccatt tatgacaatc ctgtagccaa  11700
tatcatactg aatgggcaaa agctggaagc attccctttg aaaaccagca caagacaaag  11760
atgccttctc tcaccactcc tattcaacat agtatcagaa gttctggcca gagcaatcag  11820
gcaagagaag gaagtaaagg ttattcaaat aggaagagag gacatcaaat cgtatctctt  11880
tgcagatgac atgattgtat attcagaaaa ccccatcgtc tcagcccaaa aactccttaa  11940
gctgataagc aacttcagca aagtctccgg atacaaaatc aatgtgcaaa aattacaagc  12000
attcctctac accaataata gacaagcaga cagccaaatt atgagtaaac tcccattcac  12060
aattgctaca aagaaaataa aatacctagg aatataactt acaagggagg tgaaggaatt  12120
cttcaaggag aactacaaac cactgctcaa ggaaataaga gagggcacaa acaaatggaa  12180
aaacattcca tgctcatgga taggaagaat caatatcttg aaaatggcca tactgcccaa  12240
agtaatttat agattcaagc tatccccatc aagctaccac tgactttctt cacagaacta  12300
caaaaaacta ctttaaattt catatggaat caaaaaaaga gcccatatag ccaagacaat  12360
cctaagcaaa aagaacaaag ctggaagcat caagctacct gacttcaaac tgtactacag  12420
agctacagta accaaaatag catggtactg gtaccaaaac agatatatag accaatggaa  12480
```

-continued

```
caaaacagag accccagaaa taacatcaca cgtctacaac catctgatct tcaacaaacc  12540
tgaccaaaaa agcaatgggg aaaggattcc ctatttaata aatggtgctg ggaaaactgg  12600
ctaatcatat gcagaaaaca gaaactcgac cccttcctta caccttatat aaaaattaac  12660
tcaaaatggg tgttaaagac ttaaatgtaa aacctgaaag tataaaaacc ctagaagaaa  12720
acctaggcaa tacaattcag gacataggca tgggcaaaga cttcatgact aaaacagcaa  12780
aagcaattgc aacaaaagcc aaagttgaca aatgggatct aattaaacta aagagctcag  12840
ccagtctcat tattaactga aatttcaagt ccctgaacag tagtaatttt gttcttctaa  12900
aaacacgtac attggccatt tctacaaatt tcataacatg atttcaaatt ttcttttcaa  12960
ttttcaaggg ctcttgatat atcacagata ttaaacttga tccgccttat taaaatattt  13020
aatgcaggga cccacttgag gaggcagtct gtgggtccct gacccccgag tagcctaact  13080
gggaggcacc ccccagtagg ggcatactga cgcctcccat ggtcgggtac tcctctgaga  13140
caaaacttcc agaggaacga tcaggcagca acatttgctg ctcaccaata tccgctgttc  13200
tgcagcctct gctgctgata cccaggcaaa cagagtctgg agtggacctc cagcaaactc  13260
caacagacct gcagctgagg gtcctgactg ttagatggaa aactaacaaa cagaaaggac  13320
atccaaacca aaaccccatc tgtacgtcac catcatcaaa gaccaaaggt agataaaacc  13380
acaaagatgg ggaaaaaaca gcagaaaaac tggagattct aaaaatcaga gtgcctctcc  13440
tcctccaaag gaacgcagct cctctctagc aacagaacaa agctggacag agaatgactt  13500
tgaggagtgg agagaagaag gcttcagatg atcaaactgc tctgcgctaa aggaggaagt  13560
ttgaacccat ggcaaagaag ttaaaaacct tgaaaaaaaa ttagacaaat ggctaactag  13620
aataaccaat gcagagaagt ccttaaagga cctgatggag ctgaaaacca tggcatgaga  13680
actatgtgac gaatgcacaa gcctcagtag ccaattggat caactggaag aaagggtatc  13740
agtgatggaa gatcaaatga atgaaatgaa gtgagaagag aagtttagag aaaaaagaat  13800
aaaaggaaat gaacaaatcc tccaagaaat atgggactat gtgaaaagac caagcctaag  13860
tctgattggt gtacctgaaa gtgatgggga gaatggaacc aagttggaaa acactctgca  13920
ggatatcatc caggagaact tccccaatct actaaggcag gccaacattc aaattcagga  13980
aatacagaaa acgtcacgaa gatactcctc gagaagagca gctccaagac acataattgt  14040
cagattcacc aaagttgaaa tgaacgaaaa aatgttaagt gcagccagag agaaaggtcg  14100
ggttacccac aaagggaagc ccatcaaact aacagctgat ctcttggcag aaactctaca  14160
agccagaaga gactgaagac caatattcaa cgttcttaaa gaaaagaatt ttcaacccag  14220
aatttcatat ccagccaaac taaccatcat aagtgaagga gaaataaaat cctttacaca  14280
caaacaaatg ctgagagatt ttgtcaccac gaggcctgcc ctaaaagagc tcctgaagga  14340
agcactaaac atggaaagga acaaccggta tcagccactg caaaaacatg ccaaattgta  14400
aagaccatcg aggctaggaa gaaactgcat caactaacga gcaaaataac cagctaacag  14460
cataatgata ggatcaaatt cacacataac aatattaacc ttcaatgtaa atgggctaaa  14520
tgctccaatt aaaaggcaca gactggcaaa ttggataaag agtcaagacc catcagtgtg  14580
ctgtattcag gaaacccatc tcacgtgcag agatacatat aggctcaaaa taaaaggata  14640
gaggaagatc tactaaggaa atggaaaaca aaaaaaggca ggggttgcaa tcctagtctc  14700
ggataaaaca gactttaaac caacaaagag acaaagaagg ccattatata atggtaaagg  14760
gatcaattca acaagaagag ctaactatcc caaatatata tgcacgcaat acaggagcac  14820
```

ccagattcat aaagcaagtc cttagtgacc tacaaagaga cttagactcc cataaaataa 14880
taatgggaga ctttaacacc ccactgtcaa cattagacag atcaacgaga cagaaagtta 14940
acaatgatat ccaggaattt aactcagctc tgcaccaagt ggacctaata gacatctaca 15000
gaactttcca ccccaaatca acagaatata cattcttctc agcaccacac cacacttatt 15060
ctaaaattga ccacatagtt ggaagtaaag cactcctcag caaatgtaaa agaatataaa 15120
ctataacaaa ctgtctctca gaccacagtg caatcaaact agaactcagg attaagaaac 15180
acactcaaaa ccactcaact acatggaaac tgaaaaacct gctcctgact actgggtaca 15240
tatgaaatga aggcagaaat aaagatgttc ttgaaaccaa cgagaccaca acatactaga 15300
atctctggga cacattcaaa gcagtgtgta gagggaaatt tatagcacta aatgcccaaa 15360
agagaaagca ggaaagacct aaaattgaca ccctaacatc acaattaaaa gaactagaga 15420
agcaagagca aacacattca aaagctagca gaagacaaga aataactaac atcagagcag 15480
aactgaagga aatagagaca caagaaaccc ttcaaaaaat caatgaatcc aggagctggt 15540
tttttgaaaa gatccacaaa attgatagac cactagcaag actaataaag aagaaaagag 15600
agaagaatca aacagacaca ataaaagatg ataaagggga tatcatcacc aatcccacag 15660
caatacaaac taccatcaga gaatactata aacacctcta cgcaaataaa ctagaaaatc 15720
tagaagaaat ggataaattc ctggacacat acaccctccc aagactaaac caggaagaag 15780
ttgaatctct gaatagacca ataacaggct ctgaaattga ggcaataatt aatagcttac 15840
caacccaaaa aagtccagga ccagatggat tcacagccga attctaccag aggtacaagg 15900
aggagctggt accattcctt ctgaaactat tccaatcaat agaaaaagag agaatcctcc 15960
ctaactcatt ttatgaggcc agcatcatcc tgataccaaa gtctggcaga gatacaacaa 16020
aaaaagagaa ttttagacca atacccctga tgaacatcga tgcaaaaatc ctcaataaaa 16080
tactggcaaa ccaaacccag cagcacatca aaaagcttat ccaccatgat caagtgggct 16140
tcatccctgg gatgcaaggc tggttcaaca tacacaaatc aataaacata attcagcata 16200
taaacagaac caacaacaaa aaccatatga ttatctcaat agattcagaa aaggcctttg 16260
acaaaattca acaacacttc atgctaaaaa ctctcaataa attaggtatc gatgggacat 16320
atctcaaaat aatctaagag ctatctatga caaacccaca gccaatataa tacctaatgg 16380
acaaaaactg gaagcattcc ctttgaaaac tggcacaaga cagggatgcc ctctctcaac 16440
actcctattc aacatagtgt tggaagttct agccagggca atcaggcagg agaaggaaat 16500
aaagggcatt cagttaggaa aagaggaagt caaattgtcc ctgtttgcag ttgacatgat 16560
tgtatatcta gaaaacccca tcatctcagc ccaaaatctc cttaagctga taggcaagtt 16620
cagcaaagtc tcaagataca aaatcaatgt gcaaaaatca caagcattct tatacaccaa 16680
taacagacag ccaaatcatg agtgaactcc cattcacaat tgcttcaaag gaataaaata 16740
cctaggaatc caacttacaa gggatgtgaa ggacctcttc aaggagaact acaaatcact 16800
gctcaacgaa ataaaagagg atacaaacaa atggaagaac attccatgtt catgggtagg 16860
aagaatcaat attgtgaaaa tggccatact gcccaaggta atttatagat tcaatgctat 16920
ccccatcaag ctaccattgc ctttcttcac agaattggga aaaactactt taaagttcat 16980
atagaaccaa aaaagagccc gcattgccaa gacaatccta agccaaaaga acaaagctgg 17040
aggcatcaca ctatctgact tcaaactcta ctacaaggct acagtaacca aaacagcatg 17100
gtactggtac caaaacagag atatagacca atggaacaga acacagccct cagaaataat 17160
gctgcatatc tacaaccatc tgacccagca tgcctagata ttcttgatat tcttttctcc 17220
tcttttatct ctttggaaaa tcatgggaga ttccaggata ccccaccagt ttcttctgct 17280
caaaagttat aaatggcttc agcaggaatc tagccactgg gcaatagttt cagggaccca 17340
gttcactatg gagtcaactc ttgttacgaa acttggttct cacctcacct ccaggtctgc 17400
tctatgagct ggtggcttag gactgggatt gtctgttttc agagggaagg agaggttgaa 17460
atgagctaag agatgtgttt tacaacaaga aactataaaa taacctactg cttgcagaag 17520
ctgaaggaga gggatgagtg acattggtaa ggtcccatgc ctggtgaata agagaggaaa 17580
taccacaaag agagagcgtg ttttggagat caggaggttt tgtgatagag ttagtttgag 17640
gtcacagcaa aaatatttgc ctcttagaag acatttggca ggatcaaact gcaggtcagt 17700
gactttctag gcaaagcaga ggtggcttaa aggaagtatt ttaaataact cccaggtaat 17760
tcttctaata acatttaatt tattcattca tccatctaat caatagtcta tggtcaactg 17820
ctagactccc caggaaaaga aacaatgggt aagacctgat tctgagctca tgctctggtg 17880
acttaatatc cgtggacata gagccaagat tgtctagaat tcttactggt gtcaaaggct 17940
gtaagcctga tctctaacag tgactgacca tattttatca taaaaaatat ggaaggacat 18000
tttgtctgct gagactggct tcctgtgaac gaggcacata tcagctttgg agtcttctct 18060
ccaacccttg gccacgctgc tgtgcttgtc cctggacttg caagcacacc ttcatgccca 18120
tgctgcccac acacacatac acacacattc ataaaggcac agcccatccc attctcttcc 18180
ttcatggtta ctatcatctt tgtcaaggag aatgaggaac ctagcatgac attccctcag 18240
gcattatcag gtgatccagt gtcccaacaa tctcattgga aaatagactc atttggtatg 18300
cacataaatt tcacagaggt cttcagaata tccactgaat tgtgaattcc tagaggtcac 18360
aaaacacaca cagtgtttgc ctctataaac ctaagtgttt ggatagaaaa tcactgaata 18420
cctaggagct gacaaagcag tatcttcttg attaactgct atgtttggat atcaacattt 18480
ttcactcttg acctgaacac tctcaagggt agggaactac atctgagact agaaaagaaa 18540
actattggag atggggcatc tcttagtatg acagaaatgt aaagaccata tactcctacc 18600
ttctagacca agggtatatg aaagaaggga ctatcttttt caaaagctgt attctaactt 18660
atgccataca gtaggttttc agtaaatgtt ggatggatgg atgaaataaa ttgattaatg 18720
gatgaatgta tctaatccaa aattgtatca gattccttac tctcctgtca ttcactaaga 18780
agattaaata aatcatttga ttcccatcac cttcttgaca agaaataatt agacttctca 18840
aaatcctgaa tgtacactgt acattcctaa gagagccttc gctagcctac ctatattttt 18900
aaataaaatt ttcaaagaca gggactgaat attgtccatt tttctgtctc acacactgcc 18960
ctcgttcttt taaaaaatga cattgtttaa gtgtcttcct tgtgccttat catgtgcaaa 19020
agcctcactt gatggaacca acaattcaga gaggaaggtg ctaataggcc tgttttacag 19080
ttgaggattt agattgtcta tatatagtct ttgaggtcac tgggctcata aacacagagc 19140
tcttctgatt ccaattcaaa aaactattgg cttattttaa aaactgcctt gttacacagt 19200
agacatttta atttctaagt gaagaagttt agtcacaatg atcatcacca ccaaatctga 19260
ggaaaccatc ttgattcact tattaatcct cctagcaggg ttctgcaggc cacacagcaa 19320
catggggtca ggaatgaggg ctgagcagaa ggggaggagt gtatcctagg aaggaaatgg 19380
tctctgactc aatgccacaa agaaacctgc ctagctgtgg aagcagggct tggaaaacta 19440
tacttgggga tgggaagaag ctggaatagc atacttccac aggaaagcta tggcaaggat 19500
ctctggtgtt ctcagaagtc actctttgag cctttgtcca ggcacaagct ccttaagaat 19560

-continued

```
cccctggcag ctccacgggg accagcctgg ggggggctgt gactggttaa agctccttta  19620
gacccccttc ccagagggag gtcttgggag ctcccagtgc ttccttggat tgtagggaca  19680
aggaggcagg ggaatgtgag gaatgaccca gcacgtgcct ggttgtgcaa gagccacttc  19740
ccgctcttcc cagagccaag cctgagccta taaaagacat attcagctcc agcacctcat  19800
ctgctctgac ttccccagga cgtgtctgtg ctcctgtgtg tgaccagggt gagtggcaac  19860
ctgggagcca gagggcacag gggaatggga agattaaggg aggcttcaga gagttatttc  19920
tttgattctg tgctattata tgcagaaaag agatacagtc tgacttgagt ttctggaaat  19980
cttgccttgg gctgtgagaa atgtgtatct gacagtttca tcaagggctt attcttatat  20040
ttcaaaaatg gatactttgt tgggtatgaa tactttattc aagctcatga agattagaaa  20100
atactgccta tcttctaaaa gaataagaag cttcttatta tatctgattt tcaagtatat  20160
attttcattc agcaggattt gttttctttc acttgttgat atatatgtgt gtatgtgtat  20220
atatatacac acactgagta ttattcacca tcaccatatg atttagtttt aaaagagata  20280
aaattgccat ccttggtttt tcacagctaa agggtttgac tatttcgaat ttcaggttga  20340
aaaagtcgca ctgagatgtc ctgccagcaa aaccagcagc agtgccagcc ccctcccaag  20400
tgccccccaa aatgcccacc caagtgtcct ccaaagtgcc gacctcagtg cccagcccca  20460
tgcccacctc cagtctcttc ctgctgtggt cccagctctg gggctgctg cggctccagc  20520
tctgggggct gctgcagctc tgggggtggc ggctgctgcc tgagccacca caggccccgt  20580
ctcttccacc ggcaccggca ccagagcccc gattgttgtg agtgtgaacc ttctgggggc  20640
tctggctgct gccacagctc tggggactgc tgctgaccag acctcgaaca tcacagagca  20700
acccttatgg agaaacttgc aaccaggacc tgtcccagag tgatgcttct cctgcccctt  20760
tttctccttt ccttgggctg acacaccttg tgaggtgttt tgtctgttgt catggcccaa  20820
gagcccatcc tggatcctga tcttaccttc ccactttacc tcatacaaca ataaagctct  20880
tttgcctctt cgtgaagtac cctggccatt gtcaattctt ctattctttt caaatccctt  20940
aaagtccagt gccccagccg tacactttta aggatgcttt ggtaggagtg gagtgtgaga  21000
aagaggtatg ctggaagcag tctccagagg gtcaatcctg aaagagcagc ctcacagtag  21060
ggcttctcaa tgggactgcc tgtgtgcact tggagactgt gagatgtgga ccctctcagc  21120
ccaggcaggg gcctgaaggg actgacagcc ccagggctga gaaccgctgg ccatgtgctg  21180
cttgctcagt ttaactcacc atgctgaatg taacttattt tcattttctc ttcataccat  21240
gatgacaaag ctagaaaaat ctttggtact ccaagcaaaa aggtatattt aacagaattc  21300
ttttcatctg atttaaaatg cttggtatga gaatcagaac ccttaggggc aagtttaaat  21360
gacaactcat tgccacttaa ctactctcca gggaggaaga gtctgtccag ttcttgcttt  21420
ctttcatgtt ccagcctctc cacgaaacaa ctgttaaata aatacgtaag cagtgtaagg  21480
ctgaaggaac acctcagtat gggcctgctc agttcctgtg actcaatcca tggctaagtg  21540
aagcagagta tggaacaggg gtccgggcca tgtcccactt ttattgctac gcctgcctca  21600
ctgcaaagga tcaggcctgg agggtgtgaa ggagaattat gagaaatacc actctcaaac  21660
aatatatatg aaacaaaaca taaaccaaaa taaacaaaaa agaaaaacca ctcttatgta  21720
gctgtaaaat aagctgcatg tagcccagcc tgggtctagc cctccttagg ttcaggtctc  21780
ctcagctcag cactcatatt aaaagaattt taggacggag aagcagcttg tctggatgac  21840
tggggctctg tgccttgggg aggaagtgtg aagaagagtg agggcaccac taggggaatt  21900
aaaaatagtt agtctatcag cagactgtga ggtgcttgcg gtgagatgat gagctcagtt  21960
```

```
tagagcaagg ccctgctgaa aatgggctaa taaagcatcc tgtcccttct tctgcatgat  22020
acggatgggt accaattaac atctccactt gtgttcttcc actctagtcc ctccctatca  22080
tgctttaggc ttctttcttt gctccttttt gtaattattg caactcctat aggtaattat  22140
atgtcattgt tagtttaatt tgaaatctca tagtactaat tctgagtcta tgttcatata  22200
tgtattgccc acacttttc tttttgttt ttctgcaaac tacatattca tatactctga  22260
cttatttttc actatactcc ttgttttttt ttttttcttc tggtctatct taagtatttt  22320
ccctctgcat tagccagggt tctccaaaga aacagaacca ataggagata tcggtctcga  22380
cagaaatata gatatagtta tagatatagg tagagataca aatttatgac aagaaattgg  22440
aaatggattt atgattatga aggctgagaa atctcaagat ctgtagttgg aaaactggaa  22500
acctagaaga gctgatagtt ctcatctgag tctgaaggca tggaaaccag gagagctgat  22560
ggtggaaatt gcagtctgag cacatgagaa gatcaatatc ccagcacaga gccgtcaggc  22620
agaagaaatt tcctcttact cagccctatt gttctattct ggtcatcaat tgattggatg  22680
aagcccactc atatagggaa gagtaatcta ctttaatcgg tctacaaatt caaatgttaa  22740
tttcatccaa aaacatcctc acagaaacag cccgagtaat gtttgaccaa atgtctgggc  22800
accttatggc ccagtcaagt ctccataaaa ttagccagca tacttctccc cttcctcctt  22860
atattttaat gagccatatt ggcttatagt aacattgttt gctataagac attttaaatt  22920
ttcttttatc ttgaaagttt tagacttctc ggttaagaga ttttttttca tgttcttaaa  22980
ttatacatgt agtcttcaag actttctgct aaggttttat ttgcttgctg ttttacttcc  23040
taacttgtta gtatattcat ttttattgtg agatacaacc tatatacaaa agaaaaaata  23100
aaatatattt atgtacttta aaaagaaaca caaataatac caaccacagt gaggataaga  23160
aagagaagac tgctagaact ccagaggtgc cccatgttgc ccaatcacaa gactcttctc  23220
cacccctgcc aaagtaagca tgtcacaatt tttaattttc attgtagttt taccatcgat  23280
gtatgcttct cagttgagtt tttaagcttt ataaacaagg agtcacattt ttatgtaatt  23340
tttttctctt tgttcaatgt ccagttgaga aggtaaacac ta                    23382
```

<210> SEQ ID NO 4
<211> LENGTH: 8818
<212> TYPE: DNA
<213> ORGANISM: Homo sapiens

<400> SEQUENCE: 4

```
cttagggaca gcaatcagag caggcaagga gagcagccag gaggcttgcc tgaaagcaag     60
cacctttgtt tttccttaga ttattcagtg acagttctgt aaaacagcaa agtttgttag    120
tcaggtcagt cttcttacaa tattgagaat gttgcaattg cccataatga acacaaaggt    180
gcctcagcag agacacaatc tctgatttta aatccttacc ctgaagagac agcacccggg    240
aaaacaagtg ttcctcaggt ctaaggccca tgggaaggga ccgcgacaga tgtgggaagc    300
aaggtagcac ttctggaagc attggagatg aatcatattc acttcagtgg gcaaaagcca    360
agcagatgca gggacaacca gaccataaat ggaaggaggg tctgagtctg acaaagagac    420
aacgtgcacc cctttgtaga agttcactaa aacctgacca agagaaagct caacttcaga    480
gcctttctgc ttttattgcc agagatagct ctaactttgc cagtgctacc cttgctaatt    540
cagttcctag aactctgtgg tggagaagtt gtgcagaggg ttgtcattct atttcctggc    600
ttaggtggta gtcacacaga tgttttactt tgtttaaatg cattggctga aatgcattgg    660
```

-continued

```
gctgtattct cgatgcatgt atgttacagt tcaacaaaac cacattaaaa taatacacac    720
aaatgaataa atataaaaat atccaggaca attcttaaaa ataaaattca tgtgtaggag    780
ctagttcgac tagatgtata acatattata aagctattat agttagacag tttgtactgg    840
accatgaata tacagacaga tcaatagagc atgataagtt cagagctggg aaaaaatata    900
cagaagaagc tagtacatga taagcacacc ctcaaatctg tgaaaaaaga tcagttaata    960
aatgatgttg ctacaactgg gaagccatta agaaaataaa aactctcatc ttatactagg   1020
atgagttatt taagggttaa aacattaaaa gttaactctt aagaaaatct gggggtattc   1080
ttctacactt tcaaaatggg gatcactttt ataattataa tacaacaaac aagaactaga   1140
aaataaaaaa attttaaaac gtgtttacat aattatcatt ttctatatgg ctgaaatata   1200
acaaagtcaa aggtcaaaaa acacagagga agaaatttag tttctcatag cacaaaaata   1260
acttaatttc tccaatatta tataagtgct acaaatcaat aataaagtca tcaagaatac   1320
aattaagtat taggtaagtt atgtcatcag gcagttccca gaaaatgaat gttgtggttc   1380
actaaatgta ataaaatata gttgagctta gttactaaga gcaactcaaa actactttga   1440
gatcccattt ttaacctacc agatgggcca agaacaatta gtttaaaaat acatcatttt   1500
gatgagtttg tggggaaaaa aatgcagtct tatacattgt agggagtgaa ataaatcagt   1560
gaaactcata tggaagaaac tggaaatact gatcaaatta caaaagtatt tagcctctga   1620
gtcagcaatt gcacttaaat aaatatattc tatctcctga ggaatgatgt ataaataatg   1680
tgttcactgc agcattgttt gcaagagcca aaattgggaa ctgctatata tacataggtt   1740
attatccaga ctgggaaaca aagagagaaa gtcttaatgc actgaagtgg aatgctctcc   1800
aacagatgct gttgtgaaaa aagcaatgag caaaatgatg tggagttact cttatttcat   1860
taaaagaaga aaaaatatac atgtttgtgt ggggtttttt gtgcataaaa taaccctgaa   1920
aggatatttc agaaattgat ctctgtgaac tgaagtaatt ggagtttcaa gttggggatt   1980
tcactgtgta tcctttgtaa cttctgattt taggcccaag tgaatgtgtg ataatgatca   2040
ctattaataa tattaaagga gatgggccat gctccgtggt gcatgcctat aatcccagca   2100
gtttgggaag ctgaggcagg aggatctctt gagctcagaa gttcaagacc agcctgggca   2160
atgtggcaaa atcccatctc tacaaaagat acaaaaatta gccaggtgta gtggcacgca   2220
cctgtagtcc cagctacttg ggagactgag gtggaaggat cacttgagcc caggaggtca   2280
aggctgcagt gaggcaagat cacaccactg cactacaacc tgggcaacag ggtgagaccc   2340
tgtctcaaaa aaaaaaaaaa ggacaaaaaa aattgcatta aaggagacct gcaggaagca   2400
gagcctcaaa tgctggaacc caggaagaca gcaccataag gactcgctcc gctccgttac   2460
tggatgtaat cacatcatta cattagcaaa ttcctgcaaa ctggcctcaa cttttctcac   2520
catcaattaa catagcccat gcagcaaaga aagatggtaa tagtcttccc cacttttgat   2580
aacagaggca gaaaaacata aggaggtagg agtgtggctg ccgcgggaca cattctgcta   2640
gtttggatga tgcattgaaa acagccttaa aaaatgagtt ccccaatttg gacaagcaag   2700
ttgggagtta ttggcagaaa aagtttgatt taagaaaaaa agaccaacaa tcaccattca   2760
tgcatttaac taatattttt gagtatttac tatgtattag gaactattct gactgagagc   2820
ctgagatata tcagtaaaca acatttgcct ttttggcaat gacattctaa tgagagaaga   2880
caatacataa aactataata aataaaaatt agctcatttt agtgctatga gatactggtc   2940
tttatattat acttatatta tattgtatgt gaaaagtact accaaaggaa aacaaaatag   3000
gactgtgtaa aggtgactgg agtgagggca agtgtggaag attgtcattt taattaggaa   3060
```

-continued

```
aatcagtgtg tacctcaccg agaaattgat atttaagcaa agacttgaaa tacaaacaaa   3120
aggcccttag tggcatgctt gtgcattcgt atgcatgtac acatgtgcac acacctggcc   3180
tgctgcagga acagcaagga ggtgagtgtg gctgcagcag agcaagtgac aggaagaaca   3240
gtaggagatg aggtccaagg tgtgtgtgga gttgggggtc aataatgcag ggccttgtgg   3300
gctattgtga ggacttcaat ttacccagca aggcatggaa agccacttca ggtttttgag   3360
caggagaatt acatgatatg acttatgttt taaagtccac cccaactgct ctgctgaaaa   3420
cagacaatag aggaccaaga atagagcaga gataccagtt aaaagctgat tagaaaagtc   3480
agcaagaaat catggtgtct cagagtaggt tggccacagt tacagatgga ttcattttga   3540
agttaacaga atttactgat attaactgag tgtgagttat acaagacaga agccaaggag   3600
gactcaaaag tctttagctt gagcaaatgg aagaatagag ttagcatctt ctgggctgag   3660
atgtctaggg gtagaggatg ttttcaggaa aatatcaata gctcagttgt gagcacatta   3720
aatatgagat gtctattaga tatccatgtg agaatactaa ataaataagc agttgaatat   3780
gaaagtctga agttccggag agatttctca gctgttatta acaaagtaga caccatcatc   3840
aatgacatat agatggcctt catggtcagg agactgaatg ttctaaccaa gaaaatgagt   3900
attgatggag aagaaaagag aaccaaggac tccagcagga agtagccagg cagaagaaca   3960
ggaacacaaa gagttccaag ttaatgtact ggctaaatta ttcttccatg tatttattta   4020
ctaaatgtgg atttagtacc taggatgttc catacattgt gttggaaata gaatttaaat   4080
ggtgagcaga aagtatatct atcctcacct tctagatagc cttcattagc ttaattttaa   4140
caaactaata tgcatcatgg ttaaaaattc aaatagtttg tgtgtatttg attcttctag   4200
gaaaatattt atgtatacta acatatatgt ttatcttatt ttgtatatat ctccgtatat   4260
acattctttt tataagaaaa ggaatatact aacatattgt ttactggatt gctttctttg   4320
attacatagt tgggagaatt tttcatagca tcatctacaa ctggactctg tttttattag   4380
ctatatacta tcctattaca tgattgtaaa atgaaatctc attaacagaa tatgaaaata   4440
cctgtttctc aacatattca ttaacaacta atgtgatcaa aatttcatat ttgttgccag   4500
actgtcatag aaaagccagt gtctcattga tcttctggtt tgcattcctt tagttatgaa   4560
taagcatttc ttcatagatt tgttggccat ttccacctct ctctctcact ctacctctct   4620
ctccctctcc gtactcttcc tagaaagaac ttaattctta tagattaagg ctttggtccc   4680
aactacaatg ttagagactt tgggagatgt gaataagagt agacatttta ctgagaataa   4740
attttagaga taactataag catgaagacc tgaagaagac aagtaaaaga gaaatacttg   4800
aataggctat tatagaatga aaagcacaat tcacatactt cccaagagtg ctaccctttg   4860
gccgaggtgg ttctgtcctg gacttcagac tttaaagagt ccttctctgg ctctcctcca   4920
gccatgaccc acccccatag gatgattcaa taggtccagg gtacaggccc agagctgctg   4980
tctctctcac tccagctatc caggacccca gaaatctctg tcaactggcc ctgagatcac   5040
ctttatgtgt ctatcctctt gaagactcaa acagccaata ctgtgctcac ttctaggtct   5100
caatgaccaa gagaggggca gtttgagaga tccatgtatg aaaagaacat ggacggtatg   5160
gactaggata tttacactca tgcacgcccg aggtccctcg tgacacaaga tgaagccagg   5220
gagtaggaag agaaccaggg gtgaaccaca ggggtcagaa gcctctgttt gtgctcttgc   5280
ctggtgtcct acaaatgttt atggcaggca tgcttcccag aagaacagaa tttcctagtc   5340
actgtcctca aagaggccat gctacaggaa gaaaaggaaa gagtaaacat aatgaaatgc   5400
```

-continued

```
ttctctctta tcattatttt agtcaattca ctattcaatt gattcagttt cagaatcttt   5460
tatgtgccaa ttgctcagcc agacactggg aatatcaaag tgaataaaat agggtcctgg   5520
cccctaaggc atcccagttt ctcccctgtt taaaaccttt cagtggttcc cattgtcctc   5580
aggataaagt ccaaactctt tttcttatgg cataaaggtc ctcaccaaca cagccttacc   5640
tacctaggta ggtgaatctc cccctctcc ttactcccca ctctgctcca gccacactga   5700
gcttttccac caaatagcct atactttcac atttctggat ctgaaaatgt cctcccagac   5760
acacccctat gtccaacttc ctatttccaa tttccaagtc tcagcttaaa tatcactccc   5820
tccaggaagc atatctgacc cccaaacctg acccctgtgc ttatcctacc atcattatta   5880
tcacatggta ttgttggcta ttgacttgcc tccatattga attagatctt tgagaatggg   5940
aactacatcc cattgagcta cacttcactt tttaggacag agcctggtag ataggagaca   6000
atcaatacag atttgtgttt taggttattg catgcttatg ggttagctag ggagctttct   6060
ttttatcttt caggaaagaa accaaagaga cagactctcc agcaggcagg gggcgccagt   6120
gagtgagcta ggcatagagt cttgtggaga gaattatggt gtcatagagg cttagaatct   6180
tggcattagc agggaaggga acccatctgg ttcagaaggc tttggcttct gatagtcatg   6240
gactcactag gctgctgagg aagatcaata atacctactg gaatcagtca tgagaagtca   6300
agcatggaaa ttgtgaattg tgtgtgtggc cagaccaggt aacacagaga aacattgtct   6360
tttgggtcct ctctccatgg ctttttcatg tgttcattag ttcattacgt atttacctac   6420
tgagacccat gcaatgccat tcagtgtgtt ggatgagagg attccaggat tcatcctatc   6480
tttcaggaaa aagctcctgc ttctatttaa gaggaagaca tgggagccac tgggggtggg   6540
gatagtgaga atgcctgtgt ttatggaact aacagaccac aaaagtgaga caattgggaa   6600
aataataacc actataaaaa tgtaatggga agtacagggg atccaagaaa gcctttcagg   6660
gagatggagg ttttgggtta aggaagtttt cctcgaggag tgatgtgtaa gcagagactt   6720
caggtttgaa cgatattcag tgagcatgtg gggacagaga cccaggaagg gtggtttaag   6780
ctgggaaaga gcacattcaa agacctggaa agaggtgaga aaattcagca ggtgtctgct   6840
ctgagccagt ctggtgcctg agggaacagt gtttggacat gaggctgggc ctgtgggcag   6900
agggagaagg tgccttgcca gagccctcct ggtggtttgg gctctgtatc aatcctctct   6960
gaatagagca ataagagcta ggaagatggc cctggccttg caccacaagt gtttgacatg   7020
attaggcaga tttcctgagg caggctgtgc acagcatggt tgggaaggaa gggaaatgga   7080
gcttggagag aatatttatt tatttgtttg tttcttttta tttatttatt gagatggagt   7140
ctcactctgt cacccaggct ggagtgcagt ggtgaggtct cggctcactg taacttctac   7200
ctcccggatt caagtgattc tcctgcctca gcttcccaag tagctggtat tacaggtgca   7260
cgccaccaca cccagctaat tttgtattt tcagtagaga tggagttttg ccatgttggc   7320
caggctggtc tcaaactcct gacctcaagt gattcacccg tcccagcctc ccaaagcgct   7380
gggacaacag gtgtgagcca ttgtgcccgg ccaaggagag aatcttaaga agaaactctt   7440
gcaggaggca gaggggtcca ggaggcaggt ttgttggaca ggagccaggg ttctgaaagt   7500
ggaggatata gatactattc accaggcaga aggaagacag tggagacagc actggctcag   7560
aggggcagga cctgcatcca tgggggtgag gttgcagaag gacttgatgt tgccctccct   7620
atgctacagt caacaagact ggtttccaac ctgctgtcct tctctgatat tgcacaacct   7680
ccacattcag gacctattcc caggatctca ctatggggga catgcttgga gtggggacat   7740
tggtgggact ggtgaggcaa gcccctggac ctgggctcca ggtgcctctg atgcctctgc   7800
```

acctctgatc actggaatga gaattgcttc tgtagaaaca gctcagtctg gacttgtaaa 7860
gatggacact aacaaactgg acttccaagt ggtgatgaga ctctgcactt tggtcaattc 7920
agggcactga ccttcagagt agagaaaggt aaaccagaga caaaagacag aaaggtagag 7980
acagaatgaa gaccagagaa tgatagagag gcagagagga aaaaaaaata gcaaaaggca 8040
aaaataaaca cagagaggaa caacagaaaa taaaaacaga aggggctcac tcctccctcg 8100
tccctctcaa aacctagtct taggtctgac ctctaaggga gcagattcaa acaacaagga 8160
gatacggaca gatactgggc tccctgcata ccccggcaca cccaaattca ccactgtaca 8220
gctgcagggg cacccaagtg tgtgcttgtg tgtgcgtgtg gacacacaca cacacttcct 8280
gtcaaacagc tttgaacact gcaaaggtgg tagagaacat ggccctgtac tctctcacct 8340
cttccctatt tttatactgg tctgtctccg tcttatttcc atttttggtg tgcctctcca 8400
ttgctcacct ctctccttcc tgttctctct cgggcaagtc aaggcatcgc agggcctgta 8460
tctgccacct cagcctcttt gcagcttcct ctgacctaga aggagcaata gggtgacttg 8520
tccccacccc catcctttag gagtctttgc tctagtgtct tcctcttaaa tggaagcagg 8580
ggccttttcc tgaaagatag gatgaatcca ggaataactg gcagagatag agtcatgact 8640
gaattaaagc caacatccta acccaagtca ctctcccctt tttaggtggg aactgccctt 8700
gacccagttc aggctgcagc catatagcca gggacttagg atcatgaaag gtttatacca 8760
ggtggcaggg ccttaagaga taactcttcc ctcccaatct tctctcaccc taatgctg 8818

<210> SEQ ID NO 5
<211> LENGTH: 3440
<212> TYPE: DNA
<213> ORGANISM: Homo sapeins

<400> SEQUENCE: 5
tggcctaata atgagaacaa actcattttg aaagtggaaa aattgagatt cagagcagaa 60
gtttgactaa ggtcacaaaa cagtaggatg cctcactcag ctccctgtgc ctaggtcaga 120
aaagcatcac aggaatagtt gagctaccag aatcctctgg ccaggcagga gctgtgtgtc 180
cctgggaaat ggggccctaa agggtttgct gcttaagatg cctgtggtga gtcaggaagg 240
ggttagagga agttgaccaa ctagagtggt gaaacctgtc catcaccttc aacctggagg 300
gaggccaggc tgcagaatga tataaagagt gccctgactc ctgctcagct cagcactcca 360
ccaaagcctc tgcctcagcc ttactgtgag tctggtaagt gtcggatggt agaaccaggg 420
ttgggactcg ggacctccaa cagcatacga tgtggtgggg gtgggcagcc tgggtggggg 480
tgggcattac tctggggctg gattcagctg gactttcatt ctagggggac tcgagtcaga 540
gtactgagag aaaagtgcct tggcacagaa gtgcagaaca gagagtaatc atcctatgtc 600
ccatcttttc ttgtgaccat atttttggat ttgtgtgtga gagagaatta tggaagggag 660
gaggggaata gcattcaact tctttcctaa acctcttggg ttttgacaga ccatcatttt 720
gccttcttta tggagggaga ggttcaggga agagcttcta ccttttggct atgctgcaca 780
gagggatggc agaatgggga aacctttcta tttggagaaa cctaggcaga gctgggacag 840
gaaaactcaa cttagaagta taagacttgg aagaacaacc tccaactctc agcaaccttc 900
cagctcccgc agccccaccc cagacacaag gactgcagct aaacctcaga aggtcaggag 960
agaaagcagc cctggggttg aataggccaa cctgctggct ttacaggggg gaaaaccaaa 1020
tcccaggaga ctaagtgaca tgcccagaaa cacacagcat tccaatggga gattcaggcc 1080

-continued

```
tagagcatgt cctgtggctc cagtctggag gtcacaccat gacctcttag gtcctctctg   1140
gcacggccta ttggttttct aggacttggt gttctccaag agacatttca ttccctaagg   1200
ccttactcct cactgtgaca taatcccaga acgcatctct gctccttggt cagtgaagcg   1260
atgagggtgg acacaaggac tagacaagag cagacagtga gctggcacct gacccaccct   1320
tgcagaacag ccctgcagac agatctcctt gttggctctc acctgggaac aaggaggctc   1380
ctaggaggac ctttctctgc ccctccacat ttccaccctt ctctctctgc tgcttttggg   1440
aaatgatagt ccagaggtgg tagaacagta ccctgcccaa gggaagaggg gatgctaaaa   1500
aaccagatac ttctgcagat tcccaaggtt tcatctattt cctttgcctt cagcctgtgc   1560
atcagacctc ttctgtcttt caggttgaca gtagcttcta agatgtccca gcaacacaca   1620
ctgccagtga ccctctcccc tgccctcagt caggagctcc tcaagactgt tcctcctcca   1680
gtcaataccc atcaggagca aatgaaacag ccaactccac tgcctccccc atgccagaag   1740
gtgcctgtcg agctcccagt ggaggtccca tcaaagcaag aggaaaagca catgactgct   1800
gtaaagggac tgcctgagca agaatgtgag caacagcaga aggagccaca ggagcaggag   1860
ctgcagcaac agcactggga acagcatgag gaatatcaga aagcagaaaa cccagagcag   1920
cagcttaagc aggagaaaac acaaagggat cagcagctaa acaaacagct ggaagaagag   1980
aagaagctct tagaccagca actggatcaa gagctagtca agagagatga gcaactggga   2040
atgaagaaag agcaactgtt ggagctccca gagcagcagg aggggcacct gaagcaccta   2100
gagcagcagg agggacagct gaagcacccg gagcagcagg aggggcagct ggagctccca   2160
gagcagcagg aggggcagct ggagctccca gagcagcagg aggggcagct ggagctccca   2220
gagcagcagg aggggcagct ggagctccca gagcagcagg aggggcagct ggagctccca   2280
gagcagcagg aggggcagct ggagctccca cagcagcagg aggggcagct ggagctctct   2340
gagcagcagg aggggcagct ggagctctct gagcagcagg agggacagct gaagcacctg   2400
gagcaccagg aggggcagct ggaggtccca gaggagcaga tggggcagct gaagtacctg   2460
gaacagcagg aggggcagct gaagcacctg gatcagcagg agaagcagcc agagctccca   2520
gagcagcaga tggggcagct gaagcacctg gagcagcagg aggggcagcc taagcatctg   2580
gagcagcagg aggggcaact ggagcagctg gaggagcagg aggggcagct gaagcacctg   2640
gagcagcagg aggggcagct ggagcacctg gagcaccagg aagggcagct ggggctccca   2700
gagcagcagg tgctgcagct gaagcagcta gagaagcagc aggggcagcc aaagcacctg   2760
gaggaggagg aggggcagct gaagcacctg gtgcagcagg aggggcagct gaagcatctg   2820
gtgcagcagg aggggcagct ggagcagcag gagaggcagg tggagcacct ggagcagcag   2880
gtggggcagc tgaagcacct agaggagcag gagggacaac tgaagcatct ggagcagcag   2940
caggggcagt tggaggtccc agagcagcag gtggggcagc caaagaacct ggagcaggag   3000
gagaagcaac tggagctccc agagcagcaa gagggccagg tgaagcacct ggagaagcag   3060
gaggcacagc tggagctccc agagcagcag gtaggacagc caaagcacct ggaacagcag   3120
gaaaagcacc tagagcaccc agagcagcag gacggacaac taaaacatct ggagcagcag   3180
gaggggcagc tgaaggacct ggagcagcag aaggggcagc tggagcagcc tgtgtttgcc   3240
ccagctccag gccaggtcca agacattcaa ccagccctgc ccacaaaggg agaagtattg   3300
cttcctgtag agcaccagca gcagaagcag gaggtgcagt ggccacccaa acataaataa   3360
ccacccgcag tgtccagagg ccctcagatc gtctcataca agggaagaga gagccactgg   3420
ctccacttat ttcgggtccg                                                3440
```

<210> SEQ ID NO 6
<211> LENGTH: 20
<212> TYPE: DNA
<213> ORGANISM: Artificial sequence
<220> FEATURE:
<223> OTHER INFORMATION: Oligonucleotide as PCR primer

<400> SEQUENCE: 6
agcacatagc aggcactagc 20

<210> SEQ ID NO 7
<211> LENGTH: 20
<212> TYPE: DNA
<213> ORGANISM: Artificial sequence
<220> FEATURE:
<223> OTHER INFORMATION: Oligonucleotide as PCR primer

<400> SEQUENCE: 7
cgattgtgcc actacacagt 20

<210> SEQ ID NO 8
<211> LENGTH: 23
<212> TYPE: DNA
<213> ORGANISM: Artificial sequence
<220> FEATURE:
<223> OTHER INFORMATION: Oligonucleotide as PCR primer

<400> SEQUENCE: 8
aaaaatgagt ccagtagaag cct 23

<210> SEQ ID NO 9
<211> LENGTH: 19
<212> TYPE: DNA
<213> ORGANISM: Artificial sequence
<220> FEATURE:
<223> OTHER INFORMATION: Oligonucleotide as PCR primer

<400> SEQUENCE: 9
agccagattt acatcccag 19

<210> SEQ ID NO 10
<211> LENGTH: 16
<212> TYPE: DNA
<213> ORGANISM: Artificial sequence
<220> FEATURE:
<223> OTHER INFORMATION: Oligonucleotide as PCR primer

<400> SEQUENCE: 10
tatcttgccc tgcacc 16

<210> SEQ ID NO 11
<211> LENGTH: 16
<212> TYPE: DNA
<213> ORGANISM: Artificial sequence
<220> FEATURE:
<223> OTHER INFORMATION: Oligonucleotide as PCR primer

<400> SEQUENCE: 11
aagtgggtct ccccag 16

<210> SEQ ID NO 12
<211> LENGTH: 17
<212> TYPE: DNA
<213> ORGANISM: Artificial sequence
<220> FEATURE:

<223> OTHER INFORMATION: Oligonucleotide as PCR primer

<400> SEQUENCE: 12
ttgctcggcc agagtct 17

<210> SEQ ID NO 13
<211> LENGTH: 20
<212> TYPE: DNA
<213> ORGANISM: Artificial sequence
<220> FEATURE:
<223> OTHER INFORMATION: Oligonucleotide as PCR primer

<400> SEQUENCE: 13
acgcatcaca cctggctagt 20

<210> SEQ ID NO 14
<211> LENGTH: 16
<212> TYPE: DNA
<213> ORGANISM: Artificial sequence
<220> FEATURE:
<223> OTHER INFORMATION: Oligonucleotide as PCR primer

<400> SEQUENCE: 14
gggcctatgg ctggaa 16

<210> SEQ ID NO 15
<211> LENGTH: 16
<212> TYPE: DNA
<213> ORGANISM: Artificial sequence
<220> FEATURE:
<223> OTHER INFORMATION: Oligonucleotide as PCR primer

<400> SEQUENCE: 15
ggctatgctg gggcaa 16

<210> SEQ ID NO 16
<211> LENGTH: 19
<212> TYPE: DNA
<213> ORGANISM: Artificial sequence
<220> FEATURE:
<223> OTHER INFORMATION: Oligonucleotide as PCR primer

<400> SEQUENCE: 16
tcagttccat aggctgacg 19

<210> SEQ ID NO 17
<211> LENGTH: 18
<212> TYPE: DNA
<213> ORGANISM: Artificial sequence
<220> FEATURE:
<223> OTHER INFORMATION: Oligonucleotide as PCR primer

<400> SEQUENCE: 17
cattgctgat gctggagg 18

<210> SEQ ID NO 18
<211> LENGTH: 19
<212> TYPE: DNA
<213> ORGANISM: Artificial sequence
<220> FEATURE:
<223> OTHER INFORMATION: Oligonucleotide as PCR primer

<400> SEQUENCE: 18
ccttaattgt ggtgttggt 19

-continued

<210> SEQ ID NO 19
<211> LENGTH: 20
<212> TYPE: DNA
<213> ORGANISM: Artificial sequence
<220> FEATURE:
<223> OTHER INFORMATION: Oligonucleotide as PCR primer

<400> SEQUENCE: 19
aaaaatctgg aaggcataaa 20

<210> SEQ ID NO 20
<211> LENGTH: 20
<212> TYPE: DNA
<213> ORGANISM: Artificial sequence
<220> FEATURE:
<223> OTHER INFORMATION: Oligonucleotide as PCR primer

<400> SEQUENCE: 20
agcaagaccc tgtctcaaaa 20

<210> SEQ ID NO 21
<211> LENGTH: 19
<212> TYPE: DNA
<213> ORGANISM: Artificial sequence
<220> FEATURE:
<223> OTHER INFORMATION: Oligonucleotide as PCR primer

<400> SEQUENCE: 21
tggatagctt tccaccact 19

<210> SEQ ID NO 22
<211> LENGTH: 20
<212> TYPE: DNA
<213> ORGANISM: Artificial sequence
<220> FEATURE:
<223> OTHER INFORMATION: Oligonucleotide as PCR primer

<400> SEQUENCE: 22
acaaggtgac cggaaagacc 20

<210> SEQ ID NO 23
<211> LENGTH: 20
<212> TYPE: DNA
<213> ORGANISM: Artificial sequence
<220> FEATURE:
<223> OTHER INFORMATION: Oligonucleotide as PCR primer

<400> SEQUENCE: 23
agctctggca agttgaagga 20

<210> SEQ ID NO 24
<211> LENGTH: 25
<212> TYPE: DNA
<213> ORGANISM: Artificial sequence
<220> FEATURE:
<223> OTHER INFORMATION: Oligonucleotide as PCR primer

<400> SEQUENCE: 24
atctgggttc actattaaac agagt 25

<210> SEQ ID NO 25
<211> LENGTH: 20
<212> TYPE: DNA
<213> ORGANISM: Artificial sequence
<220> FEATURE:
<223> OTHER INFORMATION: Oligonucleotide as PCR primer

<400> SEQUENCE: 25
tgggcaaggt agaatatgtg 20

<210> SEQ ID NO 26
<211> LENGTH: 19
<212> TYPE: DNA
<213> ORGANISM: Artificial sequence
<220> FEATURE:
<223> OTHER INFORMATION: Oligonucleotide as PCR primer

<400> SEQUENCE: 26
gggtgacaga gcaagactc 19

<210> SEQ ID NO 27
<211> LENGTH: 19
<212> TYPE: DNA
<213> ORGANISM: Artificial sequence
<220> FEATURE:
<223> OTHER INFORMATION: Oligonucleotide as PCR primer

<400> SEQUENCE: 27
ccctgacctc ccttacaga 19

<210> SEQ ID NO 28
<211> LENGTH: 20
<212> TYPE: DNA
<213> ORGANISM: Artificial sequence
<220> FEATURE:
<223> OTHER INFORMATION: Oligonucleotide as PCR primer

<400> SEQUENCE: 28
aactgtgtcc agcagcaact 20

<210> SEQ ID NO 29
<211> LENGTH: 20
<212> TYPE: DNA
<213> ORGANISM: Artificial sequence
<220> FEATURE:
<223> OTHER INFORMATION: Oligonucleotide as PCR primer

<400> SEQUENCE: 29
tatgtgcctg ttgtgtgcat 20

<210> SEQ ID NO 30
<211> LENGTH: 20
<212> TYPE: DNA
<213> ORGANISM: Artificial sequence
<220> FEATURE:
<223> OTHER INFORMATION: Oligonucleotide as PCR primer

<400> SEQUENCE: 30
agggtcccca aagagccttc 20

<210> SEQ ID NO 31
<211> LENGTH: 20
<212> TYPE: DNA
<213> ORGANISM: Artificial sequence
<220> FEATURE:
<223> OTHER INFORMATION: Oligonucleotide as PCR primer

<400> SEQUENCE: 31
atggcagcac atcctgcttc 20

<210> SEQ ID NO 32
<211> LENGTH: 19

<212> TYPE: DNA
<213> ORGANISM: Artificial sequence
<220> FEATURE:
<223> OTHER INFORMATION: Oligonucleotide as PCR primer

<400> SEQUENCE: 32
aatcacttga acctgggag 19

<210> SEQ ID NO 33
<211> LENGTH: 20
<212> TYPE: DNA
<213> ORGANISM: Artificial sequence
<220> FEATURE:
<223> OTHER INFORMATION: Oligonucleotide as PCR primer

<400> SEQUENCE: 33
actgactggc tgtttctgag 20

<210> SEQ ID NO 34
<211> LENGTH: 20
<212> TYPE: DNA
<213> ORGANISM: Artificial sequence
<220> FEATURE:
<223> OTHER INFORMATION: Oligonucleotide as PCR primer

<400> SEQUENCE: 34
actgcttatt cggagttgga 20

<210> SEQ ID NO 35
<211> LENGTH: 24
<212> TYPE: DNA
<213> ORGANISM: Artificial sequence
<220> FEATURE:
<223> OTHER INFORMATION: Oligonucleotide as PCR primer

<400> SEQUENCE: 35
ccaagagttt tcttagcaaa tcac 24

<210> SEQ ID NO 36
<211> LENGTH: 20
<212> TYPE: DNA
<213> ORGANISM: Artificial sequence
<220> FEATURE:
<223> OTHER INFORMATION: Oligonucleotide as PCR primer

<400> SEQUENCE: 36
ctgagcacag cagtggtctc 20

<210> SEQ ID NO 37
<211> LENGTH: 20
<212> TYPE: DNA
<213> ORGANISM: Artificial sequence
<220> FEATURE:
<223> OTHER INFORMATION: Oligonucleotide as PCR primer

<400> SEQUENCE: 37
aaggcttatc aagagcgagg 20

<210> SEQ ID NO 38
<211> LENGTH: 20
<212> TYPE: DNA
<213> ORGANISM: Artificial sequence
<220> FEATURE:
<223> OTHER INFORMATION: Oligonucleotide as PCR primer

<400> SEQUENCE: 38

-continued agacttacag cactggctgc 20

<210> SEQ ID NO 39
<211> LENGTH: 20
<212> TYPE: DNA
<213> ORGANISM: Artificial sequence
<220> FEATURE:
<223> OTHER INFORMATION: Oligonucleotide as PCR primer

<400> SEQUENCE: 39
tgctcctagg aaaggaaaca 20

<210> SEQ ID NO 40
<211> LENGTH: 17
<212> TYPE: DNA
<213> ORGANISM: Artificial sequence
<220> FEATURE:
<223> OTHER INFORMATION: Oligonucleotide as PCR primer

<400> SEQUENCE: 40
gcttctggcc tctgtca 17

<210> SEQ ID NO 41
<211> LENGTH: 18
<212> TYPE: DNA
<213> ORGANISM: Artificial sequence
<220> FEATURE:
<223> OTHER INFORMATION: Oligonucleotide as PCR primer

<400> SEQUENCE: 41
aattttgcgt gtgtgtgc 18

<210> SEQ ID NO 42
<211> LENGTH: 23
<212> TYPE: DNA
<213> ORGANISM: Artificial sequence
<220> FEATURE:
<223> OTHER INFORMATION: Oligonucleotide as PCR primer
<220> FEATURE:
<221> NAME/KEY: misc_feature
<222> LOCATION: (16)..(16)
<223> OTHER INFORMATION: n

<400> SEQUENCE: 42
tgaagtgtgc attctntaca tca 23

<210> SEQ ID NO 43
<211> LENGTH: 19
<212> TYPE: DNA
<213> ORGANISM: Artificial sequence
<220> FEATURE:
<223> OTHER INFORMATION: Oligonucleotide as PCR primer

<400> SEQUENCE: 43
cgagacattt gcatcatca 19

<210> SEQ ID NO 44
<211> LENGTH: 1762
<212> TYPE: DNA
<213> ORGANISM: Homo sapiens
<220> FEATURE:
<221> NAME/KEY: CDS
<222> LOCATION: (416)..(1453)
<223> OTHER INFORMATION: CDS

<400> SEQUENCE: 44
cgctgagagg ctgagtggag ttcactcaca tggattgagg cccagttcct gggagaagag 60

-continued

```
atgctgggca ggaaggtgtc tgcatgtggg actctgtaca gcccggtcct ctcccacgtc    120

tgggaggggc cagagtcaga caactgctgg gttcgtccct aagagaggtc atctgactgg    180

ctgttcagcc taggctgcac acacccccac tttcctctac caggccacac cggaggcagt    240

gctcacacag gcaagctacc aggccacaac aacgacaccc acctcacctc tggcacctct    300

gagcatccac gtacttgcaa gaactcttgc tcacatcagc taagagattg cacctgctga    360

cctagagatt ccggcctgtg ctcctgtgct gctgagcagg gcaaccagta gcacc atg     418
                                                             Met
                                                             1

tct gtg act ggc ggg aag atg gca ccg tcc ctc acc cag gag atc ctc      466
Ser Val Thr Gly Gly Lys Met Ala Pro Ser Leu Thr Gln Glu Ile Leu
            5                   10                  15

agc cac ctg ggc ctg gcc agc aag act gca gcg tgg ggg acc ctg ggc      514
Ser His Leu Gly Leu Ala Ser Lys Thr Ala Ala Trp Gly Thr Leu Gly
        20                  25                  30

acc ctc agg acc ttc ttg aac ttc agc gtg gac aag gat gcg cag agg      562
Thr Leu Arg Thr Phe Leu Asn Phe Ser Val Asp Lys Asp Ala Gln Arg
    35                  40                  45

cta ctg agg gcc att act ggc caa ggc gtg gac cgc agt gcc att gtg      610
Leu Leu Arg Ala Ile Thr Gly Gln Gly Val Asp Arg Ser Ala Ile Val
50                  55                  60                  65

gac gtg ctg acc aac cgg agc aga gag caa agg cag ctc atc tca cga      658
Asp Val Leu Thr Asn Arg Ser Arg Glu Gln Arg Gln Leu Ile Ser Arg
                70                  75                  80

aac ttc cag gag cgc acc caa cag gac ctg atg aag tct cta cag gca      706
Asn Phe Gln Glu Arg Thr Gln Gln Asp Leu Met Lys Ser Leu Gln Ala
            85                  90                  95

gca ctt tcc ggc aac ctg gag agg att gtg atg gct ctg ctg cag ccc      754
Ala Leu Ser Gly Asn Leu Glu Arg Ile Val Met Ala Leu Leu Gln Pro
        100                 105                 110

aca gcc cag ttt gac gcc cag gaa ttg agg aca gct ctg aag gcc tca      802
Thr Ala Gln Phe Asp Ala Gln Glu Leu Arg Thr Ala Leu Lys Ala Ser
    115                 120                 125

gat tct gct gtg gac gtg gcc att gaa att ctt gcc act cga acc cca      850
Asp Ser Ala Val Asp Val Ala Ile Glu Ile Leu Ala Thr Arg Thr Pro
130                 135                 140                 145

ccc cag ctg cag gag tgc ctg gca gtc tac aaa cac aat ttc cag gtg      898
Pro Gln Leu Gln Glu Cys Leu Ala Val Tyr Lys His Asn Phe Gln Val
                150                 155                 160

gag gct gtg gat gac atc aca tct gag acc agt ggc atc ttg cag gac      946
Glu Ala Val Asp Asp Ile Thr Ser Glu Thr Ser Gly Ile Leu Gln Asp
            165                 170                 175

ctg ctg ttg gcc ctg gcc aag ggg ggc cgt gac agc tac tct gga atc      994
Leu Leu Leu Ala Leu Ala Lys Gly Gly Arg Asp Ser Tyr Ser Gly Ile
        180                 185                 190

att gac tat aat ctg gca gaa caa gat gtc cag gca ctg cag cgg gca     1042
Ile Asp Tyr Asn Leu Ala Glu Gln Asp Val Gln Ala Leu Gln Arg Ala
    195                 200                 205

gaa gga cct agc aga gag gaa aca tgg gtc cca gtc ttc acc cag cga     1090
Glu Gly Pro Ser Arg Glu Glu Thr Trp Val Pro Val Phe Thr Gln Arg
210                 215                 220                 225

aat cct gaa cac ctc atc cga gtg ttt gat cag tac cag cgg agc act     1138
Asn Pro Glu His Leu Ile Arg Val Phe Asp Gln Tyr Gln Arg Ser Thr
                230                 235                 240

ggg caa gag ctg gag gag gct gtc cag aac cgt ttc cat gga gat gct     1186
Gly Gln Glu Leu Glu Glu Ala Val Gln Asn Arg Phe His Gly Asp Ala
            245                 250                 255
```

```
cag gtg gct ctg ctc ggc cta gct tcg gtg atc aag aac aca ccg ctg      1234
Gln Val Ala Leu Leu Gly Leu Ala Ser Val Ile Lys Asn Thr Pro Leu
        260                 265                 270

tac ttt gct gac aaa ctt cat caa gcc ctc cag gaa act gag ccc aat      1282
Tyr Phe Ala Asp Lys Leu His Gln Ala Leu Gln Glu Thr Glu Pro Asn
    275                 280                 285

tac caa gtc ctg att cgc atc ctt atc tct cga tgt gag act gac ctt      1330
Tyr Gln Val Leu Ile Arg Ile Leu Ile Ser Arg Cys Glu Thr Asp Leu
290                 295                 300                 305

ctg agt atc aga gct gag ttc agg aag aaa ttt ggg aag tcc ctc tac      1378
Leu Ser Ile Arg Ala Glu Phe Arg Lys Lys Phe Gly Lys Ser Leu Tyr
                310                 315                 320

tct tct ctc cag gat gca gtg aaa ggg gat tgc cag tca gcc ctc ctg      1426
Ser Ser Leu Gln Asp Ala Val Lys Gly Asp Cys Gln Ser Ala Leu Leu
            325                 330                 335

gcc ttg tgc agg gct gaa gac atg tga gacttccctg ccccacccca            1473
Ala Leu Cys Arg Ala Glu Asp Met
        340                 345

catgacatcc gaggatctga gatttccgtg tttggctgaa cctgggagac cagctgggcc   1533

tccaagtagg ataacccctc actgagcacc acattctcta gcttcttgtt gaggctggaa   1593

ctgtttcttt aaaatccctt aattttccca tctcaaaatt atatctgtac ctgggtcatc   1653

cagctccttc ttgggtgtgg ggaaatgagt tttctttgat agtttctgcc tcactcatcc   1713

ctcctgtacc ctggccagaa catctcactg atactcgaat tcttttggc               1762


<210> SEQ ID NO 45
<211> LENGTH: 345
<212> TYPE: PRT
<213> ORGANISM: Homo sapiens

<400> SEQUENCE: 45

Met Ser Val Thr Gly Gly Lys Met Ala Pro Ser Leu Thr Gln Glu Ile
1               5                   10                  15

Leu Ser His Leu Gly Leu Ala Ser Lys Thr Ala Ala Trp Gly Thr Leu
            20                  25                  30

Gly Thr Leu Arg Thr Phe Leu Asn Phe Ser Val Asp Lys Asp Ala Gln
        35                  40                  45

Arg Leu Leu Arg Ala Ile Thr Gly Gln Gly Val Asp Arg Ser Ala Ile
    50                  55                  60

Val Asp Val Leu Thr Asn Arg Ser Arg Glu Gln Arg Gln Leu Ile Ser
65                  70                  75                  80

Arg Asn Phe Gln Glu Arg Thr Gln Gln Asp Leu Met Lys Ser Leu Gln
                85                  90                  95

Ala Ala Leu Ser Gly Asn Leu Glu Arg Ile Val Met Ala Leu Leu Gln
            100                 105                 110

Pro Thr Ala Gln Phe Asp Ala Gln Glu Leu Arg Thr Ala Leu Lys Ala
        115                 120                 125

Ser Asp Ser Ala Val Asp Val Ala Ile Glu Ile Leu Ala Thr Arg Thr
    130                 135                 140

Pro Pro Gln Leu Gln Glu Cys Leu Ala Val Tyr Lys His Asn Phe Gln
145                 150                 155                 160

Val Glu Ala Val Asp Asp Ile Thr Ser Glu Thr Ser Gly Ile Leu Gln
                165                 170                 175

Asp Leu Leu Leu Ala Leu Ala Lys Gly Gly Arg Asp Ser Tyr Ser Gly
            180                 185                 190

Ile Ile Asp Tyr Asn Leu Ala Glu Gln Asp Val Gln Ala Leu Gln Arg
```

```
        195                 200                 205

Ala Glu Gly Pro Ser Arg Glu Glu Thr Trp Val Pro Val Phe Thr Gln
    210                 215                 220

Arg Asn Pro Glu His Leu Ile Arg Val Phe Asp Gln Tyr Gln Arg Ser
225                 230                 235                 240

Thr Gly Gln Glu Leu Glu Glu Ala Val Gln Asn Arg Phe His Gly Asp
                245                 250                 255

Ala Gln Val Ala Leu Leu Gly Leu Ala Ser Val Ile Lys Asn Thr Pro
            260                 265                 270

Leu Tyr Phe Ala Asp Lys Leu His Gln Ala Leu Gln Glu Thr Glu Pro
        275                 280                 285

Asn Tyr Gln Val Leu Ile Arg Ile Leu Ile Ser Arg Cys Glu Thr Asp
    290                 295                 300

Leu Leu Ser Ile Arg Ala Glu Phe Arg Lys Lys Phe Gly Lys Ser Leu
305                 310                 315                 320

Tyr Ser Ser Leu Gln Asp Ala Val Lys Gly Asp Cys Gln Ser Ala Leu
                325                 330                 335

Leu Ala Leu Cys Arg Ala Glu Asp Met
            340                 345


<210> SEQ ID NO 46
<211> LENGTH: 607
<212> TYPE: DNA
<213> ORGANISM: Homo sapiens
<220> FEATURE:
<221> NAME/KEY: CDS
<222> LOCATION: (55)..(387)
<223> OTHER INFORMATION: CDS

<400> SEQUENCE: 46

cagggacgtg tctgtgctcc tgcgtgtgac cagggttgac taaactctgc cagg atg       57
                                                            Met
                                                            1

tct tgc cag caa aac cag cag cag tgc cag ccc cct ccc aag tgt cct      105
Ser Cys Gln Gln Asn Gln Gln Gln Cys Gln Pro Pro Pro Lys Cys Pro
            5                   10                  15

ccc aag tgt acc cca aaa tgt cca cct aag tgt ccc cct aaa tgc ctg      153
Pro Lys Cys Thr Pro Lys Cys Pro Pro Lys Cys Pro Pro Lys Cys Leu
        20                  25                  30

ccc cag tgc cca gct cca tgt tcc cct gca gtc tct tct tgc tgt ggt      201
Pro Gln Cys Pro Ala Pro Cys Ser Pro Ala Val Ser Ser Cys Cys Gly
    35                  40                  45

ccc atc tct ggg ggc tgc tgt ggt ccc agc tct ggg ggc tgc tgc aac      249
Pro Ile Ser Gly Gly Cys Cys Gly Pro Ser Ser Gly Gly Cys Cys Asn
50                  55                  60                  65

tct ggg gct ggt ggc tgc tgc ctg agc cac cac agg ccc cgt ctc ttc      297
Ser Gly Ala Gly Gly Cys Cys Leu Ser His His Arg Pro Arg Leu Phe
                70                  75                  80

cac cgg cgc cgg cac cag agc ccc gac tgc tgt gag agt gaa cct tct      345
His Arg Arg Arg His Gln Ser Pro Asp Cys Cys Glu Ser Glu Pro Ser
            85                  90                  95

ggg ggc tct ggc tgc tgc cac agc tct ggg ggc tgc tgc tga              387
Gly Gly Ser Gly Cys Cys His Ser Ser Gly Gly Cys Cys
        100                 105                 110

cctgggctaa gaagaactct ttggacagaa tgtttaagaa cctcctacag cctgatgctt    447

aacccttccc atttcctctc attccattca tgggtggaca gcgaccacaa agactcatgg    507

ggcttccctg ggagaacttt gcacttgatg gagcacctca attgcaggtt ttgttttcct    567
```

```
cctttacctc atgttataat aaagctctga tttctgactc                        607


<210> SEQ ID NO 47
<211> LENGTH: 110
<212> TYPE: PRT
<213> ORGANISM: Homo sapiens

<400> SEQUENCE: 47

Met Ser Cys Gln Gln Asn Gln Gln Gln Cys Gln Pro Pro Pro Lys Cys
1               5                   10                  15

Pro Pro Lys Cys Thr Pro Lys Cys Pro Pro Lys Cys Pro Pro Lys Cys
            20                  25                  30

Leu Pro Gln Cys Pro Ala Pro Cys Ser Pro Ala Val Ser Ser Cys Cys
        35                  40                  45

Gly Pro Ile Ser Gly Gly Cys Cys Gly Pro Ser Ser Gly Gly Cys Cys
    50                  55                  60

Asn Ser Gly Ala Gly Gly Cys Cys Leu Ser His His Arg Pro Arg Leu
65                  70                  75                  80

Phe His Arg Arg Arg His Gln Ser Pro Asp Cys Cys Glu Ser Glu Pro
                85                  90                  95

Ser Gly Gly Ser Gly Cys Cys His Ser Ser Gly Gly Cys Cys
            100                 105                 110


<210> SEQ ID NO 48
<211> LENGTH: 592
<212> TYPE: DNA
<213> ORGANISM: Homo sapiens
<220> FEATURE:
<221> NAME/KEY: CDS
<222> LOCATION: (52)..(372)
<223> OTHER INFORMATION: CDS

<400> SEQUENCE: 48

ggacgtgtct gtgctcctgt gtgtgaccag ggttgaaaaa gtcgcactga g atg tcc      57
                                                         Met Ser
                                                         1

tgc cag caa aac cag cag cag tgc cag ccc cct ccc aag tgc ccc cca      105
Cys Gln Gln Asn Gln Gln Gln Cys Gln Pro Pro Pro Lys Cys Pro Pro
        5                   10                  15

aaa tgc cca ccc aag tgt cct cca aag tgc cga cct cag tgc cca gcc      153
Lys Cys Pro Pro Lys Cys Pro Pro Lys Cys Arg Pro Gln Cys Pro Ala
    20                  25                  30

cca tgc cca cct cca gtc tct tcc tgc tgt ggt ccc agc tct ggg ggc      201
Pro Cys Pro Pro Pro Val Ser Ser Cys Cys Gly Pro Ser Ser Gly Gly
35                  40                  45                  50

tgc tgc ggc tcc agc tct ggg ggc tgc tgc agc tct ggg ggt ggc ggc      249
Cys Cys Gly Ser Ser Ser Gly Gly Cys Cys Ser Ser Gly Gly Gly Gly
                55                  60                  65

tgc tgc ctg agc cac cac agg ccc cgt ctc ttc cac cgg cac cgg cac      297
Cys Cys Leu Ser His His Arg Pro Arg Leu Phe His Arg His Arg His
            70                  75                  80

cag agc ccc gat tgt tgt gag tgt gaa cct tct ggg ggc tct ggc tgc      345
Gln Ser Pro Asp Cys Cys Glu Cys Glu Pro Ser Gly Gly Ser Gly Cys
        85                  90                  95

tgc cac agc tct ggg gac tgc tgc tga ccagacctcg aacatcacag            392
Cys His Ser Ser Gly Asp Cys Cys
    100                 105

agcaaccctt atggagaaac ttgcaaccag gacctgtccc agagtgatgc ttctcctgcc    452

ccttttttctc ctttccttgg gctgacacac cttgtgaggt gttttgtctg ttgtcatggc    512
```

ccaagagccc atcctggatc ctgatcttac cttcccactt tacctcatac aacaataaag 572 ctcttttgcc tcttcgtgaa 592

<210> SEQ ID NO 49
<211> LENGTH: 106
<212> TYPE: PRT
<213> ORGANISM: Homo sapiens

<400> SEQUENCE: 49

```
Met Ser Cys Gln Gln Asn Gln Gln Gln Cys Gln Pro Pro Pro Lys Cys
1               5                   10                  15

Pro Pro Lys Cys Pro Pro Lys Cys Pro Pro Lys Cys Arg Pro Gln Cys
            20                  25                  30

Pro Ala Pro Cys Pro Pro Pro Val Ser Ser Cys Cys Gly Pro Ser Ser
        35                  40                  45

Gly Gly Cys Cys Gly Ser Ser Ser Gly Gly Cys Cys Ser Ser Gly Gly
    50                  55                  60

Gly Gly Cys Cys Leu Ser His His Arg Pro Arg Leu Phe His Arg His
65                  70                  75                  80

Arg His Gln Ser Pro Asp Cys Cys Glu Cys Glu Pro Ser Gly Gly Ser
                85                  90                  95

Gly Cys Cys His Ser Ser Gly Asp Cys Cys
            100                 105
```

<210> SEQ ID NO 50
<211> LENGTH: 2134
<212> TYPE: DNA
<213> ORGANISM: Homo sapiens
<220> FEATURE:
<221> NAME/KEY: CDS
<222> LOCATION: (47)..(1804)
<223> OTHER INFORMATION: CDS

<400> SEQUENCE: 50

```
ctctgcctca gccttactgt gagtctggtt gacagtagct tctaag atg tcc cag       55
                                                   Met Ser Gln
                                                   1

caa cac aca ctg cca gtg acc ctc tcc cct gcc ctc agt cag gag ctc      103
Gln His Thr Leu Pro Val Thr Leu Ser Pro Ala Leu Ser Gln Glu Leu
    5                   10                  15

ctc aag act gtt cct cct cca gtc aat acc cat cag gag caa atg aaa      151
Leu Lys Thr Val Pro Pro Pro Val Asn Thr His Gln Glu Gln Met Lys
20                  25                  30                  35

cag cca act cca ctg cct ccc cca tgc cag aag gtg cct gtc gag ctc      199
Gln Pro Thr Pro Leu Pro Pro Pro Cys Gln Lys Val Pro Val Glu Leu
                40                  45                  50

cca gtg gag gtc cca tca aag caa gag gaa aag cac atg act gct gta      247
Pro Val Glu Val Pro Ser Lys Gln Glu Glu Lys His Met Thr Ala Val
            55                  60                  65

aag gga ctg cct gag caa gaa tgt gag caa cag cag aag gag cca cag      295
Lys Gly Leu Pro Glu Gln Glu Cys Glu Gln Gln Gln Lys Glu Pro Gln
        70                  75                  80

gag cag gag ctg cag caa cag cac tgg gaa cag cat gag gaa tat cag      343
Glu Gln Glu Leu Gln Gln Gln His Trp Glu Gln His Glu Glu Tyr Gln
    85                  90                  95

aaa gca gaa aac cca gag cag cag ctt aag cag gag aaa aca caa agg      391
Lys Ala Glu Asn Pro Glu Gln Gln Leu Lys Gln Glu Lys Thr Gln Arg
100                 105                 110                 115

gat cag cag cta aac aaa cag ctg gaa gaa gag aag aag ctc tta gac      439
Asp Gln Gln Leu Asn Lys Gln Leu Glu Glu Glu Lys Lys Leu Leu Asp
```

-continued

```
                120                 125                 130

cag caa ctg gat caa gag cta gtc aag aga gat gag caa ctg gga atg      487
Gln Gln Leu Asp Gln Glu Leu Val Lys Arg Asp Glu Gln Leu Gly Met
            135                 140                 145

aag aaa gag caa ctg ttg gag ctc cca gag cag cag gag ggg cac ctg      535
Lys Lys Glu Gln Leu Leu Glu Leu Pro Glu Gln Gln Glu Gly His Leu
        150                 155                 160

aag cac cta gag cag cag gag gga cag ctg aag cac ccg gag cag cag      583
Lys His Leu Glu Gln Gln Glu Gly Gln Leu Lys His Pro Glu Gln Gln
    165                 170                 175

gag ggg cag ctg gag ctc cca gag cag cag gag ggg cag ctg gag ctc      631
Glu Gly Gln Leu Glu Leu Pro Glu Gln Gln Glu Gly Gln Leu Glu Leu
180                 185                 190                 195

cca gag cag cag gag ggg cag ctg gag ctc cca gag cag cag gag ggg      679
Pro Glu Gln Gln Glu Gly Gln Leu Glu Leu Pro Glu Gln Gln Glu Gly
            200                 205                 210

cag ctg gag ctc cca gag cag cag gag ggg cag ctg gag ctc cca gag      727
Gln Leu Glu Leu Pro Glu Gln Gln Glu Gly Gln Leu Glu Leu Pro Glu
            215                 220                 225

cag cag gag ggg cag ctg gag ctc cca cag cag cag gag ggg cag ctg      775
Gln Gln Glu Gly Gln Leu Glu Leu Pro Gln Gln Gln Glu Gly Gln Leu
        230                 235                 240

gag ctc tct gag cag cag gag ggg cag ctg gag ctc tct gag cag cag      823
Glu Leu Ser Glu Gln Gln Glu Gly Gln Leu Glu Leu Ser Glu Gln Gln
    245                 250                 255

gag gga cag ctg aag cac ctg gag cac cag gag ggg cag ctg gag gtc      871
Glu Gly Gln Leu Lys His Leu Glu His Gln Glu Gly Gln Leu Glu Val
260                 265                 270                 275

cca gag gag cag atg ggg cag ctg aag tac ctg gaa cag cag gag ggg      919
Pro Glu Glu Gln Met Gly Gln Leu Lys Tyr Leu Glu Gln Gln Glu Gly
            280                 285                 290

cag ctg aag cac ctg gat cag cag gag aag cag cca gag ctc cca gag      967
Gln Leu Lys His Leu Asp Gln Gln Glu Lys Gln Pro Glu Leu Pro Glu
            295                 300                 305

cag cag atg ggg cag ctg aag cac ctg gag cag cag gag ggg cag cct     1015
Gln Gln Met Gly Gln Leu Lys His Leu Glu Gln Gln Glu Gly Gln Pro
        310                 315                 320

aag cat ctg gag cag cag gag ggg caa ctg gag cag ctg gag gag cag     1063
Lys His Leu Glu Gln Gln Glu Gly Gln Leu Glu Gln Leu Glu Glu Gln
    325                 330                 335

gag ggg cag ctg aag cac ctg gag cag cag gag ggg cag ctg gag cac     1111
Glu Gly Gln Leu Lys His Leu Glu Gln Gln Glu Gly Gln Leu Glu His
340                 345                 350                 355

ctg gag cac cag gaa ggg cag ctg ggg ctc cca gag cag cag gtg ctg     1159
Leu Glu His Gln Glu Gly Gln Leu Gly Leu Pro Glu Gln Gln Val Leu
            360                 365                 370

cag ctg aag cag cta gag aag cag cag ggg cag cca aag cac ctg gag     1207
Gln Leu Lys Gln Leu Glu Lys Gln Gln Gly Gln Pro Lys His Leu Glu
            375                 380                 385

gag gag gag ggg cag ctg aag cac ctg gtg cag cag gag ggg cag ctg     1255
Glu Glu Glu Gly Gln Leu Lys His Leu Val Gln Gln Glu Gly Gln Leu
        390                 395                 400

aag cat ctg gtg cag cag gag ggg cag ctg gag cag cag gag agg cag     1303
Lys His Leu Val Gln Gln Glu Gly Gln Leu Glu Gln Gln Glu Arg Gln
    405                 410                 415

gtg gag cac ctg gag cag cag gtg ggg cag ctg aag cac cta gag gag     1351
Val Glu His Leu Glu Gln Gln Val Gly Gln Leu Lys His Leu Glu Glu
420                 425                 430                 435

cag gag gga caa ctg aag cat ctg gag cag cag cag ggg cag ttg gag     1399
```

```
Gln Glu Gly Gln Leu Lys His Leu Glu Gln Gln Gln Gly Gln Leu Glu
                440                 445                 450

gtc cca gag cag cag gtg ggg cag cca aag aac ctg gag cag gag gag     1447
Val Pro Glu Gln Gln Val Gly Gln Pro Lys Asn Leu Glu Gln Glu Glu
            455                 460                 465

aag caa ctg gag ctc cca gag cag caa gag ggc cag gtg aag cac ctg     1495
Lys Gln Leu Glu Leu Pro Glu Gln Gln Glu Gly Gln Val Lys His Leu
        470                 475                 480

gag aag cag gag gca cag ctg gag ctc cca gag cag cag gta gga cag     1543
Glu Lys Gln Glu Ala Gln Leu Glu Leu Pro Glu Gln Gln Val Gly Gln
    485                 490                 495

cca aag cac ctg gaa cag cag gaa aag cac cta gag cac cca gag cag     1591
Pro Lys His Leu Glu Gln Gln Glu Lys His Leu Glu His Pro Glu Gln
500                 505                 510                 515

cag gac gga caa cta aaa cat ctg gag cag cag gag ggg cag ctg aag     1639
Gln Asp Gly Gln Leu Lys His Leu Glu Gln Gln Glu Gly Gln Leu Lys
                520                 525                 530

gac ctg gag cag cag aag ggg cag ctg gag cag cct gtg ttt gcc cca     1687
Asp Leu Glu Gln Gln Lys Gly Gln Leu Glu Gln Pro Val Phe Ala Pro
            535                 540                 545

gct cca ggc cag gtc caa gac att caa cca gcc ctg ccc aca aag gga     1735
Ala Pro Gly Gln Val Gln Asp Ile Gln Pro Ala Leu Pro Thr Lys Gly
        550                 555                 560

gaa gta ttg ctt cct gta gag cac cag cag cag aag cag gag gtg cag     1783
Glu Val Leu Leu Pro Val Glu His Gln Gln Gln Lys Gln Glu Val Gln
    565                 570                 575

tgg cca ccc aaa cat aaa taa ccacccgcag tgtccagagg ccctcagatc        1834
Trp Pro Pro Lys His Lys
580                 585

gtctcataca agggaagaga gagccactgg ctccacttat ttcgggtccg ctaggtggcc   1894

cgtctcatct gtgaacttga ctctgtccct ctacatgtct ctttaatggg gtgagggtgg   1954

gggagagagg gaattattgt ccagtgccaa ccccaatgac cccaatccca acctcaggtg   2014

agcagagcct ctacttgagg gactattgtt actataggaa tccttacttc cccagtattg   2074

aagctgaatc agtgagtgtg tacaatgata cataataaat cctggaagtc ttgggatcct   2134


<210> SEQ ID NO 51
<211> LENGTH: 585
<212> TYPE: PRT
<213> ORGANISM: Homo sapiens

<400> SEQUENCE: 51

Met Ser Gln Gln His Thr Leu Pro Val Thr Leu Ser Pro Ala Leu Ser
1               5                   10                  15

Gln Glu Leu Leu Lys Thr Val Pro Pro Pro Val Asn Thr His Gln Glu
            20                  25                  30

Gln Met Lys Gln Pro Thr Pro Leu Pro Pro Pro Cys Gln Lys Val Pro
        35                  40                  45

Val Glu Leu Pro Val Glu Val Pro Ser Lys Gln Glu Glu Lys His Met
    50                  55                  60

Thr Ala Val Lys Gly Leu Pro Glu Gln Glu Cys Glu Gln Gln Gln Lys
65                  70                  75                  80

Glu Pro Gln Glu Gln Glu Leu Gln Gln Gln His Trp Glu Gln His Glu
                85                  90                  95

Glu Tyr Gln Lys Ala Glu Asn Pro Glu Gln Gln Leu Lys Gln Glu Lys
            100                 105                 110

Thr Gln Arg Asp Gln Gln Leu Asn Lys Gln Leu Glu Glu Glu Lys Lys
```

```
        115                 120                 125

Leu Leu Asp Gln Gln Leu Asp Gln Glu Leu Val Lys Arg Asp Glu Gln
    130                 135                 140

Leu Gly Met Lys Lys Glu Gln Leu Leu Glu Leu Pro Glu Gln Gln Glu
145                 150                 155                 160

Gly His Leu Lys His Leu Glu Gln Gln Glu Gly Gln Leu Lys His Pro
                165                 170                 175

Glu Gln Gln Glu Gly Gln Leu Glu Leu Pro Glu Gln Gln Glu Gly Gln
            180                 185                 190

Leu Glu Leu Pro Glu Gln Gln Glu Gly Gln Leu Glu Leu Pro Glu Gln
        195                 200                 205

Gln Glu Gly Gln Leu Glu Leu Pro Glu Gln Gln Glu Gly Gln Leu Glu
    210                 215                 220

Leu Pro Glu Gln Gln Glu Gly Gln Leu Glu Leu Pro Gln Gln Gln Glu
225                 230                 235                 240

Gly Gln Leu Glu Leu Ser Glu Gln Gln Glu Gly Gln Leu Glu Leu Ser
                245                 250                 255

Glu Gln Gln Glu Gly Gln Leu Lys His Leu Glu His Gln Glu Gly Gln
            260                 265                 270

Leu Glu Val Pro Glu Glu Gln Met Gly Gln Leu Lys Tyr Leu Glu Gln
        275                 280                 285

Gln Glu Gly Gln Leu Lys His Leu Asp Gln Gln Glu Lys Gln Pro Glu
    290                 295                 300

Leu Pro Glu Gln Gln Met Gly Gln Leu Lys His Leu Glu Gln Gln Glu
305                 310                 315                 320

Gly Gln Pro Lys His Leu Glu Gln Gln Glu Gly Gln Leu Glu Gln Leu
                325                 330                 335

Glu Glu Gln Glu Gly Gln Leu Lys His Leu Glu Gln Gln Glu Gly Gln
            340                 345                 350

Leu Glu His Leu Glu His Gln Glu Gly Gln Leu Gly Leu Pro Glu Gln
        355                 360                 365

Gln Val Leu Gln Leu Lys Gln Leu Glu Lys Gln Gln Gly Gln Pro Lys
    370                 375                 380

His Leu Glu Glu Glu Glu Gly Gln Leu Lys His Leu Val Gln Gln Glu
385                 390                 395                 400

Gly Gln Leu Lys His Leu Val Gln Gln Glu Gly Gln Leu Glu Gln Gln
                405                 410                 415

Glu Arg Gln Val Glu His Leu Glu Gln Gln Val Gly Gln Leu Lys His
            420                 425                 430

Leu Glu Glu Gln Glu Gly Gln Leu Lys His Leu Glu Gln Gln Gln Gly
        435                 440                 445

Gln Leu Glu Val Pro Glu Gln Gln Val Gly Gln Pro Lys Asn Leu Glu
    450                 455                 460

Gln Glu Glu Lys Gln Leu Glu Leu Pro Glu Gln Gln Glu Gly Gln Val
465                 470                 475                 480

Lys His Leu Glu Lys Gln Glu Ala Gln Leu Glu Leu Pro Glu Gln Gln
                485                 490                 495

Val Gly Gln Pro Lys His Leu Glu Gln Gln Glu Lys His Leu Glu His
            500                 505                 510

Pro Glu Gln Gln Asp Gly Gln Leu Lys His Leu Glu Gln Gln Glu Gly
        515                 520                 525

Gln Leu Lys Asp Leu Glu Gln Gln Lys Gly Gln Leu Glu Gln Pro Val
    530                 535                 540
```

```
Phe Ala Pro Ala Pro Gly Gln Val Gln Asp Ile Gln Pro Ala Leu Pro
545                 550                 555                 560

Thr Lys Gly Glu Val Leu Leu Pro Val Glu His Gln Gln Gln Lys Gln
                565                 570                 575

Glu Val Gln Trp Pro Pro Lys His Lys
            580                 585


<210> SEQ ID NO 52
<211> LENGTH: 694
<212> TYPE: DNA
<213> ORGANISM: Homo sapiens
<220> FEATURE:
<221> NAME/KEY: CDS
<222> LOCATION: (74)..(373)
<223> OTHER INFORMATION: CDS

<400> SEQUENCE: 52

gcccattcca gttggagaac gtagtgagtc tttcagtgga gccagggtct ggtttgtcgt      60

gaggagctcc gcg atg tcc tct caa cag agc gcc gtt tcc gcc aaa ggc       109
               Met Ser Ser Gln Gln Ser Ala Val Ser Ala Lys Gly
               1               5                   10

ttt tcc aag ggg tcg tcc cag ggc ccc gct ccg tgt ccc gcc ccg gcg      157
Phe Ser Lys Gly Ser Ser Gln Gly Pro Ala Pro Cys Pro Ala Pro Ala
        15                  20                  25

ccc acc ccg gcg ccc gcc tcc tcc tcc tcc tgc tgc ggc tcc ggc agg      205
Pro Thr Pro Ala Pro Ala Ser Ser Ser Ser Cys Cys Gly Ser Gly Arg
    30                  35                  40

ggc tgc tgc ggc gac tca ggc tgc tgc ggc tcc agc tcc acc agt tgc      253
Gly Cys Cys Gly Asp Ser Gly Cys Cys Gly Ser Ser Ser Thr Ser Cys
45                  50                  55                  60

tgc tgc ttc cca agg aga cgc cgc cga cag cgg agt agt ggt tgc tgc      301
Cys Cys Phe Pro Arg Arg Arg Arg Arg Gln Arg Ser Ser Gly Cys Cys
                65                  70                  75

tgc tgc ggg ggc ggc agc cag agg tcc cag cgc tcc aac aac cgg agc      349
Cys Cys Gly Gly Gly Ser Gln Arg Ser Gln Arg Ser Asn Asn Arg Ser
            80                  85                  90

tca gga tgc tgc tcc ggc tgc tga gaggcccgca acccccagcg ctgcgctaga     403
Ser Gly Cys Cys Ser Gly Cys
        95

gaaacccgcc cagcccagag cgggcccgcc ccgctgcggc tcccacgcgg ggctgggcct    463

cggagtttgc cccgtaaagc gaattgcact ttgatgttca gaaacccact ttgttctcag    523

ccacgcaaaa ctccctgacc ccgatgtgat ttttctcccc ggggattcga gagccatgcg    583

tgggacactg gaccctactg tctacacggg cttgcacaca gcaggtgctc agcaaatgtc    643

tattgatttg attgtctttt gaagatgtca taataaagct tctacctcct g             694


<210> SEQ ID NO 53
<211> LENGTH: 99
<212> TYPE: PRT
<213> ORGANISM: Homo sapiens

<400> SEQUENCE: 53

Met Ser Ser Gln Gln Ser Ala Val Ser Ala Lys Gly Phe Ser Lys Gly
1               5                   10                  15

Ser Ser Gln Gly Pro Ala Pro Cys Pro Ala Pro Ala Pro Thr Pro Ala
            20                  25                  30

Pro Ala Ser Ser Ser Ser Cys Cys Gly Ser Gly Arg Gly Cys Cys Gly
        35                  40                  45
```

Asp Ser Gly Cys Cys Gly Ser Ser Ser Thr Ser Cys Cys Cys Phe Pro
    50                  55                  60

Arg Arg Arg Arg Arg Gln Arg Ser Ser Gly Cys Cys Cys Cys Gly Gly
65                  70                  75                  80

Gly Ser Gln Arg Ser Gln Arg Ser Asn Asn Arg Ser Ser Gly Cys Cys
                85                  90                  95

Ser Gly Cys

<210> SEQ ID NO 54
<211> LENGTH: 5000
<212> TYPE: DNA
<213> ORGANISM: Homo sapiens

<400> SEQUENCE: 54
tcttccttct tttagttctg aatccctttc ttgtggtttt cctaagtgcc aggctttcct 60
gtagtcccta ccagactttt caaatgcttc ctcaggagaa ctgaagactg gttaactttt 120
ttttcttttt tttaagatag cagtggggag gggaagttct ggggcagaag ttggataacc 180
agggcctgag aaataaagat aagagggtat attcctcccc caggagacaa aagagaaggt 240
ggatggagaa ggggaaactg ggcctcagcc agcaccggga tgatgcgacc agctttgtca 300
gcacgcttgg ggagcataca caccgcttgc cttggctgga ccggagactg tgatcaccac 360
ccttccaacc catcccccaa cacgcaggct ggcatggcca cgcccacagt gccccaagtg 420
ctgcctgcct tgcagtgact cacttcctct gtatgggctg ctgaactgtc ccaaggagag 480
gacaggccat ctccaggcct tcagccccga gtttagatat ctgggcaggc tttgtggatg 540
ggcaagcata cagggagccc aaatgtggaa ggtaggtttt ttcaggtcag gtggaactgt 600
taacactgaa gcctatttgg gtaagaagca gagcctagct agtacctaat ggagattcag 660
gggccaggag tatcggggag gaaacatttc ctaacagaga ggtaaaatag ccaagaggag 720
tttctatgta ttctgaaatc aggcaatgga aagtatttgc agaaaagcaa tgtagggacc 780
aggcgtggtg gcttatgcct gtaatcccaa cactttggga ggccgaggtg ggtggatcac 840
ctgcggtcag gagttcaaga ccagcctgcc caacatggtg aaacctcatc tctactaaaa 900
atacaaaagt tagctaggca tggtggcaca tgcctgtagt tccagctact ttggaggctg 960
aggcaggaga attgcttgaa cctaggaggg tgaggttgca gtgagccgag atcatgccac 1020
tgccctccag cctggcaaca gagtgagact ccatctcaaa aataaataaa aggctgggtg 1080
cagtgattca tgcctataat tccagcactt tgggaggccg aggtgggcgg ataacctgag 1140
gtcaagagtt tgggaccagc ctggccaaca tggtgaaacc ctgtctctac taaaaataca 1200
aaaattagct gggtgtggtg gtgggccctg taatcccagc tactcgggag gctgaggaag 1260
gagaatcact tgaacctggg aggcagaggt tacagtgagc tgagatcaca ccactgcact 1320
ccagcctggg tgacagagta agactcggtc tcaataaata aataaataaa agcaatgtgg 1380
gacttggagg ctgaagaggt ggacatgcat gaacagtgga ggcggtgtat gtggctgcct 1440
ttcccctgta ttccactgag agggagccca aatctgcctc gcctgcattg agggatgaag 1500
aaaacactga gaggcagctg agaaacatgg atgctagttc caactccatg gcctcgggaa 1560
gtcactcaga ctccttgagt cagtaatgaa aaggtagtag attagaggct gggcgcagtg 1620
gctcatgcct gtaatcccaa cactttggga ggccgaggtg ggcggatcac aaggtcagga 1680
gttcaagacc agcctggcca acatggtgaa acactgtctc tactaaaaat acaaaaatta 1740
gctgggcatg gtggtgcatg cctgtaatcc cagctactca ggaggttgag gcaggagaat 1800

-continued

```
tgcttgaacc agggagtcgg aggttgcaat gagccgagat cgcgccattg cactctaacc   1860
tgggcaacag agtgagactc tgtctcaaaa aaaagaaaag aaaaggtggt agattagatc   1920
ctctctaaga tttcctccaa ctctgcaatt ctaaaatgta caacatgggg aaggaaggtg   1980
atcagtacaa ctgtaaacaa ctgcaatccg gccctgaagt tgaacaaaac aaaacctagg   2040
gagaggaatg agtttgtagc aggtttcaat gcagcgattg tgaacgcatc acacacacac   2100
tcctcacagg caaggacttc gcttctgcca tgtgactgag actctgttgg acttctccaa   2160
attcagagtt cagcctggca tgccggccag gagccccttg gagagattcg gcgtgaggaa   2220
acaggaggcc tcacgcttcc ttcggttctc cctaaatctg ctgggcaggt agccagaaga   2280
aactctgaag ggtacagaaa gccgagggcc agggggaccc cggctgcgga gctgcagtac   2340
cgtgtttacc cagcctaact gcggtcaccc agtctcctgc atgtgtctga ggtcagcctc   2400
gggggctccc ctgagtaggt atctacctga ggctcttccc ctgatgctac ctgcatacca   2460
attccaccca ggaacctggc gtcctcagga ggctgcactt cccaagtggg ctgagacagc   2520
cccttaatat gtggggctgg agccagagac ctcaaggggc cactaggggg ctcgagactc   2580
tcagtggctg ctgacgccct cttgtggcca ttttggggat tggccagaaa agtttcagaa   2640
gcgagccaag atcggaattc ttaaggaggt aagtaataac aacagtaaca gttaccatat   2700
aacaatactt atcgttatat atttgataac attgtgacat ttctacttaa cagcgctgtg   2760
cccagaactc ttctaagtgc tttatatgca ctgtagttat ttaattctca caacaaccta   2820
taacataaac actattactt gtctgttgat gatgaggaaa ctgagcacag aatagttgcc   2880
caaggtcaca cagaagacca gaatcccgac tctgagaagt ctggctccag aagctttgct   2940
tttagccacc acgctgagac tgagttccat tttggggttg tcaggtgaaa tacaggacac   3000
actgttaaac tataatttca gataaacaaa aaataataat tacaggcggt ggctcacgcc   3060
tgtaatccca gcactttggg agtccaaggc aggtggatca cgaggtcagg agttcgagac   3120
cagcctggcc aacatggtga aaccctatct ctactaagaa tacaaaaaat tagccaggca   3180
tgatggcagg cgcctataat cccagctact cgggaggcgg aggcaggaga atcgcttgaa   3240
cccgggaggt ggagcttgca gtgagccaac ataatgccac tgcactccag cctgggcaac   3300
agagagagac tccgcctcaa aaaaaaaaat gttagtatat ttaatgaaat atttgggtca   3360
tacttgtacc aacaaatgat tcctcattta cgtgaaattc tgattaagct gcatgtcctg   3420
tatatttatt tatttaatct aatacccccta ctttacaggg cacttttctc tgccacatgc   3480
aattacacag attacttttt tttttttttt ttttttttga gacggagtct cactctgtcg   3540
cccaggctgt ggagtgcagt ggcgccatct cagctcactg caacctctgc ctcccaggtt   3600
caagtgattc tcctgcctca gcctcccgag tagctgggat tacaggcatg cgccgccatg   3660
cccggctaat ttttttgtatt tttagtagag acggggtttc actgtgtaag ccaaggctgg   3720
tctcgatctc ctgcctcatg atccacccgc ctcggcctca caaagtgctg ggattacagg   3780
catgagccac cgtgcctggc cacattacct tatttattta tttatttatt tatttatttt   3840
tatgagttca atagtttttg gggacaaggt ggtgtttggt tacatggata agttctttag   3900
tggacacatt acttcattta atcatcccag gaaacctgtc ctcggaggcc ccagcatgtc   3960
ccacagcctc cgtctctctc aatcctccca tttagagagc tgaaaggact agcgaagctt   4020
acagaacata ggtggcagag ctggatattg aaccctcatt ctccagttct gacacaggtg   4080
catgttttcc ttttaacagg agagaaaagt gaggagcagt gattaccgcc acagaaatat   4140
cctttcatgg cgtgtcctcc ggcatggtct actcagtgtg gtggagccac tgcaggtccc   4200
```

tcctccaggg atgtaggaat gccagtgaag gccttcctga gttgggagag aggcagagga 4260
gtgagtggag gcagggctgt agcttctgtg ccccgcccct acccaggctc tccagggagg 4320
caggaaagag gctgtgttta gacctgaggg agccagctgt gaggctggag cagttgctgc 4380
atggcggggc gggggctcca cagggctgtt cacctgctgc tctgtgcaga gacagcctca 4440
agtccagctg ctggggttgc atcacctgca gctaaaacag ccacagggcc caggctgcca 4500
aaaggcaaca gaagcaatct aagaaaccag gcaagggagc ctcccccatc tccctgttgc 4560
cttttgggag catagagctt ccctctgaag gtaacaccct ttgcattttt ctctcttgac 4620
tctgttcatc aacttccact cccaaatact tgtgcccttc cttctccaca gatatacaca 4680
atccctgggc actctccacc taggtcagct ggctctagta aggcagcagt caagggagtt 4740
tctgggctgg gaccccctct ggggtgcagg ctggggtgcc ctgctggtat gtgccccaac 4800
aggtttttcc ctatcagcct tgaaatcagc ctgcagcctg tctgacctgc cccccaggga 4860
gctggagcca gaggcagagc caggtcagaa gctggggcag agccaggtca gaagctggac 4920
tttgagacta ggtctctgtg gtcccacctg gacccacagg gaaggcagtg cataaaagcc 4980
tcctgtgttt gaggctgagc 5000

<210> SEQ ID NO 55
<211> LENGTH: 5000
<212> TYPE: DNA
<213> ORGANISM: Homo sapiens

<400> SEQUENCE: 55
tttagaaagc atagttataa attatctgga aaattcatcc caccaaacaa aataattgac 60
aatctggact agacagatgg tctgacattg tgtgtgtgag tgtgtgtgtg tgtgtgtgtg 120
tgtgtgtgta tggtagtgta tctatgctgt gtgtaaactt gttgtcagaa acctgttgac 180
attatactaa aataattgaa attttttgg ttaaattttc tgaactttat tcccagctgt 240
gtgaacttgg gctatttgtt tagctctagg agcctttgtt ttctcattag tacagtggga 300
atattaatac cacctacatc acatgattag tatgaggatt aaatgagata atgtgtataa 360
aacacttaaa taatacctag aaaaaaatag atggtcagta aacatcagtt attatattac 420
tttctgttat ttttatcatt gtacacacat gtatgtatgc atgtatacac acacacacac 480
acacacacac acacacacac acacggaggc atttgaccca aaagcacaac tccactcaac 540
ctatacctca gggaaagatg gggaagtagg tagacctgaa ttggctaggg ttttgcagag 600
aaacagaaga gagagataaa tttattttaa gaaattggct catgagatga ctgtgtgggc 660
tggcaagtcc aaaatcttgg ctggaaattc agataacagt tgatgttgca gcattgagtc 720
taaattctgc aacgcagtag tctggaaaca ggcagagttt ctacattgca gtcttgagga 780
taatttattc tttgggaaac ctcagtgtcc attattaaag actgcagctg attggatgag 840
gctcatgtta gggaagataa tctgcttact cagtctactg attaaatact tacagagaaa 900
catgtggatt gctatttgat caaacaactg ggtaacacag catagcctgg gcaaaattaa 960
ccatcacaga gactgagagg atacatggag gtcactggag atatgaccca agagacagaa 1020
gagggtcaac agtgacgagg acacactaag aacatgccat gatggtttta ttttcactta 1080
ggataaaggc aaatttctgg acagaccttt ggagaatatt gggaaaacag aagcttctac 1140
ctggtaaccc catggtaagc ccaacaaagc tgtgatgtta ggaggactgg agaaagggag 1200
tgcagcatgc ggctgaggag gcccttggcc ttcgcacttt ggtttcacag aagtgtagtc 1260

-continued

```
agtacagcac ggacaaggct gctgaccact gcacagtagc tggagctctg gggactggtg   1320
attgctgcag cttcttccta tgcaggggtc acacaagaag attcggaggt gaacatgggc   1380
tgtgcactgg agtggcactg tggagggccc tttgaaggca ttggcattgc tggtggtttt   1440
ttggaaaggt atctgagttt cagaatgaat tgaataataa gtcagataaa ttagagccag   1500
gacgggcata attttgccct tttaaaccta ttcttggtgt gctggcagac agtttataaa   1560
atacatttgt atcgaattag tacctatgaa gaaacgtata accccaagtt aaaagtgtta   1620
gaactgacat gcttaaaaac agaattaatg ctaaatcaat gtcaattctg tctctcattt   1680
catttcatat ctacgtaccc acttcctacc tacagtattt catgagcttt aagaggctat   1740
caattgtaag ggacaccctt atttcatgca ccacaaggaa agaaaaaaat gctgcaaatt   1800
caacaattac gtgccaccaa tcatatggta tatactgatt taagggctgt taacaagtat   1860
tagaagactg tatcatggaa ttgatgaatt aagataagta taaaaccgat ccactttagg   1920
tcatataaat atgtatgtaa atactagacg ggccaattct tgctttgccc agaacacccc   1980
tctgctgtgc tcctccctat cactatgtct agcactagac actgctagac agtattgaca   2040
aaaaagatca aaaggcctac aaagatatgg tacaggaaaa ttttggattg gtcaatctat   2100
taaataaagg gagacaaata aaaagacatg gtaaggcttt ttcttgtact gtagataaaa   2160
taaagttccc acatttggta gggagtattt ttctggaata tatggagttt aagttcccag   2220
ggagacaaat caaggagcta cttggagaga ccagcctgca ggagagtgac ttgccagatg   2280
acatgaactt cagatgaaat gtttgaagtc acccgcaggg cattcttctc atgacaccta   2340
catgctcgtc catgtggtcc taaaatgatg cactgatcct gccaacactc atgtggcaat   2400
taagtatgtg ggtggtccct gagggagcat gggcaatgtg acccactggg tctcctggct   2460
cagagagatc acacatgatg atgtgaagac tgtggagaca gaagcaagaa tatctatagt   2520
caggtgtttc ttcactgact tgtgaaccaa ttcccaccat tttttgagat ataaagggaa   2580
aaagtgggca tgttaaagag ctgtttatct cccagttctg gtttcccaga gggtcggttc   2640
ccattagtcc ttccattgct tattcaacca ctcaatacag atgctcatgt atgtgcatgt   2700
tcatttcacc tgcactttta tatgaataca gcatacatgc acacagtgca tacatgcaca   2760
cagtgcacac atgcacacac acacacaggc ttgcctcccc tatttcctca cttacaacat   2820
tgtaacaaat atctttgtca aagagtatga ggaagctgag ggtgatatca ccatgaagac   2880
agtggaatga actaacatct tttaaacaca ttgggaaata gtgactcagg aggttcaggc   2940
ctcaaacatc atcttctttg gtatccagtt tgtctgcagt catcttcaaa aaggccacta   3000
aattctacag tctttgaggt catgggctac ttattgttca cctctatatc cctatgtttg   3060
gacatacatg ctccaagaat gttgtaggct ttcaaagaat gccttttgaa ttcactgctc   3120
taatcacact gtggacttag tttatccttg aggtaaaagc tctctgagaa caggactcgg   3180
gtctgaaaat aggactgtgt aaataggtga atagaatccc tcaggtagaa gcagacaatg   3240
ggaaactatg ctttctacct aaccaccctc caccaccaag taaacattag gcaatgtcaa   3300
ggcacggtct gtttctgttt taatcagagg tgtgaataac tatctttttc aattctaatt   3360
tcaacatctt cattgagcca taattcactt attatacagc tcatttattt aaagtgttaa   3420
ttcagtgggt ttcaatatat tcatagagtt ggacaatcac caccaaattt tagaacattt   3480
tcattactcc acaaagaaaa cctatatcca tttgttgtaa ttttctaatt tctcccagcc   3540
tgctaaagta cctggaagcc actgatattt cctcagagga tgtgcacaaa agtaaaaggc   3600
gatacaggga acagaatctt gtccaggctc tggttcctca gatgccctaa gtcagctctt   3660
```

caggcgtcca gcctgagaga ggctgtaact ggctaaagcc tcattccctt tctagttcta 3720
cagatttgcc tactctacac atttcatata aataggatca taagaaatgc agtcttttgt 3780
ggttggcttc ttccatttag cgtaaggttt tcaaagttca tcctccatat atctgtttaa 3840
aataagtgaa taaatgaatg ggtaactctg tctagtgcaa ccctgaatca gaactctgag 3900
taagtagacc cctttctgac cctctacttc atgataggaa aggaattccc tctccacaga 3960
agccacaata aatgatgtct acttcctaag ggagttttca aataaactgt cttgtaaggg 4020
ttctatatgg acaatgaatg ccacataaga cctgggtaag tatccaatac atggcattag 4080
tttttctttt aaacacatat ttattaaggg tctatcaagc acatagtgtc acactaagct 4140
ctttcttact tctcatttaa tattaaaaac agctcagtga gataagtata cctggtttat 4200
aacggccatt acatatgaga attgatactc attgtgagta tcatagtgac actctagcaa 4260
ttgttgataa ttgttgtagc aatttccaga gatcactcag ttatcatatg caagttttct 4320
gattccagta gcacattcaa tacaattcct ccgactaagg gcaatgtttt gattttagag 4380
ggaattgttt attctcaatc atattctttg ctctagacca cagaatcaac tcagatttaa 4440
tccactgaat ctgctggcca tggtgagttg gaggaaaagc agaaacacag aggccaggag 4500
gaagggctga gagcctaggc aagggaggga tgcctagaaa aagccaaggc tgtagaagcc 4560
ccctgggatg gctggatcca cagcaggaca tggaagagaa actgctcagg gtggagggag 4620
tcataatgga acatttccac aaggtcaggg aaagctgtgg ctcagaactg atgtttcctc 4680
agaggacacg aatacaaaag atgcagggaa caggatcttg tccaggcatg ggtcccttgg 4740
gtaacctaag ttaactcatt agggttccca cctggtggag gctctgactg gctaaagctt 4800
ctctagaccg cagccccaga gaggagtcct ggaagctcct gaggcctctt tggattgcag 4860
ggactaggag gcaggagaat gtcaggaatg acccagcacg tgcctggttg tgcaaaagcc 4920
acctcctcct ctttccagag ccaagcctgg gccctataaa agacacatcc agcttcagca 4980
cctcatctgc tctgactccc 5000

<210> SEQ ID NO 56
<211> LENGTH: 5000
<212> TYPE: DNA
<213> ORGANISM: Homo sapiens

<400> SEQUENCE: 56
cacccagatt cataaagcaa gtccttagtg acctacaaag agacttagac tcccataaaa 60
taataatggg agactttaac accccactgt caacattaga cagatcaacg agacagaaag 120
ttaacaatga tatccaggaa tttaactcag ctctgcacca agtggaccta atagacatct 180
acagaacttt ccaccccaaa tcaacagaat atacattctt ctcagcacca caccacactt 240
attctaaaat tgaccacata gttggaagta aagcactcct cagcaaatgt aaaagaatat 300
aaactataac aaactgtctc tcagaccaca gtgcaatcaa actagaactc aggattaaga 360
aacacactca aaaccactca actacatgga aactgaaaaa cctgctcctg actactgggt 420
acatatgaaa tgaaggcaga aataaagatg ttcttgaaac caacgagacc acaacatact 480
agaatctctg ggacacattc aaagcagtgt gtagagggaa atttatagca ctaaatgccc 540
aaaagagaaa gcaggaaaga cctaaaattg acaccctaac atcacaatta aaagaactag 600
agaagcaaga gcaaacacat tcaaaagcta gcagaagaca agaaataact aacatcagag 660
cagaactgaa ggaaatagag acacaagaaa cccttcaaaa aatcaatgaa tccaggagct 720

-continued

```
ggttttttga aaagatccac aaaattgata gaccactagc aagactaata aagaagaaaa    780
gagagaagaa tcaaacagac acaataaaag atgataaagg ggatatcatc accaatccca    840
cagcaataca aactaccatc agagaatact ataaacacct ctacgcaaat aaactagaaa    900
atctagaaga aatggataaa ttcctggaca catacaccct cccaagacta aaccaggaag    960
aagttgaatc tctgaataga ccaataacag gctctgaaat tgaggcaata attaatagct   1020
taccaaccca aaaaagtcca ggaccagatg gattcacagc cgaattctac cagaggtaca   1080
aggaggagct ggtaccattc cttctgaaac tattccaatc aatagaaaaa gagagaatcc   1140
tccctaactc attttatgag gccagcatca tcctgatacc aaagtctggc agagatacaa   1200
caaaaaaaga gaattttaga ccaatacccc tgatgaacat cgatgcaaaa atcctcaata   1260
aaatactggc aaaccaaacc cagcagcaca tcaaaaagct tatccaccat gatcaagtgg   1320
gcttcatccc tgggatgcaa ggctggttca acatacacaa atcaataaac ataattcagc   1380
atataaacag aaccaacaac aaaaaccata tgattatctc aatagattca gaaaaggcct   1440
ttgacaaaat tcaacaacac ttcatgctaa aaactctcaa taaattaggt atcgatggga   1500
catatctcaa aataatctaa gagctatcta tgacaaaccc acagccaata taatacctaa   1560
tggacaaaaa ctggaagcat tccctttgaa aactggcaca agacagggat gccctctctc   1620
aacactccta ttcaacatag tgttggaagt tctagccagg gcaatcaggc aggagaagga   1680
aataaagggc attcagttag gaaaagagga agtcaaattg tccctgtttg cagttgacat   1740
gattgtatat ctagaaaacc ccatcatctc agcccaaaat ctccttaagc tgataggcaa   1800
gttcagcaaa gtctcaagat acaaaatcaa tgtgcaaaaa tcacaagcat tcttatacac   1860
caataacaga cagccaaatc atgagtgaac tcccattcac aattgcttca aaggaataaa   1920
atacctagga atccaactta caagggatgt gaaggacctc ttcaaggaga actacaaatc   1980
actgctcaac gaaataaaag aggatacaaa caaatggaag aacattccat gttcatgggt   2040
aggaagaatc aatattgtga aaatggccat actgcccaag gtaatttata gattcaatgc   2100
tatccccatc aagctaccat tgcctttctt cacagaattg ggaaaaacta ctttaaagtt   2160
catatagaac caaaaaagag cccgcattgc caagacaatc ctaagccaaa agaacaaagc   2220
tggaggcatc acactatctg acttcaaact ctactacaag gctacagtaa ccaaaacagc   2280
atggtactgg taccaaaaca gagatataga ccaatggaac agaacacagc cctcagaaat   2340
aatgctgcat atctacaacc atctgaccca gcatgcctag atattcttga tattcttttc   2400
tcctctttta tctctttgga aaatcatggg agattccagg ataccccacc agtttcttct   2460
gctcaaaagt tataaatggc ttcagcagga atctagccac tgggcaatag tttcagggac   2520
ccagttcact atggagtcaa ctcttgttac gaaacttggt tctcacctca cctccaggtc   2580
tgctctatga gctggtggct taggactggg attgtctgtt ttcagaggga aggagaggtt   2640
gaaatgagct aagagatgtg ttttacaaca agaaactata aaataaccta ctgcttgcag   2700
aagctgaagg agagggatga gtgacattgg taaggtccca tgcctggtga ataagagagg   2760
aaataccaca aagagagagc gtgttttgga gatcaggagg ttttgtgata gagttagttt   2820
gaggtcacag caaaaatatt tgcctcttag aagacatttg gcaggatcaa actgcaggtc   2880
agtgactttc taggcaaagc agaggtggct taaaggaagt attttaaata actcccaggt   2940
aattcttcta ataacattta atttattcat tcatccatct aatcaatagt ctatggtcaa   3000
ctgctagact ccccaggaaa agaaacaatg ggtaagacct gattctgagc tcatgctctg   3060
gtgacttaat atccgtggac atagagccaa gattgtctag aattcttact ggtgtcaaag   3120
```

gctgtaagcc tgatctctaa cagtgactga ccatatttta tcataaaaaa tatggaagga 3180
cattttgtct gctgagactg gcttcctgtg aacgaggcac atatcagctt tggagtcttc 3240
tctccaaccc ttggccacgc tgctgtgctt gtccctggac ttgcaagcac accttcatgc 3300
ccatgctgcc cacacacaca tacacacaca ttcataaagg cacagcccat cccattctct 3360
tccttcatgg ttactatcat ctttgtcaag gagaatgagg aacctagcat gacattccct 3420
caggcattat caggtgatcc agtgtcccaa caatctcatt ggaaaataga ctcatttggt 3480
atgcacataa atttcacaga ggtcttcaga atatccactg aattgtgaat tcctagaggt 3540
cacaaaacac acacagtgtt tgcctctata aacctaagtg tttggataga aaatcactga 3600
atacctagga gctgacaaag cagtatcttc ttgattaact gctatgtttg gatatcaaca 3660
tttttcactc ttgacctgaa cactctcaag ggtagggaac tacatctgag actagaaaag 3720
aaaactattg gagatggggc atctcttagt atgacagaaa tgtaaagacc atatactcct 3780
accttctaga ccaagggtat atgaaagaag ggactatctt tttcaaaagc tgtattctaa 3840
cttatgccat acagtaggtt ttcagtaaat gttggatgga tggatgaaat aaattgatta 3900
atggatgaat gtatctaatc caaaattgta tcagattcct tactctcctg tcattcacta 3960
agaagattaa ataaatcatt tgattcccat caccttcttg acaagaaata attagacttc 4020
tcaaaatcct gaatgtacac tgtacattcc taagagagcc ttcgctagcc tacctatatt 4080
tttaaataaa attttcaaag acagggactg aatattgtcc atttttctgt ctcacacact 4140
gccctcgttc ttttaaaaaa tgacattgtt taagtgtctt ccttgtgcct tatcatgtgc 4200
aaaagcctca cttgatggaa ccaacaattc agagaggaag gtgctaatag gcctgtttta 4260
cagttgagga tttagattgt ctatatatag tctttgaggt cactgggctc ataaacacag 4320
agctcttctg attccaattc aaaaaactat tggcttattt taaaaactgc cttgttacac 4380
agtagacatt ttaatttcta agtgaagaag tttagtcaca atgatcatca ccaccaaatc 4440
tgaggaaacc atcttgattc acttattaat cctcctagca gggttctgca ggccacacag 4500
caacatgggg tcaggaatga gggctgagca gaaggggagg agtgtatcct aggaaggaaa 4560
tggtctctga ctcaatgcca caaagaaacc tgcctagctg tggaagcagg gcttggaaaa 4620
ctatacttgg ggatgggaag aagctggaat agcatacttc cacaggaaag ctatggcaag 4680
gatctctggt gttctcagaa gtcactcttt gagcctttgt ccaggcacaa gctccttaag 4740
aatcccctgg cagctccacg gggaccagcc tggggggggc tgtgactggt taaagctcct 4800
ttagaccccc ttcccagagg gaggtcttgg gagctcccag tgcttccttg gattgtaggg 4860
acaaggaggc aggggaatgt gaggaatgac ccagcacgtg cctggttgtg caagagccac 4920
ttcccgctct tcccagagcc aagcctgagc ctataaaaga catattcagc tccagcacct 4980
catctgctct gacttcccca 5000

<210> SEQ ID NO 57
<211> LENGTH: 5000
<212> TYPE: DNA
<213> ORGANISM: Homo sapiens

<400> SEQUENCE: 57
atggactgtg tgactgtggg gcttcatgtt tttcatgggc aaaatgagtt agttaaagct 60
gatgaacttt aaagaactta caccttcaaa actatcttta ggtaggtaac acactgtaat 120
ccatcagcaa aactttgcaa tggcccccag cgataaaata gccaacttcc tgactacaac 180

-continued

```
ctatgtgcta agcacatata ttccctcacc aaattctcac agaattctaa ggaattgtta    240
gtatccccat tttacagaca aggaaactga aattcataga ggtgaaatgt cttgtccaga    300
taaaaagacg tgcaggtgca attcaaaccc aggcctgtct gacagcaaag ccagtgccca    360
ccattgaaca gtaacattct ttcagattgg attaggctga aataaactta aacaccagac    420
ccagccagga agtggagctc cctattccca ggaccaaaga gggtcatccc aagggcattt    480
tggctgaatg agagccagag aaaactgaca ctccctccag aaaacccaga actggccatg    540
ttgaggtaag tgactgactc acagagctag aatgtgtctt tgaagtcacc tagtggaacc    600
tgtcacagcc atcagatgct caagcaccta gcaaagcagc ctgatgggga ggagagcccc    660
tgactggagg tcaggacaca tgggttccag cccagctcta tcacagcctc gctgtaggct    720
cttgggcaac tcatgttctc tccagacttc aattcctgtc agaagacaga tgagccccaa    780
tggtgagaag taggcatagg tgtgttaaga agcacctgca ttctaagcta cttgaaggca    840
gggattgtgt gttttctatt cataacccta tctccagtgc cttgcacata gtagaggctc    900
agtaagtgtt ggttgaatga atacatcaat tatattaaca actttacctt gtgacctggt    960
attaggcaaa ggcattactt cttttttgt tgaggtacaa ttcatataac ataaagttac    1020
cattttaaag tgaacagttc agtggtgttt agtacattca tatattatgc aaccaccaac   1080
tctatgtcgt tctataacat tttcatcatc cccattagca gctacatccc attctctcct   1140
cctctcactt cctggcaacc atcagtttgc tttctgtttc tatgaattta catattgtga   1200
atttaagtta ttattattag ttattattag atagataaat agagaagctc ctatgcacca   1260
ggcgcagtgt aaggcatttc ccatgcattc tctgaggact cctccatctc agacattctg   1320
ctgctggaca gagaatcaac tgtacaaaat gtgatttccc caacaatgag cccaaagggg   1380
agggaatttc ctttagttgg agaaggggga actgagtgtc tctttcctct actactggca   1440
gcctttatgc ctctgctcct cttgctgcca ccaagagcag agctgtggct gcccttccac   1500
agctctcaga tccaagaaca aaggccagaa ctggtgactg agatccagtg atccaacaag   1560
cccaggagag aaagctataa gaagatgtaa gagaggaaag caggtcagga cagacagatc   1620
cacccagaag cccaaaaagg atgagtcagc cctcttggcc ctttcttggt ctcatctccc   1680
ttccttgaat agcagacggg cacaaaaggt gagagaagag ccaaggtcag gtccaggaag   1740
caatggaaaa agatgaggag gattcaaagt ttgtggggaa ggtcgggcac cgtggctcac   1800
gcctgtaatc tcagcacttt gggaggctga ggcgggcaga ccatgaggtt aggatttcga   1860
aaccagcctg gccaacatag tgaaacccca tcactactaa aaatacaaaa attatccagg   1920
catgttggca catgcctgta gtcccagcta ctcaggaggc tgaggcagga gaatcgcttg   1980
aattggggag gcagaggttg cagtgagcca agattgcacc actgcactca agcctgagag   2040
acagagtgga ctctgtctca aaaaaaaaaa aaaaaaaaga agtgtgtggg gagacaacta   2100
gtgcaggttg gcaggttgag gactgagagc cgctgatgta ggagacagtg ccctggggag   2160
aggaggaggc ttgtgagagg gagaggaggc tagcagcctc agagcatggg gcagtgccat   2220
accaggaagc agatgaggca tggctattca agatgagaat gcatgatttt ctggcccaag   2280
tcaccttcca ggaccatctg ctatgacccc tctggcaatc tgttaagagc tgtcctcagc   2340
atccctcccc acaggacatt gaatcaccat aaccaatttc ttctgccccc taccactaag   2400
caacagctca aataggttgc ctcactcagg agagagacaa actagccagc ttctgcctcc   2460
aaatttgaaa tagccagtgc atccttaggc tggggcagag ttggggccaa agcttctcca   2520
tgtgtcatgg gatatgagct catccttatt atgttgggtg ggggttggac agttacccag   2580
```

```
acttgtcatg tggacctgga gcttatgagg tcattcacat aggcagtgaa agaacctctc   2640
ccatatacgt gaatgcctgt ctcccaaatg gggcaacctg tgggcagaat aagggacttc   2700
tcagccctag aatgttgagg tttccccaac ccctcccttg catacacaca cacacaaaca   2760
ctccctcagc tgtatccact gccctctttc ccacacccta gctttgccca gcagtcaaag   2820
gctcacacat accatcttct ccttaaggct cttattatgc cgtgagtcag agggcgggag   2880
gcagatctgg cagatactga gcccctgcta acccataaga ccggtgtgac ttccttgatc   2940
tgagtctgct gccccagact gactgtcacg ggctgggaag aggcagattc cccccagatg   3000
aagtcagcag cagagcacaa gggcatcagc gccaaagtaa ggatgcttga ttagttcttc   3060
agggcagagt gggctgtgct tcctctgccc cagaaaatgg cacagtccct gttctatggg   3120
aaaaagaatg tgaggtccct gggtgggctc agggaacaga gaggtcatga ggaggggata   3180
gcactgcaga aaccaagggt gccttgtgag tcctccctct gtctttttag gcatgatcca   3240
ggaacatgac aaaattagtg ctttaaatag atttacttgg ggctaagaga aatgtgcctg   3300
tcaggaaaac tatggggaat caggacactt ctcaaaatta gccccactga gtattgtctt   3360
tataattcct tctttttgga ttagattgta aaaaagagag tgtaaatgaa tgatgtccat   3420
ataataagtt attagccaac cattaaaaag aaagggaaga aataaatcag tttggttttt   3480
acacacacat acagacacac acatataaac attgatcaac actgaaatgt ttaatagtca   3540
ttattttcgg gtcgtaaaat tcactgttct tcaatgaata cttgtagagc acatattata   3600
tgcagtagtt ttgataggtt ctaggggtat agtggaaaac ataccaggta tacgctgctc   3660
ttagcttatt ttccagtggg aaagatagac aataagcaag tgaacaaatg caaataaatt   3720
actctagatt gttataagtg aaattaagta ccaatccttt agatatggta cacagagaag   3780
gatctctgac agaccccaac attgacactg aagctgaaag gcataaaaga accagagacc   3840
tggggagggg ccggtgggca gaaggagagc aggtgccaag cccccaggtg gagagctctg   3900
ggctcatctc aggaaccgaa ggccctcagt gaggtaagaa tatacctctc agggagagat   3960
tgacatgaat tggggcccca gaagaaggca gaagccaggt acccagggtc ttttaaacca   4020
cggcagtgag tttgaatgtt atttcaagtg tgctggtgca ctgttggcac gggggagaga   4080
tgtgctcaaa tccccactct gaaagatttc ttaagctatt tctagagtat gatttacaac   4140
aggaaatgga tgatttgatt ctgatcttta taccttcatg catttaaaaa agtacttaag   4200
aaagtagttt ggtttgtcat tataaaaagc aatacttatt tttatattgt gtagattcaa   4260
tcttgtttcc ttgcctagag tgggccgtgc tttggagttc ttatgagcat ggcattcctg   4320
agaacttctc taactgcagc ctcgggcata gaggctgggc agcaagtggc agcagcagag   4380
gactcctaga agccttctac ttgactctac ttggcctaaa gtcaaactcc ctccaccaaa   4440
gacagagttt atttccacat aggatggagt taaaaaatat attctgagag aggaagggct   4500
tgtggcccaa gagaacaccc cagaaatacc accccttcat gggaagtgac tctatcttca   4560
aacatataac ccagcctgga catccccgaa agacacataa ctttccattt catgcccttg   4620
aaagtgaatc ttttggccta ataatgagaa caaactcatt ttgaaagtgg aaaaattgag   4680
attcagagca gaagtttgac taaggtcaca aaacagtagg atgcctcact cagctccctg   4740
tgcctaggtc agaaaagcat cacaggaata gttgagctac cagaatcctc tggccaggca   4800
ggagctgtgt gtccctggga aatggggccc taaagggttt gctgcttaag atgcctgtgg   4860
tgagtcagga aggggttaga ggaagttgac caactagagt ggtgaaacct gtccatcacc   4920
```

ttcaacctgg agggaggcca ggctgcagaa tgatataaag agtgccctga ctcctgctca 4980
gctcagcact ccaccaaagc 5000

<210> SEQ ID NO 58
<211> LENGTH: 5000
<212> TYPE: DNA
<213> ORGANISM: Homo sapiens

<400> SEQUENCE: 58
ttttcttttt taaacttgca gttctaggaa ctgtgctaag aacttcatct gtatttcttt 60
attcagtgga ttaggaatgt tttcagcccc cttttccagt gatggttaag taacttgcca 120
gaggttgcac aggtggagag agcaagggtg ggaactgatg ctggatgtcc ctctccaggg 180
tctgtgttat aactgggctg atgcttctca ctgcagccca tttcaaagag catggagcta 240
aggtactgcc tttttctccc agtcttattt tctctcactg cagctttcat tgtgaatatg 300
ccatattttg gccacccttt ccagctaagt caattttgat aactatcctg gggacccaac 360
tttccctcag aatattgttt gctgagaaaa tgttttggat cccaccatgg gcttttaaaa 420
cctatatact cctcctcttc acctctccat ccaaagatta atcttctcct gaggtccttc 480
ccaggttgga tgctcttctc ttatgaatga ccagaactgg tgcctcactt ctggaaacct 540
ccagatgagt ggagagcttt tgctccaccc tcagtataca cctggtcttt gctgcctcac 600
ctcgagctgg ccaagggcac cttctttaac acgagtaaat aagccattcc tagacttctg 660 ccctttttaaa ggcattgtta gtgctgaatc ggtactgttt gtgagcagtt ttggagcatc 720
aaattcaggc aaggagagaa gcccaaccac ccacactgtc agcattagat ctgcctaaaa 780
taacatcact gagatatcaa accttccttg ttctggttat ggcatcatct agaaatgaaa 840
aaaaaatcat gttagattat ttgcttgggc ctacaatttt attttggatc tctattatta 900
ttctaaaaag ggccatttaa tttccatctt gggaattttc tccttcagtt cctataccaa 960
agagaaaaca gaacttctgt tcattccaga ggtgtagagc cgtattggcc cagctcagaa 1020
aatagaaggc atagcagagc tgcctgtgag atagataggt gccatgtgca attcacagag 1080
ctccctcacc atcctagagg cctgcagttc tcaggggatc ttcctgtggg ttaatacttg 1140
agatgcttat gcagggagga actgggtccc tgggatgcga ggggagggag tcacccatgc 1200
ctttatgaaa gatgcttcta gcgtcccgca catggtctgc acctcctgat gctaggtcag 1260
gactgaattg tataaaaggc agaagcttct gacagcacct cagtctacct gtctcctgag 1320
tgatctgctg cagtgcctga accaggtaga gtgcttctca ggaccaggat gaactcttgg 1380
tgctggtgtt ttgggcagaa agagcccctg ggtggaggtt gaggccattc ttgaagaaag 1440
acaaggataa agaaggattt tggaggggaa ggttcttctg gaaggggagg gtggaaggta 1500
ggtaaaagga atgaaggact gatgcctttc tgaagttcca agttattcat ttgaaaatat 1560
ggagttacta ggtggaaatc atttgtatca ttcttgttac tggtcttggg agactgggtt 1620
tttaaaatct ggttcatctt aggccaggag tagtggctca tgcctgtaat cccagcactt 1680
tgggaggctg aggtgggcgg gtcaagaggt caggagttcg agactgacca acatgctgaa 1740
atcccgtctc tactaaaaac acaaaaatta gctgggtgtg gtggtgcaca cctgtctgag 1800
gcaggagaat cacttgaatc cgggaggtgg aggttgcagt gagccgagat agcaccactg 1860
cactccagcc tgagtgacag agtgagactc catcccaaat aataataata atcataataa 1920
taaattctgg tcatcttaga gataaaatct tgtgaaatta tagttcaatt ttaagggcaa 1980
ggaagtgacc ttgggcttgt attgtctttc agctttattc agcttctaca gagatgtcct 2040

-continued

```
gccagcagag ccagcagcag tgccagcctc ctcccaaatg taccccctaaa tgccctccca   2100
agtgtactcc taagtgtcct cccaagtgtc ccccaaaatg ccctccccag tgttcagccc   2160
catgcccacc tccagtctct tcctgctgtg gttccagctc tgggggctgc tgcagctctg   2220
agggtggtgg ctgctgcctg agccaccaca ggccccgcca gtccctccga cgccgacctc   2280
agagttccag ctgctgtggc agtggcagtg gccagcagtc tgggggctcc agctgctgcc   2340
acagctctgg gggctctggc tgctgccaca gctctggagg ctgctgctga cctgggccat   2400
gaggagcacg gaggagaagg actggcagat cccaggtgct gaagatgtgt gtcagcctga   2460
ggcttctttt ctctcatttc ccatggaagg acttcggaaa tgccttaagt tcccctcttt   2520
atcctgccca tgttcactcc attgtagggt tgaagtctag cttgtgatat tttctggcct   2580
ggctttccct ctcagacata gctctttgga gaactaggtg ttgtaattca gttatgaagc   2640
tattttctct gtaacaataa agctttttat tcctgatatc actgcctcct gatttcattg   2700
tttgcctctc ccactcccta cctgctgcat caagccatct tcccttccct tctcttaaat   2760
gcaagcgaac actttacaaa cttgtttagg aagcacattt tggcagtgaa gctacttagg   2820
cctctggaaa acaatatttc cttctatgca ctggattctg gaactttaag cttgaaggaa   2880
agaataatgt ctgagaccat tacgccagac acaagattgt atgaggagag ccaggaatgg   2940
gtttgaagag aagaggatgg ttgtactcaa aaggttcagg ttctgagagg gtttccttca   3000
agcatgggtc acagtttgaa aaattgcttg tccccattca tggggaataa gattgcctga   3060
agtgctcatc ctgggctcta ataaatggac actctttact tttctgatta ttataagctc   3120
aggtgtttcc atcagttggc tagagggaga gctgggtggg cagtgagtga gttttggagg   3180
cagatatgaa acgtctgagc acattttccc tgcatgctga aatcctggat ttgaatctgg   3240
gtaaagaact gagaaagaca cccttctttg caaagactgt ctctatgtgg ttgggacgta   3300
cgtgtgtgtg tgtgtgtgtg tgtgtgtgtg tgtgtgtgca gtgagaggta taagagtaca   3360
ggggttttgg tccctgtgtt gggttttcca agcaacattt ctttaggaat gggctggttc   3420
cttcaggaga cactcataat gtacctagaa aagataacta gaaaagttaa ttccaaatca   3480
gcctttaata taaaagataa acaattgatg cctcctttga taagagttaa tagcgataaa   3540
taaagtaagc tggtttatga gatcatagga tgcccacaga atgagtaggc acttgcccag   3600
attatctcct tatactgatt cctaccaaac gttcttcatt cttttttttt tttttaaaa   3660
gaactttgcc cattttccca gaggagatcc tgcctctgtc ttgttatttc attacttcct   3720
tctctgttct aatattgact ttactttttg gaatgtctca cctatactca ccaacaggtg   3780
ctctaggaac tggcaacctg ttaatcaggc tctaaatcca tgttaaatga aactggtatc   3840
ttttgtgact tatctttcct cgcctagtcc cttgagccac tcccagctca ctcgccccca   3900
aacctgtctc tcatccttaa ttcctgaatt cttagtcttg gacttctgtt atagttcaca   3960
ttcacagttg tgggcaattt gattaagaag cagttctgaa gttgactgcc aaagtatcct   4020
ccaattctta aaaattagtt attctgaaaa cactatctat catgaacact ttggaccttt   4080
ggaaagaact ttctttcttt ctttctcttt tttttcttct ttccctccct cccttcttcc   4140
tttcccattt tcttttgcac tgggcagtgg ccctagggag aacttatctt caaaggcaga   4200
ttggtggttg ggggtgggat aagaagcagg agtcccacag gctgactagc ctttttgcaa   4260
ttgggccact gtcctgcaca catttttctc tttgtcatac catgctgtat tatggggata   4320
tggcaacctg actacattca caacttttct ggtcttatgg ttccttaact ttgcctaggt   4380
```

-continued

```
ttttcttcct gtctccagtg acagagagaa atcacccctg gggttcccaa aggtgcatcc   4440

ccgtcatcat cttcactcac tgcatcttga agcatatgga tgaaacccag caggcttatc   4500

gcatagcttg tggtctgccc tggggagcca aggaccaaga gccagagaga tgagaatcaa   4560

gataaaaata ggtgaactac cacctaccaa gtagatgact acataggaat ggatgtgtgg   4620

gcaagtggag ccgtctgtgt gtgtgtgtgt gtgtgtgtgt gtgtgtgtgt gtgtgtgtat   4680

tgaagacaag ggcaggggtt ccagacctcc ctgcatttga gccccatgcc ctctcttagc   4740

atacacacag cctcccaggt acaaacagtg ccctgtttgg aaagtaaaca tgccatagca   4800

atcctggcac ctctgtgaag tgacttagat gcccacatgc accacctaca atgctacctg   4860

agtgatgaat gtctctggga tgtgagtgtc agctgagcac gtctgttggg aaatgggccc   4920

ctcccaagag cctgaacctg aatacttctt ataaaaaggt tctctggctg gacgctgctc   4980

aatccactgc ctagcaggtg                                                5000
```